United States Patent
Nam et al.

(10) Patent No.: US 11,584,760 B2
(45) Date of Patent: *Feb. 21, 2023

(54) DITHIO ETP DERIVATIVES

(71) Applicants: CITY OF HOPE, Duarte, CA (US); THE REGENTS OF THE UNIVERSITY OF CALIFORNIA, Oakland, CA (US)

(72) Inventors: Sangkil Nam, Tujunga, CA (US); David Horne, Altadena, CA (US); Larry Eugene Overman, Corona Del Mar, CA (US); Brad Loertscher, Portage, MI (US)

(73) Assignees: CITY OF HOPE, Duarte, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/030,073

(22) Filed: Sep. 23, 2020

(65) Prior Publication Data
US 2021/0115066 A1   Apr. 22, 2021

Related U.S. Application Data

(63) Continuation of application No. 16/333,577, filed as application No. PCT/US2017/051902 on Sep. 15, 2017, now Pat. No. 10,822,353.

(60) Provisional application No. 62/433,678, filed on Dec. 13, 2016, provisional application No. 62/395,244, filed on Sep. 15, 2016.

(51) Int. Cl.
| | | |
|---|---|---|
| *C07D 513/18* | (2006.01) | |
| *A61K 31/706* | (2006.01) | |
| *C07D 487/04* | (2006.01) | |
| *A61K 31/548* | (2006.01) | |
| *C07D 401/12* | (2006.01) | |
| *A61K 45/06* | (2006.01) | |
| *C07D 513/08* | (2006.01) | |
| *A61P 35/00* | (2006.01) | |

(52) U.S. Cl.
CPC .......... *C07D 513/18* (2013.01); *A61K 31/548* (2013.01); *A61K 31/706* (2013.01); *A61K 45/06* (2013.01); *A61P 35/00* (2018.01); *C07D 401/12* (2013.01); *C07D 487/04* (2013.01); *C07D 513/08* (2013.01)

(58) Field of Classification Search
CPC .. C07D 513/08; C07D 401/12; C07D 487/04; A61K 31/548; A61K 31/706; A61P 35/00
See application file for complete search history.

(56) References Cited

U.S. PATENT DOCUMENTS

| | | | |
|---|---|---|---|
| 4,396,589 A | 8/1983 | Bogdanovic | |
| 5,380,923 A | 1/1995 | Wright et al. | |
| 7,186,721 B2 | 3/2007 | Peschke et al. | |
| 8,044,103 B2 | 10/2011 | Kozikowski et al. | |
| 9,527,868 B2 * | 12/2016 | Overman | C07D 513/18 |
| 9,856,273 B2 | 1/2018 | Overman et al. | |
| 10,822,353 B2 | 11/2020 | Nam et al. | |
| 11,230,560 B2 | 1/2022 | Horne et al. | |
| 2007/0037816 A1 | 2/2007 | Edwards et al. | |
| 2009/0131311 A1 | 5/2009 | Becker et al. | |
| 2010/0305182 A1 | 12/2010 | Blackwell et al. | |
| 2014/0187500 A1 | 7/2014 | Movassaghi et al. | |
| 2015/0291622 A1 | 10/2015 | Overman et al. | |
| 2017/0037058 A1 | 2/2017 | Overman et al. | |

FOREIGN PATENT DOCUMENTS

| | | |
|---|---|---|
| CN | 1215433 A | 4/1999 |
| CN | 101248071 A | 8/2008 |
| EP | 0926242 A1 | 6/1999 |
| GB | 1409085 A | 10/1975 |
| GB | 1409185 A | 10/1975 |
| JP | 2007504235 A | 3/2007 |
| JP | 2008503477 A | 2/2008 |
| JP | 2009504735 A | 2/2009 |
| WO | WO-9748706 A1 | 12/1997 |
| WO | WO-9824926 A1 | 6/1998 |
| WO | WO-9940931 A1 | 8/1999 |
| WO | WO-2005023815 A2 | 3/2005 |
| WO | WO-2005110982 A2 | 11/2005 |
| WO | WO-2005110982 A3 | 1/2006 |
| WO | WO-2006009789 A2 | 1/2006 |
| WO | WO-2006066775 A1 | 6/2006 |
| WO | WO-2007021574 A1 | 2/2007 |
| WO | WO-2007117180 A1 | 10/2007 |
| WO | WO-2008112014 A1 | 9/2008 |
| WO | WO-2010075282 A1 | 7/2010 |
| WO | WO 2014/066435 A1 * | 5/2014 |
| WO | WO-2014189343 A1 | 11/2014 |

(Continued)

OTHER PUBLICATIONS

Baumann et al., Tricyclic analogues of epidithiodioxopiperazine alkaloids with promising in vitro and in vivo antitumor activity, Chemical Science, vol. 6, pp. 4451-4457 (2015).*
Acute Leukemia, Merck Manual (Online Edition) 6 pages, pp. 1-6 (2013).
Fujishiro, S. et al. (Feb. 1, 2013, e-published Dec. 5, 2012). "Epidithiodiketopiperazine as a pharmacophore for protein lysine methyltransferase G9a inhibitors: reducing cytotoxicity by structural simplification," Bioorg Med Chem Lett 23(3):733-736.
Gura, Systems for identifying New Drugs are Often Faulty, Cancer Models, Science, vol. 278, No. 5340, pp. 1041-1042, Nov. 1997.
Häusler J. et al. (1974). "Hydroxylsubstituierte Cyclodipeptide durch Ringschluß von Pyruvoylaminosäure-amiden," Chem Ber 107:2804-2815. (English Translation of Abstract only).

(Continued)

*Primary Examiner* — Deepak R Rao
(74) *Attorney, Agent, or Firm* — Wilson Sonsini Goodrich & Rosati

(57) ABSTRACT

Disclosed herein, inter alia, are compositions and methods of using the same for the treatment of cancer.

19 Claims, 4 Drawing Sheets

(56) References Cited

FOREIGN PATENT DOCUMENTS

| WO | WO-2018053345 A1 | 3/2018 |
| WO | WO-2018217811 A1 | 11/2018 |

OTHER PUBLICATIONS

Johnson et al., Relationships between drug activity in NCI preclinical in vitro and in vivo models and early clinical trials, British Journal of Cancer (2001) 64(10): 1424-1431.
Overman, L.E. et al. (Dec. 6, 2007, e-published Nov. 15, 2007). "Construction of epidithiodioxopiperazines by directed oxidation of hydroxyproline-derived dioxopiperazines," *Org Lett* 9(25):5267-5270.
Pearce et al., Failure modes in anticancer drug discovery and development, Cancer Drug Design and Discovery Edited by Stephen Neidle, Chapter 18, pp. 424-435 (2008).
Simone, Oncology: Introduction, Cecil Textbook of Medicine, 20th Edition, vol. 1, pp. 1004-1010, 1996.
International Search Report dated Jan. 17, 2018, for PCT Application No. PCT/US2017/051902, filed Sep. 15, 2017, 4 pages.
Written Opinion dated Jan. 17, 2018, for PCT Application No. PCT/US2017/051902, filed Sep. 15, 2017, 5 pages.
Australia Patent Application No. 2013334707 Examination Report No. 1 dated Feb. 3, 2017.
Banfi et al., A convergent synthesis of enantiopure bicyclic scaffolds through multicomponent Ugi reaction. ScienceDirect, Tetrahedron, 64:1114-1134, 2008.
Baumann et al. Tricyclic analogues of epidithiodioxopiperazine alkaloids with promising in vitro and in vivo antitumor activity. Chemical Science 6:4451-4457 (2015).
Blaha et al., Collection Czechoslovak Chern. Cornrnun. [vol. 52] [1987] pp. 2295-2308.
Canadian Patent Application No. 2,900,335 Office Action dated Dec. 2, 2019.
Chen et al., "Convergent diversity-oriented synthesis of small-molecule hybrids," Angew Chern Int Ed Engl., 44(15):2249-2252 (2005).
Chen et al., "Supporting Information-Convergent diversity-oriented synthesis of small-molecule hybrids," pp. 1-38 (2005).
Chinese Patent Application No. 201380065997.2 First Office Action dated Apr. 19, 2016.
Chinese Patent Applpication No. 201380065997.2 Second Office Action dated Dec. 19, 2016.
DeLorbe et al., J Am Chern Soc. Mar. 13, 2013; 135(1 0) pp. 1-30.
Extended European Supplementary Search Report in EP 13 84 9813 dated Mar. 21, 2016, 13 pages.
Guenoun et al., Pyrrolidinopiperazinedione as chiral auxiliary and its use in asymmetric Mannich synthesis. Tetrahedron Letters, 38(9):1563-1566, 1997.

Imamura et al.: Cyclo (His-Pro) potentiates GABA/ethanol-mediated chloride uptake by neurosynaptosomes. Peptides 24:445-448 (2003).
International Search Report in International Publication No. PCT/US2013/066252 dated Feb. 11, 2014, 5 pages.
Jainta et al., "Microwave-assisted stereo selective one-pot synthesis of symmetrical and unsymmetrical 2,5-Diketopiperazines from unprotected amino acids," European Journal of Organic Chemistry, 32:5418-5424 (2008).
Japanese Patent Application No. 2016-558595 Office Action dated May 8, 2018.
Japanese Patent Application No. 2020-079037 Notice of Rejection dated Jun. 1, 2021.
Kobayashi et al., Chem. Pharm. Bull. 42(12) 2449-2451 (1994).
Lopez-Rodriguez et al., "Synthesis and structure-activity relationships of a new model of arylpiperazines. 8. Computational simulation of ligand-receptor interaction of 5-HT(IA)R agonists with selectivity over alpha1-adrenoceptors," Journal of Medicinal Chemistry, 48(7):2548-2558 (2005).
Moldvai et al., "Enantioefficient synthesis of alpha-ergocryptine: first direct synthesis of (+)-lysergic acid," Journal of Organic Chemistry, 69(18):5993-6000 (2004).
Monbaliu et al., "A new benzotriazole-mediated stereoflexible gateway to hetero-2,5-diketopiperazines," Chemistry—A European Journal, 18(9):2632-2638 (2012).
Occelli et al., Sostanze attive sul sistema nervoso centrale. Il Farmaco, 39(8):718-738, 1984. (English abstract provided).
Oehler, E. and U. Schmidt, Uber Aminosauren und Peptide, XV-1,2. "Hydroxylsubstituierte cyclodipeptide durch ringschlufi von pyruvoylaminosaureamiden, II-3, Zweifacher Ringschlufi," Chemische Berichte, 108(9):2907-2916 (1975). In German with an English Language abstract.
PCT/US2018/033967 International Search Report and Written Opinion dated Aug. 2, 2018.
Poisel, H. and U. Schmidt, Ueber Aminosaeuren und Peptide, XVI-1, "Ueber dehydro-aminosaeuren, III. Additionen an alpha-iminocaronsaeuren," Chemische Berichte, 108(9):2917-2922 (1975). In German with an English Language abstract.
PubChemCompound, datasheet [online compound summary] for CID 98951, retrieved from the Internet:<URL:pubchem.ncbi.nlm.nih.gov/search!search.cgi>, 14 pages, create date Mar. 26, 2005.
Stark et al., "Structures, sensory activity, and dose/response functions of 2,5 diketopiperazines in roasted cocoa nibs (*Theobroma cacao*)," Journal of Agricultural and Food Chemistry, American Chemical Society, 53(18):7222-7231 (2005).
U.S. Appl. No. 14/689,682 Notice of Allowance dated Jul. 28, 2016.
U.S. Appl. No. 14/689,682 Office Action dated Oct. 23, 2015.
U.S. Appl. No. 15/242,318 Office Action dated Apr. 10, 2017.
U.S. Appl. No. 16/333,577 Office Action dated Mar. 3, 2020.
Wang, L. and D. Clive, "Synthetic studies related to MPC1001: formation of a model epidithiodiketopiperazine," Tetrahedron Letters, 53(12): 1504-1506 (2012).

\* cited by examiner

| Entry | Name | R–X | Solvent/Temp | Base | Yield (2 steps) | IC$_{50}$ ($\mu$M) DU145 | IC$_{50}$ ($\mu$M) A2058 |
|---|---|---|---|---|---|---|---|
| 1 | LEO-16-1833 | Me-C(O)- | EtOAc, 0 °C | K$_2$CO$_3$ | 92% yield | 0.29 | 0.16 |
| 2 | LEO-16-1836 | Ph-C(O)- | EtOAc, rt | K$_2$CO$_3$ | 66% yield | 0.80 | 0.20 |
| 3 | LEO-16-1835 | PhCH$_2$-C(O)- | EtOAc, rt | K$_2$CO$_3$ | 70% yield | 0.48 | 0.20 |
| 4 | LEO-16-1837 | MeO-C(O)- | EtOAc, rt | K$_2$CO$_3$ | 57% yield | > 5 | > 5 |
| 5 | LEO-16-1840 | Cl-CH$_2$-C(O)- | EtOAc, rt | K$_2$CO$_3$ | 36% yield | 1.78 | 0.87 |
| 6 | LEO-16-1841 | PhO-C(O)- | THF, 0 °C | Et$_3$N | 69% yield | 1.78 | 0.87 |
| 7 | LEO-16-1843 | Me$_2$N-C(O)- | THF, 0 °C | Et$_3$N | 33% yield | > 5 | > 5 |
| 8 | LEO-16-1844 | MeO-CH$_2$-C(O)- | THF, -78 °C to -25 °C | Et$_3$N | 58% yield | 0.61 | 0.58 |

FIG. 2B                                                                      IC$_{50}$(μM)

| Entry | Name | Structure | DU-145 | A2058 |
|---|---|---|---|---|
| 1 | Leo-16-1862v (R,S,S,S)-enantiomer | 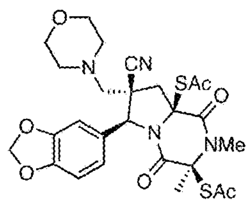 | 0.397 | 0.096 |
| 2 | Leo-16-1866 (racemate) | 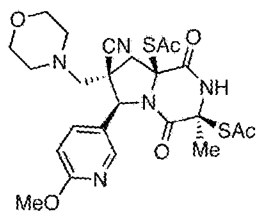 | 0.87 | 0.23 |
| 3 | Leo-16-1867 (racemate) | 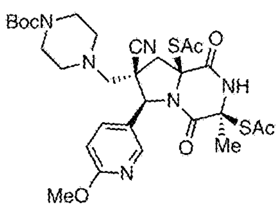 | 0.55 | 0.21 |
| 4 | Leo-16-1868 (racemate) | 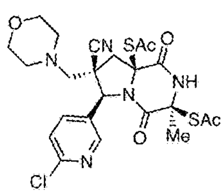 | 0.66 | 0.47 |
| 5 | Leo-16-1869 | 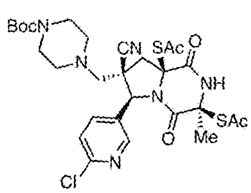 | 0.43 | 0.27 |
| 6 | Leo-17-1876 (S, R, R, R)-enantiomer | 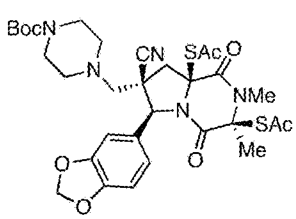 | 0.36 | 0.086 |

DITHIO ETP DERIVATIVES

CROSS REFERENCES TO RELATED APPLICATIONS

This application is a continuation of U.S. patent application Ser. No. 16/333,577 filed on Mar. 14, 2019, now U.S. Pat. No. 10,822,353, which is a U.S. National Stage of International Patent Application No. PCT/US17/51902 filed on Sep. 15, 2017, which claims the benefit of priority of U.S. Provisional Application No. 62/395,244 filed on Sep. 15, 2016 and U.S. Provisional Application No. 62/433,678 filed on Dec. 13, 2016, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. 1F32CA180741 awarded by the National Institutes of Health. The government has certain rights in the invention.

BACKGROUND

ETP natural products represent an intriguing class of (typically) fungal secondary metabolites with a large variety of biological activities ranging from antibiotic to antiviral to antimalarial properties. High levels of toxicity, however, have so far prevented any clinical studies of known ETP structures. Furthermore, modification of properties such as water solubility, membrane permeability or metabolic stability in biological systems is critical. Accordingly, a synthetic route to synthesize ETP analogues for medicinal purposes is imperative and has significant value. Disclosed herein, inter alia, are solutions to these and other problems in the art.

BRIEF SUMMARY OF THE INVENTION

In an aspect is provided a compound having the formula:

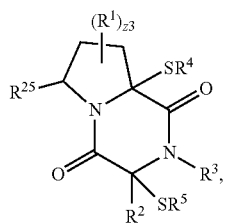

(I)

or a pharmaceutically acceptable salt thereof. $R^1$ is hydrogen, halogen, $-N_3$, $-CF_3$, $-CCl_3$, $-CBr_3$, $-CI_3$, $-CN$, $-CHO$, $-OR^{1A}$, $-NR^{1B}R^{1C}$, $-C(O)OR^{1A}$, $-C(O)NR^{1B}R^{1C}$, $-NO_2$, $-SR^{1D}$, $-S(O)_{n1}R^{1B}$, $-SO_{v1}NR^{1B}R^{1C}$, $-NHNR^{1B}R^{1C}$, $-ONR^{1B}R^{1C}$, $-NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, $-CF_3$, $-CCl_3$, $-CBr_3$, $-CI_3$, $-CN$, $-CHO$, $-COOR^{2A}$, $-CONR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-CHO$, $-OR^{3A}$, $-R^{3B}R^{3C}$, $-COOR^{3A}$, $-CONR^{3B}R^{3C}$, $-NO_2$, $-SR^{3D}$, $-SO_{n3}R^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is $-C(O)-L^1-R^{18}$ or $-C(S)-L^1-R^{18}$. $R^5$ is $-C(O)-L^2-R^{19}$ or $-C(S)-L^2-R^{19}$. $R^4$ and $R^5$ may optionally be joined to form

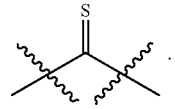

$L^1$ is a bond, $-O-$, $-NH-$, substituted or unsubstituted alkylene, substituted or unsubstituted heteroalkylene. $L^2$ is a bond, $-O-$, $-NH-$, substituted or unsubstituted alkylene, substituted or unsubstituted heteroalkylene. $R^{18}$ and $R^{19}$ are independently halogen, substituted or unsubstituted $C_1$-$C_3$alkyl, substituted or unsubstituted aryl. $R^{25}$ is hydrogen, halogen, $-N_3$, $-CF_3$, $-CCl_3$, $-CBr_3$, $-CI_3$, $-CN$, $-CHO$, $-OR^{25A}$, $-NR^{25B}R^{25C}$, $-C(O)OR^{25A}$, $-C(O)NR^{25B}R^{25C}$, $-NO_2$, $-SR^{25D}$, $-S(O)_{n25}R^{25B}$, $-SO_{v25}NR^{25B}R^{25C}$, $-NHNR^{25B}R^{25C}$, $ONR^{25B}R^{25C}$, $-NHC(O)NHNR^{25B}R^{25C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{25A}$, $R^{25B}$, $R^{25C}$, and $R^{25D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH2$, $-NHC(O)NHNH_2$, $-NHC(O)NH_2$, $-NHSO_2H$, $-NHC(O)H$, $-NHC(O)-OH$, $-NHOH$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl or substituted or unsubstituted heteroaryl. The symbol z3 is an integer from 0 to 5. The symbols n1, n3, and n25 are independently an integer from 0 to 4. The symbols v1, v3, and v25 are independently 1 or 2.

In an aspect is provided a pharmaceutical composition including a compound as described herein and a pharmaceutically acceptable excipient.

In an aspect is provided a pharmaceutical composition including a pharmaceutically acceptable excipient, a compound as described herein, and at least one anticancer agent.

In an aspect is provided a method of treating cancer, including administering to a subject in need thereof a therapeutically effective amount of a compound as described herein, including embodiments.

In another aspect is provided a method of inhibiting the growth of a cancer cell, comprising administering to a subject in need thereof a therapeutically effective amount of a compound or composition described herein.

BRIEF DESCRIPTION OF THE DRAWINGS

FIGS. 2A and 2B. In vitro cytotoxicity against two invasive cancer cell lines, DU145 (human prostate cancer) and A2058 (human melanoma) were determined for different analogs.

DETAILED DESCRIPTION

Figure 1:
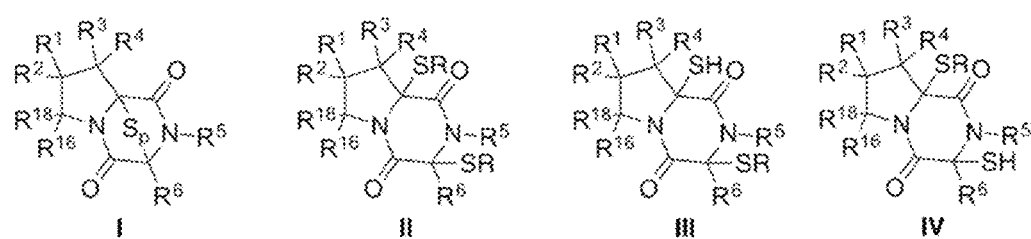
FIG. 1. Chemical scaffolds I-IV. Each R is independently a group that could be removed in vivo, such as for example —C(O)R, —C(S)R', —C(O)NR'$_2$, —SR', —S(O$_2$)R', —S(O) R', or —S(O)NR$_2$.

Provided herein, inter alia, are synthetic analogues of ETP compounds. The analogues may be used in the treatment of cancer and may be effective when synergistically combined with other cancer treating compounds. Methods of synthesis and use are also provided.

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to:
—CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. A 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ~~~ " denotes the point of attachment of a chemical moiety to the remainder of a molecule or chemical formula.

The term "oxo," as used herein, means an oxygen that is double bonded to a carbon atom.

The term "thio," as used herein, means a sulfur that is single bonded to carbon or to another sulfur.

The term "alkylarylene" as an arylene moiety covalently bonded to an alkylene moiety (also referred to herein as an alkylene linker). In embodiments, the alkylarylene group has the formula:

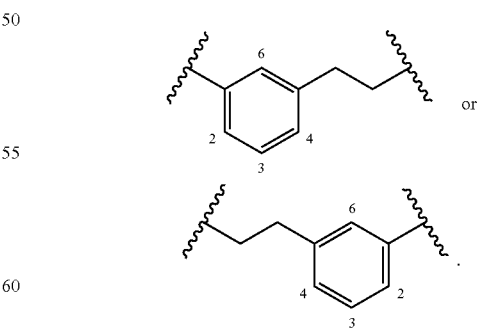

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O) NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl,", "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R',
—C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —NRSO$_2$R", —NR'C=(O)R", —NR'C (O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen,
—SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R",
—NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—,
—CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH2, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C1-C8 alkyl, C1-C6 alkyl, or C1-C4 alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C3-C$_8$ cycloalkyl, C3-C6 cycloalkyl, or C5-C6 cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$,
—NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$,—OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo,
halogen, —CCl$_3$, —CBr$_3$, —CF$_3$, —OH, —NH$_2$, —COOH, —CONH$_2$, —NO$_2$, —SH, —O$_3$H, —SO$_4$H, —SO$_2$NH$_2$, —NHNH$_2$, —ONH$_2$, —NHC(O)NHNH$_2$,—NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C3-C$_8$ cycloalkyl, C3-C6 cycloalkyl, or C5-C6 cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C6-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo,
halogen, —CCl$_3$, —CBr$_3$, —CF$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$,
—NHC(O)NH$_2$, —NHSO$_2$H,
—NHC(O)H, —NHC(O)OH, —NHOH, —OCCl$_3$, —OCF$_3$, —OCBr$_3$, —OCI$_3$,—OCHCl$_2$, —OCHBr$_2$,
—OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"$S_p$", "$S_t$", or "$S_n$" refers to a sulfide bridge having p, t, or n sulfurs (e.g. $S_2$ is —S—S—, $S_3$ is —S—S—S—, $S_4$ is —S—S—S—S—).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

"Analog," or "analogue" is used in accordance with its plain ordinary meaning within Chemistry and Biology and refers to a chemical compound that is structurally similar to another compound (i.e., a so-called "reference" compound)

but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, treating does not include preventing.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies, for example epigenetic inhibitors or multi-kinase inhibitors. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alfa, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by (in whole or in part), a symptom of the disease is caused by (in whole or inpart) the substance or substance activity or function, or a side-effect of the compound (e.g. toxicity) is caused by (in whole or inpart) the substance or substance activity or function.

As used herein, the term "cancer" refers to all types of cancer, neoplasm, or malignant tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein include cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Examples of HDAC inhibitors include Vorinostat, romidepsin, CI-994, Belinostat, Panobinostat, Givinostat, Entinostat, Mocetinostat, SRT501, CUDC-101, JNJ-26481585, or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases.

Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Selective" or "selectivity" or the like of a compound refers to the compound's ability to discriminate between molecular targets (e.g. a compound having selectivity toward HMT SUV39H1 and/or HMT G9a).

"Specific", "specifically", "specificity", or the like of a compound refers to the compound's ability to cause a particular action, such as inhibition, to a particular molecular target with minimal or no action to other proteins in the cell (e.g. a compound having specificity towards HMT SUV39H1 and/or HMT G9a displays inhibition of the activity of those HMTs whereas the same compound displays little-to-no inhibition of other HMTs such as DOT1, EZH1, EZH2, GLP, MLL1, MLL2, MLL3, MLL4, NSD2, SET1b, SET7/9, SET8, SETMAR, SMYD2, SUV39H2).

"HMT SUV39H1," "SUV39H1," or "suppressor of varigation 3-9 homolgue 1" is a histone methyltransferase protein that trimethylates H3K9 (NCBI GI No. 49456451). HMT SUV39H1 may methylate H3K9.

"HMT G9a" or "G9a" is a histone methyltranserfse that dimethylates H3K9 (NCBI GI No. 287865). HMT G9a may dimethylate H3K9.

"H3K9 trimetylation" refers to tri-methylation of lysine 9 of Histone H3. H3K9 trimethylation may be performed by histone methyl transferases such as SUV39H1.

Azacitidine is an epigenetic inhibitor having the formula:

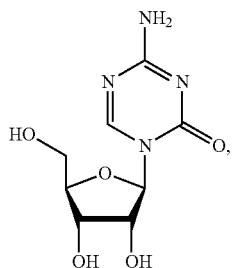

including pharmaceutically acceptable salts thereof.

Azacitidine is an anti-cancer epigenetic inhibitor.

Decitabine is an epigenetic inhibitor having the formula:

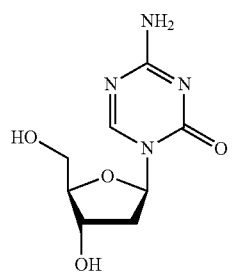 [SMILES: Nc1ncn([C@H]2C[C@@H](O)[C@@H](CO)O2)c(=O)n1]

including pharmaceutically acceptable salts thereof.

Decitabine is an anti-cancer epigenetic inhibitor.

Sorafenib is a multi-kinase inhibitor having the formula:

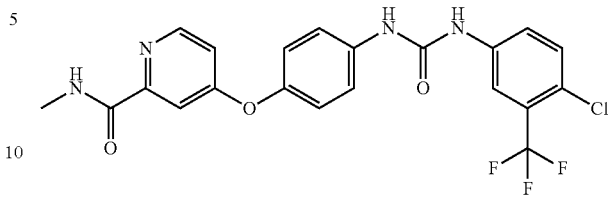

including pharmaceutically acceptable salts thereof.

Sorafenib is an anti-cancer multi-kinase inhibitor.

The terms "synergy", "synergism" "synergistic" and "synergistic therapeutic effect" are used herein interchangeably and refer to a measured effect of compounds administered in combination where the measured effect is greater than the sum of the individual effects of each of the compounds administered alone as a single agent.

II. COMPOUNDS

In an aspect is provided a compound having the formula:

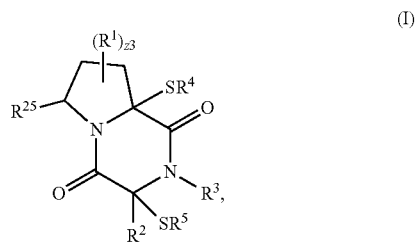

or a pharmaceutically acceptable salt thereof.

$R^1$ is halogen, $-N_3$, $-CF_3$, $-CCl_3$, $-CBr_3$, $-CI_3$, $-CN$, $-CHO$, $-OR^{1A}$, $-NR^{1B}R^{1C}$, $-C(O)OR^{1A}$, $-C(O)NR^{1B}R^{1C}$, $-NO_2$, $-SR^{1D}$, $-S(O)_{n1}R^{1B}$, $-SO_{v1}NR^{1B}R^{1C}$, $-NHNR^{1B}R^{1C}$, $ONR^{1B}R^{1C}$, $-NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, $-CF_3$, $-CCl_3$, $-CBr_3$, $-CI_3$, $-CN$, $-CHO$, $-COOR^{2A}$, $-CONR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is $C_1$-$C_3$alkyl. In embodiments, $R^2$ is methyl.

$R^3$ is hydrogen, halogen, $-N_3$, $-CF_3$, $-CCl_3$, $-CBr_3$, $-CI_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is $C_1$-$C_3$alkyl. In embodiments, $R^3$ is methyl.

$R^4$ is —C(O)—O-$L^1$-$R^{18}$ or —C(S)-$L^1$-$R^{18}$. $R^5$ is —C(O)-$L^2$-$R^{19}$ or —C(S)-$L^2$-$R^{19}$. $R^4$ and $R^5$ may optionally be joined to form:

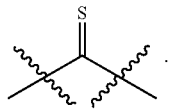 [SMILES: *C(*)=S]

$L^1$ is a bond, —O—, —NH—, substituted or unsubstituted alkylene, substituted or unsubstituted heteroalkylene. $L^2$ is a bond, —O—, —NH—, substituted or unsubstituted alkylene, substituted or unsubstituted heteroalkylene. $R^4$ and $R^5$ may optionally be joined to form:

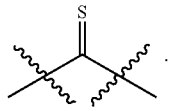 [SMILES: *C(*)=S]

$R^{18}$ and $R^{19}$ are independently halogen, OH, substituted or unsubstituted alkyl, substituted or unsubstituted aryl.

In embodiments, $R^{18}$ and $R^{19}$ are independently halogen. In embodiments V and $R^{19}$ are independently —Cl. In embodiments $R^{18}$ and $R^{19}$ are independently —OH. In embodiments, $R^{18}$ and $R^{19}$ are independently substituted or unsubstituted $C_1$-$C_3$ alkyl or substituted or unsubstituted aryl. In embodiments, $R^{18}$ and $R^{19}$ are independently unsubstituted $C_1$-$C_3$ alkyl or unsubstituted aryl.

$R^{25}$ is hydrogen, halogen, —$N_3$, —$CF_3$, —$CCl_3$, —$CBr_3$, —$CI_3$, —CN, —CHO, —$OR^{25A}$, —$NR^{25B}R^{25C}$, —C(O)$OR^{25A}$, —C(O)$NR^{25B}R^{25C}$, —$NO_2$, —$SR^{25D}$, —S(O)$_{n25}R^{25B}$, —$SO_{v25}R^{25B}R^{25C}$, —$NHNR^{25B}R^{25C}$, $ONR^{25B}R^{25C}$, —NHC(O)$NHNR^{25B}R^{25C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{25A}$, $R^{25B}$, $R^{25C}$, and $R^{25D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl or substituted or unsubstituted heteroaryl.

The symbol z3 is an integer from 0 to 5. The symbols n1, n3, and n25 are independently an integer from 0 to 4. The symbols v1, v3, and v25 are independently 1 or 2.

In embodiments, $R^2$ is hydrogen. In embodiments, $R^3$ is hydrogen. In embodiments, $R^{25}$ is hydrogen.

In embodiments, the compound has the formula:

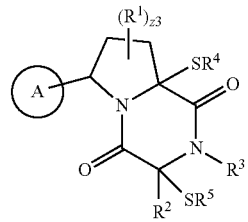

(Ia), wherein $R^1$, z3, $R^2$, $R^3$, $R^4$, and $R^5$ are as described herein.

Ring A is a substituted or unsubstituted cycloalkyl, substituted or unsubstituted heterocycloalkyl, substituted or unsubstituted aryl, or substituted or unsubstituted heteroaryl. In embodiments, Ring A is substituted or unsubstituted phenyl, substituted or unsubstituted pyridyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted furanyl, substituted or unsubstituted pyrrolyl, or substituted or unsubstituted thienyl. In embodiments, Ring A is substituted or unsubstituted phenyl, pyridinyl, pyridazinyl, pyrimidinyl, pyrazinyl, or triazinyl.

In embodiments, the compound has the formula:

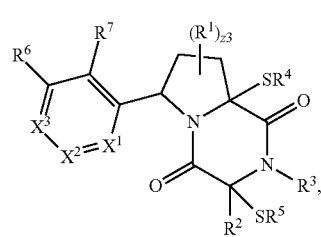

(II)

wherein $R^1$, z3, $R^2$, $R^3$, $R^4$, and $R^5$ are as described herein.

$X^1$ is N or $CR^{10}$. $X^2$ is N or $CR^{11}$. $X^3$ is N or $CR^{12}$. $R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{v6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $X^1$ is $CR^{10}$ and $X^3$ is $CR^{12}$. In embodiments, $X^1$ is $CR^{10}$; $X^2$ is N; $X^3$ is $CR^{12}$; $R^6$, $R^7$ and $R^{10}$ are independently hydrogen; and $R^{12}$ is —$OCH_3$.

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{v6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —$CONR^{7B}R^{7C}$, —$NO_2$, —$SR^{7D}$, —$SO_{n7}R^{7B}$, —$SO_{v7}NR^{7B}R^{7C}$, —$NHNR^{7B}R^{7C}$, —$ONR^{7B}R^{7C}$, —NHC (O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{10}$ is hydrogen, halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —CONR$^{10B}$R$^{10C}$, —NO$_2$, —SR$^{10D}$, —SO$_{n10}$R$^{10B}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{11}$ is hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —CONR$^{11B}$R$^{11C}$, —NO$_2$, —SR$^{11D}$, —SO$_{n11}$R$^{11B}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ and R$^{11}$ may optionally be joined to form a substituted or unsubstituted cycloalkyl, substituted or unsubstituted heterocycloalkyl.

R$^{12}$ is hydrogen, halogen, —N$_3$, —CF$_3$, —CCl$_3$, —CBr$_3$, —CI$_3$, —CN, —CHO, —OR$^{12A}$, —NR$^{12B}$R$^{12C}$, —COOR$^{12A}$, —CONR$^{12B}$R$^{12C}$, —NO$_2$, —SR$^{12D}$, —SO$_{n12}$R$^{12B}$, —SO$_{v12}$NR$^{12B}$R$^{12C}$, —NHNR$^{12B}$R$^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ and R$^{12}$ may optionally be joined to form a substituted or unsubstituted cycloalkyl, substituted or unsubstituted heterocycloalkyl.

In embodiments, R$^2$ is hydrogen. In embodiments, R$^3$ is hydrogen. In embodiments, R$^6$ is hydrogen. In embodiments, R$^7$ is hydrogen. In embodiments, R$^{10}$ is hydrogen. In embodiments, R$^{11}$ is hydrogen. In embodiments, R$^{12}$ is hydrogen.

R$^{6A}$, R$^{6B}$, R$^{6C}$, R$^{6D}$, R$^{7A}$, R$^{7B}$, R$^{7C}$, R$^{7D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, and R$^{12D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{6B}$ and R$^{6C}$, R$^{7B}$ and R$^{7C}$, R$^{10B}$ and R$^{10C}$, R$^{11B}$ and R$^{11C}$, and R$^{12B}$ and R$^{12C}$, substituents bonded to the same nitrogen atom may independently optionally be joined to form a substituted or unsubstituted heterocycloalkyl or substituted or unsubstituted heteroaryl.

The symbols n6, n7, n10, n11 and n12 are independently an integer from 0 to 4. Each occurrence of v6, v7, v10, v11, v12, is independently 1 or 2.

In embodiments, R$^{10}$ and R$^{11}$ or R$^{11}$ and R$^{12}$ are optionally joined to form a substituted or unsubstituted cycloalkyl or substituted or unsubstituted heterocycloalkyl having structural formula:

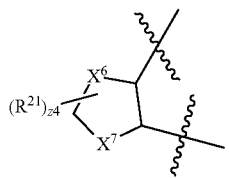 or 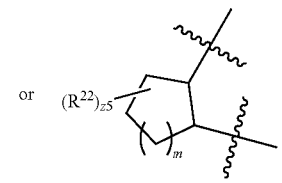

In embodiments, R$^{10}$ and R$^{11}$ are optionally joined to form a substituted or unsubstituted cycloalkyl or substituted or unsubstituted heterocycloalkyl having structural formula:

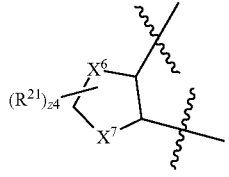 or 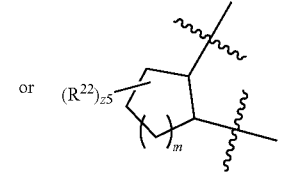

In embodiments, R$^{11}$ and R$^{12}$ are optionally joined to form a substituted or unsubstituted cycloalkyl or substituted or unsubstituted heterocycloalkyl having structural formula:

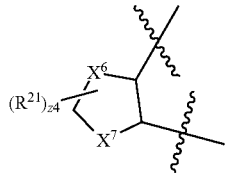 or 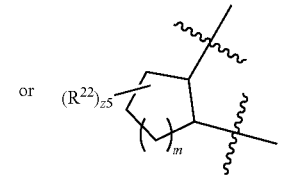

In embodiments, R$^{10}$ and R$^{11}$ or R$^{11}$ and R$^{12}$ are optionally joined to form a substituted or unsubstituted cycloalkyl or substituted or unsubstituted heterocycloalkyl having structural formula:

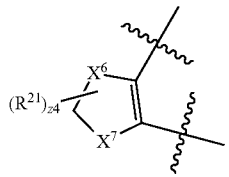 or 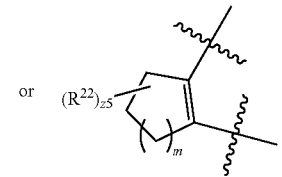

In embodiments, R$^{10}$ and R$^{11}$ are optionally joined to form a substituted or unsubstituted cycloalkyl or substituted or unsubstituted heterocycloalkyl having structural formula:

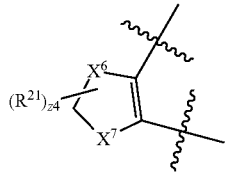 or 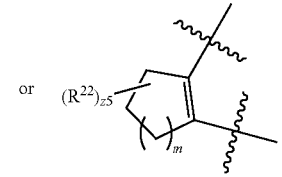

In embodiments, R$^{11}$ and R$^{12}$ are optionally joined to form a substituted or unsubstituted cycloalkyl or substituted or unsubstituted heterocycloalkyl having structural formula:

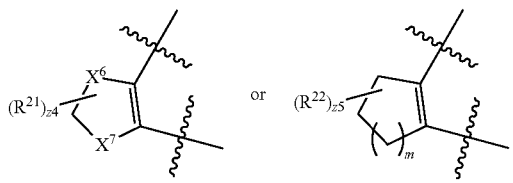

$X^6$ is O, $NR^{23A}$, or S. $X^7$ is O, $NR^{24A}$, or S. The symbol z4 is an integer from 0 to 2. The symbol z5 is an integer from 0 to 8. The symbol m is 1 or 2. $R^{21}$ and $R^{22}$ are independently halogen, $-N_3$, $-CF_3$, $-CCl_3$, $-CBr_3$, $-CI_3$, $-CN$, $-CHO$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the symbol z4 is 0. In embodiments, the symbol z4 is 0.

$R^{23A}$, and $R^{24A}$ are independently hydrogen, halogen, $-N_3$, $-CF_3$, $-CCl_3$, $-CBr_3$, $-CI_3$, $-CN$, $-CHO$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound has the formula:

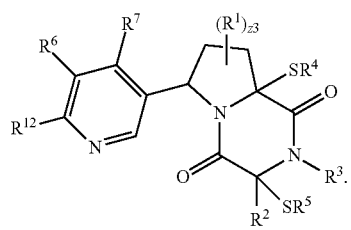

In embodiments, the compound or the pharmaceutically acceptable salt thereof has the formula:

(IIIa(S))

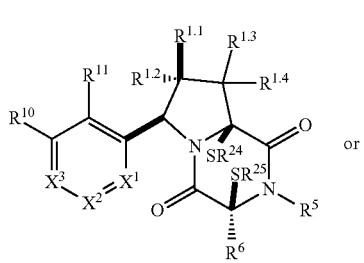

or (IVb (R))

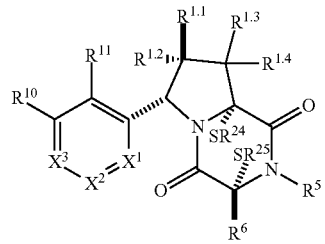

wherein $R^5$, $R^6$, $R^{10}$, $R^{11}$, $X^1$, $X^2$, and $X^3$ are as described herein. $R^{1.1}$, $R^{1.2}$, $R^{1.3}$, and $R^{1.4}$ are encompassed by the definition of $R^1$ or are independently hydrogen. $R^{24}$ is $-C(O)-L^1-R^{18}$ or $-C(S)-L^1-R^{18}$. $R^{25}$ is $-C(O)-L^2-R^{19}$ or $-S(S)-L^2-R^{19}$. $R^{24}$ and $R^{25}$ may optionally be joined to form:

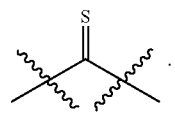

$L^1$ is a bond, $-O-$, $-NH-$, substituted or unsubstituted alkylene, substituted or unsubstituted heteroalkylene. $L^2$ is a bond, $-O-$, $-NH-$, substituted or unsubstituted alkylene, substituted or unsubstituted heteroalkylene. $R^{18}$ and $R^{19}$ are as described herein.

In embodiments, the compound has the formula:

(III)

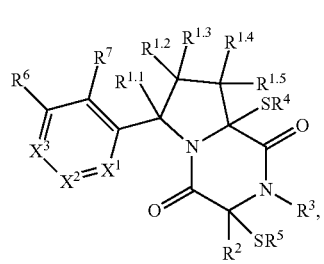

wherein $R^2$, $R^3$, $R^4$, and $R^5$ are as described herein. $R^{1.1}$, $R^{1.2}$, $R^{1.3}$, $R^{1.4}$, and $R^{1.5}$ are substituents encompassed by the definitions of $R^1$ or hydrogen.

In embodiments, $R^2$ is hydrogen. In embodiments, $R^3$ is hydrogen. In embodiments, $R^4$ is hydrogen. In embodiments, $R^5$ is hydrogen. In embodiments, $R^6$ is hydrogen. In embodiments, $R^7$ is hydrogen.

$R^{1.1}$ is hydrogen, halogen, $-CF_3$, $-CCl_3$, $-CBr_3$, $-CI_3$, $-CN$, $-CHO$, $-COOR^{1.1A}$, $-CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1.2}$ is hydrogen, halogen, $-N_3$, $-CF_3$, $-CCl_3$, $-CBr_3$, $-CI_3$, $-CN$, $-CHO$, $-OR^{1.2A}$, $-NR^{1.2B}R^{1.2C}$, $-COOR^{1.2A}$, $-CONR^{1.2B}R^{1.2C}$, $-NO_2$, $-SR^{1.2D}$, $-SO_{n1.2}R^{1.2B}$, $-SO_{v1.2}NR^{1.2B}R^{1.2C}$, $-NHNR^{1.2B}R^{1.2C}$, $-ONR^{1.2B}R^{1.2C}$, $-NHC(O)NHNR^{1.2B}R^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1.2}$ is hydrogen, —CN, —CHO, —OR$^{1.2A}$, —NR$^{1.2B}$R$^{1.2C}$, —C(O)OR$^{1.2A}$, —C(O)NR$^{1.2B}$R$^{1.2C}$, —NO$_2$, —SR$^{1.2D}$, —S(O)$_{n1.2}$R$^{1.2B}$, —SO$_{v1.2}$NR$^{1.2B}$R$^{1.2C}$, —NHNR$^{1.2B}$R$^{1.2C}$, ONR$^{1.2B}$R$^{1.2C}$, —NHC(O)NHNR$^{1.2B}$R$^{1.2C}$, or substituted or unsubstituted alkyl. In embodiments, $R^{1.2}$ is hydrogen, —CN, —CHO, —OCH$_3$, —N(CH$_3$)$_2$, —NH$_2$, —C(O)OCH$_3$, —S(O)$_2$R$^{1.2B}$, or substituted or unsubstituted alkyl. In embodiments, $R^{1.2}$ is —C(O)OR$^{1.2A}$ wherein $R^{1.2A}$ is substituted or unsubstituted alkyl (e.g., $C_1$-$C_8$ alkyl, $C_1$-$C_6$ alkyl, or $C_1$-$C_4$ alkyl). In embodiments, $R^{1.2}$ is an unsubstituted $C_1$-$C_3$ alkyl. In embodiments, $R^{1.2}$ is —CN. In embodiments, $R^{1.2}$ is hydrogen, —CH$_3$, —N(CH$_3$)$_2$, —CN, —CH$_2$OCH$_3$, —C(O)OCH$_3$, —C(O)OCH$_2$CH$_2$CH$_2$CH$_3$, —C(O)OC(CH$_3$)$_3$, or

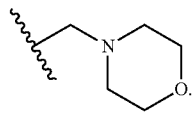

In embodiments, $R^{1.2}$ is methyl substituted with substituted or unsubstituted cycloalkyl, substituted or unsubstituted heterocycloalkyl, substituted or unsubstituted aryl, or substituted or unsubstituted heteroaryl, and $R^{1.3}$ is CN. These embodiments apply to all formulae in the application.

In embodiments, $R^{1.2}$ is methyl substituted with morpholinyl, and $R^{1.3}$ is CN. In embodiments, $R^{1.2}$ is methyl substituted with BOC substituted piperazinyl, and $R^{1.3}$ is CN.

$R^{1.3}$ is hydrogen, halogen, —N$_3$, —CF$_3$, —CCl$_3$, —CBr$_3$, —CI$_3$, —CN, —CHO, —OR$^{1.3A}$, —NR$^{1.3B}$R$^{1.3C}$, —COOR$^{1.3A}$, —CON$^{1.3B}$R$^{1.3C}$, —NO$_2$, —SR$^{1.3D}$, —SO$_{n1.3}$R$^{1.3B}$, —SO$_{v1.3}$NR$^{1.3B}$R$^{1.3C}$, —NHNR$^{1.3B}$R$^{1.3C}$, —ONR$^{1.3B}$R$^{1.3C}$, —NHC(O)NHNR$^{1.3B}$R$^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.3}$ is —CN. In embodiments, $R^{1.3}$ is —CN and $R^{1.2}$ is an unsubstituted $C_1$-$C_3$ alkyl. In embodiments, $R^{1.3}$ is —CN and $R^{1.2}$ is methyl.

In embodiments, $R^{1.3}$ is hydrogen, —CN, —CHO, —OR$^{1.3A}$, —NR$^{1.3B}$R$^{1.3C}$, —C(O)OR$^{1.3A}$, —C(O)NR$^{1.3B}$R$^{1.3C}$, —NO$_2$, —SR$^{1.3D}$, —S(O)$_{n1.3}$R$^{1.3B}$, —SO$_{v1.3}$NR$^{1.3B}$R$^{1.3C}$, —NHNR$^{1.3B}$R$^{1.3C}$, ONR$^{1.3B}$R$^{1.3C}$, —NHC(O)NHNR$^{1.3B}$R$^{1.3C}$, or substituted or unsubstituted alkyl. In embodiments, $R^{1.3}$ is hydrogen, —CN, —CHO, —OCH$_3$, —N(CH$_3$)$_2$, —NH$_2$, —C(O)OCH$_3$, —S(O)$_2$R$^{1.3B}$, or substituted or unsubstituted alkyl. In embodiments, $R^{1.3}$ is —C(O)OR$^{1.3A}$ wherein $R^{1.3A}$ is substituted or unsubstituted alkyl (e.g., $C_1$-$C_8$ alkyl, $C_1$-$C_6$ alkyl, or $C_1$-$C_4$ alkyl). In embodiments, $R^{1.3}$ is hydrogen, —CH$_3$, —N(CH$_3$)$_2$, —CN, —CH$_2$OCH$_3$, —C(O)OCH$_3$, —C(O)OCH$_2$CH$_2$CH$_2$CH$_3$, —C(O)OC(CH$_3$)$_3$, or

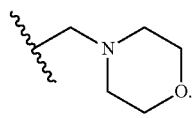

$R^{1.4}$ is hydrogen, halogen, —N$_3$, —CF$_3$, —CCl$_3$, —CBr$_3$, —CI$_3$, —CN, —CHO, —OR$^{1.4A}$, —NR$^{1.4B}$R$^{1.4C}$, —COOR$^{1.4A}$, —CONR$^{1.4B}$R$^{1.4C}$, —NO$_2$, —SR$^{1.4D}$, —SO$_{n1.4}$R$^{1.4B}$, —SO$_{v1.4}$NR$^{1.4B}$R$^{1.4C}$, —NHNR$^{1.4B}$R$^{1.4C}$, —ONR$^{1.4B}$R$^{1.4C}$, —NHC(O)NHNR$^{1.4B}$R$^{1.4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1.5}$ is hydrogen, halogen, —N$_3$, —CF$_3$, —CCl$_3$, —CBr$_3$, —CI$_3$, —CN, —CHO, —OR$^{1.5A}$, —NR$^{1.5B}$R$^{1.5C}$, —COOR$^{1.5A}$, —CONR$^{1.5B}$R$^{1.5C}$, —NO$_2$, —SR$^{1.5D}$, —SO$_{n1.5}$R$^{1.5B}$, —SO$_{v1.5}$NR$^{1.5B}$R$^{1.5C}$, —NHNR$^{1.5B}$R$^{1.5C}$, —ONR$^{1.5B}$R$^{1.5C}$, —NHC(O)NHNR$^{1.5B}$R$^{1.5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1.1A}$, $R^{1.1B}$, $R^{1.1C}$, $R^{1.2A}$, and $R^{1.2B}$, $R^{1.2C}$, $R^{1.2D}$, $R^{1.3A}$, $R^{1.3B}$, and $R^{1.3C}$, $R^{1.3D}$, $R^{1.4A}$, $R^{1.4B}$, $R^{1.4C}$, and $R^{1.5D}$, $R^{1.5A}$, $R^{1.5B}$, $R^{1.5C}$, and $R^{1.5D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1.1B}$ and $R^{1.1C}$, $R^{1.2B}$ and $R^{1.2C}$, and $R^{1.3B}$ and $R^{1.3C}$ substituents bonded to the same nitrogen atom may independently optionally be joined to form a substituted or unsubstituted heterocycloalkyl or substituted or unsubstituted heteroaryl. The symbols n1.2, n1.3, n1.4, and n1.5 are independently an integer from 0 to 4. The symbols, v1.2, v1.3, v1.4, and v1.5 are independently 1 or 2.

$L^1$ is a bond, —O—, —NH—, substituted or unsubstituted alkylene, substituted or unsubstituted heteroalkylene. $L^2$ is a bond, —O—, —NH—, substituted or unsubstituted alkylene, substituted or unsubstituted hetero alkylene.

In embodiments, $L^1$ is —O—. In embodiments, $L^1$ is —NH—. In embodiments, $L^1$ is a bond. In embodiments, $L^2$ is —O—. In embodiments, $L^2$ is —NH—. In embodiments, $L^2$ is a bond.

In embodiments, $R^2$ is hydrogen. In embodiments, $R^3$ is hydrogen.

In embodiments, the compound has the formula:

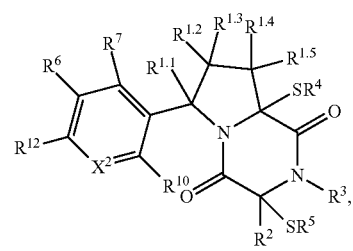

(IV)

wherein $R^{1.1}$, $R^{1.2}$, $R^{1.3}$, $R^{1.4}$, $R^{1.5}$, $R^2$, $R^3$, $R^4$, $R^5$, $R^6$, $R^7$, $R^{10}$, $R^{12}$, and $X^2$ are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen. In embodiments, $R^{12}$ is hydrogen.

In embodiments, the compound has the formula:

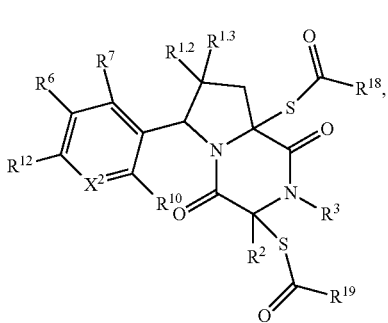
(IVa)

wherein $R^{1.2}$, $R^{1.3}$, $R^2$, $R^3$, $R^6$, $R^7$, $R^{10}$, $R^{12}$, $R^{18}$, $R^{19}$, and $X^2$ are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen. In embodiments, $R^{12}$ is hydrogen.

In embodiments, the compound has the formula:

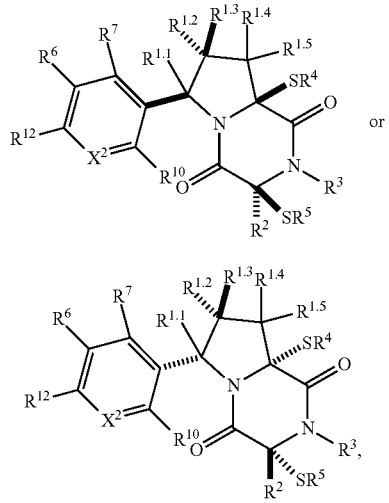
(V (S))

or (VI (R))

wherein $R^{1.1}$, $R^{1.2}$, $R^{1.3}$, $R^{1.4}$, $R^{1.5}$, $R^2$, $R^3$, $R^4$, $R^5$, $R^6$, $R^7$, $R^{10}$, $R^{12}$, and $X^2$ are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen. In embodiments, $R^{12}$ is hydrogen.

In embodiments, the compound has the formula:

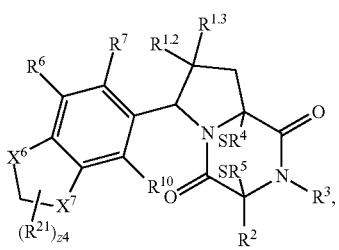
(VII)

wherein $R^{1.2}$, $R^{1.3}$, $R^2$, $R^3$, $R^4$, $R^5$, $R^6$, $R^7$, $R^{10}$, $X^6$, $X^7$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen. In embodiments, $R^{21}$ is hydrogen.

In embodiments, the compound has the formula:

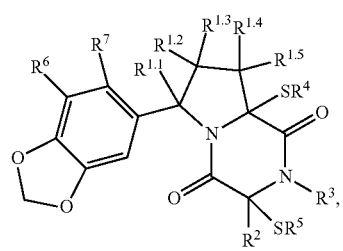

wherein $R^{1.1}$, $R^{1.2}$, $R^{1.3}$, $R^{1.4}$, $R^{1.5}$, $R^2$, $R^3$, $R^4$, $R^5$, $R^6$, and $R^7$ are as described herein.

In embodiments, $R^2$ is hydrogen. In embodiments, $R^3$ is hydrogen. In embodiments, $R^4$ is hydrogen. In embodiments, $R^5$ is hydrogen. In embodiments, $R^6$ is hydrogen. In embodiments, $R^7$ is hydrogen.

In embodiments, the compound has the formula:

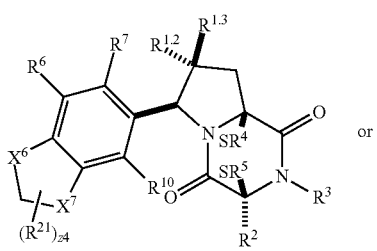
(VIII (S))

or

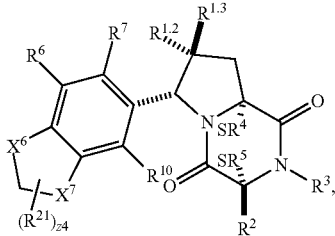
(IX (R))

wherein $R^{1.2}$, $R^{1.3}$, $R^2$, $R^3$, $R^4$, $R^5$, $R^6$, $R^7$, $R^{10}$, $X^6$, $X^7$, $R^{21}$, and z4 are as described herein.

In embodiments, $R^2$ is hydrogen. In embodiments, $R^3$ is hydrogen. In embodiments, $R^4$ is hydrogen. In embodiments, $R^5$ is hydrogen. In embodiments, $R^6$ is hydrogen. In embodiments, $R^7$ is hydrogen. In embodiments, $R^{10}$ is hydrogen.

In embodiments, the compound has the formula:

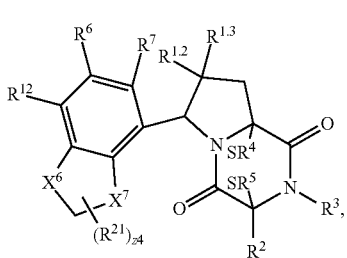

(X)

wherein $R^{1.2}$, $R^{1.3}$, $R^2$, $R^3$, $R^4$, $R^5$, $R^6$, $R^7$, $R^{12}$, $X^6$, $X^7$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{12}$ is hydrogen.

In embodiments, the compound has the formula:

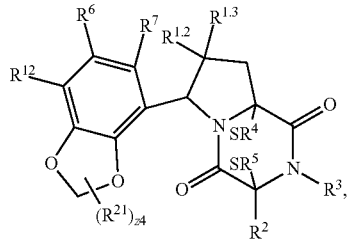

wherein $R^{1.2}$, $R^{1.3}$, $R^2$, $R^3$, $R^4$, $R^5$, $R^6$, $R^7$, $R^{12}$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{12}$ is hydrogen.

In embodiments, the compound has the formula:

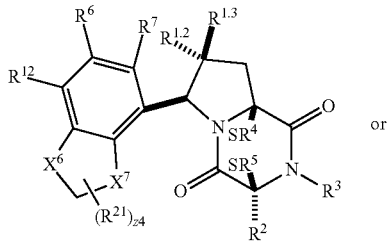

(XI (S))

or (XII (R))

wherein $R^{1.2}$, $R^{1.3}$, $R^2$, $R^3$, $R^4$, $R^5$, $R^6$, $R^7$, $R^{12}$, $X^6$, $X^7$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{12}$ is hydrogen.

In embodiments, the compound has the formula:

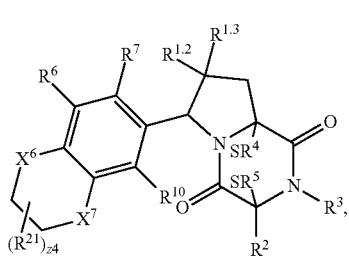

(XIII)

wherein $R^{1.2}$, $R^{1.3}$, $R^2$, $R^3$, $R^4$, $R^5$, $R^6$, $R^7$, $R^{10}$, $X^6$, $X^7$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen.

In embodiments, the compound has the formula:

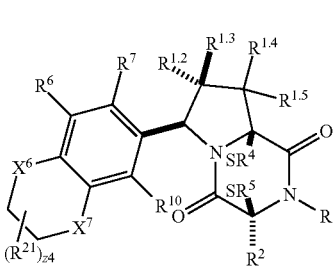

(XIV (S))

or

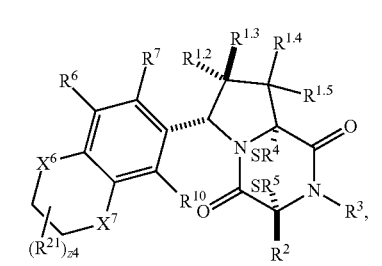

(XV (R))

wherein $R^{1.2}$, $R^{1.3}$, $R^{1.4}$, $R^{1.5}$, $R^2$, $R^3$, $R^4$, $R^5$, $R^6$, $R^7$, $R^{10}$, $X^6$, $X^7$, $R^{21}$, and z4 are as described herein.

In embodiments, $R^2$ is hydrogen. In embodiments, $R^3$ is hydrogen. In embodiments, $R^6$ is hydrogen. In embodiments, $R^7$ is hydrogen. In embodiments, $R^{10}$ is hydrogen.

In embodiments, the compound has the formula:

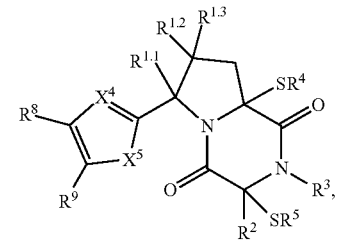

(XVI)

wherein $R^{1.1}$, $R^{1.2}$, $R^{1.3}$, $R^2$, $R^3$, $R^4$, and $R^5$ are as described herein. $X^4$ is N or $CR^{13}$. $X^5$ is $CR^{14}R^{15}$, S, O, or $NR^{20.4}$.

$R^8$ is hydrogen, halogen, $-N_3$, $-CF_3$, $-CCl_3$, $-CBr_3$, $-CI_3$, $-CN$, $-CHO$, $-OR^{8A}$, $-NR^{8B}R^{8C}$, $-COOR^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, NO$_2$, —SR$^{13D}$, —SO$_{n13}$R$^{13B}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{14}$ is hydrogen, halogen, —N$_3$, —CF$_3$, —CCl$_3$, —CBr$_3$, —CI$_3$, —CN, —CHO, —OR$^{14A}$, —NR$^{14B}$R$^{14C}$, —COOR$^{14A}$, —CONR$^{14B}$R$^{14C}$, —NO$_2$, —SR$^{14D}$, —SO$_{n14}$R$^{14B}$, —SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{15}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, —CONR$^{15B}$R$^{15C}$, —NO$_2$, —SR$^{15D}$, —SO$_{n15}$R$^{15B}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{20A}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, —CONR$^{15B}$R$^{15C}$, —NO$_2$, —SR$^{15D}$, —SO$_{n15}$R$^{15B}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^2$ is hydrogen. In embodiments, R$^3$ is hydrogen. In embodiments, R$^8$ is hydrogen. In embodiments, R$^9$ is hydrogen. In embodiments, R$^{13}$ is hydrogen. In embodiments, R$^{14}$ is hydrogen. In embodiments, R$^{15}$ is hydrogen. In embodiments, R$^{20A}$ is hydrogen.

In embodiments, the compound or the pharmaceutically acceptable salt thereof has the formula:

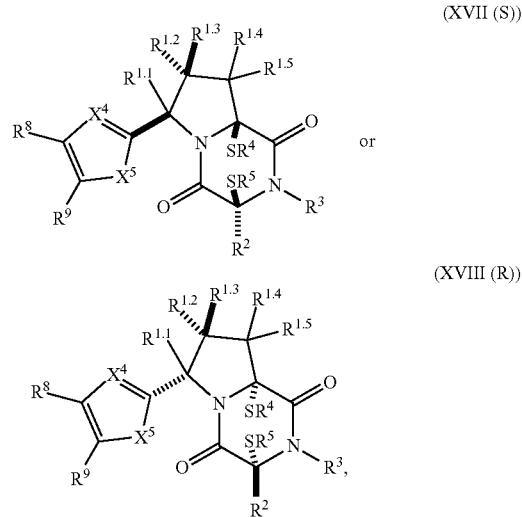

wherein R$^{1.1}$, R$^{1.2}$, R$^{1.3}$, R$^{1.4}$, R$^{1.5}$, R$^2$, R$^3$, R$^4$, R$^5$, X$^4$, X$^5$, R$^8$, R$^9$, R$^{13}$, R$^{14}$, and R$^{15}$ are as described herein.

R$^{8A}$, R$^{8B}$, R$^{8C}$, R$^{8D}$, R$^{9A}$, R$^{9B}$, R$^{9C}$, R$^{9D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, and R$^{20A}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{13B}$ and R$^{13C}$, R$^{14B}$ and R$^{14C}$, and R$^{15B}$ and R$^{15C}$, substituents bonded to the same nitrogen atom may independently optionally be joined to form a substituted or unsubstituted heterocycloalkyl or substituted or unsubstituted heteroaryl.

In embodiments, R$^{13B}$ and R$^{13C}$, R$^{14B}$ and R$^{14C}$, and R$^{15B}$ and R$^{15C}$ substituents bonded to the same nitrogen atom may independently optionally be joined to form a substituted or unsubstituted heterocycloalkyl or substituted or unsubstituted heteroaryl.

The symbols n8, n9, n13, n14, and n15 are independently an integer from 0 to 4. The symbols v8, v9, v13, v14, and v15 are independently 1 or 2.

R$^{8A}$, R$^{8B}$, R$^{8C}$, R$^{8D}$, R$^{9A}$, R$^{9B}$, R$^{9C}$, R$^{9D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, and R$^{15D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^2$ is hydrogen. In embodiments, R$^3$ is hydrogen. In embodiments, R$^8$ is hydrogen. In embodiments, R⁹ is hydrogen. In embodiments, R¹³ is hydrogen. In embodiments, R¹⁴ is hydrogen. In embodiments, R¹⁵ is hydrogen.

In embodiments, the compound is S,S'-3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) diethanethioate.

In embodiments, the compound is a compound described herein in Example 2.

In embodiments, $R^1$ is halogen, —$N_3$, —$CF_3$, —$CCl_3$, —$CBr_3$, —$CI_3$, —CN, —CHO, —$OR^{1A}$, —$NR^{1B}R^{1C}$, —$C(O)OR^{1A}$, —$C(O)NR^{1B}R^{1C}$, —$NO_2$, —$SR^{1D}$, —$S(O)_{n1}R^{1B}$, —$SO_{v1}NR^{1B}R^{1C}$, —$NHNR^{1B}R^{1C}$, $ONR^{1B}R^{1C}$, —$NHC(O)NHNR^{1B}R^{1C}$, x substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^1$ is substituted or unsubstituted alkyl (e.g., $C_1$-$C_8$ alkyl, $C_1$-$C_6$ alkyl, or $C_1$-$C_4$ alkyl). In embodiments, $R^1$ is substituted alkyl (e.g., $C_1$-$C_8$ alkyl, $C_1$-$C_6$ alkyl, or $C_1$-$C_4$ alkyl). In embodiments, $R^1$ is unsubstituted alkyl (e.g., $C_1$-$C_8$ alkyl, $C_1$-$C_6$ alkyl, or $C_1$-$C_4$ alkyl). In embodiments, $R^1$ is substituted or unsubstituted $C_1$-$C_6$ alkyl. In embodiments, $R^1$ is substituted or unsubstituted $C_1$-$C_4$ alkyl. In embodiments, $R^1$ is unsubstituted $C_1$-$C_6$ alkyl. In embodiments, $R^1$ is unsubstituted $C_1$-$C_4$ alkyl. In embodiments, $R^1$ is —CN or —$CH_3$. In embodiments, $R^1$ is —CN. In embodiments, $R^1$ is —$CH_3$.

In embodiments, $R^1$ is hydrogen, —CN, —CHO, —$OR^{1A}$, —$NR^{1B}R^{1C}$, —$C(O)OR^{1A}$, —$C(O)NR^{1B}R^{1C}$, —$NO_2$, —$SR^{1D}$, —$S(O)_{n1}R^{1B}$, —$SO_{v1}NR^{1B}R^{1C}$, —$NHNR^{1B}R^{1C}$, —$ONR^{1B}R^{1C}$, —$NHC(O)NHNR^{1B}R^{1C}$, or substituted or unsubstituted alkyl. In embodiments, $R^1$ is hydrogen, —CN, —CHO, —$OCH_3$, —$N(CH_3)_2$, —$NH_2$, —$C(O)OCH_3$, —$S(O)_2R^{1B}$, or substituted or unsubstituted alkyl. In embodiments, $R^1$ is —$C(O)OR^{1A}$ wherein $R^{1A}$ is substituted or unsubstituted alkyl (e.g., $C_1$-$C_8$ alkyl, $C_1$-$C_6$ alkyl, or $C_1$-$C_4$ alkyl). In embodiments, $R^1$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

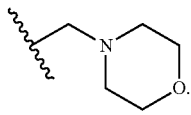

In embodiments, $R^1$ is $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^1$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{26}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl).

In embodiments, $R^1$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^{26}$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl).

In embodiments, $R^1$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, le is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^1$ is $R^{26}$-substituted or unsubstituted aryl (e.g., $C_6$-$C_{10}$ aryl, $C_{10}$ aryl, or phenyl). In embodiments, $R^1$ is $R^{26}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl).

In embodiments, $R^1$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{26}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^{1A}$ is $R^{26A}$-substituted or unsubstituted alkyl (e.g., $C_1$-$C_8$ alkyl, $C_1$-$C_6$ alkyl, or $C_1$-$C_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1B}$ is $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1C}$ is $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1D}$ is $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^2$ is hydrogen, $-CF_3$, $-CCl_3$, $-CBr_3$, $-CI_3$, $-CN$, $-CHO$, $-COOR^{2A}$, $-CONR^{2B}R^{2C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^2$ is substituted or unsubstituted alkyl (e.g., $C_1$-$C_8$ alkyl, $C_1$-$C_6$ alkyl, or $C_1$-$C_4$ alkyl). In embodiments, $R^2$ is substituted alkyl (e.g., $C_1$-$C_8$ alkyl, $C_1$-$C_6$ alkyl, or $C_1$-$C_4$ alkyl). In embodiments, $R^2$ is unsubstituted alkyl (e.g., $C_1$-$C_8$ alkyl, $C_1$-$C_6$ alkyl, or $C_1$-$C_4$ alkyl). In embodiments, $R^2$ is substituted or unsubstituted $C_1$-$C_6$ alkyl. In embodiments, $R^2$ is substituted or unsubstituted $C_1$-$C_4$ alkyl. In embodiments, $R^2$ is unsubstituted $C_1$-$C_6$ alkyl. In embodiments, $R^2$ is unsubstituted $C_1$-$C_4$ alkyl. In embodiments, $R^2$ is $-CH_3$.

In embodiments, $R^2$ is $R^{27}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl).

In embodiments, $R^2$ is $R^{27}$-substituted or unsubstituted alkyl (e.g., $C_1$-$C_8$ alkyl, $C_1$-$C_6$ alkyl, or $C_1$-$C_4$ alkyl). In embodiments, $R^2$ is $R^{27}$-substituted alkyl (e.g., $C_1$-$C_8$ alkyl, $C_1$-$C_6$ alkyl, or $C_1$-$C_4$ alkyl). In embodiments, $R^2$ is an unsubstituted alkyl (e.g., $C_1$-$C_8$ alkyl, $C_1$-$C_6$ alkyl, or $C_1$-$C_4$ alkyl).

In embodiments, $R^2$ is $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^2$ is $R^{27}$-substituted heteroalkyl (e.g., 2 to 8 membered heteroalkyl, 2 to 6 membered heteroalkyl, or 2 to 4 membered heteroalkyl). In embodiments, $R^2$ is an unsubstituted heteroalkyl (e.g., 2 to 8 membered heteroalkyl, 2 to 6 membered heteroalkyl, or 2 to 4 membered heteroalkyl).

In embodiments, $R^2$ is $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^2$ is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^2$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^2$ is $R^{27}$-substituted or unsubstituted aryl (e.g., $C_6$-$C_{10}$ aryl, $C_{10}$ aryl, or phenyl). In embodiments, $R^2$ is $R^{27}$-substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl).

In embodiments, $R^2$ is $R^{27}$-substituted or unsubstituted heteroaryl (e.g., 5 to 10 membered heteroaryl, 5 to 9 membered heteroaryl, or 5 to 6 membered heteroaryl). In embodiments, $R^2$ is $R^{27}$-substituted heteroaryl (e.g., 5 to 10 membered heteroaryl, 5 to 9 membered heteroaryl, or 5 to 6 membered heteroaryl). In embodiments, $R^2$ is an unsubstituted heteroaryl (e.g., 5 to 10 membered heteroaryl, 5 to 9 membered heteroaryl, or 5 to 6 membered heteroaryl).

In embodiments, $R^{2A}$ is $R^{27A}$-substituted or unsubstituted alkyl (e.g., $C_1$-$C_8$ alkyl, $C_1$-$C_6$ alkyl, or $C_1$-$C_4$ alkyl), $R^{27A}$-substituted or unsubstituted heteroalkyl (e.g., 2 to 8 membered heteroalkyl, 2 to 6 membered heteroalkyl, or 2 to 4 membered heteroalkyl), $R^{27A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27A}$-substituted or unsubstituted aryl (e.g., $C_6$-$C_{10}$ aryl, $C_{10}$ aryl, or phenyl), or $R^{27A}$-substituted or unsubstituted heteroaryl (e.g., 5 to 10 membered heteroaryl, 5 to 9 membered heteroaryl, or 5 to 6 membered heteroaryl).

In embodiments, $R^{2B}$ is $R^{27B}$-substituted or unsubstituted alkyl (e.g., $C_1$-$C_8$ alkyl, $C_1$-$C_6$ alkyl, or $C_1$-$C_4$ alkyl), $R^{27B}$-substituted or unsubstituted heteroalkyl (e.g., 2 to 8 membered heteroalkyl, 2 to 6 membered heteroalkyl, or 2 to 4 membered heteroalkyl), $R^{27B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27B}$-substituted or unsubstituted aryl (e.g., $C_6$-$C_{10}$ aryl, $C_{10}$ aryl, or phenyl), or $R^{27B}$-substituted or unsubstituted heteroaryl (e.g., 5 to 10 membered heteroaryl, 5 to 9 membered heteroaryl, or 5 to 6 membered heteroaryl).

In embodiments, $R^{2C}$ is $R^{27C}$-substituted or unsubstituted alkyl (e.g., $C_1$-$C_8$ alkyl, $C_1$-$C_6$ alkyl, or $C_1$-$C_4$ alkyl), $R^{27C}$-substituted or unsubstituted heteroalkyl (e.g., 2 to 8 membered heteroalkyl, 2 to 6 membered heteroalkyl, or 2 to 4 membered heteroalkyl), $R^{27C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27C}$-substituted or unsubstituted aryl (e.g., $C_6$-$C_{10}$ aryl, $C_{10}$ aryl, or phenyl), or $R^{27C}$-substituted or unsubstituted heteroaryl (e.g., 5 to 10 membered heteroaryl, 5 to 9 membered heteroaryl, or 5 to 6 membered heteroaryl).

In embodiments, $R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_{n3}R^{3B}$, —$SO_{v3}NR^{3B}R^{3C}$, —$NHNR^{3B}R^{3C}$, —$ONR^{3B}R^{3C}$, —$NHC(O)NHNR^{3B}R^{3C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is substituted or unsubstituted alkyl (e.g., $C_1$-$C_8$ alkyl, $C_1$-$C_6$ alkyl, or $C_1$-$C_4$ alkyl). In embodiments, $R^3$ is substituted alkyl (e.g., $C_1$-$C_8$ alkyl, $C_1$-$C_6$ alkyl, or $C_1$-$C_4$ alkyl). In embodiments, $R^3$ is unsubstituted alkyl (e.g., $C_1$-$C_8$ alkyl, $C_1$-$C_6$ alkyl, or $C_1$-$C_4$ alkyl). In embodiments, $R^3$ is substituted or unsubstituted $C_1$-$C_6$ alkyl. In embodiments, $R^3$ is substituted or unsubstituted $C_1$-$C_4$ alkyl. In embodiments, $R^3$ is unsubstituted $C_1$-$C_6$ alkyl. In embodiments, $R^3$ is unsubstituted $C_1$-$C_4$ alkyl. In embodiments, $R^3$ is —$CH_3$.

In embodiments, $R^3$ is an unsubstituted cyclopropyl. In embodiments, $R^3$ is an unsubstituted cyclobutyl. In embodiments, $R^3$ is an unsubstituted cyclopentyl. In embodiments, $R^3$ is an unsubstituted cyclohexyl. In embodiments, $R^3$ is an unsubstituted $C_2$-$C_4$ alkyene. In embodiments, $R^3$ is an unsubstituted $C_4$ alkyene.

In embodiments, $R^3$ is $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl).

In embodiments, $R^3$ is $R^{28}$-substituted or unsubstituted $C_1$-$C_4$ alkyl, wherein $R^{28}$ is substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is $R^{28}$-substituted or unsubstituted $C_1$-$C_4$ alkyl, wherein $R^{28}$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is morpholino.

In embodiments, $R^3$ is $R^{28}$-substituted or unsubstituted alkyl (e.g., $C_1$-$C_8$ alkyl, $C_1$-$C_6$ alkyl, or $C_1$-$C_4$ alkyl). In embodiments, $R^3$ is $R^{28}$-substituted alkyl (e.g., $C_1$-$C_8$ alkyl, $C_1$-$C_6$ alkyl, or $C_1$-$C_4$ alkyl). In embodiments, $R^3$ is an unsubstituted alkyl (e.g., $C_1$-$C_8$ alkyl, $C_1$-$C_6$ alkyl, or $C_1$-$C_4$ alkyl).

In embodiments, $R^3$ is $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^{28}$-substituted heteroalkyl (e.g., 2 to 8 membered heteroalkyl, 2 to 6 membered heteroalkyl, or 2 to 4 membered heteroalkyl). In embodiments, $R^3$ is an unsubstituted heteroalkyl (e.g., 2 to 8 membered heteroalkyl, 2 to 6 membered heteroalkyl, or 2 to 4 membered heteroalkyl).

In embodiments, $R^3$ is $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{28}$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^3$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^3$ is $R^{28}$-substituted or unsubstituted aryl (e.g., $C_6$-$C_{10}$ aryl, $C_{10}$ aryl, or phenyl). In embodiments, $R^3$ is $R^{28}$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl).

In embodiments, $R^3$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^3$ is $R^{28}$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^{3A}$ is $R^{28A}$-substituted or unsubstituted alkyl (e.g., $C_1$-$C_8$ alkyl, $C_1$-$C_6$ alkyl, or $C_1$-$C_4$ alkyl), $R^{28A}$-substituted or unsubstituted heteroalkyl (e.g., 2 to 8 membered heteroalkyl, 2 to 6 membered heteroalkyl, or 2 to 4 membered heteroalkyl), $R^{28A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28A}$-substituted or unsubstituted aryl (e.g., $C_6$-$C_{10}$ aryl, $C_{10}$ aryl, or phenyl), or $R^{28A}$-substituted or unsubstituted heteroaryl (e.g., 5 to 10 membered heteroaryl, 5 to 9 membered heteroaryl, or 5 to 6 membered heteroaryl).

In embodiments, $R^{3B}$ is $R^{28B}$-substituted or unsubstituted alkyl (e.g., $C_1$-$C_8$ alkyl, $C_1$-$C_6$ alkyl, or $C_1$-$C_4$ alkyl), $R^{28B}$-substituted or unsubstituted heteroalkyl (e.g., 2 to 8 membered heteroalkyl, 2 to 6 membered heteroalkyl, or 2 to 4 membered heteroalkyl), $R^{28B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28B}$-substituted or unsubstituted aryl (e.g., $C_6$-$C_{10}$ aryl, $C_{10}$ aryl, or phenyl), or $R^{28B}$-substituted or unsubstituted heteroaryl (e.g., 5 to 10 membered heteroaryl, 5 to 9 membered heteroaryl, or 5 to 6 membered heteroaryl).

In embodiments, $R^{3C}$ is $R^{28C}$-substituted or unsubstituted alkyl (e.g., $C_1$-$C_8$ alkyl, $C_1$-$C_6$ alkyl, or $C_1$-$C_4$ alkyl), $R^{28C}$-substituted or unsubstituted heteroalkyl (e.g., 2 to 8 membered heteroalkyl, 2 to 6 membered heteroalkyl, or 2 to 4 membered heteroalkyl), $R^{28C}$ substituted or unsubstituted cycloalkyl (e.g., $C_3$-$C_8$ cycloalkyl, $C_3$-$C_6$ cycloalkyl, or $C_5$-$C_6$ cycloalkyl), $R^{28C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28C}$-substituted or unsubstituted aryl (e.g., $C_6$-$C_{10}$ aryl, $C_{10}$ aryl, or phenyl), or $R^{28C}$-substituted or unsubstituted heteroaryl (e.g., 5 to 10 membered heteroaryl, 5 to 9 membered heteroaryl, or 5 to 6 membered heteroaryl).

In embodiments, $R^{3D}$ is $R^{28D}$-substituted or unsubstituted alkyl (e.g., $C_1$-$C_8$ alkyl, $C_1$-$C_6$ alkyl, or $C_1$-$C_4$ alkyl), $R^{28D}$-substituted or unsubstituted heteroalkyl (e.g., 2 to 8 membered heteroalkyl, 2 to 6 membered heteroalkyl, or 2 to 4 membered heteroalkyl), $R^{28D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28D}$-substituted or unsubstituted aryl (e.g., $C_6$-$C_{10}$ aryl, $C_{10}$ aryl, or phenyl), or $R^{28D}$-substituted or unsubstituted heteroaryl (e.g., 5 to 10 membered heteroaryl, 5 to 9 membered heteroaryl, or 5 to 6 membered heteroaryl).

$R^4$ is —C(O)-$L^1$-$R^{18}$ or —C(S)-$L^1$-$R^{18}$. $R^5$ is —C(O)-$L^2$-$R^{19}$ or —C(S)-$L^2$-$R^{19}$. $R^4$ and $R^5$ may optionally be joined to form

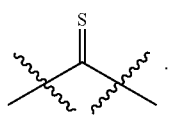

In embodiments, $R^4$ and $R^5$ are joined together to form:

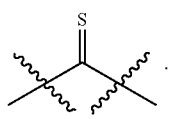

In embodiments, $L^1$ is -$L^{1A}$-$L^{1B}$-, wherein $L^{1A}$ is bonded to —C(O)— or —C(S)—. $L^{1A}$ is a bond or —(CH$_2$)$_{z1}$—. $L^{1B}$ is a bond, —O—, or —NR$^{16B}$—. In embodiments, $L^2$ is -$L^{2A}$-$L^{2B}$-, wherein $L^{2A}$ is bonded to —C(O)— or —C(S)—. $L^{2A}$ is a bond or —(CH$_2$)$_{z2}$—. $L^{2B}$ is a bond, —O—, or —NR$^{17B}$—. The symbols z1 and z2 are independently an integer from 1 to 10. $R^{16B}$ and $R^{17B}$ are independently hydrogen or substituted or unsubstituted alkyl. The symbols z1 and z2 are independently an integer from 1 to 10. In embodiments, $L^{1A}$ is —CH$_2$—. In embodiments, $L^{2A}$ is —CH$_2$—. In embodiments, $L^{1A}$ and $L^{2A}$ are independently —CH$_2$—. In embodiments, $L^{1A}$ is —CH$_2$—. In embodiments, $L^{2A}$ is —CH$_2$—. In embodiments, $L^{1B}$ is —O—. In embodiments, $L^{2B}$ is —O—.

In embodiments, $R^4$ has the formula:

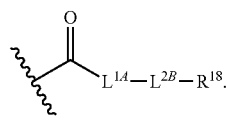

In embodiments, $R^4$ has the formula:

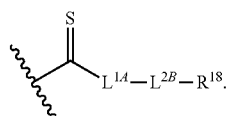

In embodiments, $R^4$ has the formula:

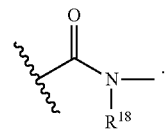

In embodiments, $R^4$ has the formula:

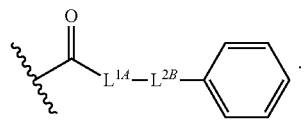

In embodiments, $R^5$ has the formula:

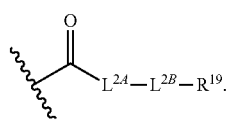

In embodiments, $R^5$ has the formula:

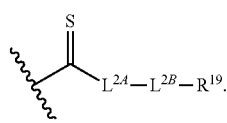

In embodiments, $R^5$ has the formula:

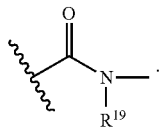

In embodiments, $R^5$ has the formula:

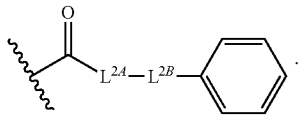

In embodiments, $L^{1B}$ is —$NR^{16B}$; $L^{2B}$ is —$NR^{17B}$; and $R^{16B}$ and $R^{17B}$ are independently unsubstituted $C_1$-$C_3$alkyl.

In embodiments, $R^4$ is —C(O)-$L^1$-$R^{18}$. In embodiments, $R^4$ is —C(S)-$L^1$-$R^{18}$. In embodiments, $R^5$ is —C(O)-$L^2$-$R^{19}$. In embodiments, $R^5$ is —C(S)-$L^2$-$R^{19}$. In embodiments, $R^4$ is —C(O)-$L^1$-$R^{18}$ and $R^5$ is —C(O)-$L^2$-$R^{19}$. In embodiments, $R^4$ is —C(S)-$L^1$-$R^{18}$ and $R^5$ is —C(S)-$L^2$-$R^{19}$.

In embodiments, $R^4$ is

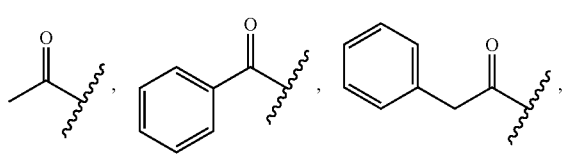

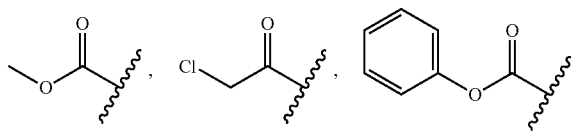

In embodiments, $R^4$ is

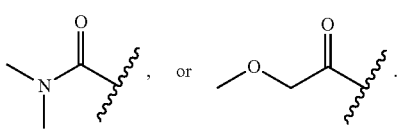

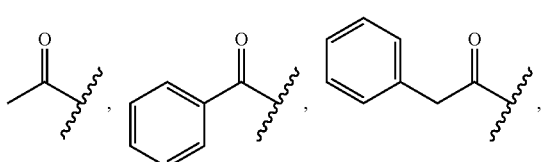

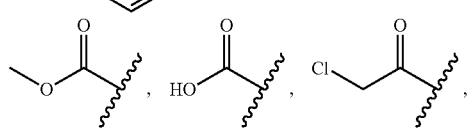

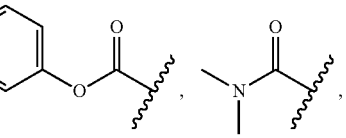

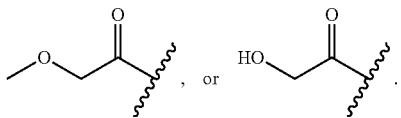

In embodiments, $R^4$ is

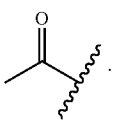 [SMILES: *C(C)=O]

In embodiments, $R^4$ is

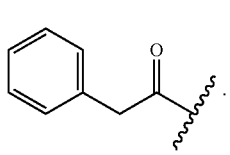 [SMILES: *C(=O)Cc1ccccc1]

In embodiments, $R^4$ is

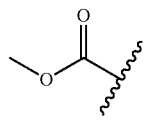

In embodiments, $R^4$ is

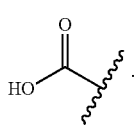

In embodiments, $R^4$ is

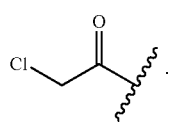

In embodiments, R⁴ is

[structure: phenyl ester]

In embodiments, R⁴ is

[structure: N,N-dimethylamide]

In embodiments, R⁴ is

[structure: methoxymethyl ketone]

In embodiments, R⁴ is

[structure: hydroxymethyl ketone]

In embodiments, R⁵ is

[structures: methyl ketone, phenyl ketone, benzyl ketone, methyl ester, chloromethyl ketone, phenyl ester, N,N-dimethylamide, or methoxymethyl ketone]

In embodiments, R⁵ is

[structures: methyl ketone, phenyl ketone, benzyl ketone,

-continued methyl ester, carboxylic acid, chloromethyl ketone, phenyl ester, N,N-dimethylamide, methoxymethyl ketone, or hydroxymethyl ketone]

In embodiments, R⁵ is

[structure: methyl ketone]

In embodiments, R⁵ is

[structure: phenyl ketone]

In embodiments, R⁵ is

[structure: benzyl ketone]

In embodiments, R⁵ is

[structure: methyl ester]

In embodiments, R⁵ is

[structure: carboxylic acid]

In embodiments, $R^5$ is

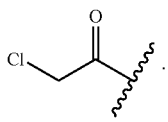

In embodiments, $R^5$ is

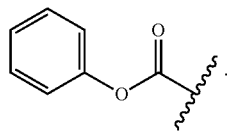 [SMILES: *C(=O)Oc1ccccc1]

In embodiments, $R^5$ is

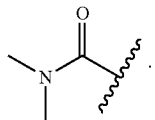 [SMILES: *C(=O)N(C)C]

In embodiments, $R^5$ is

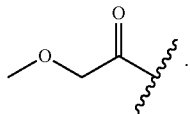

In embodiments, $R^5$ is

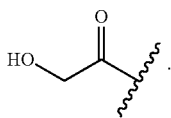

In embodiments, $R^{18}$ is halogen, OH, substituted or unsubstituted $C_1$-$C_3$alkyl, substituted or unsubstituted aryl. In embodiments, $R^{18}$ is substituted or unsubstituted aryl (e.g., $C_6$-$C_{10}$ aryl, $C_{10}$ aryl, or phenyl). In embodiments, $R^{18}$ is halogen. In embodiments, $R^{18}$ is OH. In embodiments, $R^{18}$ is substituted or unsubstituted phenyl. In embodiments, $R^{18}$ is unsubstituted phenyl. In embodiments, $R^{18}$ is Cl. In embodiments, $R^{18}$ is substituted or unsubstituted $C_1$-$C_3$alkyl. In embodiments, $R^{18}$ is unsubstituted $C_1$-$C_3$alkyl. In embodiments, $R^{18}$ is substituted $C_1$-$C_3$alkyl. In embodiments, $R^{18}$ is an unsubstituted $C_3$ alkyl. In embodiments, $R^{18}$ is Cl. In embodiments, $R^{18}$ is F. In embodiments, $R^{18}$ is —$CH_3$.

In embodiments, $R^{19}$ is halogen, OH, substituted or unsubstituted $C_1$-$C_3$alkyl, substituted or unsubstituted aryl. In embodiments, $R^{19}$ is substituted or unsubstituted aryl (e.g., $C_6$-$C_{10}$ aryl, $C_{10}$ aryl, or phenyl). In embodiments, $R^{19}$ is halogen. In embodiments, $R^{19}$ is substituted or unsubstituted phenyl. In embodiments, $R^{19}$ is unsubstituted phenyl. In embodiments, $R^{19}$ is Cl. In embodiments, $R^{19}$ is substituted or unsubstituted $C_1$-$C_3$alkyl. In embodiments, $R^{19}$ is unsubstituted $C_1$-$C_3$alkyl. In embodiments, $R^{19}$ is substituted $C_1$-$C_3$alkyl. In embodiments, $R^{19}$ is an unsubstituted $C_3$ alkyl. In embodiments, $R^{19}$ is F. In embodiments, $R^{19}$ is Cl. In embodiments, $R^{19}$ is —$CH_3$.

In embodiments, $R^{25}$ is hydrogen, halogen, —$N_3$, —$CF_3$, —$CCl_3$, —CN, —, —CHO, —$OR^{25A}$, —$NR^{25B}R^{25C}$, —C(O)$OR^{25A}$, —C(O)$NR^{25B}R^{25C}$, —$NO_2$, —$SR^{25D}$, —S(O)$_{n25}R^{25B}$, —SO$_{v25}NR^{25B}R^{2C}$, —$NHNR^{25B}R^{25C}$, —$ONR^{25B}R^{25C}$, —NHC(O)$NHNR^{25B}R^{25C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{25}$ is $R^{55}$-substituted or unsubstituted alkyl (e.g., $C_1$-$C_8$ alkyl, $C_1$-$C_6$ alkyl, or $C_1$-$C_4$ alkyl), $R^{55}$-substituted or unsubstituted heteroalkyl (e.g., 2 to 8 membered heteroalkyl, 2 to 6 membered heteroalkyl, or 2 to 4 membered heteroalkyl), $R^{55}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55}$-substituted or unsubstituted aryl (e.g., $C_6$-$C_{10}$ aryl, $C_{10}$ aryl, or phenyl), or $R^{55}$-substituted or unsubstituted heteroaryl (e.g., 5 to 10 membered heteroaryl, 5 to 9 membered heteroaryl, or 5 to 6 membered heteroaryl).

In embodiments, $R^{25}$ is $R^{55}$-substituted or unsubstituted alkyl (e.g., $C_1$-$C_8$ alkyl, $C_1$-$C_6$ alkyl, or $C_1$-$C_4$ alkyl). In embodiments, $R^{25}$ is $R^{55}$-substituted alkyl (e.g., $C_1$-$C_8$ alkyl, $C_1$-$C_6$ alkyl, or $C_1$-$C_4$ alkyl). In embodiments, $R^{25}$ is an unsubstituted alkyl (e.g., $C_1$-$C_8$ alkyl, $C_1$-$C_6$ alkyl, or $C_1$-$C_4$ alkyl).

In embodiments, $R^{25}$ is $R^{55}$-substituted or unsubstituted heteroalkyl (e.g., 2 to 8 membered heteroalkyl, 2 to 6 membered heteroalkyl, or 2 to 4 membered heteroalkyl). In embodiments, $R^{25}$ is $R^{55}$-substituted heteroalkyl (e.g., 2 to 8 membered heteroalkyl, 2 to 6 membered heteroalkyl, or 2 to 4 membered heteroalkyl). In embodiments, $R^{25}$ is an unsubstituted heteroalkyl (e.g., 2 to 8 membered heteroalkyl, 2 to 6 membered heteroalkyl, or 2 to 4 membered heteroalkyl).

In embodiments, $R^{25}$ is $R^{55}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is $R^{55}$-substituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{25}$ is $R^{55}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is $R^{55}$-substituted heterocycloalkyl (e.g., 3 to 8 membered heterocycloalkyl, 3 to 6 membered heterocycloalkyl, or 5 to 6 membered heterocycloalkyl). In embodiments, $R^{25}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{25}$ is $R^{55}$-substituted or unsubstituted aryl (e.g., $C_6$-$C_{10}$ aryl, $C_{10}$ aryl, or phenyl). In embodiments, $R^{25}$ is $R^{55}$-substituted aryl (e.g., $C_6$-$C_{10}$ aryl, $C_{10}$ aryl, or phenyl). In embodiments, $R^{25}$ is an unsubstituted aryl (e.g., $C_6$-$C_{10}$ aryl, $C_{10}$ aryl, or phenyl).

In embodiments, $R^{25}$ is $R^{55}$-substituted or unsubstituted heteroaryl (e.g., 5 to 10 membered heteroaryl, 5 to 9 membered heteroaryl, or 5 to 6 membered heteroaryl). In embodiments, $R^{25}$ is $R^{55}$-substituted heteroaryl (e.g., 5 to 10 membered heteroaryl, 5 to 9 membered heteroaryl, or 5 to 6 membered heteroaryl). In embodiments, $R^{25}$ is an unsubstituted heteroaryl (e.g., 5 to 10 membered heteroaryl, 5 to 9 membered heteroaryl, or 5 to 6 membered heteroaryl).

In embodiments, $R^{25A}$ is $R^{55A}$-substituted or unsubstituted alkyl (e.g., $C_1$-$C_8$ alkyl, $C_1$-$C_6$ alkyl, or $C_1$-$C_4$ alkyl), $R^{55A}$-substituted or unsubstituted heteroalkyl (e.g., 2 to 8 membered heteroalkyl, 2 to 6 membered heteroalkyl, or 2 to 4 membered heteroalkyl), $R^{55A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55A}$-substituted or unsubstituted aryl (e.g., $C_6$-$C_{10}$ aryl, $C_{10}$ aryl, or phenyl), or $R^{55A}$-substituted or unsubstituted heteroaryl (e.g., 5 to 10 membered heteroaryl, 5 to 9 membered heteroaryl, or 5 to 6 membered heteroaryl).

In embodiments, $R^{25B}$ is $R^{55B}$-substituted or unsubstituted alkyl (e.g., $C_1$-$C_8$ alkyl, $C_1$-$C_6$ alkyl, or $C_1$-$C_4$ alkyl), $R^{55B}$-substituted or unsubstituted heteroalkyl (e.g., 2 to 8 membered heteroalkyl, 2 to 6 membered heteroalkyl, or 2 to 4 membered heteroalkyl), $R^{55B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55B}$-substituted or unsubstituted aryl (e.g., $C_6$-$C_{10}$ aryl, $C_{10}$ aryl, or phenyl), or $R^{55B}$-substituted or unsubstituted heteroaryl (e.g., 5 to 10 membered heteroaryl, 5 to 9 membered heteroaryl, or 5 to 6 membered heteroaryl).

In embodiments, $R^{25C}$ is $R^{55C}$-substituted or unsubstituted alkyl (e.g., $C_1$-$C_8$ alkyl, $C_1$-$C_6$ alkyl, or $C_1$-$C_4$ alkyl), $R^{55C}$-substituted or unsubstituted heteroalkyl (e.g., 2 to 8 membered heteroalkyl, 2 to 6 membered heteroalkyl, or 2 to 4 membered heteroalkyl), $R^{55C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55C}$-substituted or unsubstituted aryl (e.g., $C_6$-$C_{10}$ aryl, $C_{10}$ aryl, or phenyl), or $R^{55C}$-substituted or unsubstituted heteroaryl (e.g., 5 to 10 membered heteroaryl, 5 to 9 membered heteroaryl, or 5 to 6 membered heteroaryl).

In embodiments, $R^{25D}$ is $R^{55D}$-substituted or unsubstituted alkyl (e.g., $C_1$-$C_8$ alkyl, $C_1$-$C_6$ alkyl, or $C_1$-$C_4$ alkyl), $R^{55D}$-substituted or unsubstituted heteroalkyl (e.g., 2 to 8 membered heteroalkyl, 2 to 6 membered heteroalkyl, or 2 to 4 membered heteroalkyl), $R^{55D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55D}$-substituted or unsubstituted aryl (e.g., $C_6$-$C_{10}$ aryl, $C_{10}$ aryl, or phenyl), or $R^{55D}$-substituted or unsubstituted heteroaryl (e.g., 5 to 10 membered heteroaryl, 5 to 9 membered heteroaryl, or 5 to 6 membered heteroaryl).

In embodiments, $R^{25}$ is Ring A. In embodiments, Ring A is a substituted or unsubstituted cycloalkyl, substituted or unsubstituted heterocycloalkyl, substituted or unsubstituted aryl, or substituted or unsubstituted heteroaryl. In embodiments, Ring A is $R^{55}$-substituted or unsubstituted heteroaryl (e.g., 5 to 10 membered heteroaryl, 5 to 9 membered heteroaryl, or 5 to 6 membered heteroaryl). In embodiments, Ring A is $R^{55}$-substituted heteroaryl (e.g., 5 to 10 membered heteroaryl, 5 to 9 membered heteroaryl, or 5 to 6 membered heteroaryl). In embodiments, Ring A is an unsubstituted heteroaryl (e.g., 5 to 10 membered heteroaryl, 5 to 9 membered heteroaryl, or 5 to 6 membered heteroaryl).

In embodiments, Ring A is substituted or unsubstituted phenyl, substituted or unsubstituted pyridyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted furanyl, substituted or unsubstituted pyrrolyl, or substituted or unsubstituted thienyl. In embodiments, Ring A is substituted or unsubstituted phenyl, pyridinyl, pyridazinyl, pyrimidinyl, pyrazinyl, or triazinyl.

In embodiments, $R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{25A}$, $R^{25B}$, $R^{25C}$, $R^{25D}$, $R^{55A}$, $R^{55B}$, $R^{55C}$, and $R^{55D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2N_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{25A}$, $R^{25B}$, $R^{25C}$, $R^{25D}$, $R^{55A}$, $R^{55B}$, $R^{55C}$, and $R^{55D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{25A}$, $R^{25B}$, $R^{25C}$, $R^{25D}$, $R^{55A}$, $R^{55B}$, $R^{55C}$, and $R^{55D}$ are independently hydrogen.

In embodiments, $X^1$ is $CR^{10}$. In embodiments, $X^1$ is N. In embodiments, $X^2$ is $CR^{11}$. In embodiments, $X^2$ is N. In embodiments, $X^3$ is $CR^{12}$. In embodiments, $X^3$ is N. In embodiments, $X^1$ is $CR^{10}$ and $X^2$ is N and $X^3$ is $CR^{12}$ and $R^6$, $R^7$ and $R^{10}$ are independently hydrogen and $R^{12}$ is —$OCH_3$. In embodiments, $X^1$ is CH and $X^2$ is N and $X^3$ is CH and $R^6$ and $R^7$ are independently hydrogen. In embodiments, $X^1$ is $CR^{10}$ and $X^3$ is $CR^{12}$. In embodiments, $X^1$ is CH and $X^3$ is CH. In embodiments, $R^{12}$ is —$OCH_3$.

In embodiments, $X^4$ is N. In embodiments, $X^4$ is $CR^{13}$. In embodiments, $X^5$ is $CR^{14}R^{15}$. In embodiments, $X^5$ is S. In embodiments, $X^5$ is O. In embodiments, $X^5$ is $NR_{20A}$. In embodiments, $X^4$ is CH. In embodiments, $X^5$ is $CHR^{15}$. In embodiments, $X^5$ is $CH_2$. In embodiments, $X^5$ is NH.

In embodiments, $X^6$ is O. In embodiments, $X^6$ is O or S. In embodiments, $X^6$ is $NR^{23A}$. In embodiments, $X^6$ is S. In embodiments, $X^7$ is O. In embodiments, $X^7$ is O or S. In embodiments, $X^7$ is $NR^{24A}$. In embodiments, $X^7$ is S. In embodiments, $X^6$ is O and $X^7$ is O.

In embodiments, $R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{v6}NR^{6B}R^{6C}$, —$NHNR^{6B}R^{6C}$, —$ONR^{6B}R^{6C}$, —$NHC(O)NHNR^{6B}R^{6C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^6$ is hydrogen.

In embodiments, $R^6$ is hydrogen, halogen, —$OCH_3$, $SO_2$, $SO_2$—$R^{6B}$, —$OR^{6A}$, —$NR^{6B}R^{6C}$, or substituted or unsubstituted aryl (e.g., $C_6$-$C_{10}$ aryl, $C_{10}$ aryl, or phenyl). In embodiments, $R^6$ is hydrogen. In embodiments, $R^6$ is Br. In embodiments, $R^6$ is Cl. In embodiments, $R^6$ is $SO_2$—$R^{6B}$ wherein $R^{6B}$ is substituted or unsubstituted aryl (e.g., $C_6$-$C_{10}$ aryl, $C_{10}$ aryl, or phenyl). In embodiments, $R^6$ is $SO_2$—$R^{6B}$ wherein $R^{6B}$ is unsubstituted aryl (e.g., $C_6$-$C_{10}$ aryl, $C_{10}$ aryl, or phenyl). In embodiments, $R^6$ is $SO_2$—$R^{6B}$ wherein $R^{6B}$ is phenyl. In embodiments, $R^6$ is phenyl. In embodiments, $R^6$ is —$OR^{6A}$, wherein $R^{6A}$ is substituted or unsubstituted alkyl (e.g., $C_1$-$C_8$ alkyl, $C_1$-$C_6$ alkyl, or $C_1$-$C_4$ alkyl). In embodiments, $R^6$ is —$OR^{6A}$, wherein $R^{6A}$ is unsubstituted alkyl (e.g., $C_1$-$C_8$ alkyl, $C_1$-$C_6$ alkyl, or $C_1$-$C_4$ alkyl). In embodiments, $R^6$ is —$OR^{6A}$, wherein $R^{6A}$ is substituted or unsubstituted $C_1$-$C_8$ alkyl. In embodiments, $R^6$ is —$OR^{6A}$, wherein $R^{6A}$ is substituted or unsubstituted $C_1$-$C_4$ alkyl. In embodiments, $R^6$ is —$OR^{6A}$, wherein $R^{6A}$ is substituted or unsubstituted $C_1$-$C_2$ alkyl. In embodiments, $R^6$ is —$NR^{6B}R^{6C}$, wherein $R^{6B}$ and $R^{6C}$ are unsubstituted alkyl (e.g., $C_1$-$C_8$ alkyl, $C_1$-$C_6$ alkyl, or $C_1$-$C_4$ alkyl). In embodiments, $R^6$ is —$NR^{6B}R^{6C}$, wherein $R^{6B}$ and $R^{6C}$ are substituted or unsubstituted $C_1$-$C_8$ alkyl. In embodiments, $R^6$ is —$NR^{6B}R^{6C}$, wherein $R^{6B}$ and $R^{6C}$ are substituted or unsubstituted $C_1$-$C_4$ alkyl. In embodiments, $R^6$ is —$NR^{6B}R^{6C}$, wherein $R^{6B}$ and $R^{6C}$ are substituted or unsubstituted $C_1$-$C_2$ alkyl.

In embodiments, $R^6$ is $R^{35}$-substituted or unsubstituted alkyl (e.g., $C_1$-$C_8$ alkyl, $C_1$-$C_6$ alkyl, or $C_1$-$C_4$ alkyl), $R^{35}$-substituted or unsubstituted heteroalkyl (e.g., 2 to 8 membered heteroalkyl, 2 to 6 membered heteroalkyl, or 2 to 4 membered heteroalkyl), $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl).

In embodiments, $R^6$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^6$ is $R^{35}$-substituted alkyl (e.g., $C_1$-$C_8$ alkyl, $C_1$-$C_6$ alkyl, or $C_1$-$C_4$ alkyl). In embodiments, $R^6$ is an unsubstituted alkyl (e.g., $C_1$-$C_8$ alkyl, $C_1$-$C_6$ alkyl, or $C_1$-$C_4$ alkyl).

In embodiments, $R^6$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^6$ is $R^{35}$-substituted heteroalkyl (e.g., 2 to 8 membered heteroalkyl, 2 to 6 membered heteroalkyl, or 2 to 4 membered heteroalkyl). In embodiments, $R^6$ is an unsubstituted heteroalkyl (e.g., 2 to 8 membered heteroalkyl, 2 to 6 membered heteroalkyl, or 2 to 4 membered heteroalkyl).

In embodiments, $R^6$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^6$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^6$ is $R^{35}$-substituted or unsubstituted aryl (e.g., $C_6$-$C_{10}$ aryl, $C_{10}$ aryl, or phenyl). In embodiments, $R^6$ is $R^{35}$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^6$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^6$ is $R^{35}$-substituted heteroaryl (e.g., 5 to 10 membered heteroaryl, 5 to 9 membered heteroaryl, or 5 to 6 membered heteroaryl). In embodiments, $R^6$ is an unsubstituted heteroaryl (e.g., 5 to 10 membered heteroaryl, 5 to 9 membered heteroaryl, or 5 to 6 membered heteroaryl).

In embodiments, $R^{6A}$ is $R^{35A}$-substituted or unsubstituted alkyl (e.g., $C_1$-$C_8$ alkyl, $C_1$-$C_6$ alkyl, or $C_1$-$C_4$ alkyl), $R^{35A}$- substituted or unsubstituted heteroalkyl (e.g., 2 to 8 membered heteroalkyl, 2 to 6 membered heteroalkyl, or 2 to 4 membered heteroalkyl), $R^{35A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35A}$-substituted or unsubstituted aryl (e.g., $C_6$-$C_{10}$ aryl, $C_{10}$ aryl, or phenyl), or $R^{35A}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is $R^{35B}$-substituted or unsubstituted alkyl (e.g., $C_1$-$C_8$ alkyl, $C_1$-$C_6$ alkyl, or $C_1$-$C_4$ alkyl), $R^{35B}$-substituted or unsubstituted heteroalkyl (e.g., 2 to 8 membered heteroalkyl, 2 to 6 membered heteroalkyl, or 2 to 4 membered heteroalkyl), $R^{35B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35B}$-substituted or unsubstituted aryl (e.g., $C_6$-$C_{10}$ aryl, $C_{10}$ aryl, or phenyl), or $R^{35B}$-substituted or unsubstituted heteroaryl (e.g., 5 to 10 membered heteroaryl, 5 to 9 membered heteroaryl, or 5 to 6 membered heteroaryl).

In embodiments, $R^{6C}$ is $R^{35C}$-substituted or unsubstituted alkyl (e.g., $C_1$-$C_8$ alkyl, $C_1$-$C_6$ alkyl, or $C_1$-$C_4$ alkyl), $R^{35C}$-substituted or unsubstituted heteroalkyl (e.g., 2 to 8 membered heteroalkyl, 2 to 6 membered heteroalkyl, or 2 to 4 membered heteroalkyl), $R^{35C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35C}$-substituted or unsubstituted aryl (e.g., $C_6$-$C_{10}$ aryl, $C_{10}$ aryl, or phenyl), or $R^{35C}$-substituted or unsubstituted heteroaryl (e.g., 5 to 10 membered heteroaryl, 5 to 9 membered heteroaryl, or 5 to 6 membered heteroaryl).

In embodiments, $R^{6D}$ is $R^{35D}$-substituted or unsubstituted alkyl (e.g., $C_1$-$C_8$ alkyl, $C_1$-$C_6$ alkyl, or $C_1$-$C_4$ alkyl), $R^{35D}$-substituted or unsubstituted heteroalkyl (e.g., 2 to 8 membered heteroalkyl, 2 to 6 membered heteroalkyl, or 2 to 4 membered heteroalkyl), $R^{35D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35D}$-substituted or unsubstituted aryl (e.g., $C_6$-$C_{10}$ aryl, $C_{10}$ aryl, or phenyl), or $R^{35D}$-substituted or unsubstituted heteroaryl (e.g., 5 to 10 membered heteroaryl, 5 to 9 membered heteroaryl, or 5 to 6 membered heteroaryl).

In embodiments, $R^7$ is hydrogen, halogen, $-N_3$, $-CF_3$, $-CCl_3$, $-CBr_3$, $-CI_3$, $-CN$, $-CHO$, $-OR^{7A}$, $-NR^{7B}R^{7C}$, $-COOR^{7A}$, $-CONR^{7B}R^{7C}$, $-NO_2$, $-SR^{7D}$, $-SO_{n7}R^{7B}$, $-SO_{v7}NR^{7B}R^{7C}$, $-NHNR^{7B}R^{7C}$, $-ONR^{7B}R^{7C}$, $-NHC(O)NHNR^{7B}R^{7C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^7$ is hydrogen.

In embodiments, $R^7$ is hydrogen, halogen, $-OCH_3$, $SO_2$, $SO_2-R^{7B}$, $-OR^{7A}$, $-NR^{7B}R^{7C}$, or substituted or unsubstituted aryl (e.g., $C_6$-$C_{10}$ aryl, $C_{10}$ aryl, or phenyl). In embodiments, $R^7$ is hydrogen. In embodiments, $R^7$ is Br. In embodiments, $R^7$ is Cl. In embodiments, $R^7$ is $SO_2-R^{7B}$ wherein $R^{7B}$ is substituted or unsubstituted aryl (e.g., $C_6$-$C_{10}$ aryl, $C_{10}$ aryl, or phenyl). In embodiments, $R^7$ is $SO_2-R^{7B}$ wherein $R^{7B}$ is unsubstituted aryl (e.g., $C_6$-$C_{10}$ aryl, $C_{10}$ aryl, or phenyl). In embodiments, $R^7$ is $SO_2-R^{7B}$ wherein $R^{7B}$ is phenyl. In embodiments, $R^7$ is phenyl. In embodiments, $R^7$ is $-OR^{7A}$, wherein $R^{7A}$ is substituted or unsubstituted alkyl (e.g., $C_1$-$C_8$ alkyl, $C_1$-$C_6$ alkyl, or $C_1$-$C_4$ alkyl). In embodiments, $R^7$ is $-OR^{7A}$, wherein $R^{7A}$ is unsubstituted alkyl (e.g., $C_1$-$C_8$ alkyl, $C_1$-$C_6$ alkyl, or $C_1$-$C_4$ alkyl). In embodiments, $R^7$ is $-OR^{7A}$, wherein $R^{7A}$ is substituted or unsubstituted $C_1$-$C_8$ alkyl. In embodiments, $R^7$ is $-OR^{7A}$, wherein $R^{7A}$ is substituted or unsubstituted $C_1$-$C_4$ alkyl. In embodiments, $R^7$ is $-OR^{7A}$, wherein $R^{7A}$ is substituted or unsubstituted $C_1$-$C_2$ alkyl. In embodiments, $R^7$ is $-NR^{7B}R^{7C}$, wherein $R^{7B}$ and $R^{7C}$ are unsubstituted alkyl (e.g., $C_1$-$C_8$ alkyl, $C_1$-$C_6$ alkyl, or $C_1$-$C_4$ alkyl). In embodiments, $R^7$ is $-NR^{7B}R^{7C}$, wherein $R^{7B}$ and $R^{7C}$ are substituted or unsubstituted $C_1$-$C_8$ alkyl. In embodiments, $R^7$ is $-NR^{7B}R^{7C}$, wherein $R^{7B}$ and $R^{7C}$ are substituted or unsubstituted $C_1$-$C_4$ alkyl. In embodiments, $R^7$ is $-NR^{7B}R^{7C}$, wherein $R^{7B}$ and $R^{7C}$ are substituted or unsubstituted $C_1$-$C_2$ alkyl.

In embodiments, $R^7$ is $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl).

In embodiments, $R^7$ is $R^{36}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{36}$-substituted alkyl (e.g., $C_1$-$C_8$ alkyl, $C_1$-$C_6$ alkyl, or $C_1$-$C_4$ alkyl). In embodiments, $R^7$ is an unsubstituted alkyl (e.g., $C_1$-$C_8$ alkyl, $C_1$-$C_6$ alkyl, or $C_1$-$C_4$ alkyl).

In embodiments, $R^7$ is $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{36}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl).

In embodiments, $R^7$ is $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^7$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^7$ is $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^7$ is $R^{36}$-substituted or unsubstituted aryl (e.g., $C_6$-$C_{10}$ aryl, $C_{10}$ aryl, or phenyl). In embodiments, $R^7$ is $R^{36}$-substituted aryl (e.g., $C_6$-$C_{10}$ aryl, $C_{10}$ aryl, or phenyl). In embodiments, $R^7$ is an unsubstituted aryl (e.g., $C_6$-$C_{10}$ aryl, $C_{10}$ aryl, or phenyl).

In embodiments, $R^7$ is $R^{36}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{36}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl).

In embodiments, $R^{7A}$ is $R^{36A}$-substituted or unsubstituted alkyl (e.g., $C_1$-$C_8$ alkyl, $C_1$-$C_6$ alkyl, or $C_1$-$C_4$ alkyl), $R^{36A}$-substituted or unsubstituted heteroalkyl (e.g., 2 to 8 membered heteroalkyl, 2 to 6 membered heteroalkyl, or 2 to 4 membered heteroalkyl), $R^{36A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36A}$-substituted or unsubstituted aryl (e.g., $C_6$-$C_{10}$ aryl, $C_{10}$ aryl, or phenyl), or $R^{36A}$-substituted or unsubstituted heteroaryl (e.g., 5 to 10 membered heteroaryl, 5 to 9 membered heteroaryl, or 5 to 6 membered heteroaryl).

In embodiments, $R^{7B}$ is $R^{36B}$-substituted or unsubstituted alkyl (e.g., $C_1$-$C_8$ alkyl, $C_1$-$C_6$ alkyl, or $C_1$-$C_4$ alkyl), $R^{36B}$-substituted or unsubstituted heteroalkyl (e.g., 2 to 8 membered heteroalkyl, 2 to 6 membered heteroalkyl, or 2 to 4 membered heteroalkyl), $R^{36B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36B}$-substituted or unsubstituted aryl (e.g., $C_6$-$C_{10}$ aryl, $C_{10}$ aryl, or phenyl), or $R^{36B}$-substituted or unsubstituted heteroaryl (e.g., 5 to 10 membered heteroaryl, 5 to 9 membered heteroaryl, or 5 to 6 membered heteroaryl).

In embodiments, $R^{7C}$ is $R^{36C}$-substituted or unsubstituted alkyl (e.g., $C_1$-$C_8$ alkyl, $C_1$-$C_6$ alkyl, or $C_1$-$C_4$ alkyl), $R^{36C}$-substituted or unsubstituted heteroalkyl (e.g., 2 to 8 membered heteroalkyl, 2 to 6 membered heteroalkyl, or 2 to 4 membered heteroalkyl), $R^{36C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36C}$-substituted or unsubstituted aryl (e.g., $C_6$-$C_{10}$ aryl, $C_{10}$ aryl, or phenyl), or $R^{36C}$-substituted or unsubstituted heteroaryl (e.g., 5 to 10 membered heteroaryl, 5 to 9 membered heteroaryl, or 5 to 6 membered heteroaryl).

In embodiments, $R^{7D}$ is $R^{36D}$-substituted or unsubstituted alkyl (e.g., $C_1$-$C_8$ alkyl, $C_1$-$C_6$ alkyl, or $C_1$-$C_4$ alkyl), $R^{36D}$-substituted or unsubstituted heteroalkyl (e.g., 2 to 8 membered heteroalkyl, 2 to 6 membered heteroalkyl, or 2 to 4 membered heteroalkyl), $R^{36D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36D}$-substituted or unsubstituted aryl (e.g., $C_6$-$C_{10}$ aryl, $C_{10}$ aryl, or phenyl), or $R^{36D}$-substituted or unsubstituted heteroaryl (e.g., 5 to 10 membered heteroaryl, 5 to 9 membered heteroaryl, or 5 to 6 membered heteroaryl).

In embodiments, $R^8$ is hydrogen, halogen, $-N_3$, $-CF_3$, $-CCl_3$, $-CBr_3$, $-CI_3$, $-CN$, $-CHO$, $-OR^{8A}$, $-NR^{8B}R^{8C}$, $-COOR^{8A}$, $-CONR^{8B}R^{8C}$, $-NO_2$, $-SO_{n8}R^{8B}$, $-SO_{v8}NR^{8B}R^{8C}$, $-NHNR^{8B}R^{8C}$, $-ONR^{8B}R^{8C}$, $-NHC(O)NHNR^{8B}R^{8C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^8$ is $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl).

In embodiments, $R^8$ is $R^{37}$-substituted or unsubstituted alkyl (e.g., $C_1$-$C_8$ alkyl, $C_1$-$C_6$ alkyl, or $C_1$-$C_4$ alkyl). In embodiments, $R^8$ is $R^{37}$-substituted alkyl (e.g., $C_1$-$C_8$ alkyl, $C_1$-$C_6$ alkyl, or $C_1$-$C_4$ alkyl). In embodiments, $R^8$ is an unsubstituted alkyl (e.g., $C_1$-$C_8$ alkyl, $C_1$-$C_6$ alkyl, or $C_1$-$C_4$ alkyl).

In embodiments, $R^8$ is $R^{37}$-substituted or unsubstituted heteroalkyl (e.g., 2 to 8 membered heteroalkyl, 2 to 6 membered heteroalkyl, or 2 to 4 membered heteroalkyl). In embodiments, $R^8$ is $R^{37}$-substituted heteroalkyl (e.g., 2 to 8 membered heteroalkyl, 2 to 6 membered heteroalkyl, or 2 to 4 membered heteroalkyl). In embodiments, $R^8$ is an unsubstituted heteroalkyl (e.g., 2 to 8 membered heteroalkyl, 2 to 6 membered heteroalkyl, or 2 to 4 membered heteroalkyl).

In embodiments, $R^8$ is $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^8$ is $R^{37}$-substituted cycloalkyl (e.g., $C_3$-$C_8$ cycloalkyl, $C_3$-$C_6$ cycloalkyl, or $C_5$-$C_6$ cycloalkyl). In embodiments, $R^8$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^8$ is $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^8$ is $R^{37}$-substituted heterocycloalkyl (e.g., 3 to 8 membered heterocycloalkyl, 3 to 6 membered heterocycloalkyl, or 5 to 6 membered heterocycloalkyl). In embodiments, $R^8$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^8$ is $R^{37}$-substituted or unsubstituted aryl (e.g., $C_6$-$C_{10}$ aryl, $C_{10}$ aryl, or phenyl). In embodiments, $R^8$ is $R^{37}$-substituted aryl (e.g., $C_6$-$C_{10}$ aryl, $C_{10}$ aryl, or phenyl). In embodiments, $R^8$ is an unsubstituted aryl (e.g., $C_6$-$C_{10}$ aryl, $C_{10}$ aryl, or phenyl).

In embodiments, $R^8$ is $R^{37}$-substituted or unsubstituted heteroaryl (e.g., 5 to 10 membered heteroaryl, 5 to 9 membered heteroaryl, or 5 to 6 membered heteroaryl). In embodiments, $R^8$ is $R^{37}$-substituted heteroaryl (e.g., 5 to 10 membered heteroaryl, 5 to 9 membered heteroaryl, or 5 to 6 membered heteroaryl). In embodiments, $R^8$ is an unsubstituted heteroaryl (e.g., 5 to 10 membered heteroaryl, 5 to 9 membered heteroaryl, or 5 to 6 membered heteroaryl).

In embodiments, $R^{8A}$ is $R^{37A}$-substituted or unsubstituted alkyl (e.g., $C_1$-$C_8$ alkyl, $C_1$-$C_6$ alkyl, or $C_1$-$C_4$ alkyl), $R^{37A}$-substituted or unsubstituted heteroalkyl (e.g., 2 to 8 membered heteroalkyl, 2 to 6 membered heteroalkyl, or 2 to 4 membered heteroalkyl), $R^{37A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37A}$-substituted or unsubstituted aryl (e.g., $C_6$-$C_{10}$ aryl, $C_{10}$ aryl, or phenyl), or $R^{37A}$-substituted or unsubstituted heteroaryl (e.g., 5 to 10 membered heteroaryl, 5 to 9 membered heteroaryl, or 5 to 6 membered heteroaryl).

In embodiments, $R^{8B}$ is $R^{37B}$-substituted or unsubstituted alkyl (e.g., $C_1$-$C_8$ alkyl, $C_1$-$C_6$ alkyl, or $C_1$-$C_4$ alkyl), $R^{37B}$-substituted or unsubstituted heteroalkyl (e.g., 2 to 8 membered heteroalkyl, 2 to 6 membered heteroalkyl, or 2 to 4 membered heteroalkyl), $R^{37B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37B}$-substituted or unsubstituted aryl (e.g., $C_6$-$C_{10}$ aryl, $C_{10}$ aryl, or phenyl), or $R^{37B}$-substituted or unsubstituted heteroaryl (e.g., 5 to 10 membered heteroaryl, 5 to 9 membered heteroaryl, or 5 to 6 membered heteroaryl).

In embodiments, $R^{8C}$ is $R^{37C}$-substituted or unsubstituted alkyl (e.g., $C_1$-$C_8$ alkyl, $C_1$-$C_6$ alkyl, or $C_1$-$C_4$ alkyl), $R^{37C}$-substituted or unsubstituted heteroalkyl (e.g., 2 to 8 membered heteroalkyl, 2 to 6 membered heteroalkyl, or 2 to 4 membered heteroalkyl), $R^{37C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37C}$-substituted or unsubstituted aryl (e.g., $C_6$-$C_{10}$ aryl, $C_{10}$ aryl, or phenyl), or $R^{37C}$-substituted or unsubstituted heteroaryl (e.g., 5 to 10 membered heteroaryl, 5 to 9 membered heteroaryl, or 5 to 6 membered heteroaryl).

In embodiments, $R^{8D}$ is $R^{37D}$-substituted or unsubstituted alkyl (e.g., $C_1$-$C_8$ alkyl, $C_1$-$C_6$ alkyl, or $C_1$-$C_4$ alkyl), $R^{37D}$-substituted or unsubstituted heteroalkyl (e.g., 2 to 8 membered heteroalkyl, 2 to 6 membered heteroalkyl, or 2 to 4 membered heteroalkyl), $R^{37D}$-substituted or unsubstituted cycloalkyl (e.g., C3-$C_8$ cycloalkyl, $C_3$-$C_6$ cycloalkyl, or $C_5$-$C_6$ cycloalkyl), $R^{37D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37D}$-substituted or unsubstituted aryl (e.g., $C_6$-$C_{10}$ aryl, $C_{10}$ aryl, or phenyl), or $R^{37D}$-substituted or unsubstituted heteroaryl (e.g., 5 to 10 membered heteroaryl, 5 to 9 membered heteroaryl, or 5 to 6 membered heteroaryl).

In embodiments, $R^9$ is hydrogen, halogen, —$N_3$, —$CF_3$, —$CCl_3$, —$CBr_3$, —$CI_3$, —CN, —CHO, —$OR^{9A}$, —$NR^{9B}R^{9C}$, —$COOR^{9A}$, —$CONR^{9B}R^{9C}$, —$NO_2$, —$SR^{9D}$, —$SO_{n9}R^{9B}$, —$SO_{v9}NR^{9B}R^{9C}$, —$NHNR^{9B}R^{9C}$, —$ONR^{9B}R^{9C}$, —NHC(O)NHN$R^{9B}R^{9C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^9$ is $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl).

In embodiments, $R^9$ is $R^{38}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{38}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{38}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{38}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{38}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is $R^{38}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{38}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is $R^{38}$-substituted or unsubstituted aryl (e.g., $C_6$-$C_{10}$ aryl, $C_{10}$ aryl, or phenyl). In embodiments, $R^9$ is $R^{38}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl).

In embodiments, $R^9$ is $R^{38}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{38}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl).

In embodiments, $R^{9A}$ is $R^{38A}$-substituted or unsubstituted alkyl (e.g., $C_1$-$C_8$ alkyl, $C_1$-$C_6$ alkyl, or $C_1$-$C_4$ alkyl), $R^{38A}$-substituted or unsubstituted heteroalkyl (e.g., 2 to 8 membered heteroalkyl, 2 to 6 membered heteroalkyl, or 2 to 4 membered heteroalkyl), $R^{38A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38A}$-substituted or unsubstituted aryl (e.g., $C_6$-$C_{10}$ aryl, $C_{10}$ aryl, or phenyl), or $R^{38A}$-substituted or unsubstituted heteroaryl (e.g., 5 to 10 membered heteroaryl, 5 to 9 membered heteroaryl, or 5 to 6 membered heteroaryl).

In embodiments, $R^{9B}$ is $R^{38B}$-substituted or unsubstituted alkyl (e.g., $C_1$-$C_8$ alkyl, $C_1$-$C_6$ alkyl, or $C_1$-$C_4$ alkyl), $R^{38B}$-substituted or unsubstituted heteroalkyl (e.g., 2 to 8 membered heteroalkyl, 2 to 6 membered heteroalkyl, or 2 to 4 membered heteroalkyl), $R^{38B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38B}$-substituted or unsubstituted aryl (e.g., $C_6$-$C_{10}$ aryl, $C_{10}$ aryl, or phenyl), or $R^{38B}$-substituted or unsubstituted heteroaryl (e.g., 5 to 10 membered heteroaryl, 5 to 9 membered heteroaryl, or 5 to 6 membered heteroaryl).

In embodiments, $R^{9C}$ is $R^{38C}$-substituted or unsubstituted alkyl (e.g., $C_1$-$C_8$ alkyl, $C_1$-$C_6$ alkyl, or $C_1$-$C_4$ alkyl), $R^{38C}$-substituted or unsubstituted heteroalkyl (e.g., 2 to 8 membered heteroalkyl, 2 to 6 membered heteroalkyl, or 2 to 4 membered heteroalkyl), $R^{38C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38C}$-substituted or unsubstituted aryl (e.g., $C_6$-$C_{10}$ aryl, $C_{10}$ aryl, or phenyl), or $R^{38C}$-substituted or unsubstituted heteroaryl (e.g., 5 to 10 membered heteroaryl, 5 to 9 membered heteroaryl, or 5 to 6 membered heteroaryl).

In embodiments, $R^{9D}$ is $R^{38D}$-substituted or unsubstituted alkyl (e.g., $C_1$-$C_8$ alkyl, $C_1$-$C_6$ alkyl, or $C_1$-$C_4$ alkyl), $R^{38D}$-substituted or unsubstituted heteroalkyl (e.g., 2 to 8 membered heteroalkyl, 2 to 6 membered heteroalkyl, or 2 to 4 membered heteroalkyl), $R^{38D}$-substituted or unsubstituted cycloalkyl (e.g., $C_3$-$C_8$ cycloalkyl, $C_3$-$C_6$ cycloalkyl, or $C_5$-$C_6$ cycloalkyl), R'-substituted or unsubstituted heterocycloalkyl (e.g., 3 to 8 membered heterocycloalkyl, 3 to 6 membered heterocycloalkyl, or 5 to 6 membered heterocycloalkyl), R'-substituted or unsubstituted aryl (e.g., $C_6$-$C_{10}$ aryl, $C_{10}$ aryl, or phenyl), or $R^{38D}$-substituted or unsubstituted heteroaryl (e.g., 5 to 10 membered heteroaryl, 5 to 9 membered heteroaryl, or 5 to 6 membered heteroaryl).

In embodiments, $R^{10}$ is hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-CONR^{10B}R^{10C}$, $-NO_2$, $-SR^{10D}$, $-SO_{n10}R^{10B}$, $-SO_{v10}NR^{10B}R^{10C}$, $-NHNR^{10B}R^{10C}$, $-ONR^{10B}R^{10C}$, $-NHC(O)NHNR^{10B}R^{10C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10}$ is hydrogen, halogen, $-OCH_3$, $SO_2$, $SO_2-R^{10B}$, $-OR^{10A}$, $-NR^{10B}R^{10C}$ or substituted or unsubstituted aryl (e.g., $C_6$-$C_{10}$ aryl, $C_{10}$ aryl, or phenyl). In embodiments, $R^{10}$ is hydrogen. In embodiments, R'° is Br. In embodiments, R'° is Cl. In embodiments, $R^{10}$ is $SO_2-R^{10B}$ wherein $R^{10B}$ is substituted or unsubstituted aryl (e.g., $C_6$-$C_{10}$ aryl, $C_{10}$ aryl, or phenyl). In embodiments, $R^{10}$ is $SO_2-R^{10B}$ wherein $R^{10B}$ is unsubstituted aryl (e.g., $C_6$-$C_{10}$ aryl, $C_{10}$ aryl, or phenyl). In embodiments, $R^{10}$ is $SO_2-R^{10B}$ wherein $R^{10B}$ is phenyl. In embodiments, $R^{10}$ is phenyl. In embodiments, $R^{10}$ is $-OR^{10A}$, wherein $R^{10A}$ is substituted or unsubstituted alkyl (e.g., $C_1$-$C_8$ alkyl, $C_1$-$C_6$ alkyl, or $C_1$-$C_4$ alkyl). In embodiments, $R^{10}$ is $-OR^{10A}$, wherein $R^{10A}$ is unsubstituted alkyl (e.g., $C_1$-$C_8$ alkyl, $C_1$-$C_6$ alkyl, or $C_1$-$C_4$ alkyl). In embodiments, $R^{10}$ is $-OR^{10A}$, wherein $R^{10A}$ is substituted or unsubstituted $C_1$-$C_8$ alkyl. In embodiments, $R^{10}$ is $-OR^{10A}$, wherein $R^{10A}$ is substituted or unsubstituted $C_1$-$C_4$ alkyl. In embodiments, $R^{10}$ is $-OR^{10A}$, wherein $R^{10A}$ is substituted or unsubstituted $C_1$-$C_2$ alkyl. In embodiments, $R^{10}$ is $-NR^{10B}R^{10C}$, wherein $R^{10B}$ and $R^{10C}$ are unsubstituted alkyl (e.g., $C_1$-$C_8$ alkyl, $C_1$-$C_6$ alkyl, or $C_1$-$C_4$ alkyl). In embodiments, $R^{10}$ is $-NR^{10B}R^{10C}$, wherein $R^{10B}$ and $R^{1C}$ are substituted or unsubstituted $C_1$-$C_8$ alkyl. In embodiments, $R^{10}$ is $-NR^{10B}R^{10C}$, wherein $R^{10B}$ and $R^{10C}$ are substituted or unsubstituted $C_1$-$C_4$ alkyl. In embodiments, $R^{10}$ is $-NR^{10B}R^{10C}$, wherein $R^{10B}$ and $R^{10C}$ are substituted or unsubstituted $C_1$-$C_2$ alkyl.

In embodiments, $R^{10}$ is $R^{39}$-substituted or unsubstituted alkyl (e.g., $C_1$-$C_8$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

In embodiments, $R^{10}$ is $R^{39}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{39}$-substituted alkyl (e.g., $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl).

In embodiments, $R^{10}$ is $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{39}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl).

In embodiments, $R^{10}$ is $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{10}$ is $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{10}$ is $R^{39}$-substituted or unsubstituted aryl (e.g., $C_6$-$C_{10}$ aryl, $C_{10}$ aryl, or phenyl). In embodiments, $R^{10}$ is $R^{39}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl).

In embodiments, $R^{10}$ is $R^{39}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{39}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl).

In embodiments, $R^{10A}$ is $R^{39A}$-substituted or unsubstituted alkyl (e.g., $C_1$-$C_8$ alkyl, $C_1$-$C_6$ alkyl, or $C_1$-$C_4$ alkyl), $R^{39A}$-substituted or unsubstituted heteroalkyl (e.g., 2 to 8 membered heteroalkyl, 2 to 6 membered heteroalkyl, or 2 to 4 membered heteroalkyl), $R^{39A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39A}$-substituted or unsubstituted aryl (e.g., $C_6$-$C_{10}$ aryl, $C_{10}$ aryl, or phenyl), or $R^{39A}$-substituted or unsubstituted heteroaryl (e.g., 5 to 10 membered heteroaryl, 5 to 9 membered heteroaryl, or 5 to 6 membered heteroaryl).

In embodiments, $R^{10B}$ is $R^{39B}$-substituted or unsubstituted alkyl (e.g., $C_1$-$C_8$ alkyl, $C_1$-$C_6$ alkyl, or $C_1$-$C_4$ alkyl), $R^{39B}$-substituted or unsubstituted heteroalkyl (e.g., 2 to 8 membered heteroalkyl, 2 to 6 membered heteroalkyl, or 2 to 4 membered heteroalkyl), $R^{39B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39B}$-substituted or unsubstituted aryl (e.g., $C_6$-$C_{10}$ aryl, $C_{10}$ aryl, or phenyl), or $R^{39B}$-substituted or unsubstituted heteroaryl (e.g., 5 to 10 membered heteroaryl, 5 to 9 membered heteroaryl, or 5 to 6 membered heteroaryl).

In embodiments, $R^{10C}$ is $R^{39C}$-substituted or unsubstituted alkyl (e.g., $C_1$-$C_8$ alkyl, $C_1$-$C_6$ alkyl, or $C_1$-$C_4$ alkyl), $R^{39C}$-substituted or unsubstituted heteroalkyl (e.g., 2 to 8 membered heteroalkyl, 2 to 6 membered heteroalkyl, or 2 to 4 membered heteroalkyl), $R^{39C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39C}$-substituted or unsubstituted aryl (e.g., $C_6$-$C_{10}$ aryl, $C_{10}$ aryl, or phenyl), or $R^{39C}$-substituted or unsubstituted heteroaryl (e.g., 5 to 10 membered heteroaryl, 5 to 9 membered heteroaryl, or 5 to 6 membered heteroaryl).

In embodiments, $R^{10D}$ is $R^{39D}$-substituted or unsubstituted alkyl (e.g., $C_1$-$C_8$ alkyl, $C_1$-$C_6$ alkyl, or $C_1$-$C_4$ alkyl), $R^{39D}$-substituted or unsubstituted heteroalkyl (e.g., 2 to 8 membered heteroalkyl, 2 to 6 membered heteroalkyl, or 2 to 4 membered heteroalkyl), $R^{39D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39D}$-substituted or unsubstituted aryl (e.g., $C_6$-$C_{10}$ aryl, $C_{10}$ aryl, or phenyl), or $R^{39D}$-substituted or unsubstituted heteroaryl (e.g., 5 to 10 membered heteroaryl, 5 to 9 membered heteroaryl, or 5 to 6 membered heteroaryl).

In embodiments, $R^{18}$ is hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-CONR^{11B}R^{11C}$, $-NO_2$, $-SR^{11D}$, $-SO_{n11}R^{11B}$, $-SO_{v11}NR^{11B}R^{11C}$, $-NHNR^{11B}R^{11C}$, $-ONR^{11B}R^{11C}$, $-NHC(O)NHNR^{11B}R^{11C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl); $R^{10}$ and $R^{11}$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl) or substituted or unsubstituted heteroaryl (e.g., 5 to 10 membered heteroaryl, 5 to 9 membered heteroaryl, or 5 to 6 membered heteroaryl).

In embodiments, $R^{11}$ is hydrogen, halogen, $-OCH_3$, $SO_2$, $SO_2-R^{11B}$, $-OR^{11A}$, $-NR^{11B}R^{11C}$ or substituted or unsubstituted aryl (e.g., $C_6$-$C_{10}$ aryl, $C_{10}$ aryl, or phenyl). In embodiments, $R^{11}$ is hydrogen. In embodiments, $R^{11}$ is Br. In embodiments, $R^{11}$ is Cl. In embodiments, $R^{11}$ is $SO_2-R^{11B}$ wherein $R^{11B}$ is substituted or unsubstituted aryl (e.g., $C_6$-$C_{10}$ aryl, $C_{10}$ aryl, or phenyl). In embodiments, $R^{11}$ is $SO_2-R^{11B}$ wherein $R^{11B}$ is unsubstituted aryl (e.g., $C_6$-$C_{10}$ aryl, $C_{10}$ aryl, or phenyl). In embodiments, $R^{11}$ is $SO_2-R^{11B}$ wherein $R^{11B}$ is phenyl. In embodiments, $R^{11}$ is phenyl. In embodiments, $R^{11}$ is $-OR^{11A}$, wherein $R^{11A}$ is substituted or unsubstituted alkyl (e.g., $C_1$-$C_8$ alkyl, $C_1$-$C_6$ alkyl, or $C_1$-$C_4$ alkyl). In embodiments, $R^{18}$ is $-OR^{11A}$, wherein $R^{11A}$ is unsubstituted alkyl (e.g., $C_1$-$C_8$ alkyl, $C_1$-$C_6$ alkyl, or $C_1$-$C_4$ alkyl). In embodiments, $R^{11}$ is $-OR^{11A}$, wherein $R^{11A}$ is substituted or unsubstituted $C_1$-$C_8$ alkyl. In embodiments, $R^{11}$ is $-OR^{11A}$, wherein $R^{11A}$ is substituted or unsubstituted $C_1$-$C_4$ alkyl. In embodiments, $R^{11}$ is $-OR^{11A}$, wherein $R^{11A}$ is substituted or unsubstituted $C_1$-$C_2$ alkyl. In embodiments, $R^{11}$ is $-NR^{11B}R^{11C}$, wherein $R^{11B}$ and $R^{11C}$ are unsubstituted alkyl (e.g., $C_1$-$C_8$ alkyl, $C_1$-$C_6$ alkyl, or $C_1$-$C_4$ alkyl). In embodiments, $R^{11}$ is $-NR^{11B}R^{11C}$, wherein $R^{11B}$ and $R^{11C}$ are substituted or unsubstituted $C_1$-$C_8$ alkyl. In embodiments, $R^{11B}$ is $-NR^{11B}R^{11C}$, wherein $R^{11B}$ and $R^{11C}$ are substituted or unsubstituted $C_1$-$C_4$ alkyl. In embodiments, $R^{11}$ is $-NR^{11B}R^{11C}$, wherein $R^{11B}$ and $R^{11C}$ are substituted or unsubstituted $C_1$-$C_2$ alkyl.

In embodiments, $R^{11}$ is $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), 10-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{41}$-substituted or unsubstituted heteroaryl (e.g., 5 to 10 membered heteroaryl, 5 to 9 membered heteroaryl, or 5 to 6 membered heteroaryl).

In embodiments, $R^{11}$ is $R^{41}$-substituted or unsubstituted alkyl (e.g., $C_1$-$C_8$ alkyl, $C_1$-$C_6$ alkyl, or $C_1$-$C_4$ alkyl). In embodiments, $R^{11}$ is $R^{41}$-substituted alkyl (e.g., $C_1$-$C_8$ alkyl, $C_1$-$C_6$ alkyl, or $C_1$-$C_4$ alkyl). In embodiments, $R^{11}$ is an unsubstituted alkyl (e.g., $C_1$-$C_8$ alkyl, $C_1$-$C_6$ alkyl, or $C_1$-$C_4$ alkyl).

In embodiments, $R^{11}$ is $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{11}$ is $R^{41}$-substituted heteroalkyl (e.g., 2 to 8 membered heteroalkyl, 2 to 6 membered heteroalkyl, or 2 to 4 membered heteroalkyl). In embodiments, $R^{11}$ is an unsubstituted heteroalkyl (e.g., 2 to 8 membered heteroalkyl, 2 to 6 membered heteroalkyl, or 2 to 4 membered heteroalkyl).

In embodiments, $R^{11}$ is $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{11}$ is $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{11}$ is $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{11}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{11}$ is $R^{41}$-substituted or unsubstituted aryl (e.g., $C_6$-$C_{10}$ aryl, Cm aryl, or phenyl). In embodiments, $R^{11}$ is $R^{41}$-substituted aryl (e.g., $C_6$-$C_{10}$ aryl, $C_{10}$ aryl, or phenyl). In embodiments, $R^{11}$ is an unsubstituted aryl (e.g., $C_6$-$C_{10}$ aryl, $C_{10}$ aryl, or phenyl).

In embodiments, $R^{11}$ is $R^{41}$-substituted or unsubstituted heteroaryl (e.g., 5 to 10 membered heteroaryl, 5 to 9 membered heteroaryl, or 5 to 6 membered heteroaryl). In embodiments, $R^{11}$ is $R^{41}$-substituted heteroaryl (e.g., 5 to 10 membered heteroaryl, 5 to 9 membered heteroaryl, or 5 to 6 membered heteroaryl). In embodiments, $R^{11}$ is an unsubstituted heteroaryl (e.g., 5 to 10 membered heteroaryl, 5 to 9 membered heteroaryl, or 5 to 6 membered heteroaryl).

In embodiments, $R^{11A}$ is $R^{41A}$-substituted or unsubstituted alkyl (e.g., $C_1$-$C_8$ alkyl, $C_1$-$C_6$ alkyl, or $C_1$-$C_4$ alkyl), $R^{41A}$-substituted or unsubstituted heteroalkyl (e.g., 2 to 8 membered heteroalkyl, 2 to 6 membered heteroalkyl, or 2 to 4 membered heteroalkyl), $R^{41A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41A}$-substituted or unsubstituted aryl (e.g., $C_6$-$C_{10}$ aryl, $C_{10}$ aryl, or phenyl), or $R^{41A}$-substituted or unsubstituted heteroaryl (e.g., 5 to 10 membered heteroaryl, 5 to 9 membered heteroaryl, or 5 to 6 membered heteroaryl).

In embodiments, $R^{11B}$ is $R^{41B}$-substituted or unsubstituted alkyl (e.g., $C_1$-$C_8$ alkyl, $C_1$-$C_6$ alkyl, or $C_1$-$C_4$ alkyl), $R^{41B}$-substituted or unsubstituted heteroalkyl (e.g., 2 to 8 membered heteroalkyl, 2 to 6 membered heteroalkyl, or 2 to 4 membered heteroalkyl), $R^{41B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41B}$-substituted or unsubstituted aryl (e.g., $C_6$-$C_{10}$ aryl, $C_{10}$ aryl, or phenyl), or $R^{41B}$-substituted or unsubstituted heteroaryl (e.g., 5 to 10 membered heteroaryl, 5 to 9 membered heteroaryl, or 5 to 6 membered heteroaryl).

In embodiments, $R^{11C}$ is $R^{41C}$-substituted or unsubstituted alkyl (e.g., $C_1$-$C_8$ alkyl, $C_1$-$C_6$ alkyl, or $C_1$-$C_4$ alkyl), $R^{41B}$-substituted or unsubstituted heteroalkyl (e.g., 2 to 8 membered heteroalkyl, 2 to 6 membered heteroalkyl, or 2 to 4 membered heteroalkyl), $R^{41C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41C}$-substituted or unsubstituted aryl (e.g., $C_6$-$C_{10}$ aryl, $C_{10}$ aryl, or phenyl), or $R^{41C}$-substituted or unsubstituted heteroaryl (e.g., 5 to 10 membered heteroaryl, 5 to 9 membered heteroaryl, or 5 to 6 membered heteroaryl).

In embodiments, $R^{11D}$ is $R^{41D}$-substituted or unsubstituted alkyl (e.g., $C_1$-$C_8$ alkyl, $C_1$-$C_6$ alkyl, or $C_1$-$C_4$ alkyl), $R^{41D}$-substituted or unsubstituted heteroalkyl (e.g., 2 to 8 membered heteroalkyl, 2 to 6 membered heteroalkyl, or 2 to 4 membered heteroalkyl), $R^{41D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41D}$-substituted or unsubstituted aryl (e.g., $C_6$-$C_{10}$ aryl, $C_{10}$ aryl, or phenyl), or $R^{41D}$-substituted or unsubstituted heteroaryl (e.g., 5 to 10 membered heteroaryl, 5 to 9 membered heteroaryl, or 5 to 6 membered heteroaryl).

In embodiments, $R^{12}$ is hydrogen, halogen, $-N_3$, $-CF_3$, $-CCl_3$, $-CBr_3$, $-CI_3$, $-CN$, $-CHO$, $-OR^{12A}$, $-NR^{12B}R^{12C}$, $-COOR^{12A}$, $-CONR^{12B}R^{12C}$, $-NO_2$, $-SR^{12D}$, $-SO_{n12}R^{12B}$, $-SO_{v12}NR^{12B}R^{12C}$, $-NHNR^{12B}R^{12C}$, $-ONR^{12B}R^{12C}$, $-NHC(O)NHNR^{12B}R^{12C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{11}$ and $R^{12}$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl) or substituted or unsubstituted heteroaryl (e.g., 5 to 10 membered heteroaryl, 5 to 9 membered heteroaryl, or 5 to 6 membered heteroaryl).

In embodiments, $R^{12}$ is hydrogen, halogen, $-OCH_3$, $SO_2$, $SO_2-R^{12B}$, $-OR^{12A}$, $-NR^{12B}R^{12C}$, or substituted or unsubstituted aryl (e.g., $C_6$-$C_{10}$ aryl, $C_{10}$ aryl, or phenyl). In embodiments, $R^{12}$ is hydrogen. In embodiments, $R^{12}$ is Br. In embodiments, $R^{12}$ is Cl. In embodiments, $R^{12}$ is $SO_2-R^{12B}$ wherein $R^{12B}$ is substituted or unsubstituted aryl (e.g., $C_6$-$C_{10}$ aryl, $C_{10}$ aryl, or phenyl). In embodiments, $R^{12}$ is $SO_2-R^{12B}$ wherein $R^{12B}$ is unsubstituted aryl (e.g., $C_6$-$C_{10}$ aryl, $C_{10}$ aryl, or phenyl). In embodiments, $R^{12}$ is $SO_2$—$R^{12B}$ wherein $R^{12B}$ is phenyl. In embodiments, $R^{12}$ is phenyl. In embodiments, $R^{12}$ is —$OR^{12A}$, wherein $R^{12A}$ is substituted or unsubstituted alkyl (e.g., $C_1$-$C_8$ alkyl, $C_1$-$C_6$ alkyl, or $C_1$-$C_4$ alkyl). In embodiments, $R^{12}$ is —$OR^{12A}$, wherein $R^{12A}$ is unsubstituted alkyl (e.g., $C_1$-$C_8$ alkyl, $C_1$-$C_6$ alkyl, or $C_1$-$C_4$ alkyl). In embodiments, $R^{12}$ is —$OR^{12A}$, wherein $R^{12A}$ is substituted or unsubstituted $C_1$-$C_8$ alkyl. In embodiments, $R^{12}$ is —$OR^{12A}$, wherein $R^{12A}$ is substituted or unsubstituted $C_1$-$C_4$ alkyl. In embodiments, $R^{12}$ is —$OR^{12A}$, wherein $R^{12A}$ is substituted or unsubstituted $C_1$-$C_2$ alkyl. In embodiments, $R^{12}$ is —$NR^{12B}R^{12C}$, wherein $R^{12B}$ and $R^{12C}$ are unsubstituted alkyl (e.g., $C_1$-$C_8$ alkyl, $C_1$-$C_6$ alkyl, or $C_1$-$C_4$ alkyl). In embodiments, $R^{12}$ is —$NR^{12B}R^{12C}$, wherein $R^{12B}$ and $R^{12C}$ are substituted or unsubstituted $C_1$-$C_8$ alkyl. In embodiments, $R^{12}$ is —$NR^{12B}R^{12C}$, wherein $R^{12B}$ and $R^{12C}$ are substituted or unsubstituted $C_1$-$C_4$ alkyl. In embodiments, $R^{12}$ is —$NR^{12B}R^{12C}$, wherein $R^{12B}$ and $R^{12C}$ are substituted or unsubstituted $C_1$-$C_2$ alkyl.

In embodiments, $R^{12}$ is $R^{43}$-substituted or unsubstituted alkyl (e.g., $C_1$-$C_8$ alkyl, $C_1$-$C_6$ alkyl, or $C_1$-$C_4$ alkyl), $R^{43}$-substituted or unsubstituted heteroalkyl (e.g., 2 to 8 membered heteroalkyl, 2 to 6 membered heteroalkyl, or 2 to 4 membered heteroalkyl), $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43}$-substituted or unsubstituted aryl (e.g., $C_6$-$C_{10}$ aryl, $C_{10}$ aryl, or phenyl), or $R^{43}$-substituted or unsubstituted heteroaryl (e.g., 5 to 10 membered heteroaryl, 5 to 9 membered heteroaryl, or 5 to 6 membered heteroaryl).

In embodiments, $R^{12}$ is $R^{43}$-substituted or unsubstituted alkyl (e.g., $C_1$-$C_8$ alkyl, $C_1$-$C_6$ alkyl, or $C_1$-$C_4$ alkyl). In embodiments, $R^{12}$ is $R^{43}$-substituted alkyl (e.g., $C_1$-$C_8$ alkyl, $C_1$-$C_6$ alkyl, or $C_1$-$C_4$ alkyl). In embodiments, $R^u$ is an unsubstituted alkyl (e.g., $C_1$-$C_8$ alkyl, $C_1$-$C_6$ alkyl, or $C_1$-$C_4$ alkyl).

In embodiments, $R^{12}$ is $R^{43}$-substituted or unsubstituted heteroalkyl (e.g., 2 to 8 membered heteroalkyl, 2 to 6 membered heteroalkyl, or 2 to 4 membered heteroalkyl). In embodiments, $R^{12}$ is $R^{43}$-substituted heteroalkyl (e.g., 2 to 8 membered heteroalkyl, 2 to 6 membered heteroalkyl, or 2 to 4 membered heteroalkyl). In embodiments, $R^{12}$ is an unsubstituted heteroalkyl (e.g., 2 to 8 membered heteroalkyl, 2 to 6 membered heteroalkyl, or 2 to 4 membered heteroalkyl).

In embodiments, $R^{12}$ is $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is $R^{43}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{12}$ is $R^{43}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{12}$ is $R^{43}$-substituted heterocycloalkyl (e.g., 3 to 8 membered heterocycloalkyl, 3 to 6 membered heterocycloalkyl, or 5 to 6 membered heterocycloalkyl). In embodiments, $R^{12}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{12}$ is $R^{43}$-substituted or unsubstituted aryl (e.g., $C_6$-$C_{10}$ aryl, $C_{10}$ aryl, or phenyl). In embodiments, $R^{12}$ is $R^{43}$-substituted aryl (e.g., $C_6$-$C_{10}$ aryl, $C_{10}$ aryl, or phenyl). In embodiments, $R^{12}$ is an unsubstituted aryl (e.g., $C_6$-$C_{10}$ aryl, $C_{10}$ aryl, or phenyl).

In embodiments, $R^{12}$ is $R^{43}$-substituted or unsubstituted heteroaryl (e.g., 5 to 10 membered heteroaryl, 5 to 9 membered heteroaryl, or 5 to 6 membered heteroaryl). In embodiments, $R^{12}$ is $R^{43}$-substituted heteroaryl (e.g., 5 to 10 membered heteroaryl, 5 to 9 membered heteroaryl, or 5 to 6 membered heteroaryl). In embodiments, $R^{12}$ is an unsubstituted heteroaryl (e.g., 5 to 10 membered heteroaryl, 5 to 9 membered heteroaryl, or 5 to 6 membered heteroaryl).

In embodiments, $R^{12A}$ is $R^{43A}$-substituted or unsubstituted alkyl (e.g., $C_1$-$C_8$ alkyl, $C_1$-$C_6$ alkyl, or $C_1$-$C_4$ alkyl), $R^{43A}$-substituted or unsubstituted heteroalkyl (e.g., 2 to 8 membered heteroalkyl, 2 to 6 membered heteroalkyl, or 2 to 4 membered heteroalkyl), $R^{43A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43A}$-substituted or unsubstituted aryl (e.g., $C_6$-$C_{10}$ aryl, $C_{10}$ aryl, or phenyl), or $R^{43A}$-substituted or unsubstituted heteroaryl (e.g., 5 to 10 membered heteroaryl, 5 to 9 membered heteroaryl, or 5 to 6 membered heteroaryl).

In embodiments, $R^{12B}$ is $R^{43B}$-substituted or unsubstituted alkyl (e.g., $C_1$-$C_8$ alkyl, $C_1$-$C_6$ alkyl, or $C_1$-$C_4$ alkyl), $R^{43B}$-substituted or unsubstituted heteroalkyl (e.g., 2 to 8 membered heteroalkyl, 2 to 6 membered heteroalkyl, or 2 to 4 membered heteroalkyl), $R^{43B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43B}$-substituted or unsubstituted aryl (e.g., $C_6$-$C_{10}$ aryl, $C_{10}$ aryl, or phenyl), or $R^{43B}$-substituted or unsubstituted heteroaryl (e.g., 5 to 10 membered heteroaryl, 5 to 9 membered heteroaryl, or 5 to 6 membered heteroaryl).

In embodiments, $R^{12C}$ is $R^{43C}$-substituted or unsubstituted alkyl (e.g., $C_1$-$C_8$ alkyl, $C_1$-$C_6$ alkyl, or $C_1$-$C_4$ alkyl), $R^{43C}$-substituted or unsubstituted heteroalkyl (e.g., 2 to 8 membered heteroalkyl, 2 to 6 membered heteroalkyl, or 2 to 4 membered heteroalkyl), $R^{43C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43C}$-substituted or unsubstituted aryl (e.g., $C_6$-$C_{10}$ aryl, $C_{10}$ aryl, or phenyl), or $R^{43C}$-substituted or unsubstituted heteroaryl (e.g., 5 to 10 membered heteroaryl, 5 to 9 membered heteroaryl, or 5 to 6 membered heteroaryl).

In embodiments, $R^{12D}$ is $R^{43D}$-substituted or unsubstituted alkyl (e.g., $C_1$-$C_8$ alkyl, $C_1$-$C_6$ alkyl, or $C_1$-$C_4$ alkyl), $R^{43D}$-substituted or unsubstituted heteroalkyl (e.g., 2 to 8 membered heteroalkyl, 2 to 6 membered heteroalkyl, or 2 to 4 membered heteroalkyl), $R^{43D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43D}$-substituted or unsubstituted aryl (e.g., $C_6$-$C_{10}$ aryl, $C_{10}$ aryl, or phenyl), or $R^{43D}$-substituted or unsubstituted heteroaryl (e.g., 5 to 10 membered heteroaryl, 5 to 9 membered heteroaryl, or 5 to 6 membered heteroaryl).

In embodiments, $R^{10}$ and $R^{11}$ are optionally joined to form a substituted or unsubstituted cycloalkyl or substituted or unsubstituted heterocycloalkyl having structural formula

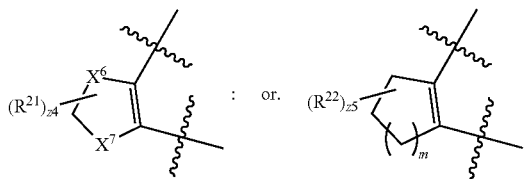

In embodiments, $R^{10}$ and $R^{11}$ are optionally joined to form a substituted or unsubstituted cycloalkyl or substituted or unsubstituted heterocycloalkyl having structural formula:

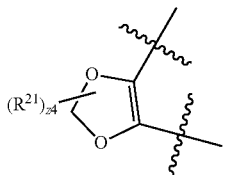

In embodiments, $R^{10}$ and $R^{11}$ are optionally joined to form a substituted or unsubstituted cycloalkyl or substituted or unsubstituted heterocycloalkyl having structural formula:

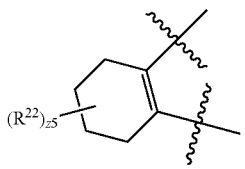

In embodiments, $R^{11}$ and $R^{12}$ are optionally joined to form a substituted or unsubstituted cycloalkyl or substituted or unsubstituted heterocycloalkyl having structural formula:

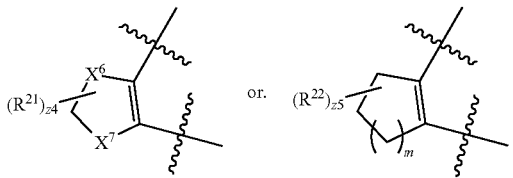

In embodiments, $R^{11}$ and $R^{12}$ are optionally joined to form a substituted or unsubstituted cycloalkyl or substituted or unsubstituted heterocycloalkyl having structural formula:

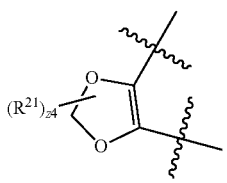

In embodiments, $R^{11}$ and $R^{12}$ are optionally joined to form a substituted or unsubstituted cycloalkyl or substituted or unsubstituted heterocycloalkyl having structural formula:

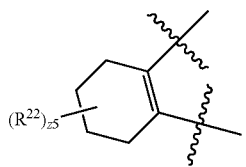

In embodiments, $R^{13}$ is hydrogen, halogen, $-N_3$, $-CF_3$, $-CCl_3$, $-CBr_3$, $-CI_3$, $-CN$, $-CHO$, $-OR^{13A}$, $-NR^{13B}R^{13C}$, $-COOR^{13A}$, $-CONR^{13B}R^{13C}$, $-NO_2$, $-SR^{13D}$, $-SO_{n13}R^{13B}$, $-SO_{v13}NR^{13B}R^{13C}$, $-NHNR^{13B}R^{13C}$, $-ONR^{13B}R^{13C}$, $-NHC(O)NHNR^{13B}R^{13C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{13}$ is $R^{45}$-substituted or unsubstituted alkyl (e.g., $C_1$-$C_8$ alkyl, $C_1$-$C_6$ alkyl, or $C_1$-$C_4$ alkyl), $R^{45}$-substituted or unsubstituted heteroalkyl (e.g., 2 to 8 membered heteroalkyl, 2 to 6 membered heteroalkyl, or 2 to 4 membered heteroalkyl), $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45}$-substituted or unsubstituted aryl (e.g., $C_6$-$C_{10}$ aryl, $C_{10}$ aryl, or phenyl), or $R^{45}$-substituted or unsubstituted heteroaryl (e.g., 5 to 10 membered heteroaryl, 5 to 9 membered heteroaryl, or 5 to 6 membered heteroaryl).

In embodiments, $R^{13}$ is $R^{45}$-substituted or unsubstituted alkyl (e.g., $C_1$-$C_8$ alkyl, $C_1$-$C_6$ alkyl, or $C_1$-$C_4$ alkyl). In embodiments, $R^{13}$ is $R^{45}$-substituted alkyl (e.g., $C_1$-$C_8$ alkyl, $C_1$-$C_6$ alkyl, or $C_1$-$C_4$ alkyl). In embodiments, $R^n$ is an unsubstituted alkyl (e.g., $C_1$-$C_8$ alkyl, $C_1$-$C_6$ alkyl, or $C_1$-$C_4$ alkyl).

In embodiments, $R^{13}$ is $R^{45}$-substituted or unsubstituted heteroalkyl (e.g., 2 to 8 membered heteroalkyl, 2 to 6 membered heteroalkyl, or 2 to 4 membered heteroalkyl). In embodiments, $R^{13}$ is $R^{45}$-substituted heteroalkyl (e.g., 2 to 8 membered heteroalkyl, 2 to 6 membered heteroalkyl, or 2 to 4 membered heteroalkyl). In embodiments, $R^{13}$ is an unsubstituted heteroalkyl (e.g., 2 to 8 membered heteroalkyl, 2 to 6 membered heteroalkyl, or 2 to 4 membered heteroalkyl).

In embodiments, $R^{13}$ is $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is $R^{45}$-substituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{13}$ is $R^{45}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13}$ is $R^{45}$-substituted heterocycloalkyl (e.g., 3 to 8 membered heterocycloalkyl, 3 to 6 membered heterocycloalkyl, or 5 to 6 membered heterocycloalkyl). In embodiments, $R^{13}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{13}$ is $R^{45}$-substituted or unsubstituted aryl (e.g., $C_6$-$C_{10}$ aryl, $C_{10}$ aryl, or phenyl). In embodiments, $R^{13}$ is $R^{45}$-substituted aryl (e.g., $C_6$-$C_{10}$ aryl, $C_{10}$ aryl, or phenyl). In embodiments, $R^{13}$ is an unsubstituted aryl (e.g., $C_6$-$C_{10}$ aryl, $C_{10}$ aryl, or phenyl).

In embodiments, $R^{13}$ is $R^{45}$-substituted or unsubstituted heteroaryl (e.g., 5 to 10 membered heteroaryl, 5 to 9 membered heteroaryl, or 5 to 6 membered heteroaryl). In embodiments, $R^{13}$ is $R^{45}$-substituted heteroaryl (e.g., 5 to 10 membered heteroaryl, 5 to 9 membered heteroaryl, or 5 to 6 membered heteroaryl). In embodiments, $R^{13}$ is an unsubstituted heteroaryl (e.g., 5 to 10 membered heteroaryl, 5 to 9 membered heteroaryl, or 5 to 6 membered heteroaryl).

In embodiments, $R^{13A}$ is $R^{45A}$-substituted or unsubstituted alkyl (e.g., $C_1$-$C_8$ alkyl, $C_1$-$C_6$ alkyl, or $C_1$-$C_4$ alkyl), $R^{45A}$-substituted or unsubstituted heteroalkyl (e.g., 2 to 8 membered heteroalkyl, 2 to 6 membered heteroalkyl, or 2 to 4 membered heteroalkyl), $R^{45A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45A}$-substituted or unsubstituted aryl (e.g., $C_6$-$C_{10}$ aryl, $C_{10}$ aryl, or phenyl), or $R^{45A}$-substituted or unsubstituted heteroaryl (e.g., 5 to 10 membered heteroaryl, 5 to 9 membered heteroaryl, or 5 to 6 membered heteroaryl).

In embodiments, $R^{13B}$ is $R^{45B}$-substituted or unsubstituted alkyl (e.g., $C_1$-$C_8$ alkyl, $C_1$-$C_6$ alkyl, or $C_1$-$C_4$ alkyl), $R^{45B}$-substituted or unsubstituted heteroalkyl (e.g., 2 to 8 membered heteroalkyl, 2 to 6 membered heteroalkyl, or 2 to 4 membered heteroalkyl), $R^{45B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45B}$-substituted or unsubstituted aryl (e.g., $C_6$-$C_{10}$ aryl, $C_{10}$ aryl, or phenyl), or $R^{45B}$-substituted or unsubstituted heteroaryl (e.g., 5 to 10 membered heteroaryl, 5 to 9 membered heteroaryl, or 5 to 6 membered heteroaryl).

In embodiments, $R^{13C}$ is $R^{45C}$-substituted or unsubstituted alkyl (e.g., $C_1$-$C_8$ alkyl, $C_1$-$C_6$ alkyl, or $C_1$-$C_4$ alkyl), $R^{45C}$-substituted or unsubstituted heteroalkyl (e.g., 2 to 8 membered heteroalkyl, 2 to 6 membered heteroalkyl, or 2 to 4 membered heteroalkyl), $R^{45C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45C}$-substituted or unsubstituted aryl (e.g., $C_6$-$C_{10}$ aryl, $C_{10}$ aryl, or phenyl), or $R^{45C}$-substituted or unsubstituted heteroaryl (e.g., 5 to 10 membered heteroaryl, 5 to 9 membered heteroaryl, or 5 to 6 membered heteroaryl).

In embodiments, $R^{13D}$ is $R^{45D}$-substituted or unsubstituted alkyl (e.g., $C_1$-$C_8$ alkyl, $C_1$-$C_6$ alkyl, or $C_1$-$C_4$ alkyl), $R^{45D}$-substituted or unsubstituted heteroalkyl (e.g., 2 to 8 membered heteroalkyl, 2 to 6 membered heteroalkyl, or 2 to 4 membered heteroalkyl), $R^{45D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45D}$-substituted or unsubstituted aryl (e.g., $C_6$-$C_{10}$ aryl, $C_{10}$ aryl, or phenyl), or $R^{45D}$-substituted or unsubstituted heteroaryl (e.g., 5 to 10 membered heteroaryl, 5 to 9 membered heteroaryl, or 5 to 6 membered heteroaryl).

In embodiments, $R^{14}$ is hydrogen, halogen, $-N_3$, $-CF_3$, $-CCl_3$, $-CBr_3$, $-CI_3$, $-CN$, $-CHO$, $-OR^{14A}$, $-NR^{14B}R^{14C}$, $-COOR^{14A}$, $-CONR^{14B}R^{14C}$, $-NO_2$, $-SR^{14D}$, $-SO_{n14}R^{14B}$, $-SO_{v14}NR^{14B}R^{14C}$, $-NHNR^{14B}R^{14C}$, $-ONR^{14B}R^{14C}$, $-NHC(O)NHNR^{14B}R^{14C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{14}$ is $R^{46}$-substituted or unsubstituted alkyl (e.g., $C_1$-$C_8$ alkyl, $C_1$-$C_6$ alkyl, or $C_1$-$C_4$ alkyl), $R^{46}$-substituted or unsubstituted heteroalkyl (e.g., 2 to 8 membered heteroalkyl, 2 to 6 membered heteroalkyl, or 2 to 4 membered heteroalkyl), $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46}$-substituted or unsubstituted aryl (e.g., $C_6$-$C_{10}$ aryl, $C_{10}$ aryl, or phenyl), or $R^{46}$-substituted or unsubstituted heteroaryl (e.g., 5 to 10 membered heteroaryl, 5 to 9 membered heteroaryl, or 5 to 6 membered heteroaryl).

In embodiments, $R^{14}$ is $R^{46}$-substituted or unsubstituted alkyl (e.g., $C_1$-$C_8$ alkyl, $C_1$-$C_6$ alkyl, or $C_1$-$C_4$ alkyl). In embodiments, $R^{14}$ is $R^{46}$-substituted alkyl (e.g., $C_1$-$C_8$ alkyl, $C_1$-$C_6$ alkyl, or $C_1$-$C_4$ alkyl). In embodiments, $R^{14}$ is an unsubstituted alkyl (e.g., $C_1$-$C_8$ alkyl, $C_1$-$C_6$ alkyl, or $C_1$-$C_4$ alkyl).

In embodiments, $R^{14}$ is $R^{46}$-substituted or unsubstituted heteroalkyl (e.g., 2 to 8 membered heteroalkyl, 2 to 6 membered heteroalkyl, or 2 to 4 membered heteroalkyl). In embodiments, $R^{14}$ is $R^{46}$-substituted heteroalkyl (e.g., 2 to 8 membered heteroalkyl, 2 to 6 membered heteroalkyl, or 2 to 4 membered heteroalkyl). In embodiments, $R^{14}$ is an unsubstituted heteroalkyl (e.g., 2 to 8 membered heteroalkyl, 2 to 6 membered heteroalkyl, or 2 to 4 membered heteroalkyl).

In embodiments, $R^{14}$ is $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is $R^{46}$-substituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{14}$ is $R^{46}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{14}$ is $R^{46}$-substituted heterocycloalkyl (e.g., 3 to 8 membered heterocycloalkyl, 3 to 6 membered heterocycloalkyl, or 5 to 6 membered heterocycloalkyl). In embodiments, $R^{14}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{14}$ is $R^{46}$-substituted or unsubstituted aryl (e.g., $C_6$-$C_{10}$ aryl, $C_{10}$ aryl, or phenyl). In embodiments, $R^{14}$ is $R^{46}$-substituted aryl (e.g., $C_6$-$C_{10}$ aryl, $C_{10}$ aryl, or phenyl). In embodiments, $R^{14}$ is an unsubstituted aryl (e.g., $C_6$-$C_{10}$ aryl, $C_{10}$ aryl, or phenyl).

In embodiments, $R^{14}$ is $R^{46}$-substituted or unsubstituted heteroaryl (e.g., 5 to 10 membered heteroaryl, 5 to 9 membered heteroaryl, or 5 to 6 membered heteroaryl). In embodiments, $R^{14}$ is $R^{46}$-substituted heteroaryl (e.g., 5 to 10 membered heteroaryl, 5 to 9 membered heteroaryl, or 5 to 6 membered heteroaryl). In embodiments, $R^{14}$ is an unsubstituted heteroaryl (e.g., 5 to 10 membered heteroaryl, 5 to 9 membered heteroaryl, or 5 to 6 membered heteroaryl).

In embodiments, $R^{14A}$ is $R^{46A}$-substituted or unsubstituted alkyl (e.g., $C_1$-$C_8$ alkyl, $C_1$-$C_6$ alkyl, or $C_1$-$C_4$ alkyl), $R^{46A}$-substituted or unsubstituted heteroalkyl (e.g., 2 to 8 membered heteroalkyl, 2 to 6 membered heteroalkyl, or 2 to 4 membered heteroalkyl), $R^{46A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46A}$-substituted or unsubstituted aryl (e.g., $C_6$-$C_{10}$ aryl, $C_{10}$ aryl, or phenyl), or $R^{46A}$-substituted or unsubstituted heteroaryl (e.g., 5 to 10 membered heteroaryl, 5 to 9 membered heteroaryl, or 5 to 6 membered heteroaryl).

In embodiments, $R^{14B}$ is $R^{46B}$-substituted or unsubstituted alkyl (e.g., $C_1$-$C_8$ alkyl, $C_1$-$C_6$ alkyl, or $C_1$-$C_4$ alkyl), $R^{46B}$-substituted or unsubstituted heteroalkyl (e.g., 2 to 8 membered heteroalkyl, 2 to 6 membered heteroalkyl, or 2 to 4 membered heteroalkyl), $R^{46B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46B}$-substituted or unsubstituted aryl (e.g., $C_6$-$C_{10}$ aryl, $C_{10}$ aryl, or phenyl), or $R^{46B}$-substituted or unsubstituted heteroaryl (e.g., 5 to 10 membered heteroaryl, 5 to 9 membered heteroaryl, or 5 to 6 membered heteroaryl).

In embodiments, $R^{14C}$ is $R^{46C}$-substituted or unsubstituted alkyl (e.g., $C_1$-$C_8$ alkyl, $C_1$-$C_6$ alkyl, or $C_1$-$C_4$ alkyl), $R^{46C}$-substituted or unsubstituted heteroalkyl (e.g., 2 to 8 membered heteroalkyl, 2 to 6 membered heteroalkyl, or 2 to 4 membered heteroalkyl), $R^{46C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46C}$-substituted or unsubstituted aryl (e.g., $C_6$-$C_{10}$ aryl, $C_{10}$ aryl, or phenyl), or $R^{46C}$-substituted or unsubstituted heteroaryl (e.g., 5 to 10 membered heteroaryl, 5 to 9 membered heteroaryl, or 5 to 6 membered heteroaryl).

In embodiments, $R^{14D}$ is $R^{46D}$-substituted or unsubstituted alkyl (e.g., $C_1$-$C_8$ alkyl, $C_1$-$C_6$ alkyl, or $C_1$-$C_4$ alkyl), $R^{46D}$-substituted or unsubstituted heteroalkyl (e.g., 2 to 8 membered heteroalkyl, 2 to 6 membered heteroalkyl, or 2 to 4 membered heteroalkyl), $R^{45D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46D}$-substituted or unsubstituted aryl (e.g., $C_6$-$C_{10}$ aryl, $C_{10}$ aryl, or phenyl), or $R^{45D}$-substituted or unsubstituted heteroaryl (e.g., 5 to 10 membered heteroaryl, 5 to 9 membered heteroaryl, or 5 to 6 membered heteroaryl).

In embodiments, $R^{15}$ is hydrogen, halogen, —$N_3$, —$CF_3$, —$CCl_3$, —$CBr_3$, —$CI_3$, —CN, —CHO, —$OR^{15A}$, —$NR^{15B}R^{15C}$, —$COOR^{15A}$, —$CONR^{15B}R^{15C}$, —$NO_2$, —$SR^{15D}$, —$SO_{n15}R^{15B}$, —$SO_{v15}NR^{15B}R^{15C}$, —$NHNR^{15B}R^{15C}$, —$ONR^{15B}R^{15C}$, —NHC(O)$NHNR^{15B}R^{15C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{15}$ is $R^{47}$-substituted or unsubstituted alkyl (e.g., $C_1$-$C_8$ alkyl, $C_1$-$C_6$ alkyl, or $C_1$-$C_4$ alkyl), $R^{47}$-substituted or unsubstituted heteroalkyl (e.g., 2 to 8 membered heteroalkyl, 2 to 6 membered heteroalkyl, or 2 to 4 membered heteroalkyl), $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47}$-substituted or unsubstituted aryl (e.g., $C_6$-$C_{10}$ aryl, $C_{10}$ aryl, or phenyl), or $R^{47}$-substituted or unsubstituted heteroaryl (e.g., 5 to 10 membered heteroaryl, 5 to 9 membered heteroaryl, or 5 to 6 membered heteroaryl).

In embodiments, $R^{15}$ is $R^{47}$-substituted or unsubstituted alkyl (e.g., $C_1$-$C_8$ alkyl, $C_1$-$C_6$ alkyl, or $C_1$-$C_4$ alkyl). In embodiments, $R^{15}$ is $R^{47}$-substituted alkyl (e.g., $C_1$-$C_8$ alkyl, $C_1$-$C_6$ alkyl, or $C_1$-$C_4$ alkyl). In embodiments, $R^{15}$ is an unsubstituted alkyl (e.g., $C_1$-$C_8$ alkyl, $C_1$-$C_6$ alkyl, or $C_1$-$C_4$ alkyl).

In embodiments, $R^{15}$ is $R^{47}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{47}$-substituted heteroalkyl (e.g., 2 to 8 membered heteroalkyl, 2 to 6 membered heteroalkyl, or 2 to 4 membered heteroalkyl). In embodiments, $R^{15}$ is an unsubstituted heteroalkyl (e.g., 2 to 8 membered heteroalkyl, 2 to 6 membered heteroalkyl, or 2 to 4 membered heteroalkyl).

In embodiments, $R^{15}$ is $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is $R^{47}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{15}$ is $R^{47}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{47}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{15}$ is $R^{47}$-substituted or unsubstituted aryl (e.g., $C_6$-$C_{10}$ aryl, $C_{10}$ aryl, or phenyl). In embodiments, $R^{15}$ is $R^{47}$-substituted aryl (e.g., $C_6$-$C_{10}$ aryl, $C_{10}$ aryl, or phenyl). In embodiments, $R^{15}$ is an unsubstituted aryl (e.g., $C_6$-$C_{10}$ aryl, $C_{10}$ aryl, or phenyl).

In embodiments, $R^{15}$ is $R^{47}$-substituted or unsubstituted heteroaryl (e.g., 5 to 10 membered heteroaryl, 5 to 9 membered heteroaryl, or 5 to 6 membered heteroaryl). In embodiments, $R^{15}$ is $R^{47}$-substituted heteroaryl (e.g., 5 to 10 membered heteroaryl, 5 to 9 membered heteroaryl, or 5 to 6 membered heteroaryl). In embodiments, $R^{15}$ is an unsubstituted heteroaryl (e.g., 5 to 10 membered heteroaryl, 5 to 9 membered heteroaryl, or 5 to 6 membered heteroaryl).

In embodiments, $R^{15A}$ is $R^{47A}$-substituted or unsubstituted alkyl (e.g., $C_1$-$C_8$ alkyl, $C_1$-$C_6$ alkyl, or $C_1$-$C_4$ alkyl), $R^{47A}$-substituted or unsubstituted heteroalkyl (e.g., 2 to 8 membered heteroalkyl, 2 to 6 membered heteroalkyl, or 2 to 4 membered heteroalkyl), $R^{47A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47A}$-substituted or unsubstituted aryl (e.g., $C_6$-$C_{10}$ aryl, $C_{10}$ aryl, or phenyl), or $R^{47A}$-substituted or unsubstituted heteroaryl (e.g., 5 to 10 membered heteroaryl, 5 to 9 membered heteroaryl, or 5 to 6 membered heteroaryl).

In embodiments, $R^{15B}$ is $R^{47B}$-substituted or unsubstituted alkyl (e.g., $C_1$-$C_8$ alkyl, $C_1$-$C_6$ alkyl, or $C_1$-$C_4$ alkyl), $R^{47B}$-substituted or unsubstituted heteroalkyl (e.g., 2 to 8 membered heteroalkyl, 2 to 6 membered heteroalkyl, or 2 to 4 membered heteroalkyl), $R^{47B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47B}$-substituted or unsubstituted aryl (e.g., $C_6$-$C_{10}$ aryl, $C_{10}$ aryl, or phenyl), or $R^{47B}$-substituted or unsubstituted heteroaryl (e.g., 5 to 10 membered heteroaryl, 5 to 9 membered heteroaryl, or 5 to 6 membered heteroaryl).

In embodiments, $R^{15C}$ is $R^{47C}$-substituted or unsubstituted alkyl (e.g., $C_1$-$C_8$ alkyl, $C_1$-$C_6$ alkyl, or $C_1$-$C_4$ alkyl), $R^{47C}$-substituted or unsubstituted heteroalkyl (e.g., 2 to 8 membered heteroalkyl, 2 to 6 membered heteroalkyl, or 2 to 4 membered heteroalkyl), $R^{47C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47C}$-substituted or unsubstituted aryl (e.g., $C_6$-$C_{10}$ aryl, $C_{10}$ aryl, or phenyl), or $R^{47C}$-substituted or unsubstituted heteroaryl (e.g., 5 to 10 membered heteroaryl, 5 to 9 membered heteroaryl, or 5 to 6 membered heteroaryl).

In embodiments, $R^{15D}$ is $R^{47D}$-substituted or unsubstituted alkyl (e.g., $C_1$-$C_8$ alkyl, $C_1$-$C_6$ alkyl, or $C_1$-$C_4$ alkyl), $R^{47D}$-substituted or unsubstituted heteroalkyl (e.g., 2 to 8 membered heteroalkyl, 2 to 6 membered heteroalkyl, or 2 to 4 membered heteroalkyl), $R^{47D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47D}$-substituted or unsubstituted aryl (e.g., $C_6$-$C_{10}$ aryl, $C_{10}$ aryl, or phenyl), or $R^{47D}$-substituted or unsubstituted heteroaryl (e.g., 5 to 10 membered heteroaryl, 5 to 9 membered heteroaryl, or 5 to 6 membered heteroaryl).

In embodiments, $L^1$ is a bond, —O—, —NH—, $R^{16}$-substituted or unsubstituted alkylene, $R^{16}$-substituted or unsubstituted heteroalkylene. In embodiments, $L^2$ is a bond, —O—, —NH—, $R^{17}$-substituted or unsubstituted alkylene, $R^{17}$-substituted or unsubstituted heteroalkylene.

$R^{16}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{29}$-substituted or unsubstituted alkyl (e.g., $C_1$-$C_8$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl).

$R^{16B}$ is independently hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{29B}$-substituted or unsubstituted alkyl (e.g., $C_1$-$C_8$ alkyl, $C_1$-$C_6$ alkyl, or $C_1$-$C_4$ alkyl), $R^{29B}$-substituted or unsubstituted heteroalkyl (e.g., 2 to 8 membered heteroalkyl, 2 to 6 membered heteroalkyl, or 2 to 4 membered heteroalkyl), $R^{29B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29B}$-substituted or unsubstituted aryl (e.g., $C_6$-$C_{10}$ aryl, $C_{10}$ aryl, or phenyl), or $R^{29B}$-substituted or unsubstituted heteroaryl (e.g., 5 to 10 membered heteroaryl, 5 to 9 membered heteroaryl, or 5 to 6 membered heteroaryl).

$R^{17}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

$R^{17B}$ is independently hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{32B}$-substituted or unsubstituted alkyl (e.g., $C_1$-$C_8$ alkyl, $C_1$-$C_6$ alkyl, or $C_1$-$C_4$ alkyl), $R^{32B}$-substituted or unsubstituted heteroalkyl (e.g., 2 to 8 membered heteroalkyl, 2 to 6 membered heteroalkyl, or 2 to 4 membered heteroalkyl), $R^{32B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32B}$-substituted or unsubstituted aryl (e.g., $C_6$-$C_{10}$ aryl, $C_{10}$ aryl, or phenyl), or $R^{32B}$-substituted or unsubstituted heteroaryl (e.g., 5 to 10 membered heteroaryl, 5 to 9 membered heteroaryl, or 5 to 6 membered heteroaryl).

In embodiments, $R^{17B}$ is independently hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{32B}$-substituted or unsubstituted alkyl (e.g., C$_1$-C$_8$ alkyl, C$_1$-C$_6$ alkyl, or C$_1$-C$_4$ alkyl), $R^{32B}$-substituted or unsubstituted heteroalkyl (e.g., 2 to 8 membered heteroalkyl, 2 to 6 membered heteroalkyl, or 2 to 4 membered heteroalkyl), $R^{32B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{32B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32B}$-substituted or unsubstituted aryl (e.g., C$_6$-C$_{10}$ aryl, C$_{10}$ aryl, or phenyl), or $R^{32B}$-substituted or unsubstituted heteroaryl (e.g., 5 to 10 membered heteroaryl, 5 to 9 membered heteroaryl, or 5 to 6 membered heteroaryl). In embodiments, $R^{17B}$ is hydrogen. In embodiments, $R^{17B}$ is —CH$_3$.

$R^{20A}$ is hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{50A}$-substituted or unsubstituted alkyl (e.g., C$_1$-C$_8$ alkyl, C$_1$-C$_6$ alkyl, or C$_1$-C$_4$ alkyl), $R^{50A}$-substituted or unsubstituted heteroalkyl (e.g., 2 to 8 membered heteroalkyl, 2 to 6 membered heteroalkyl, or 2 to 4 membered heteroalkyl), $R^{50A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{50A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50A}$-substituted or unsubstituted aryl (e.g., C$_6$-C$_{10}$ aryl, C$_{10}$ aryl, or phenyl), or $R^{50A}$-substituted or unsubstituted heteroaryl (e.g., 5 to 10 membered heteroaryl, 5 to 9 membered heteroaryl, or 5 to 6 membered heteroaryl).

In embodiments, $R^{20A}$ is hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{50A}$-substituted or unsubstituted alkyl (e.g., C$_1$-C$_8$ alkyl, C$_1$-C$_6$ alkyl, or C$_1$-C$_4$ alkyl), $R^{50A}$-substituted or unsubstituted heteroalkyl (e.g., 2 to 8 membered heteroalkyl, 2 to 6 membered heteroalkyl, or 2 to 4 membered heteroalkyl), $R^{50A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{50A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50A}$-substituted or unsubstituted aryl (e.g., C$_6$-C$_{10}$ aryl, C$_{10}$ aryl, or phenyl), or $R^{50A}$-substituted or unsubstituted heteroaryl (e.g., 5 to 10 membered heteroaryl, 5 to 9 membered heteroaryl, or 5 to 6 membered heteroaryl).

$R^{21}$ is hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{21}$ is hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH—OCCl$_3$, —OCF$_3$, —OCBr$_3$, —OCI$_3$, —OCHCl$_2$, —OCHBr$_2$, —OCHI$_2$, —OCHF$_2$, $R^{51}$-substituted or unsubstituted alkyl (e.g., C$_1$-C$_8$ alkyl, C$_1$-C$_6$ alkyl, or C$_1$-C$_4$ alkyl), $R^{51}$-substituted or unsubstituted heteroalkyl (e.g., 2 to 8 membered heteroalkyl, 2 to 6 membered heteroalkyl, or 2 to 4 membered heteroalkyl), $R^{51}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{51}$-substituted or unsubstituted heterocycloalkyl (e.g., 3 to 8 membered heterocycloalkyl, 3 to 6 membered heterocycloalkyl, or 5 to 6 membered heterocycloalkyl), $R^{51}$-substituted or unsubstituted aryl (e.g., C$_6$-C$_{10}$ aryl, C$_{10}$ aryl, or phenyl), or $R^{51}$-substituted or unsubstituted heteroaryl (e.g., 5 to 10 membered heteroaryl, 5 to 9 membered heteroaryl, or 5 to 6 membered heteroaryl). In embodiments, $R^{21}$ is hydrogen or halogen. In embodiments, $R^{21}$ is F. In embodiments, $R^{21}$ is Cl.

$R^{22}$ is hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{22}$ is hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{52}$-substituted or unsubstituted alkyl (e.g., C$_1$-C$_6$ alkyl, or C$_1$-C$_4$ alkyl), $R^{52}$-substituted or unsubstituted heteroalkyl (e.g., 2 to 8 membered heteroalkyl, 2 to 6 membered heteroalkyl, or 2 to 4 membered heteroalkyl), $R^{52}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{52}$- substituted or unsubstituted heterocycloalkyl (e.g., 3 to 8 membered heterocycloalkyl, 3 to 6 membered heterocycloalkyl, or 5 to 6 membered heterocycloalkyl), $R^{52}$-substituted or unsubstituted aryl (e.g., $C_6$-$C_{10}$ aryl, $C_{10}$ aryl, or phenyl), or $R^{52}$-substituted or unsubstituted heteroaryl (e.g., 5 to 10 membered heteroaryl, 5 to 9 membered heteroaryl, or 5 to 6 membered heteroaryl).

$R^{23A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{23A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{53A}$-substituted or unsubstituted alkyl (e.g., $C_1$-$C_8$ alkyl, $C_1$-$C_6$ alkyl, or $C_1$-$C_4$ alkyl), $R^{53A}$-substituted or unsubstituted heteroalkyl (e.g., 2 to 8 membered heteroalkyl, 2 to 6 membered heteroalkyl, or 2 to 4 membered heteroalkyl), $R^{53A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53A}$-substituted or unsubstituted aryl (e.g., $C_6$-$C_{10}$ aryl, $C_{10}$ aryl, or phenyl), or $R^{53A}$-substituted or unsubstituted heteroaryl (e.g., 5 to 10 membered heteroaryl, 5 to 9 membered heteroaryl, or 5 to 6 membered heteroaryl).

$R^{24A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{24A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{54A}$-substituted or unsubstituted alkyl (e.g., $C_1$-$C_8$ alkyl, $C_1$-$C_6$ alkyl, or $C_1$-$C_4$ alkyl), $R^{54A}$-substituted or unsubstituted heteroalkyl (e.g., 2 to 8 membered heteroalkyl, 2 to 6 membered heteroalkyl, or 2 to 4 membered heteroalkyl), $R^{54A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{54A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{54A}$-substituted or unsubstituted aryl (e.g., $C_6$-$C_{10}$ aryl, $C_{10}$ aryl, or phenyl), or $R^{54A}$-substituted or unsubstituted heteroaryl (e.g., 5 to 10 membered heteroaryl, 5 to 9 membered heteroaryl, or 5 to 6 membered heteroaryl).

$R^{30}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{31}$-substituted or unsubstituted alkyl (e.g., $C_1$-$C_8$ alkyl, $C_1$-$C_6$ alkyl, or $C_1$-$C_4$ alkyl), $R^{31}$-substituted or unsubstituted heteroalkyl (e.g., 2 to 8 membered heteroalkyl, 2 to 6 membered heteroalkyl, or 2 to 4 membered heteroalkyl), $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31}$-substituted or unsubstituted aryl (e.g., $C_6$-$C_{10}$ aryl, $C_{10}$ aryl, or phenyl), or $R^{31}$-substituted or unsubstituted heteroaryl (e.g., 5 to 10 membered heteroaryl, 5 to 9 membered heteroaryl, or 5 to 6 membered heteroaryl).

$R^{33}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

$R^{39}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40}$-substituted or unsubstituted alkyl (e.g., $C_1$-$C_8$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

$R^{39A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40A}$-substituted or unsubstituted alkyl (e.g., $C_1$-$C_8$ alkyl, $C_1$-$C_6$ alkyl, or $C_1$-$C_4$ alkyl), $R^{40A}$-substituted or unsubstituted heteroalkyl (e.g., 2 to 8 membered heteroalkyl, 2 to 6 membered heteroalkyl, or 2 to 4 membered heteroalkyl), $R^{40A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40A}$-substituted or unsubstituted aryl (e.g., $C_6$-$C_{10}$ aryl, $C_{10}$ aryl, or phenyl), or $R^{40A}$-substituted or unsubstituted heteroaryl (e.g., 5 to 10 membered heteroaryl, 5 to 9 membered heteroaryl, or 5 to 6 membered heteroaryl).

$R^{39B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40B}$-substituted or unsubstituted alkyl (e.g., $C_1$-$C_8$ alkyl, $C_1$-$C_6$ alkyl, or $C_1$-$C_4$ alkyl), $R^{40B}$-substituted or unsubstituted heteroalkyl (e.g., 2 to 8 membered heteroalkyl, 2 to 6 membered heteroalkyl, or 2 to 4 membered heteroalkyl), $R^{40B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40B}$-substituted or unsubstituted aryl (e.g., $C_6$-$C_{10}$ aryl, $C_{10}$ aryl, or phenyl), or $R^{40B}$-substituted or unsubstituted heteroaryl (e.g., 5 to 10 membered heteroaryl, 5 to 9 membered heteroaryl, or 5 to 6 membered heteroaryl).

$R^{39C}$ is independently oxo, halogen, —$CCl_3$, —$CBr_3$, —$CF_3$, —$CI_3$, —N, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40C}$-substituted or unsubstituted alkyl (e.g., $C_1$-$C_8$ alkyl, $C_1$-$C_6$ alkyl, or $C_1$-$C_4$ alkyl), $R^{40C}$-substituted or unsubstituted heteroalkyl (e.g., 2 to 8 membered heteroalkyl, 2 to 6 membered heteroalkyl, or 2 to 4 membered heteroalkyl), $R^{40C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40C}$-substituted or unsubstituted aryl (e.g., $C_6$-$C_{10}$ aryl, $C_{10}$ aryl, or phenyl), or $R^{40C}$-substituted or unsubstituted heteroaryl (e.g., 5 to 10 membered heteroaryl, 5 to 9 membered heteroaryl, or 5 to 6 membered heteroaryl).

$R^{39D}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{40D}$-substituted or unsubstituted alkyl (e.g., $C_1$-$C_8$ alkyl, $C_1$-$C_6$ alkyl, or $C_1$-$C_4$ alkyl), $R^{40D}$-substituted or unsubstituted heteroalkyl (e.g., 2 to 8 membered heteroalkyl, 2 to 6 membered heteroalkyl, or 2 to 4 membered heteroalkyl), $R^{40D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40D}$-substituted or unsubstituted aryl (e.g., $C_6$-$C_{10}$ aryl, $C_{10}$ aryl, or phenyl), or $R^{40D}$-substituted or unsubstituted heteroaryl (e.g., 5 to 10 membered heteroaryl, 5 to 9 membered heteroaryl, or 5 to 6 membered heteroaryl).

$R^{41}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl).

$R^{41A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{42A}$-substituted or unsubstituted alkyl (e.g., $C_1$-$C_8$ alkyl, $C_1$-$C_6$ alkyl, or $C_1$-$C_4$ alkyl), $R^{42A}$-substituted or unsubstituted heteroalkyl (e.g., 2 to 8 membered heteroalkyl, 2 to 6 membered heteroalkyl, or 2 to 4 membered heteroalkyl), $R^{42A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42A}$-substituted or unsubstituted aryl (e.g., $C_6$-$C_{10}$ aryl, $C_{10}$ aryl, or phenyl), or $R^{42A}$-substituted or unsubstituted heteroaryl (e.g., 5 to 10 membered heteroaryl, 5 to 9 membered heteroaryl, or 5 to 6 membered heteroaryl).

$R^{41B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{42B}$-substituted or unsubstituted alkyl (e.g., $C_1$-$C_8$ alkyl, $C_1$-$C_6$ alkyl, or $C_1$-$C_4$ alkyl), $R^{42B}$-substituted or unsubstituted heteroalkyl (e.g., 2 to 8 membered heteroalkyl, 2 to 6 membered heteroalkyl, or 2 to 4 membered heteroalkyl), $R^{42B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42B}$-substituted or unsubstituted aryl (e.g., $C_6$-$C_{10}$ aryl, $C_{10}$ aryl, or phenyl), or $R^{42B}$-substituted or unsubstituted heteroaryl (e.g., 5 to 10 membered heteroaryl, 5 to 9 membered heteroaryl, or 5 to 6 membered heteroaryl).

$R^{1C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{42C}$-substituted or unsubstituted alkyl (e.g., $C_1$-$C_8$ alkyl, $C_1$-$C_6$ alkyl, or $C_1$-$C_4$ alkyl), $R^{42C}$-substituted or unsubstituted heteroalkyl (e.g., 2 to 8 membered heteroalkyl, 2 to 6 membered heteroalkyl, or 2 to 4 membered heteroalkyl), $R^{42C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42C}$-substituted or unsubstituted aryl (e.g., $C_6$-$C_{10}$ aryl, $C_{10}$ aryl, or phenyl), or $R^{42C}$-substituted or unsubstituted heteroaryl (e.g., 5 to 10 membered heteroaryl, 5 to 9 membered heteroaryl, or 5 to 6 membered heteroaryl).

$R^{41D}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{42D}$-substituted or unsubstituted alkyl (e.g., $C_1$-$C_8$ alkyl, $C_1$-$C_6$ alkyl, or $C_1$-$C_4$ alkyl), $R^{42D}$-substituted or unsubstituted heteroalkyl (e.g., 2 to 8 membered heteroalkyl, 2 to 6 membered heteroalkyl, or 2 to 4 membered heteroalkyl), $R^{42D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42D}$-substituted or unsubstituted aryl (e.g., $C_6$-$C_{10}$ aryl, $C_{10}$ aryl, or phenyl), or $R^{42D}$-substituted or unsubstituted heteroaryl (e.g., 5 to 10 membered heteroaryl, 5 to 9 membered heteroaryl, or 5 to 6 membered heteroaryl).

$R^{43}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44}$-substituted or unsubstituted alkyl (e.g., $C_1$-$C_8$ alkyl, $C_1$-$C_6$ alkyl, or $C_1$-$C_4$ alkyl), $R^{44}$-substituted or unsubstituted heteroalkyl (e.g., 2 to 8 membered heteroalkyl, 2 to 6 membered heteroalkyl, or 2 to 4 membered heteroalkyl), $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44}$-substituted or unsubstituted aryl (e.g., $C_6$-$C_{10}$ aryl, $C_{10}$ aryl, or phenyl), or $R^{44}$-substituted or unsubstituted heteroaryl (e.g., 5 to 10 membered heteroaryl, 5 to 9 membered heteroaryl, or 5 to 6 membered heteroaryl).

$R^{43A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44A}$-substituted or unsubstituted alkyl (e.g., $C_1$-$C_8$ alkyl, $C_1$-$C_6$ alkyl, or $C_1$-$C_4$ alkyl), $R^{44A}$-substituted or unsubstituted heteroalkyl (e.g., 2 to 8 membered heteroalkyl, 2 to 6 membered heteroalkyl, or 2 to 4 membered heteroalkyl), $R^{44A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44A}$-substituted or unsubstituted aryl (e.g., $C_6$-$C_{10}$ aryl, $C_{10}$ aryl, or phenyl), or $R^{44A}$-substituted or unsubstituted heteroaryl (e.g., 5 to 10 membered heteroaryl, 5 to 9 membered heteroaryl, or 5 to 6 membered heteroaryl).

$R^{43B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44B}$-substituted or unsubstituted alkyl (e.g., $C_1$-$C_8$ alkyl, $C_1$-$C_6$ alkyl, or $C_1$-$C_4$ alkyl), $R^{44B}$-substituted or unsubstituted heteroalkyl (e.g., 2 to 8 membered heteroalkyl, 2 to 6 membered heteroalkyl, or 2 to 4 membered heteroalkyl), $R^{44B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44B}$-substituted or unsubstituted aryl (e.g., $C_6$-$C_{10}$ aryl, $C_{10}$ aryl, or phenyl), or $R^{44B}$-substituted or unsubstituted heteroaryl (e.g., 5 to 10 membered heteroaryl, 5 to 9 membered heteroaryl, or 5 to 6 membered heteroaryl).

$R^{43C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44C}$-substituted or unsubstituted alkyl (e.g., $C_1$-$C_8$ alkyl, $C_1$-$C_6$ alkyl, or $C_1$-$C_4$ alkyl), $R^{44C}$-substituted or unsubstituted heteroalkyl (e.g., 2 to 8 membered heteroalkyl, 2 to 6 membered heteroalkyl, or 2 to 4 membered heteroalkyl), $R^{44C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44C}$-substituted or unsubstituted aryl (e.g., $C_6$-$C_{10}$ aryl, $C_{10}$ aryl, or phenyl), or $R^{44C}$-substituted or unsubstituted heteroaryl (e.g., 5 to 10 membered heteroaryl, 5 to 9 membered heteroaryl, or 5 to 6 membered heteroaryl).

$R^{43D}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{44D}$-substituted or unsubstituted alkyl (e.g., $C_1$-$C_8$ alkyl, $C_1$-$C_6$ alkyl, or $C_1$-$C_4$ alkyl), $R^{44D}$-substituted or unsubstituted heteroalkyl (e.g., 2 to 8 membered heteroalkyl, 2 to 6 membered heteroalkyl, or 2 to 4 membered heteroalkyl), $R^{44D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44D}$-substituted or unsubstituted aryl (e.g., $C_6$-$C_{10}$ aryl, $C_{10}$ aryl, or phenyl), or $R^{44D}$-substituted or unsubstituted heteroaryl (e.g., 5 to 10 membered heteroaryl, 5 to 9 membered heteroaryl, or 5 to 6 membered heteroaryl).

$R^{55}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{56}$-substituted or unsubstituted alkyl (e.g., $C_1$-$C_8$ alkyl, $C_1$-$C_6$ alkyl, or $C_1$-$C_4$ alkyl), $R^{56}$-substituted or unsubstituted heteroalkyl (e.g., 2 to 8 membered heteroalkyl, 2 to 6 membered heteroalkyl, or 2 to 4 membered heteroalkyl), $R^{56}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56}$-substituted or unsubstituted aryl (e.g., $C_6$-$C_{10}$ aryl, $C_{10}$ aryl, or phenyl), or $R^{56}$-substituted or unsubstituted heteroaryl (e.g., 5 to 10 membered heteroaryl, 5 to 9 membered heteroaryl, or 5 to 6 membered heteroaryl).

$R^{55A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{56A}$-substituted or unsubstituted alkyl (e.g., $C_1$-$C_8$ alkyl, $C_1$-$C_6$ alkyl, or $C_1$-$C_4$ alkyl), $R^{56A}$-substituted or unsubstituted heteroalkyl (e.g., 2 to 8 membered heteroalkyl, 2 to 6 membered heteroalkyl, or 2 to 4 membered heteroalkyl), $R^{56A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56A}$-substituted or unsubstituted aryl (e.g., $C_6$-$C_{10}$ aryl, $C_{10}$ aryl, or phenyl), or $R^{56A}$-substituted or unsubstituted heteroaryl (e.g., 5 to 10 membered heteroaryl, 5 to 9 membered heteroaryl, or 5 to 6 membered heteroaryl).

$R^{55B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{56B}$-substituted or unsubstituted alkyl (e.g., $C_1$-$C_8$ alkyl, $C_1$-$C_6$ alkyl, or $C_1$-$C_4$ alkyl), $R^{56B}$-substituted or unsubstituted heteroalkyl (e.g., 2 to 8 membered heteroalkyl, 2 to 6 membered heteroalkyl, or 2 to 4 membered heteroalkyl), $R^{56B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56B}$-substituted or unsubstituted aryl (e.g., $C_6$-$C_{10}$ aryl, $C_{10}$ aryl, or phenyl), or $R^{56B}$-substituted or unsubstituted heteroaryl (e.g., 5 to 10 membered heteroaryl, 5 to 9 membered heteroaryl, or 5 to 6 membered heteroaryl).

$R^{55C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{56C}$-substituted or unsubstituted alkyl (e.g., $C_1$-$C_8$ alkyl, $C_1$-$C_6$ alkyl, or $C_1$-$C_4$ alkyl), $R^{56C}$-substituted or unsubstituted heteroalkyl (e.g., 2 to 8 membered heteroalkyl, 2 to 6 membered heteroalkyl, or 2 to 4 membered heteroalkyl), $R^{56C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56C}$-substituted or unsubstituted aryl (e.g., $C_6$-$C_{10}$ aryl, $C_{10}$ aryl, or phenyl), or $R^{56C}$-substituted or unsubstituted heteroaryl (e.g., 5 to 10 membered heteroaryl, 5 to 9 membered heteroaryl, or 5 to 6 membered heteroaryl).

$R^{55D}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{56D}$-substituted or unsubstituted alkyl (e.g., $C_1$-$C_8$ alkyl, $C_1$-$C_6$ alkyl, or $C_1$-$C_4$ alkyl), $R^{56D}$-substituted or unsubstituted heteroalkyl (e.g., 2 to 8 membered heteroalkyl, 2 to 6 membered heteroalkyl, or 2 to 4 membered heteroalkyl), $R^{56D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56D}$-substituted or unsubstituted aryl (e.g., $C_6$-$C_{10}$ aryl, $C_{10}$ aryl, or phenyl), or $R^{56D}$-substituted or unsubstituted heteroaryl (e.g., 5 to 10 membered heteroaryl, 5 to 9 membered heteroaryl, or 5 to 6 membered heteroaryl).

$R^{56}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{57}$-substituted or unsubstituted alkyl (e.g., $C_1$-$C_8$ alkyl, $C_1$-$C_6$ alkyl, or $C_1$-$C_4$ alkyl), $R^{57}$-substituted or unsubstituted heteroalkyl (e.g., 2 to 8 membered heteroalkyl, 2 to 6 membered heteroalkyl, or 2 to 4 membered heteroalkyl), $R^{57}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57}$-substituted or unsubstituted aryl (e.g., $C_6$-$C_{10}$ aryl, $C_{10}$ aryl, or phenyl), or $R^{57}$-substituted or unsubstituted heteroaryl (e.g., 5 to 10 membered heteroaryl, 5 to 9 membered heteroaryl, or 5 to 6 membered heteroaryl).

$R^{56A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{57A}$-substituted or unsubstituted alkyl (e.g., $C_1$-$C_8$ alkyl, $C_1$-$C_6$ alkyl, or $C_1$-$C_4$ alkyl), $R^{57A}$-substituted or unsubstituted heteroalkyl (e.g., 2 to 8 membered heteroalkyl, 2 to 6 membered heteroalkyl, or 2 to 4 membered heteroalkyl), $R^{57A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57A}$-substituted or unsubstituted aryl (e.g., $C_6$-$C_{10}$ aryl, $C_{10}$ aryl, or phenyl), or $R^{57A}$-substituted or unsubstituted heteroaryl (e.g., 5 to 10 membered heteroaryl, 5 to 9 membered heteroaryl, or 5 to 6 membered heteroaryl).

$R^{56B}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{57B}$-substituted or unsubstituted alkyl (e.g., $C_1$-$C_8$ alkyl, $C_1$-$C_6$ alkyl, or $C_1$-$C_4$ alkyl), $R^{57B}$-substituted or unsubstituted heteroalkyl (e.g., 2 to 8 membered heteroalkyl, 2 to 6 membered heteroalkyl, or 2 to 4 membered heteroalkyl), $R^{57B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57B}$-substituted or unsubstituted aryl (e.g., $C_6$-$C_{10}$ aryl, $C_{10}$ aryl, or phenyl), or $R^{57B}$-substituted or unsubstituted heteroaryl (e.g., 5 to 10 membered heteroaryl, 5 to 9 membered heteroaryl, or 5 to 6 membered heteroaryl).

$R^{56C}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHF_2$, $R^{57C}$-substituted or unsubstituted alkyl (e.g., $C_1$-$C_8$ alkyl, $C_1$-$C_6$ alkyl, or $C_1$-$C_4$ alkyl), $R^{57C}$-substituted or unsubstituted heteroalkyl (e.g., 2 to 8 membered heteroalkyl, 2 to 6 membered heteroalkyl, or 2 to 4 membered heteroalkyl), $R^{57C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57C}$-substituted or unsubstituted aryl (e.g., $C_6$-$C_{10}$ aryl, $C_{10}$ aryl, or phenyl), or $R^{57C}$-substituted or unsubstituted heteroaryl (e.g., 5 to 10 membered heteroaryl, 5 to 9 membered heteroaryl, or 5 to 6 membered heteroaryl).

$R^{56D}$ is independently oxo, halogen, $-CCl_3$, $-CF_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHF_2$, $R^{57D}$-substituted or unsubstituted alkyl (e.g., $C_1$-$C_8$ alkyl, $C_1$-$C_6$ alkyl, or $C_1$-$C_4$ alkyl), $R^{57D}$-substituted or unsubstituted heteroalkyl (e.g., 2 to 8 membered heteroalkyl, 2 to 6 membered heteroalkyl, or 2 to 4 membered heteroalkyl), $R^{57D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57D}$-substituted or unsubstituted aryl (e.g., $C_6$-$C_{10}$ aryl, $C_{10}$ aryl, or phenyl), or $R^{57D}$-substituted or unsubstituted heteroaryl (e.g., 5 to 10 membered heteroaryl, 5 to 9 membered heteroaryl, or 5 to 6 membered heteroaryl).

In embodiments, $R^{1.1}$ is hydrogen, halogen, $-CF_3$, $-CCl_3$, $-CI_3$, $-CN$, $-CHO$, $-COOR^{1.1A}$, $-CONR^{1.1B}R^{1.1C}$, substituted or unsubstituted alkyl (e.g., $C_1$-$C_8$ alkyl, $C_1$-$C_6$ alkyl, or $C_1$-$C_4$ alkyl) substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{1.1}$ is $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{1.1}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{1.1}$ is $R^{26}$-substituted alkyl (e.g., $C_1$-$C_8$ alkyl, $C_1$-$C_6$ alkyl, or $C_1$-$C_4$ alkyl). In embodiments, $R^{18}$ is an unsubstituted alkyl (e.g., $C_1$-$C_8$ alkyl, $C_1$-$C_6$ alkyl, or $C_1$-$C_4$ alkyl).

In embodiments, $R^{1.1}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{1.1}$ is $R^{26}$-substituted heteroalkyl (e.g., 2 to 8 membered heteroalkyl, 2 to 6 membered heteroalkyl, or 2 to 4 membered heteroalkyl). In embodiments, $R^{1.1}$ is an unsubstituted heteroalkyl (e.g., 2 to 8 membered heteroalkyl, 2 to 6 membered heteroalkyl, or 2 to 4 membered heteroalkyl).

In embodiments, $R^{1.1}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1.1}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1.1}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1.1}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1.1}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{1.1}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1.1}$ is $R^{26}$-substituted or unsubstituted aryl (e.g., $C_6$-$C_{10}$ aryl, $C_{10}$ aryl, or phenyl). In embodiments, $R^{1.1}$ is $R^{26}$-substituted aryl (e.g., $C_6$-$C_{10}$ aryl, $C_{10}$ aryl, or phenyl). In embodiments, $R^{1.1}$ is an unsubstituted aryl (e.g., $C_6$-$C_{10}$ aryl, $C_{10}$ aryl, or phenyl).

In embodiments, $R^{1.1}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{1.1}$ is $R^{26}$-substituted heteroaryl (e.g., 5 to 10 membered heteroaryl, 5 to 9 membered heteroaryl, or 5 to 6 membered heteroaryl). In embodiments, $R^{1.1}$ is an unsubstituted heteroaryl (e.g., 5 to 10 membered heteroaryl, 5 to 9 membered heteroaryl, or 5 to 6 membered heteroaryl).

In embodiments, $R^{1.1A}$ is $R^{26A}$-substituted or unsubstituted alkyl (e.g., $C_1$-$C_8$ alkyl, $C_1$-$C_6$ alkyl, or $C_1$-$C_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1.1B}$ is $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1.1C}$ is $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1.1D}$ is $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^{1.2}$ is hydrogen, halogen, —$N_3$, —$CF_3$, —$CCl_3$, —$CBr_3$, —$CI_3$, —CN, —CHO, —$OR^{1.2A}$, —$NR^{1.2B}R^{1.2C}$, —$COOR^{1.2A}$, —$CONR^{1.2B}R^{1.2C}$, —$NO_2$, —$SR^{1.2D}$, —$SO_{n1.2}R^{1.2B}$, —$SO_{v1.2}NR^{1.2B}R^{1.2C}$, —$NHNR^{1.2B}R^{1.2C}$, —$ONR^{1.2B}R^{1.2C}$, —NHC(O)NHNR$^{1.2B}R^{1.2C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{1.2}$ is —CN. In embodiments, $R^{1.2}$ is an unsubstituted $C_1$-$C_3$ alkyl. In embodiments, $R^{1.2}$ is hydrogen, —CN, —CHO, —$OR^{1.2A}$, —$NR^{1.2B}R^{1.2C}$, —$C(O)OR^{1.2A}$, —$C(O)NR^{1.2B}R^{1.2C}$, —$NO_2$, —$SR^{1.2D}$, —$S(O)_{n1}R^{1.2B}$, —$SO_{v1}NR^{1.2B}R^{1.2C}$, —$NHNR^{1.2B}R^{1.2C}$, $ONR^{1.2B}R^{1.2C}$, —NHC(O)NHNR$^{1.2B}R^{1.2C}$, or substituted or unsubstituted alkyl. In embodiments, $R^{1.2}$ is hydrogen, —CN, —CHO, —$OCH_3$, —$N(CH_3)_2$, —$NH_2$, —$C(O)OCH_3$, —$S(O)_2R^{1.2B}$, or substituted or unsubstituted alkyl. In embodiments, $R^{1.2}$ is —$C(O)OR^{1.2A}$ wherein $R^{1.2A}$ is substituted or unsubstituted alkyl (e.g., $C_1$-$C_8$ alkyl, $C_1$-$C_6$ alkyl, or $C_1$-$C_4$ alkyl). In embodiments, $R^{1.2}$ is hydrogen, —$CH_3$, —$N(CH_3)_2$, —CN, —$CH_2OCH_3$, —$C(O)OCH_3$, —$C(O)OCH_2CH_2CH_3$, —$C(O)OC(CH_3)_4$, or

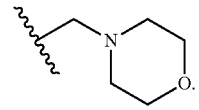

In embodiments, $R^{1.2}$ is hydrogen. In embodiments, $R^{1.2}$ is —$CH_3$. In embodiments, $R^{1.2}$ is —$N(CH_3)_2$. In embodiments, $R^{1.2}$ is —CN. In embodiments, $R^{1.2}$ is —$CH_2OCH_3$. In embodiments, $R^{1.2}$ is —$C(O)OCH_3$. In embodiments, $R^{1.2}$ is —$C(O)OCH_2CH_2CH_3$. In embodiments, $R^{1.2}$ is —$C(O)OC(CH_3)_4$. In embodiments, $R^{1.2}$ is

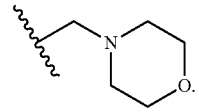

In embodiments, $R^{1.2}$ is $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{1.2}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{1.2}$ is $R^{26}$-substituted alkyl (e.g., $C_1$-$C_8$ alkyl, $C_1$-$C_6$ alkyl, or $C_1$-$C_4$ alkyl). In embodiments, $R^{1.2}$ is an unsubstituted alkyl (e.g., $C_1$-$C_8$ alkyl, $C_1$-$C_6$ alkyl, or $C_1$-$C_4$ alkyl).

In embodiments, $R^{1.2}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{1.2}$ is $R^{26}$-substituted heteroalkyl (e.g., 2 to 8 membered heteroalkyl, 2 to 6 membered heteroalkyl, or 2 to 4 membered heteroalkyl). In embodiments, $R^{1.2}$ is an unsubstituted heteroalkyl (e.g., 2 to 8 membered heteroalkyl, 2 to 6 membered heteroalkyl, or 2 to 4 membered heteroalkyl).

In embodiments, $R^{1.2}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1.2}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, R"2 is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1.2}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1.2}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{1.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1.2}$ is $R^{26}$-substituted or unsubstituted aryl (e.g., $C_6$-$C_{10}$ aryl, $C_{10}$ aryl, or phenyl). In embodiments, $R^{1.2}$ is $R^{26}$-substituted aryl (e.g., $C_6$-$C_{10}$ aryl, $C_{10}$ aryl, or phenyl). In embodiments, $R^{1.2}$ is an unsubstituted aryl (e.g., $C_6$-$C_{10}$ aryl, $C_{10}$ aryl, or phenyl).

In embodiments, $R^{1.2}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{1.2}$ is $R^{26}$-substituted heteroaryl (e.g., 5 to 10 membered heteroaryl, 5 to 9 membered heteroaryl, or 5 to 6 membered heteroaryl). In embodiments, $R^{1.2}$ is an unsubstituted heteroaryl (e.g., 5 to 10 membered heteroaryl, 5 to 9 membered heteroaryl, or 5 to 6 membered heteroaryl).

In embodiments, $R^{1.2}$ is methyl substituted with substituted or unsubstituted cycloalkyl, substituted or unsubstituted heterocycloalkyl, substituted or unsubstituted aryl, or substituted or unsubstituted heteroaryl, and $R^{1.3}$ is CN.

In embodiments, $R^{1.2A}$ is $R^{26A}$ substituted or unsubstituted alkyl (e.g., $C_1$-$C_8$ alkyl, $C_1$-$C_6$ alkyl, or $C_1$-$C_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1.2B}$ is $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1.2C}$ is $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1.2D}$ is $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^{1.3}$ is hydrogen, halogen, $-N_3$, $-CF_3$, $-CCl_3$, $-CBr_3$, $-CI_3$, $-CN$, $-CHO$, $-OR^{1.3A}$, $-NR^{1.3B}R^{1.3C}$, $-COOR^{1.3A}$, $-CONR^{1.3B}R^{1.3C}$, $-NO_2$, $-SR^{13D}$, $-SO_{n1.3}R^{1.3B}$, $-SO_{v1.3}NR^{1.3B}R^{1.3C}$, $-NHNR^{1.3B}R^{1.3C}$, $-ONR^{1.3B}R^{1.3C}$, $-NHC(O)NHNR^{1.3B}R^{1.3C}$ substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{1.3}$ is $-CN$. In embodiments, $R^{1.3}$ is $-CN$ and $R^{1.2}$ is an unsubstituted $C_1$-$C_3$ alkyl. In embodiments, $R^{1.3}$ is $-CN$ and $R^{1.2}$ is methyl. In embodiments, $R^{1.3}$ is hydrogen, $-CN$, $-CHO$, $-OR^{1.3A}$, $-NR^{1.3B}R^{1.3C}$, $-C(O)OR^{1.3A}$, $-C(O)NR^{1.3B}R^{1.3C}$, $-NO_2$, $-SR^{1.3D}$, $-S(O)_{n1}R^{1.3B}$, $-SO_{v1}NR^{1.3B}R^{1.3C}$, $-NHNR^{1.3B}R^{1.3C}$ $ONR^{1.3B}R^{1.3C}$, $-NHC(O)NHNR^{1.3B}R^{1.3C}$, or substituted or unsubstituted alkyl. In embodiments, $R^{1.3}$ is hydrogen, $-CN$, $-CHO$, $-OCH_3$, $-N(CH_3)_2$, $-NH_2$, $-C(O)OCH_3$, $-S(O)_2R^{1.3B}$, or substituted or unsubstituted alkyl. In embodiments, $R^{1.3}$ is $-C(O)OR^{13A}$ wherein $R^{13A}$ is substituted or unsubstituted alkyl (e.g., $C_1$-$C_8$ alkyl, $C_1$-$C_6$ alkyl, or $C_1$-$C_4$ alkyl). In embodiments, $R^{1.3}$ is hydrogen, $-CH_3$, $-N(CH_3)_2$, $-CN$, $-CH_2OCH_3$, $-C(O)OCH_3$, $-C(O)OCH_2CH_2CH_3$, $-C(O)OC(CH_3)_4$, or

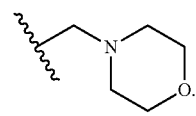

In embodiments, $R^{1.3}$ is hydrogen. In embodiments, $R^{1.3}$ is $-CH_3$. In embodiments, $R^{1.3}$ is $-N(CH_3)_2$. In embodiments, $R^{1.3}$ is $-CN$. In embodiments, $R^{1.3}$ is $-CH_2OCH_3$. In embodiments, $R^{1.3}$ is $-C(O)OCH_3$. In embodiments, $R^{1.3}$ is —C(O)OCH$_2$CH$_2$CH$_3$. In embodiments, $R^{1.3}$ is —C(O)OC(CH$_3$)$_4$. In embodiments, $R^{1.3}$ is

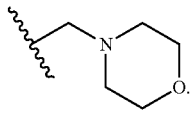

In embodiments, $R^{1.3}$ is $R^{26}$-substituted or unsubstituted alkyl (e.g., C$_1$-C$_8$ alkyl, C$_1$-C$_6$ alkyl, or C$_1$-C$_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., C$_6$-C$_{10}$ aryl, C$_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{1.3}$ is $R^{26}$-substituted or unsubstituted alkyl (e.g., C$_1$-C$_8$ alkyl, C$_1$-C$_6$ alkyl, or C$_1$-C$_4$ alkyl). In embodiments, $R^{1.3}$ is $R^{26}$-substituted alkyl (e.g., C$_1$-C$_8$ alkyl, C$_1$-C$_6$ alkyl, or C$_1$-C$_4$ alkyl). In embodiments, $R^{1.3}$ is an unsubstituted alkyl (e.g., C$_1$-C$_8$ alkyl, C$_1$-C$_6$ alkyl, or C$_1$-C$_4$ alkyl).

In embodiments, $R^{1.3}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{1.3}$ is $R^{26}$-substituted heteroalkyl (e.g., 2 to 8 membered heteroalkyl, 2 to 6 membered heteroalkyl, or 2 to 4 membered heteroalkyl). In embodiments, $R^{1.3}$ is an unsubstituted heteroalkyl (e.g., 2 to 8 membered heteroalkyl, 2 to 6 membered heteroalkyl, or 2 to 4 membered heteroalkyl).

In embodiments, $R^{1.3}$ is $R^{26}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{1.3}$ is $R^{26}$-substituted cycloalkyl (e.g., C$_3$-C$_8$ cycloalkyl, C$_3$-C$_6$ cycloalkyl, or C$_5$-C$_6$ cycloalkyl). In embodiments, $R^{1.3}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{1.3}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1.3}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{1.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1.3}$ is $R^{26}$-substituted or unsubstituted aryl (e.g., C$_6$-C$_{10}$ aryl, C$_{10}$ aryl, or phenyl). In embodiments, $R^{1.3}$ is $R^{26}$-substituted aryl (e.g., C$_6$-C$_{10}$ aryl, C$_{10}$ aryl, or phenyl). In embodiments, $R^{1.3}$ is an unsubstituted aryl (e.g., C$_6$-C$_{10}$ aryl, C$_{10}$ aryl, or phenyl).

In embodiments, $R^{1.3}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{1.3}$ is $R^{26}$-substituted heteroaryl (e.g., 5 to 10 membered heteroaryl, 5 to 9 membered heteroaryl, or 5 to 6 membered heteroaryl). In embodiments, $R^{1.3}$ is an unsubstituted heteroaryl (e.g., 5 to 10 membered heteroaryl, 5 to 9 membered heteroaryl, or 5 to 6 membered heteroaryl).

In embodiments, $R^{1.2}$ is methyl substituted with substituted or unsubstituted cycloalkyl, substituted or unsubstituted heterocycloalkyl, substituted or unsubstituted aryl, or substituted or unsubstituted heteroaryl, and $R^{1.3}$ is CN.

In embodiments, $R^{1.3A}$ is $R^{26A}$-substituted or unsubstituted alkyl (e.g., C$_1$-C$_8$ alkyl, C$_1$-C$_6$ alkyl, or C$_1$-C$_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., C$_6$-C$_{10}$ aryl, C$_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1.3B}$ is $R^{26B}$-substituted or unsubstituted alkyl (e.g., C$_1$-C$_8$ alkyl, C$_1$-C$_6$ alkyl, or C$_1$-C$_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., C$_6$-C$_{10}$ aryl, C$_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1.3C}$ is $R^{26C}$-substituted or unsubstituted alkyl (e.g., C$_1$-C$_8$ alkyl, C$_1$-C$_6$ alkyl, or C$_1$-C$_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., C$_6$-C$_{10}$ aryl, C$_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1.3D}$ is $R^{26D}$-substituted or unsubstituted alkyl (e.g., C$_1$-C$_8$ alkyl, C$_1$-C$_6$ alkyl, or C$_1$-C$_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., C$_6$-C$_{10}$ aryl, C$_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^{1.4}$ is hydrogen, halogen, —N$_3$, —CF$_3$, —CCl$_3$, —CBr$_3$, —CI$_3$, —CN, —CHO, —OR$^{1.4A}$, —NR$^{1.4B}$R$^{1.4C}$, —COOR$^{1.4A}$, —CONR$^{1.4B}$R$^{1.4C}$, —NO$_2$, —SR$^{1.4D}$, —SO$_{n1.4}$R$^{1.4B}$, —SO$_{v1.4}$NR$^{1.4B}$R$^{1.4C}$, —NHNR$^{1.4B}$R$^{1.4C}$, —ONR$^{1.4B}$R$^{1.4C}$, —NHC(O)NHNR$^{1.4B}$R$^{1.4C}$ substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{1.4}$ is $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{1.4}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{1.4}$ is $R^{26}$-substituted alkyl (e.g., $C_1$-$C_8$ alkyl, $C_1$-$C_6$ alkyl, or $C_1$-$C_4$ alkyl). In embodiments, $R^{1.4}$ is an unsubstituted alkyl (e.g., $C_1$-$C_8$ alkyl, $C_1$-$C_6$ alkyl, or $C_1$-$C_4$ alkyl).

In embodiments, $R^{1.4}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{1.4}$ is $R^{26}$-substituted heteroalkyl (e.g., 2 to 8 membered heteroalkyl, 2 to 6 membered heteroalkyl, or 2 to 4 membered heteroalkyl). In embodiments, $R^{1.4}$ is an unsubstituted heteroalkyl (e.g., 2 to 8 membered heteroalkyl, 2 to 6 membered heteroalkyl, or 2 to 4 membered heteroalkyl).

In embodiments, $R^{1.4}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1.4}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1.4}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1.4}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{1.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1.4}$ is $R^{26}$-substituted or unsubstituted aryl (e.g., $C_6$-$C_{10}$ aryl, $C_{10}$ aryl, or phenyl). In embodiments, $R^{1.4}$ is $R^{26}$-substituted aryl (e.g., $C_6$-$C_{10}$ aryl, $C_{10}$ aryl, or phenyl). In embodiments, $R^{1.4}$ is an unsubstituted aryl (e.g., $C_6$-$C_{10}$ aryl, $C_{10}$ aryl, or phenyl).

In embodiments, $R^{1.4}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{1.4}$ is $R^{26}$-substituted heteroaryl (e.g., 5 to 10 membered heteroaryl, 5 to 9 membered heteroaryl, or 5 to 6 membered heteroaryl). In embodiments, $R^{1.4}$ is an unsubstituted heteroaryl (e.g., 5 to 10 membered heteroaryl, 5 to 9 membered heteroaryl, or 5 to 6 membered heteroaryl).

In embodiments, $R^{1.4A}$ is $R^{26A}$-substituted or unsubstituted alkyl (e.g., $C_1$-$C_8$ alkyl, $C_1$-$C_6$ alkyl, or $C_1$-$C_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1.4B}$ is $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1.4C}$ is $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1.4D}$ is $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^{1.5}$ is hydrogen, halogen, $-N_3$, $-CF_3$, $-CCl_3$, $-CBr_3$, $-CI_3$, $-CN$, $-CHO$, $-OR^{1.5A}$, $-NR^{1.5B}R^{1.5C}$, $-COOR^{1.5A}$, $-CONR^{1.5B}R^{1.5C}$, $-NO_2$, $-SR^{1.5D}$, $-SO_{n1.5}R^{1.5B}$, $-SO_{v1.5}NR^{1.5B}R^{1.5C}$, $-NHNR^{1.5B}R^{1.5C}$, $-ONR^{1.5B}R^{1.5C}$, $-NHC(O)NHNR^{1.5B}R^{1.5C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{1.5}$ is $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{1.5}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{1.5}$ is $R^{26}$-substituted alkyl (e.g., $C_1$-$C_8$ alkyl, $C_1$-$C_6$ alkyl, or $C_1$-$C_4$ alkyl). In embodiments, $R^{1.5}$ is an unsubstituted alkyl (e.g., $C_1$-$C_8$ alkyl, $C_1$-$C_6$ alkyl, or $C_1$-$C_4$ alkyl).

In embodiments, $R^{1.5}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{1.5}$ is $R^{26}$-substituted heteroalkyl (e.g., 2 to 8 membered heteroalkyl, 2 to 6 membered heteroalkyl, or 2 to 4 membered heteroalkyl). In embodiments, $R^{1.5}$ is an unsubstituted heteroalkyl (e.g., 2 to 8 membered heteroalkyl, 2 to 6 membered heteroalkyl, or 2 to 4 membered heteroalkyl).

In embodiments, $R^{1.5}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1.5}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1.5}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1.5}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{1.5}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1.5}$ is $R^{26}$-substituted or unsubstituted aryl (e.g., $C_6$-$C_{10}$ aryl, $C_{10}$ aryl, or phenyl). In embodiments, $R^{1.5}$ is $R^{26}$-substituted aryl (e.g., $C_6$-$C_{10}$ aryl, $C_{10}$ aryl, or phenyl). In embodiments, $R^{1.5}$ is an unsubstituted aryl (e.g., $C_6$-$C_{10}$ aryl, $C_{10}$ aryl, or phenyl).

In embodiments, $R^{1.5}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{1.5}$ is $R^{26}$-substituted heteroaryl (e.g., 5 to 10 membered heteroaryl, 5 to 9 membered heteroaryl, or 5 to 6 membered heteroaryl). In embodiments, $R^{1.5}$ is an unsubstituted heteroaryl (e.g., 5 to 10 membered heteroaryl, 5 to 9 membered heteroaryl, or 5 to 6 membered heteroaryl).

In embodiments, $R^{1.5A}$ is $R^{26A}$-substituted or unsubstituted alkyl (e.g., $C_1$-$C_8$ alkyl, $C_1$-$C_6$ alkyl, or $C_1$-$C_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{1.5B}$ is $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{1.5C}$ is $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{1.5}$ D is $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, the compound has the formula:

wherein $R^4$, $R^5$, and $R^{12}$ are as described herein. In embodiments, $R^4$ and $R^5$ are independently —C(O)CH$_3$. In embodiments, $R^4$ and $R^5$ are both —C(O)CH$_3$. In embodiments, $R^{12}$ is —OCH$_3$. In embodiments, $R^4$ and $R^5$ are independently —C(O)CH$_3$, —C(O)OPh, —C(O)CH$_2$OCH$_3$, C(O)NHPh, or —C(S)OPh.

In embodiments, the compound has the formula:

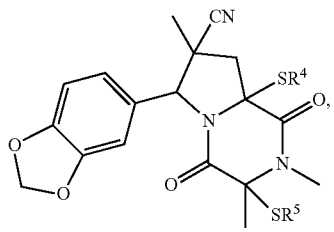

wherein $R^4$ and $R^5$ are as described herein. In embodiments, $R^4$ and $R^5$ are independently —C(O)CH$_3$. In embodiments, $R^4$ and $R^5$ are both —C(O)CH$_3$. In embodiments, $R^{12}$ is —OCH$_3$. In embodiments, $R^4$ and $R^5$ are independently —C(O)CH$_3$, —C(O)OPh, —C(O)CH$_2$OCH$_3$, C(O)NHPh, or —C(S)OPh.

In embodiments, $R^{1A}$, $R^{1.1A}$, $R^{1.1B}$, $R^{1.1C}$, $R^{1.2A}$, $R^{1.2B}$, $R^{1.2C}$, $R^{1.2D}$, $R^{1.3A}$, $R^{1.3B}$, $R^{1.3C}$, $R^{1.3D}$, $R^{1.4A}$, $R^{1.4B}$, $R^{1.4C}$, $R^{1.4D}$, $R^{1.5A}$, $R^{1.5B}$, $R^{1.5C}$, $R^{1.5D}$, $R^{2A}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, and $R^{20A}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl); and $R^{1.1B}$ and $R^{1.1C}$, $R^{1.2B}$ and $R^{1.2C}$, and $R^{1.3B}$ and $R^{1.3C}$ substituents bonded to the same nitrogen atom may independently optionally be joined to form a substituted or unsubstituted cycloalkyl (e.g., C$_3$-C$_8$ cycloalkyl, C$_3$-C$_6$ cycloalkyl, or C$_5$-C$_6$ cycloalkyl) or substituted or unsubstituted heteroaryl (e.g., 5 to 10 membered heteroaryl, 5 to 9 membered heteroaryl, or 5 to 6 membered heteroaryl). In embodiments, $R^{1.1B}$ and $R^{1.1C}$, $R^{1.2B}$ and $R^{1.2C}$, and $R^{1.3B}$ and $R^{1.3C}$, $R^{13B}$ and $R^{13C}$, $R^{14B}$ and $R^{14C}$, and $R^{15B}$ and $R^{15C}$, $R^{6B}$ and $R^{6C}$, $R^{7B}$ and $R^{7C}$, $R^{10B}$ and $R^{10C}$, $R^{11B}$ and $R^{11C}$, and $R^{12B}$ and $R^{12C}$ substituents bonded to the same nitrogen atom may independently optionally be joined to form a substituted or unsubstituted cycloalkyl (e.g., C$_3$-C$_8$ cycloalkyl, C$_3$-C$_6$ cycloalkyl, or C$_5$-C$_6$ cycloalkyl) or substituted or unsubstituted heteroaryl (e.g., 5 to 10 membered heteroaryl, 5 to 9 membered heteroaryl, or 5 to 6 membered heteroaryl). In embodiments, $R^{1A}$, $R^{1.1A}$, $R^{1.1B}$, $R^{1.1C}$, $R^{1.2A}$, $R^{1.2B}$, $R^{1.2C}$, $R^{1.2D}$, $R^{1.3A}$, $R^{1.3B}$, $R^{1.3C}$, $R^{1.3D}$, $R^{1.4A}$, $R^{1.4B}$, $R^{1.4C}$, and $R^{1.4D}$, $R^{1.5A}$, $R^{1.5B}$, $R^{1.5C}$, and $R^{1.5D}$, $R^{2A}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, and $R^{20A}$ are independently hydrogen, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

The symbols z1 and z2 are independently an integer from 1 to 10. In embodiments, the symbols z1 and z2 are independently an integer from 1 to 5. In embodiments, the symbols z1 and z2 are independently an integer from 1 to 3. The symbol z3 is an integer from 0 to 5. The symbols n1.2, n1.3, n1.4, n1.5, n1, n2, n3, n6, n7, n8, n9, n10, n11, n12, n13, n14, n15, and n25 are independently an integer from 0 to 4. The symbols m, v1.2, v1.3, v1.4, v1.5, v1, v2, v3, v6, v7, v8, v9, v10, v11, v12, v13, v14, v15, and v25 are independently 1 or 2. The symbol z4 is an integer from 0 to 2. The symbol z5 is an integer from 0 to 8.

$R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCH$_{12}$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently hydrogen, halogen, —CF$_3$, —CCl$_3$, —CBr$_3$, —CI$_3$, —OH, —COOH, —CONH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). In embodiments $R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently hydrogen, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently halogen, —$CF_3$, —$CCl_3$, —$CBr_3$, —$CI_3$, —OH, —COOH, —$CONH_2$, —$NO_2$, —SH, —$SO_3H$, —$SO_4H$, —$SO_2NH_2$, —$NHNH_2$, —$ONH_2$, -MIC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently halogen, —$CF_3$, —$CCl_3$, —$CBr_3$, —$CI_3$, —OH, —COOH, —$CONH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26A}$, $R^{26B}$, $R^{26C}$, $R^{26D}$, $R^{27A}$, $R^{27B}$, $R^{27C}$, $R^{28A}$, $R^{28B}$, $R^{28C}$, $R^{28D}$, $R^{35A}$, $R^{35B}$, $R^{35C}$, $R^{35D}$, $R^{36A}$, $R^{36B}$, $R^{36C}$, $R^{36D}$, $R^{37A}$, $R^{37B}$, $R^{37C}$, $R^{37D}$, $R^{38A}$, $R^{38B}$, $R^{38C}$, $R^{38D}$, $R^{40A}$, $R^{40B}$, $R^{40C}$, $R^{40D}$, $R^{42A}$, $R^{42B}$, $R^{42C}$, $R^{42D}$, $R^{44A}$, $R^{44B}$, $R^{44C}$, $R^{44D}$, $R^{45A}$, $R^{45B}$, $R^{45C}$, $R^{45D}$, $R^{46A}$, $R^{46B}$, $R^{46C}$, $R^{46D}$, $R^{47A}$, $R^{47B}$, $R^{47C}$, $R^{47D}$, $R^{57A}$, $R^{57B}$, $R^{57C}$, and $R^{57D}$ are independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{26}$, $R^{27}$, $R^{28}$, $R^{35}$, $R^{36}$, $R^{37}$, $R^{38}$, $R^{40}$, $R^{42}$, $R^{44}$, $R^{45}$, $R^{46}$, $R^{47}$, $R^{29}$, $R^{29B}$, $R^{32}$, $R^{32B}$, $R^{48}$, $R^{49}$, $R^{31}$, $R^{34}$, $R^{50A}$, $R^{51}$, $R^{52}$, $R^{53A}$, $R^{54A}$, and $R^{57}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26}$, $R^{27}$, $R^{28}$, $R^{35}$, $R^{36}$, $R^{37}$, $R^{38}$, $R^{40}$, $R^{42}$, $R^{44}$, $R^{45}$, $R^{46}$, $R^{47}$, $R^{29}$, $R^{29B}$, $R^{32}$, $R^{32B}$, $R^{48}$, $R^{49}$, $R^{31}$, $R^{34}$, $R^{50A}$, $R^{51}$, $R^{52}$, $R^{53A}$, $R^{54A}$, and $R^{57}$ are independently, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, z1 is 1. In embodiments, z1 is 2. In embodiments, z1 is 3. In embodiments, z1 is 4. In embodiments, z1 is 5. In embodiments, z1 is 6. In embodiments, z1 is 7. In embodiments, z1 is 8. In embodiments, z1 is 9. In embodiments, z1 is 10.

In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9. In embodiments, z2 is 10. In embodiments, z1 and z2 are independently an integer from 1 to 5. In embodiments, z1 and z2 are independently an integer from 1 to 3.

In embodiments z3 is 0. In embodiments, z3 is 1. In embodiments, z3 is 2. In embodiments, z3 is 3. In embodiments, z3 is 4. In embodiments, z3 is 5.

In embodiments, z4 is 0. In embodiments, z4 is 1. In embodiments, z4 is 2.

In embodiments, z5 is 0. In embodiments, z5 is 1. In embodiments, z5 is 2. In embodiments, z5 is 3. In embodiments, z5 is 4. In embodiments, z5 is 5. In embodiments, z5 is 6. In embodiments, z5 is 7. In embodiments, z5 is 8.

In embodiments, n1.2 is 0. In embodiments, n1.2 is 1. In embodiments, n1.2 is 2. In embodiments, n1.2 is 3. In embodiments, n1.2 is 4. In embodiments, n1.3 is 0. In embodiments, n1.3 is 1. In embodiments, n1.3 is 2. In embodiments, n1.3 is 3. In embodiments, n1.3 is 4. In embodiments, n1.4 is 0. In embodiments, n1.4 is 1. In embodiments, n1.4 is 2. In embodiments, n1.4 is 3. In embodiments, n1.4 is 4. In embodiments, n1.5 is 0. In embodiments, n1.5 is 1. In embodiments, n1.5 is 2. In embodiments, n1.5 is 3. In embodiments, n1.5 is 4. In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n6 is 0. In embodiments, n6 is 1. In embodiments, n6 is 2. In embodiments, n6 is 3. In embodiments, n6 is 4. In embodiments, n7 is 0. In embodiments, n7 is 1. In embodiments, n7 is 2. In embodiments, n7 is 3. In embodiments, n7 is 4. In embodiments, n8 is 0. In embodiments, n8 is 1. In embodiments, n8 is 2. In embodiments, n8 is 3. In embodiments, n8 is 4. In embodiments, n9 is 0. In embodiments, n9 is 1. In embodiments, n9 is 2. In embodiments, n9 is 3. In embodiments, n9 is 4. In embodiments, n10 is 0. In embodiments, n10 is 1. In embodiments, n10 is 2. In embodiments, n10 is 3. In embodiments, n10 is 4. In embodiments, n11 is 0. In embodiments, n11 is 1. In embodiments, n11 is 2. In embodiments, n11 is 3. In embodiments, n11 is 4. In embodiments, n12 is 0. In embodiments, n12 is 1. In embodiments, n12 is 2. In embodiments, n12 is 3. In embodiments, n12 is 4. In embodiments, n13 is 0. In embodiments, n13 is 1. In embodiments, n13 is 2. In embodiments, n13 is 3. In embodiments, n13 is 4. In embodiments, n14 is 0. In embodiments, n14 is 1. In embodiments, n14 is 2. In embodiments, n14 is 3. In embodiments, n14 is 4. In embodiments, n15 is 0. In embodiments, n15 is 1. In embodiments, n15 is 2. In embodiments, n15 is 3. In embodiments, n15 is 4. In embodiments, n25 is 0. In embodiments, n25 is 1. In embodiments, n25 is 2. In embodiments, n25 is 3. In embodiments, n25 is 4.

In embodiments, m is 1. In embodiments, m is 2.

In embodiments, v1.2 is 1. In embodiments, v1.2 is 2. In embodiments, v1.3 is 1. In embodiments, v1.3 is 2. In embodiments, v1.4 is 1. In embodiments, v1.4 is 2. In embodiments, v1.5 is 1. In embodiments, v1.5 is 2. In embodiments, v1 is 1. In embodiments, v1 is 2. In embodiments, v2 is 1. In embodiments, v2 is 2. In embodiments, v3 is 1. In embodiments, v3 is 2. In embodiments, v6 is 1. In embodiments, v6 is 2. In embodiments, v7 is 1. In embodiments, v7 is 2. In embodiments, v8 is 1. In embodiments, v8 is 2. In embodiments, v9 is 1. In embodiments, v9 is 2. In embodiments, v10 is 1. In embodiments, v10 is 2. In embodiments, v11 is 1. In embodiments, v11 is 2. In embodiments, v12 is 1. In embodiments, v12 is 2. In embodiments, v13 is 1. In embodiments, v13 is 2. In embodiments, v14 is 1. In embodiments, v14 is 2. In embodiments, v15 is 1. In embodiments, v15 is 2. In embodiments, v25 is 1. In embodiments, v25 is 2.

In embodiments, the compound has the formula:

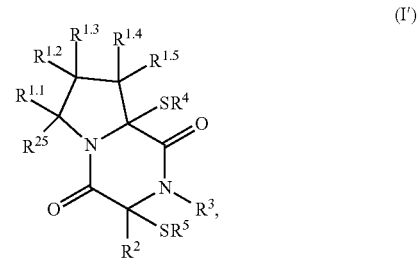

(I')

or a pharmaceutically acceptable salt thereof,
wherein:
$R^{1.1}$ is hydrogen, halogen, —$CF_3$, —$CCl_3$, —$CBr_3$, —$CI_3$, —CN, —CHO, —$COOR^{1.1A}$, —$CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.2}$ is hydrogen, halogen, —$N_3$, —$CF_3$, —$CCl_3$, —$CBr_3$, —$CI_3$, —CN, —CHO, —$OR^{1.2A}$, —$NR^{1.2B}R^{1.2C}$, —$COOR^{1.2A}$, —$CONR^{1.2B}R^{1.2C}$, —$NO_2$, —$SR^{1.2D}$, —$SO_{n1.2}R^{1.2B}$, —$SO_{v1.2}NR^{1.2B}R^{1.2C}$, —$NHNR^{1.2B}R^{1.2C}$, —$ONR^{1.2B}R^{1.2C}$, —$NHC(O)NHNR^{1.2B}R^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.3}$ is hydrogen, halogen, —$N_3$, —$CF_3$, —$CCl_3$, —$CBr_3$, —$CI_3$, —CN, —CHO, —$OR^{1.3A}$, —$NR^{1.3B}R^{1.3C}$, —$COOR^{1.3A}$, —$CONR^{1.3B}R^{1.3C}$, —$NO_2$, —$SR^{1.3D}$, —$SO_{n1.3}R^{1.3B}$, —$SO_{v1.3}NR^{1.3B}R^{1.3C}$, —$NHNR^{1.3B}R^{1.3C}$, —$ONR^{1.3B}R^{1.3C}$, —$NHC(O)NHNR^{1.3B}R^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.4}$ is hydrogen, halogen, —$N_3$, —$CF_3$, —$CCl_3$, —$CBr_3$, —$CI_3$, —CN, —CHO, —$OR^{1.4A}$, —$NR^{1.4B}R^{1.4C}$, —$COOR^{1.4A}$, —$CONR^{1.4B}R^{1.4C}$, —$NO_2$, —$SR^{1.4D}$, —$SO_{n1.4}R^{1.4B}$, —$SO_{v1.4}NR^{1.4B}R^{1.4C}$, —$NHNR^{1.4B}R^{1.4C}$, —$ONR^{1.4B}R^{1.4C}$, —$NHC(O)NHNR^{1.4B}R^{1.4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.5}$ is hydrogen, halogen, —$N_3$, —$CF_3$, —$CCl_3$, —$CBr_3$, —$CI_3$, —CN, —CHO, —$OR^{1.5A}$, —$NR^{1.5B}R^{1.5C}$, —$COOR^{1.5A}$, —$CONR^{1.5B}R^{1.5C}$, —$NO_2$, —$SR^{1.5D}$, —$SO_{n1.5}R^{1.5B}$, —$SO_{v1.5}NR^{1.5B}R^{1.5C}$, —$NHNR^{1.5B}R^{1.5C}$, —$ONR^{1.5B}R^{1.5C}$, —$NHC(O)NHNR^{1.5B}R^{1.5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.1A}$, $R^{1.1B}$, $R^{1.1C}$, $R^{1.2A}$, and $R^{1.2B}$, $R^{1.2C}$, $R^{1.2D}$, $R^{1.3A}$, $R^{1.3B}$, and $R^{1.3C}$, $R^{1.3D}$, $R^{1.4A}$, $R^{1.4B}$, $R^{1.4C}$, $R^{1.4D}$, $R^{1.5A}$, $R^{1.5B}$, $R^{1.5C}$, and $R^{1.5D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1.1B}$ and $R^{1.1C}$, $R^{1.2B}$ and $R^{1.2C}$, $R^{1.3B}$ and $R^{1.3C}$, $R^{1.4B}$ and $R^{1.4C}$, and $R^{1.5B}$ and $R^{1.5C}$ substituents bonded to the same nitrogen atom may independently optionally be joined to form a substituted or unsubstituted heterocycloalkyl or substituted or unsubstituted heteroaryl;

$R^2$ is hydrogen, $-CF_3$, $-CCl_3$, $-CBr_3$, $-CI_3$, $-CN$, $-CHO$, $-COOR^{2A}$, $-CONR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is $-C(O)-L^1-R^{18}$ or $-C(S)-L^1-R^{18}$;
$R^5$ is $-C(O)-L^2-R^{19}$ or $-C(S)-L^2-R^{19}$; or
$R^4$ and $R^5$ may optionally be joined to form

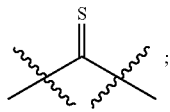 [SMILES: *C(*)=S]

$L^1$ is a bond, $-O-$, $-NH-$, substituted or unsubstituted alkylene, substituted or unsubstituted heteroalkylene;
$L^2$ is a bond, $-O-$, $-NH-$, substituted or unsubstituted alkylene, substituted or unsubstituted heteroalkylene;
$R^{18}$ and $R^{19}$ are independently halogen, substituted or unsubstituted $C_1$-$C_3$ alkyl, substituted or unsubstituted aryl;
$R^{25}$ is hydrogen, halogen, $-N_3$, $-CF_3$, $-CCl_3$, $-CBr_3$, $-CI_3$, $-CN$, $-CHO$, $-OR^{25A}$, $-NR^{25B}R^{25C}$, $-C(O)OR^{25A}$, $-C(O)NR^{25B}R^{25C}$, $-SR^{25D}$, $-S(O)_{n25}R^{25B}$, $-SO_{v25}NR^{25B}R^{25C}$, $-NHNR^{25B}R^{25C}$, $ONR^{25B}R^{25C}$, $-NHC(O)NHNR^{25B}R^{25C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{25A}$, $R^{25B}$, $R^{25C}$, and $R^{25D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl or substituted or unsubstituted heteroaryl;

n1, n3, and n25 are independently an integer from 0 to 4;
v1, v3, and v25 are independently 1 or 2;
n1.2, n1.3, n1.4, and n1.5 are independently an integer from 0 to 4; and
v1.2, v1.3, v1.4, and v1.5 are independently 1 or 2.

In embodiments, the compound or pharmaceutically acceptable salt thereof, has the formula:

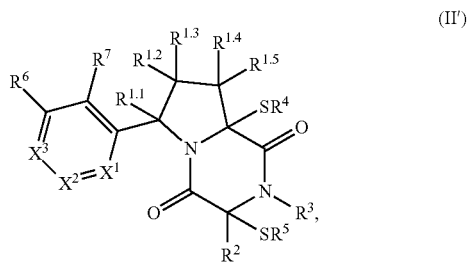

(II')

or a pharmaceutically acceptable salt thereof,
wherein:
$X^1$ is N or $CR^{10}$;
$X^2$ is N or $CR^{11}$;
$X^3$ is N or $CR^{12}$;

$R^6$ is hydrogen, halogen, $-N_3$, $-CF_3$, $-CCl_3$, $-CBr_3$, $-CI_3$, $-CN$, $-CHO$, $-OR^{6A}$, $-NR^{6B}R^{6C}$, $-COOR^{6A}$, $-CONR^{6B}R^{6C}$, $-NO_2$, $-SR^{6D}$, $-SO_{n6}R^{6B}$, $-SO_{v6}NR^{6B}R^{6C}$, $-NHNR^{6B}R^{6C}$, $-ONR^{6B}R^{6C}$, $-NHC(O)NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-N_3$, $-CF_3$, $-CCl_3$, $-CBr_3$, $-CI_3$, $-CN$, $-CHO$, $-OR^{7A}$, $-NR^{7B}R^{7C}$, $-COOR^{7A}$, $-CONR^{7B}R^{7C}$, $-NO_2$, $-SR^{7D}$, $-SO_{n7}R^{7B}$, $-SO_{v7}NR^{7B}R^{7C}$, $-NHNR^{7B}R^{7C}$, $-ONR^{7B}R^{7C}$, $-NHC(O)NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-CONR^{10B}R^{10C}$, $-NO_2$, $-SR^{10D}$, $-SO_{n10}R^{10B}$, $-SO_{v10}NR^{10B}R^{10C}$, $-NHNR^{10B}R^{10C}$, $-ONR^{10B}R^{10C}$, $-NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-CONR^{11B}R^{11C}$, $-NO_2$, $-SR^{11D}$, $-SO_{n11}R^{11B}$, $-SO_{v11}NR^{11B}R^{11C}$, $-NHNR^{11B}R^{11C}$, $-ONR^{11B}R^{11C}$, $-NHC(O)NHNR^{11B}R^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ may optionally be joined to form a substituted or unsubstituted cycloalkyl, substituted or unsubstituted heterocycloalkyl;

$R^{12}$ is hydrogen, halogen, $-N_3$, $-CF_3$, $-CCl_3$, $-CBr_3$, $-CI_3$, $-CN$, $-CHO$, $-OR^{12A}$, $-NR^{12B}R^{12C}$, $-COOR^{12A}$, $-CONR^{12B}R^{12C}$, $-NO_2$, $-SR^{12D}$, $-SO_{n12}R^{12B}$, $-SO_{v12}NR^{12B}R^{12C}$, $-NHNR^{12B}R^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ and R$^{12}$ may optionally be joined to form a substituted or unsubstituted cycloalkyl, substituted or unsubstituted heterocycloalkyl; R$^{6A}$, R$^{6B}$, R$^{6C}$, R$^{6D}$, R$^{7A}$, R$^{7B}$, R$^{7C}$, R$^{7D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, and R$^{12D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{6B}$ and R$^{6C}$, R$^{7B}$ and R$^{7C}$, R$^{10B}$ and R$^{10C}$, R$^{11B}$ and R$^{11C}$, and R$^{12B}$ and R$^{12C}$, substituents bonded to the same nitrogen atom may optionally be joined to form a substituted or unsubstituted heterocycloalkyl or substituted or unsubstituted heteroaryl; n6, n7, n10, n11 and n12 are independently an integer from 0 to 4; and v6, v7, v10, v11 and v12, are independently 1 or 2.

In embodiments, the compound or pharmaceutically acceptable salt thereof, has the formula:

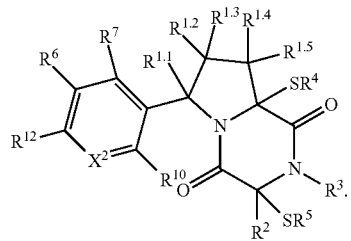

(IV)

In some embodiments, R$^{10}$ and R$^{11}$ or R$^{11}$ and R$^{12}$ are optionally joined to form a substituted or unsubstituted cycloalkyl or substituted or unsubstituted heterocycloalkyl having structural formula:

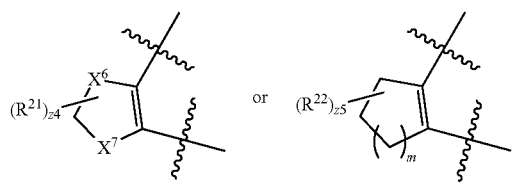

wherein:
X$^6$ is O, NR$^{23A}$, or S;
X$^7$ is O, NR$^{24A}$, or S;
z4 is an integer from 0 to 2;
z5 is an integer from 0 to 8;
m is 1 or 2;
R$^{21}$, R$^{22}$, R$^{23A}$, and R$^{24A}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound or pharmaceutically acceptable salt thereof, has the formula:

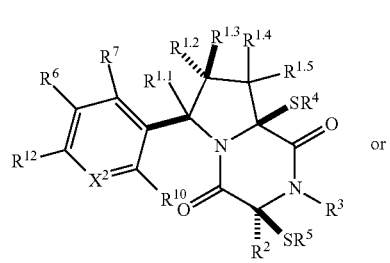

(V (S))

or

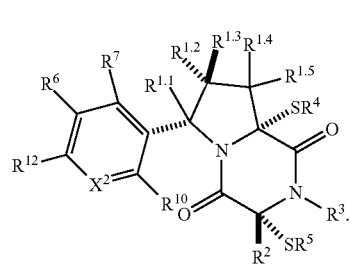

(VI (R))

In embodiments, the compound or pharmaceutically acceptable salt thereof, has the formula:

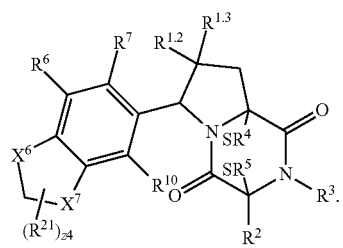

(VII)

In embodiments, the compound or pharmaceutically acceptable salt thereof, has the formula:

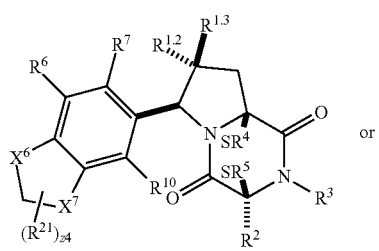

(VIII (S))

or

-continued

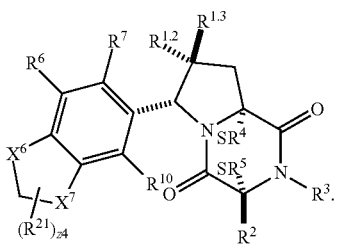
(IX (R))

In embodiments, the compound or pharmaceutically acceptable salt thereof, has the formula:

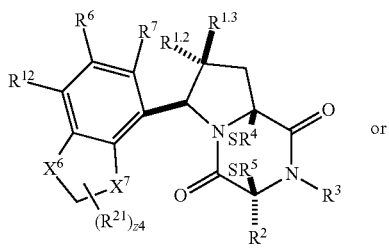
(X)

In embodiments, the compound or pharmaceutically acceptable salt thereof, has the formula:

(XI (S))

In embodiments, the compound or pharmaceutically acceptable salt thereof, has the formula:

(XII (R))

In embodiments, the compound or pharmaceutically acceptable salt thereof, has the formula:

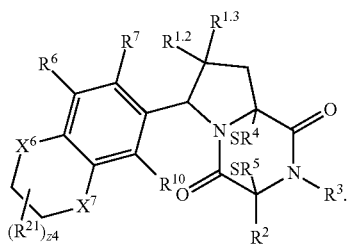
(XIII)

In embodiments, the compound or pharmaceutically acceptable salt thereof, has the formula:

(XIV (S))

or (XV (R))

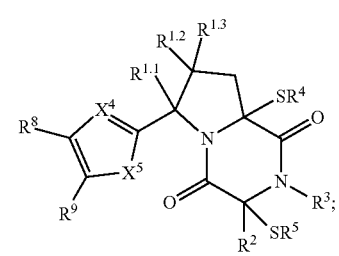

In embodiments, the compound or pharmaceutically acceptable salt thereof, has the formula:

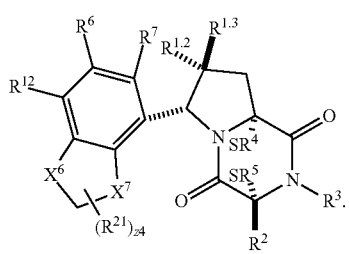
(XVI)

wherein:

$R^{1.1}$ is hydrogen, halogen, —$CF_3$, —$CCl_3$, —$CBr_3$, —$CI_3$, —CN, —CHO, —$COOR^{1.1A}$, —$CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, —$N_3$, —$CF_3$, —$CCl_3$, —$CBr_3$, —$CI_3$, —CN, —CHO, —$OR^{1.2A}$, —$NR^{1.2B}R^{1.2C}$, —$COOR^{1.2A}$, —$CONR^{1.2B}R^{1.2C}$, —$NO_2$, —$SR^{1.2D}$, —$SO_{n1.2}R^{1.2B}$, —$SO_{v1.2}NR^{1.2B}R^{1.2C}$, —$NHNR^{1.2B}R^{1.2C}$, —ONR$^{1.2B}$R$^{1.2C}$, —NHC(O)NHNR$^{1.2B}$R$^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1.3}$ is hydrogen, halogen, —N$_3$, —CF$_3$, —CCl$_3$, —CBr$_3$, —CI$_3$, —CN, —CHO, —OR$^{1.3A}$, —NR$^{1.3B}$R$^{1.3C}$, —COOR$^{1.3A}$, —CONR$^{1.3B}$R$^{1.3C}$, —NO$_2$, —SR$^{1.3D}$, —SO$_{n1.3}$R$^{1.3B}$, —SO$_{v1.3}$NR$^{1.3B}$R$^{1.3C}$, —NHNR$^{1.3B}$R$^{1.3C}$, —ONR$^{1.3B}$R$^{1.3C}$, —NHC(O)NHNR$^{1.3B}$R$^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^4$ is N or CR$^{13}$;

X$^5$ is CR$^{14}$R$^{15}$, S, O, or NR$^{20A}$;

R$^8$ is hydrogen, halogen, —N$_3$, —CF$_3$, —CCl$_3$, —CBr$_3$, —CI$_3$, —CN, —CHO, —OR$^{8A}$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, NO$_2$, —SR$^{13D}$, —SO$_{n13}$R$^{13B}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$ is hydrogen, halogen, —N$_3$, —CF$_3$, —CCl$_3$, —CBr$_3$, —CI$_3$, —CN, —CHO, —OR$^{14A}$, —NR$^{14B}$R$^{14C}$, —COOR$^{14A}$, —CONR$^{14B}$R$^{14C}$, —NO$_2$, —SR$^{14D}$, —SO$_{n14}$R$^{14B}$, —SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, —CONR$^{15B}$R$^{15C}$, —NO$_2$, —SR$^{15D}$, —SO$_{n15}$R$^{15B}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1.1A}$, R$^{1.1B}$, R$^{1.1C}$, R$^{1.2A}$, R$^{1.2B}$, R$^{1.2C}$, R$^{1.2D}$, R$^{1.3A}$, R$^{1.3B}$, R$^{1.3C}$, R$^{1.3D}$, R$^{8A}$, R$^{8B}$, R$^{8C}$, R$^{8D}$, R$^{9A}$, R$^{9B}$, R$^{9C}$, R$^{9D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, and R$^{20A}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{1.1B}$ and R$^{1.1C}$, R$^{1.2B}$ and R$^{1.2C}$, R$^{1.3B}$ and R$^{1.3C}$, R$^{13B}$ and R$^{13C}$, R$^{14B}$ and R$^{14C}$, and R$^{15B}$ and R$^{15C}$, substituents bonded to the same nitrogen atom may optionally be joined to form a substituted or unsubstituted heterocycloalkyl or substituted or unsubstituted heteroaryl;

n1.2, n1.3, n8, n9, n13, n14, and n15 are independently an integer from 0 to 4; and v1.2, v1.3, v8, v9, v13, v14, and v15 are independently 1 or 2.

In embodiments, the compound or pharmaceutically acceptable salt thereof, has the formula:

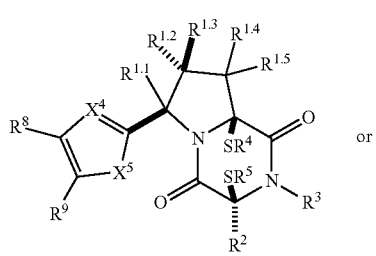

(XVII (S))

or

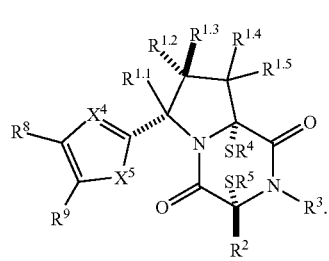

(XVIII (R))

In some embodiments, R$^6$ and R$^7$ are independently hydrogen. In some embodiments, X$^2$ is N. In some embodiments, R$^{1.2}$ is —OCH$_3$. In some embodiments, R$^{1.2}$ is substituted or unsubstituted alkyl.

In some embodiments, R$^{1.2}$ is substituted or unsubstituted C$_1$-C$_3$alkyl. In some embodiments, R$^{1.2}$ is methyl. In some embodiments, R$^{1.3}$ is —CN. In some embodiments, R$^4$ is —C(O)-L$^1$-R$^{18}$ or —C(S)-L$^1$-R$^{18}$; and R$^5$ is —C(O)-L$^2$-R$^{19}$ or —C(S)-L$^2$-R$^{19}$.

In some embodiments, R$^4$ is —C(O)-L$^1$-R$^{18}$; and R$^5$ is —C(O)-L$^2$-R$^{19}$.

In some embodiments, R$^4$ is —C(S)-L$^1$-R$^{18}$; and R$^5$ is —C(S)-L$^2$-R$^{19}$.

In some embodiments, L$^1$ and L$^2$ are independently —O—.

In some embodiments, $L^1$ and $L^2$ are independently —NH—.

In some embodiments, $L^1$ and $L^2$ are independently a bond.

In some embodiments, $L^1$ is -$L^{1A}$-$L^{1B}$-, wherein $L^{1A}$ is bonded to —C(O)— or —C(S)—; and $L^2$ is -$L^{2A}$-$L^{2B}$-, wherein $L^{2A}$ is bonded to —C(O)— or —C(S)—; $L^{1A}$ is a bond or —(CH$_2$)$_{z1}$—; $L^{1B}$ is a bond, —O— or —NR$^{16B}$—; $L^{2A}$ is a bond or —(CH$_2$)$_{z2}$—; $L^{2B}$ is a bond, —O— or —NR$^{17B}$—; z1 and z2 are independently an integer from 1 to 10; and $R^{16B}$ and $R^{17B}$ are independently hydrogen or substituted or unsubstituted alkyl.

In some embodiments, $L^{1A}$ and $L^{2A}$ are independently —CH$_2$—.

In some embodiments, $L^{1B}$ is —NR$^{16B}$; $L^{2B}$ is —NR$^{17B}$; and $R^{16B}$ and $R^{17B}$ are independently unsubstituted $C_1$-$C_3$alkyl.

In some embodiments, $R^{18}$ and $R^{19}$ are independently unsubstituted $C_1$-$C_3$alkyl or unsubstituted aryl.

In some embodiments, $R^{18}$ and $R^{19}$ are independently unsubstituted aryl.

In some embodiments, $R^{18}$ and $R^{19}$ are independently halogen.

In some embodiments, $R^4$ and $R^5$ are joined together to form:

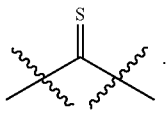 [SMILES: *C(*)=S]

In some embodiments, $R^2$ is methyl.

In some embodiments, the compound or pharmaceutically acceptable salt thereof, has the structure:

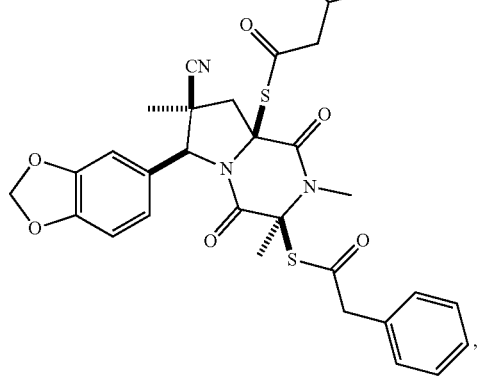

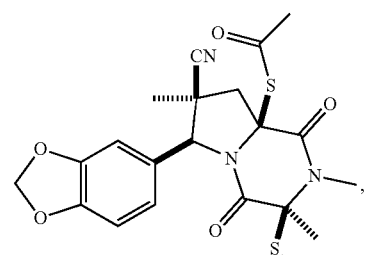

-continued

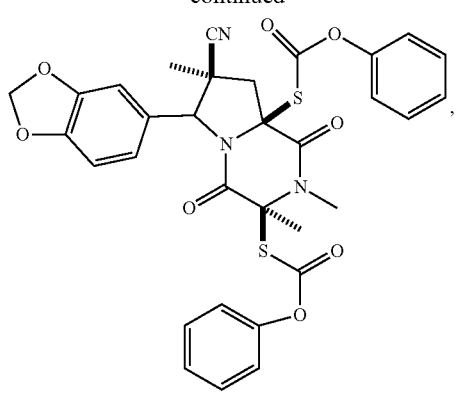

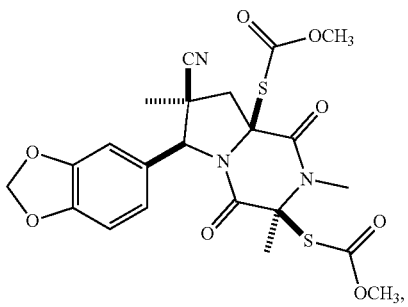

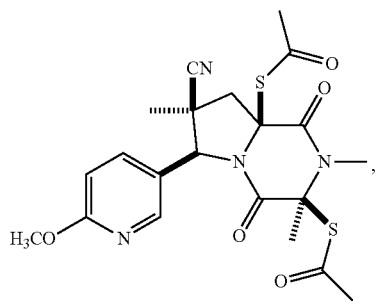

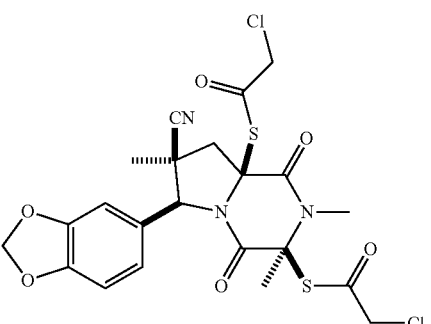

115
-continued
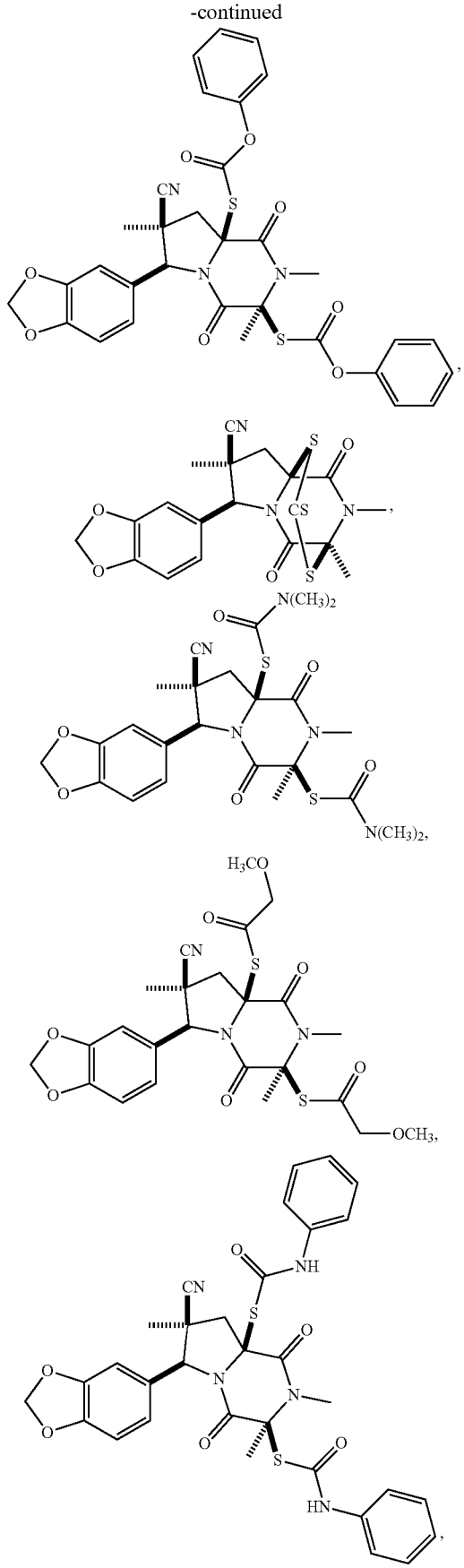
116
-continued
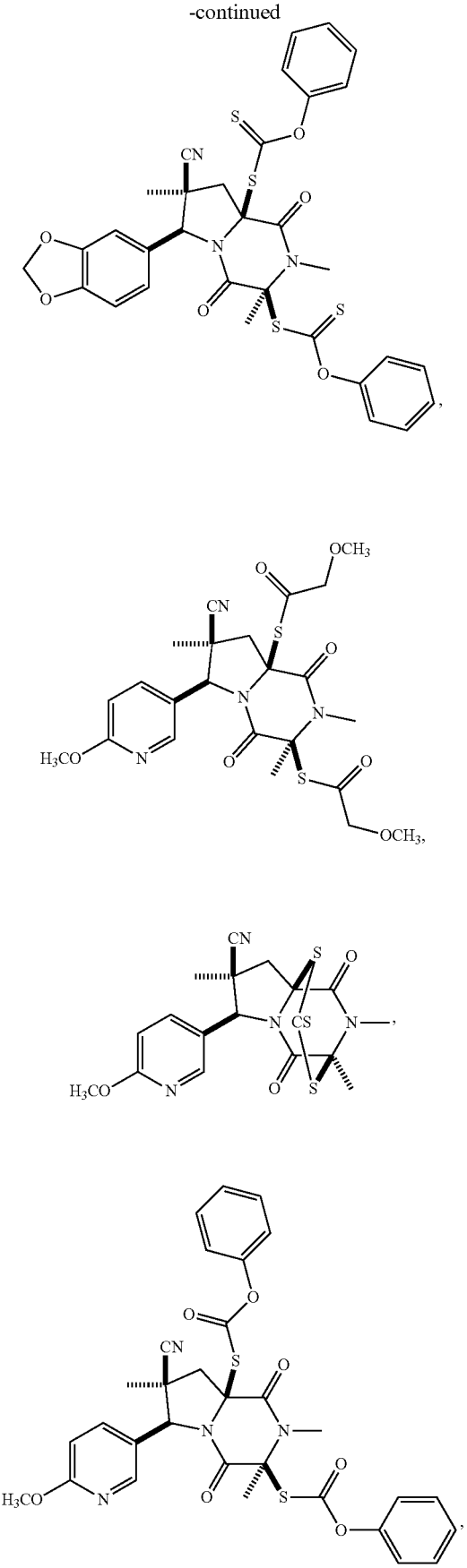

117
-continued
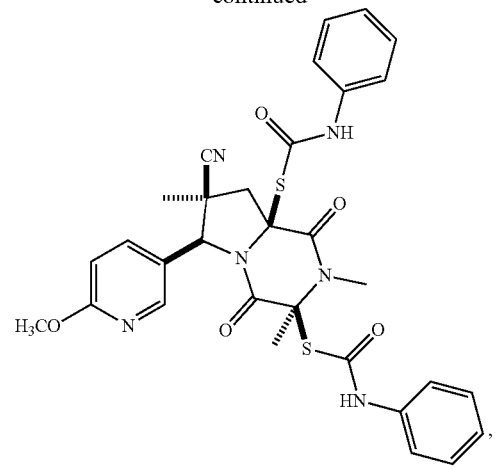
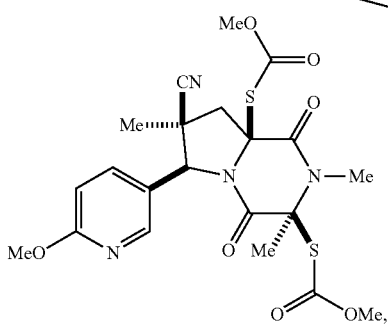
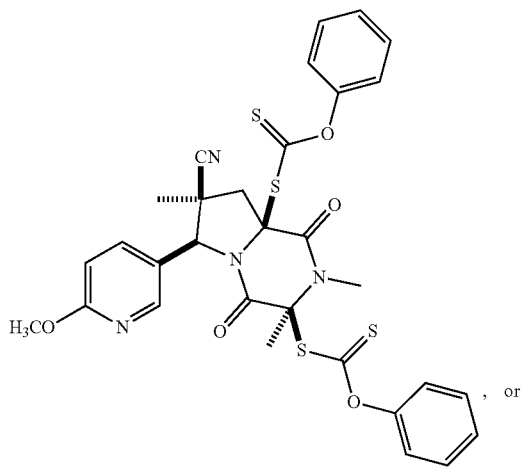, or
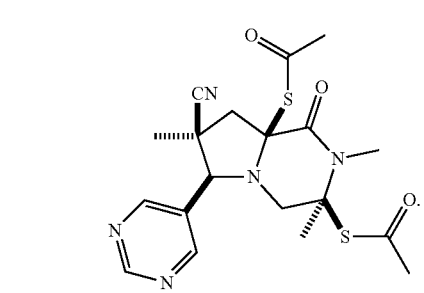
118
In embodiments, the compound has the structure:
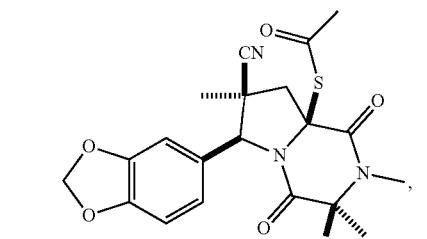
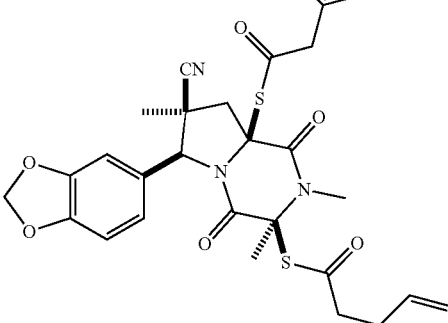,
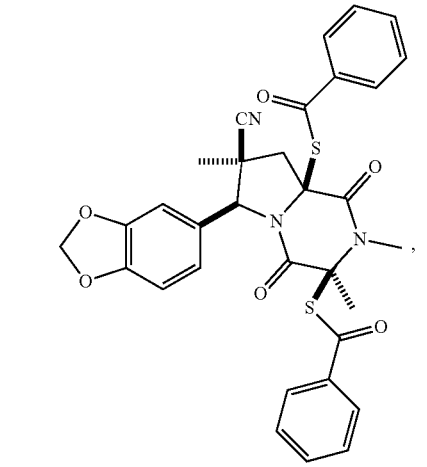,
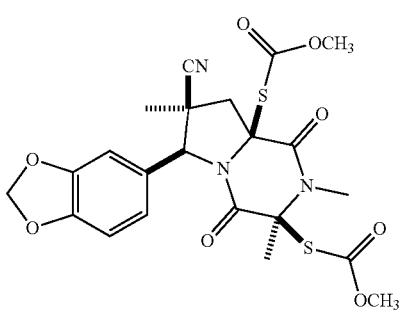

119
-continued
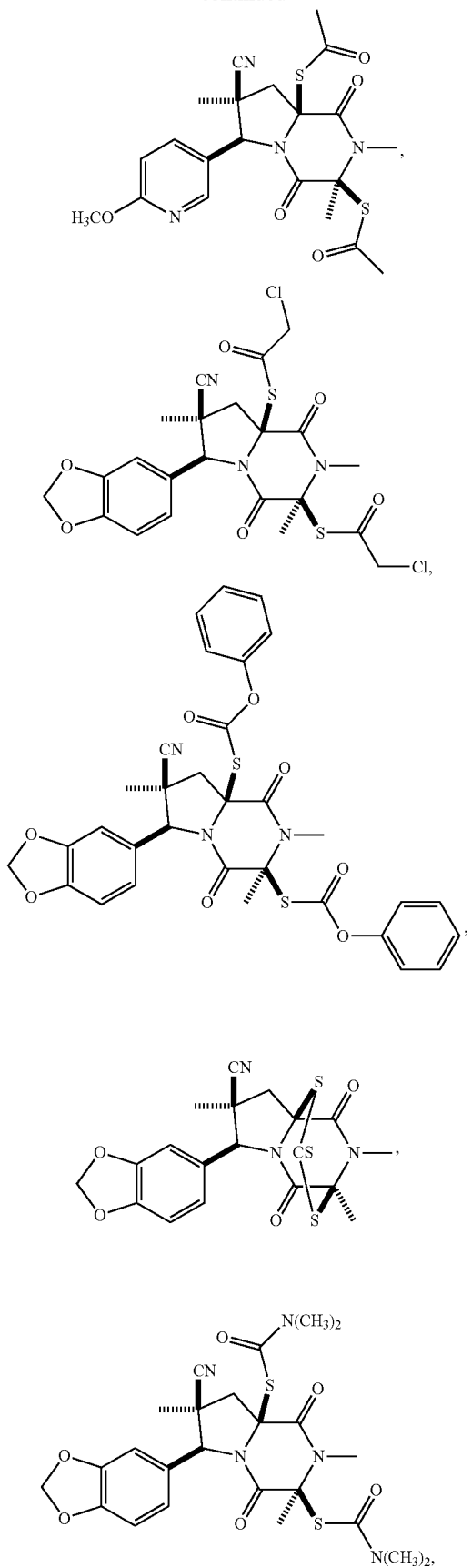
120
-continued
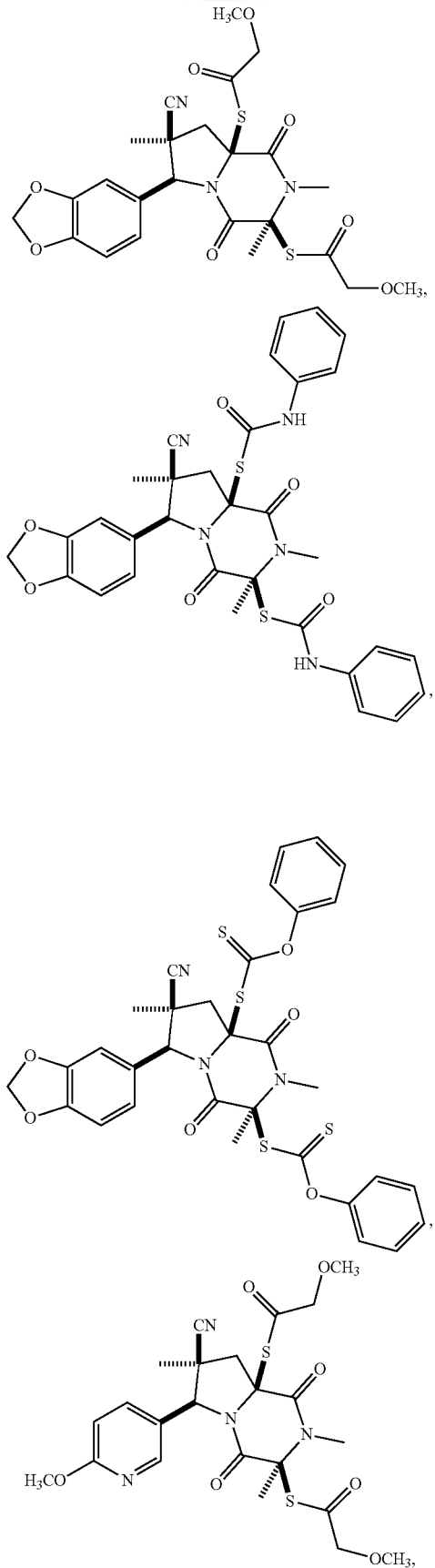

121
-continued
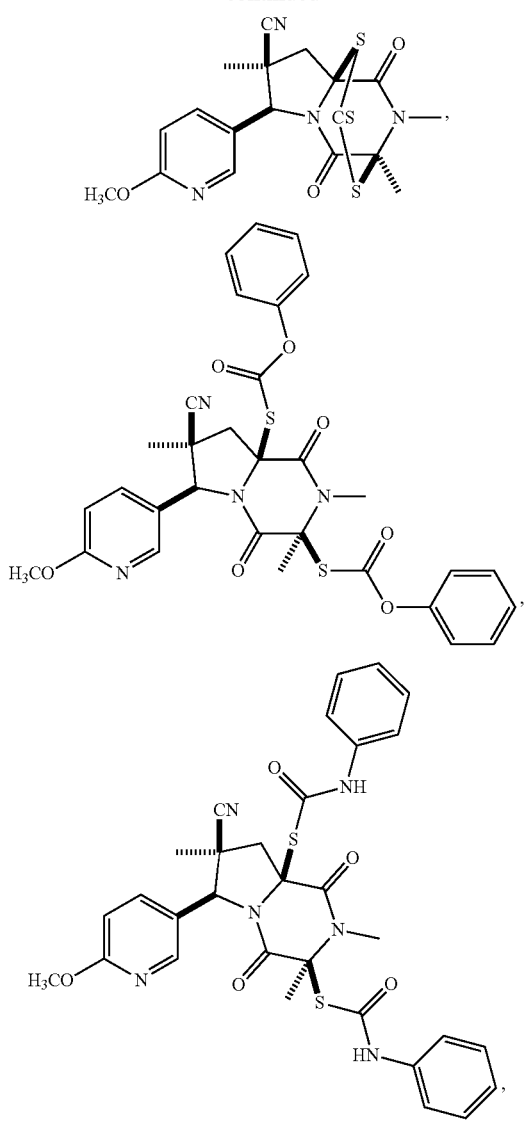
, or
122
-continued
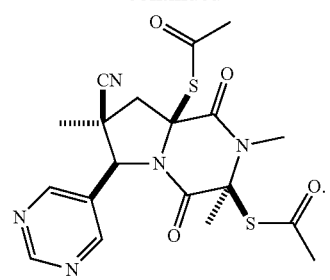
In embodiments, the compound has the structure:
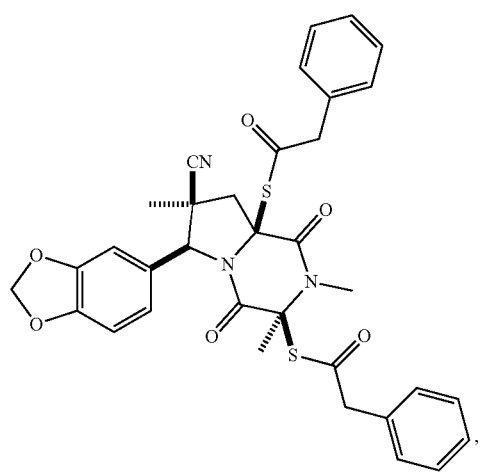
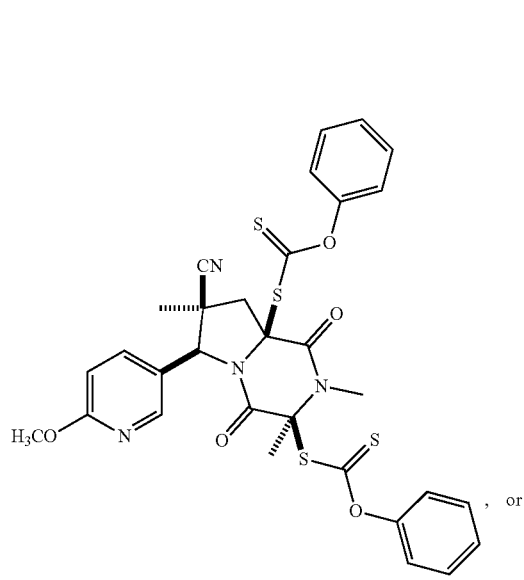
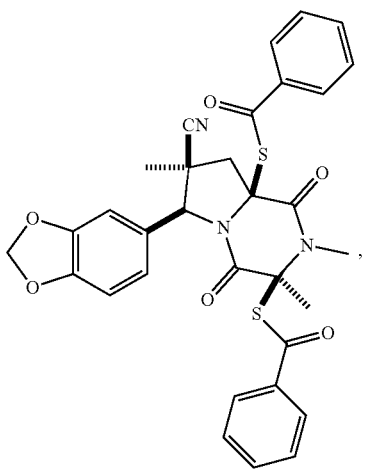
, 123
-continued
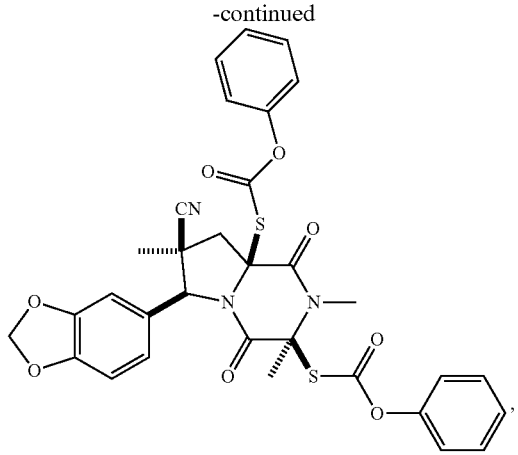
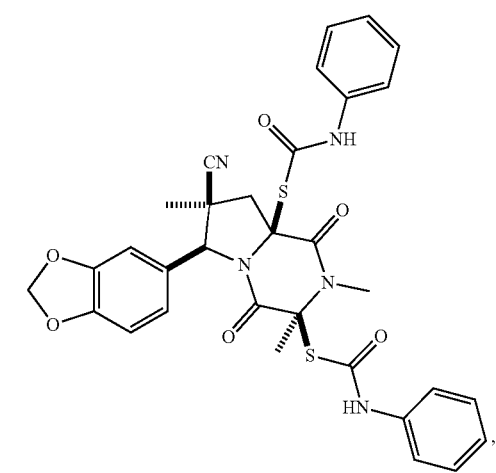
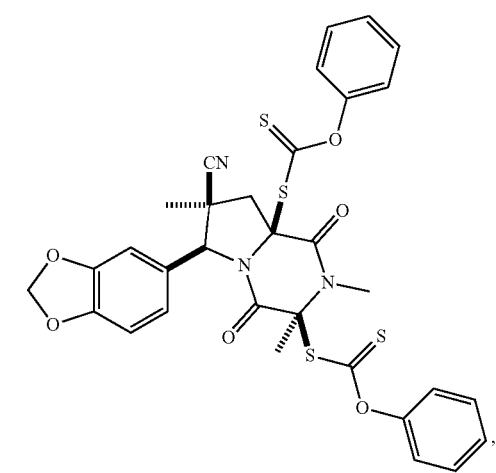
124
-continued
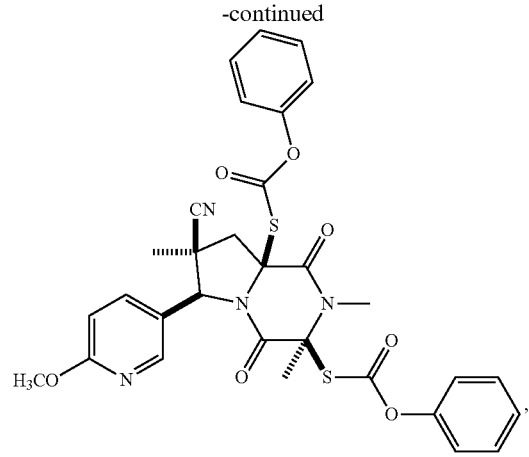
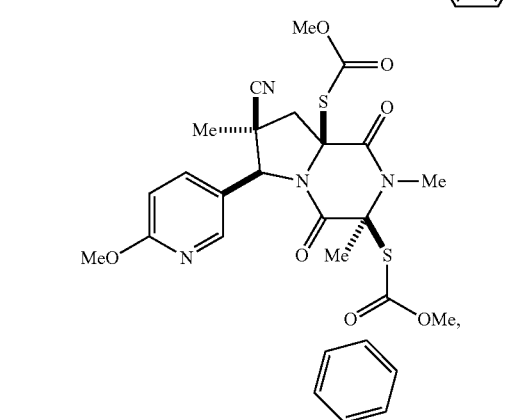
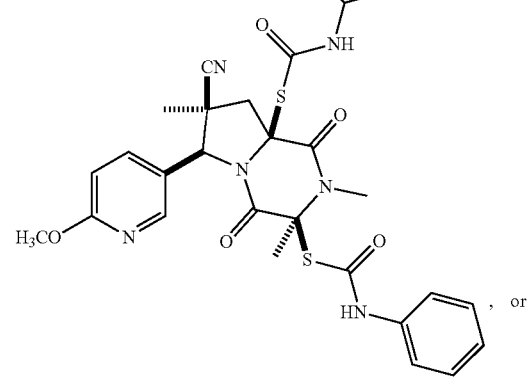
, or
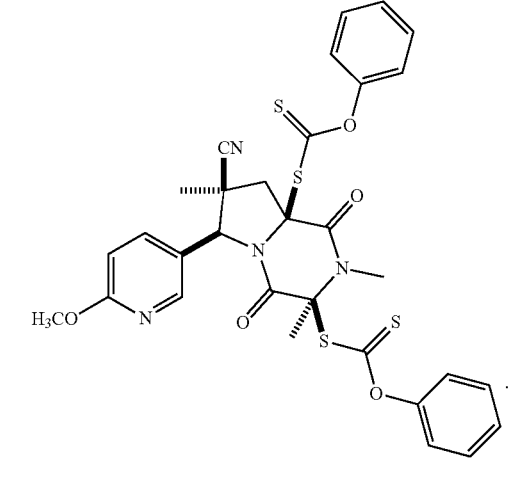

In embodiments, the compound has the structure:

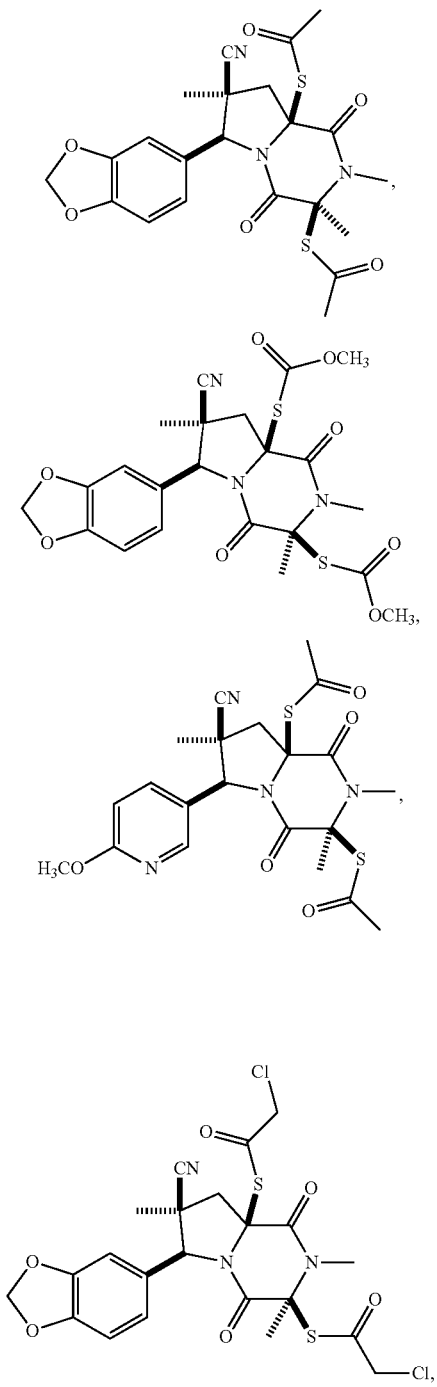

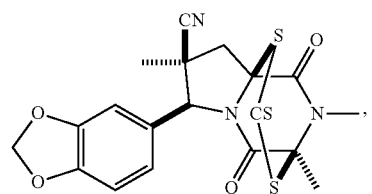

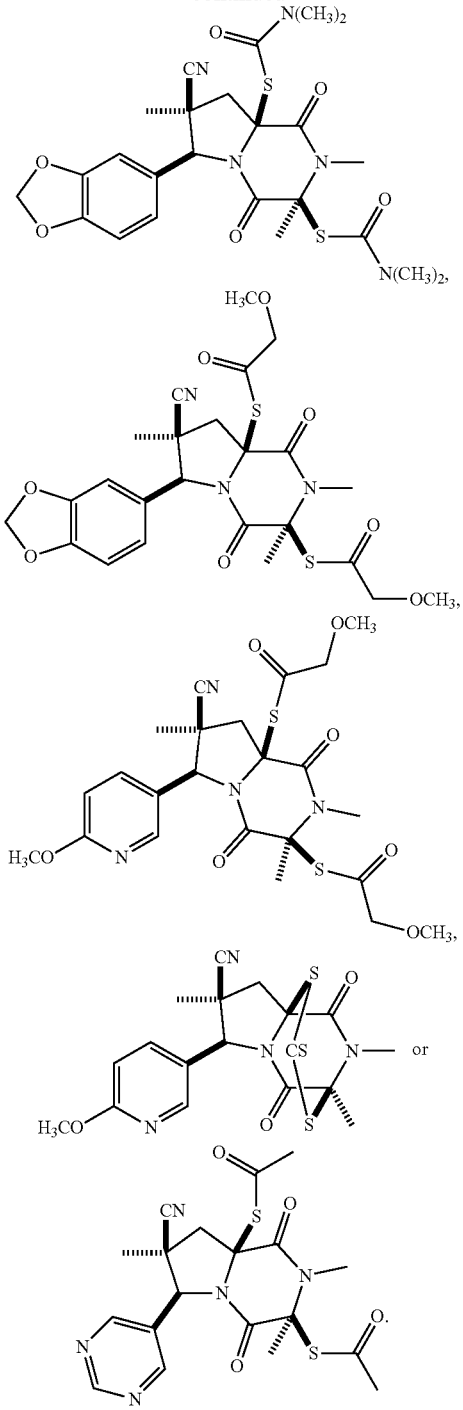

III. PHARMACEUTICAL COMPOSITIONS

In an aspect, is provided a pharmaceutical composition including a compound as described herein, or salt thereof, and a pharmaceutically acceptable excipient.

In an aspect is provided a pharmaceutical composition including a pharmaceutically acceptable excipient and a combination of a compound as described herein at least one additional anticancer agent.

In embodiments, the at least one additional anticancer agent includes an epigenetic inhibitor or a multi-kinase inhibitor.

In embodiments, the combination includes a first amount of the compound and a second amount of a epigenetic inhibitor, wherein the first amount and second amount are together an effective amount to provide a synergistic therapeutic effect.

In embodiments, the combination includes a first amount of the compound and a second amount of a multi-kinase inhibitor, wherein the first amount and second amount are together an effective amount to provide a synergistic therapeutic effect.

In embodiments, the combination includes a first amount of the compound, a second amount of a multi-kinase inhibitor, and a third amount of a epigenetic inhibitor, wherein the first amount, the second amount, and the third amount are together an effective amount to provide a synergistic therapeutic effect.

In embodiments, the additional anticancer agent is a multi-kinase inhibitor. In embodiments, the multi-kinase inhibitor is sorafenib.

In embodiments, the additional anticancer agent is an epigenetic inhibitor. In embodiments, the epigenetic inhibitor is azacitidine or decitabine. In embodiments, the epigenetic inhibitor is azacitidine. In embodiments, the epigenetic inhibitor is decitabine.

In embodiments, the pharmaceutical composition is for use in cancer. In embodiments, the pharmaceutical composition is for use in solid and blood tumors, including ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer. In embodiments, the pharmaceutical composition is for use in non-small cell lung cancer.

In embodiments, the compound as described herein and the multi-kinase inhibitor or the epigenetic inhibitor are co-administered as a single dosage form.

Methods of Use

In an aspect is provided a method of treating cancer, including administering to a subject in need thereof a therapeutically effective amount of a compound as described herein, or salt thereof, including embodiments.

In embodiments, the cancer is a solid or blood tumor.

In embodiments, the cancer is ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer. In embodiments, the cancer is ovarian cancer.

In embodiments, the method includes further including administering at least one additional anticancer agent. In embodiments, the at least one additional anticancer agent includes an epigenetic inhibitor or a multi-kinase inhibitor.

In embodiments, the additional anticancer agent is a multi-kinase inhibitor. In embodiments, the multi-kinase inhibitor is sorafenib.

In embodiments, the additional anticancer agent is an epigenetic inhibitor. In embodiments, the epigenetic inhibitor is azacitidine or decitabine. In embodiments, the epigenetic inhibitor is azacitidine. In embodiments, the epigenetic inhibitor is decitabine.

In embodiments, the method includes administering a first amount of the compound and a second amount of at least one additional anticancer agent, wherein the first amount and second amount are together an effective amount to provide a synergistic therapeutic effect.

In embodiments, the compound and the epigenetic inhibitor are co-administered as a pharmaceutical composition. In embodiments, the compound and the multi-kinase inhibitor are co-administered as a pharmaceutical composition.

In a further aspect is provided a method of inhibiting the growth of a cancer cell, comprising administering to a subject in need thereof a therapeutically effective amount of a compound or composition described herein. In embodiments, the cancer cell is an ovarian cancer cell, breast cancer cell, lung cancer cell, leukemia cell, AML cell, CML cell, lymphoma cell, pancreatic cancer cell, kidney cancer cell, melanoma cell, liver cancer cell, colon cancer cell, sarcoma cell, multiple myeloma cell, brain cancer cell, or prostate cancer cell.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Dithio Analogs of 1,4-Dioxohexahydro-6H-3,8a-epidithiopyrrolo[1,2-a]pyrazines Having Anticancer Activity 1,4-Dioxohexahydro-6H-3,8a-epidithiopyrrolo[1,2-c]pyrazines, see compound (I) in FIG. 1 for example, have been shown to suppresses tumor growth in mouse xenograft models of melanoma and lung cancer, without obvious signs of toxicity, following either intraperitoneal (IP) or oral administration (PCT/US2013/066252). Additional background can be found in the cited patent application.

Molecules of structure II as found in FIG. 1, which could be converted in vivo to the corresponding dithiol II (R=H), mono-thio derivatives III or IV, or compounds of structure I (p=2), exhibit significant in vitro antitumor activity. Careful control of the substituents effects bioavailability of the compounds, their physical properties, and the rate at which the R substituent would be cleaved in vivo, while improving the antitumor activity relative to compound I.

Pharmaceutical compositions comprising molecules II and a pharmaceutical acceptable expedient alone or in conjunction with another antitumor agent are of utility for treating cancer.

Figure 2A:
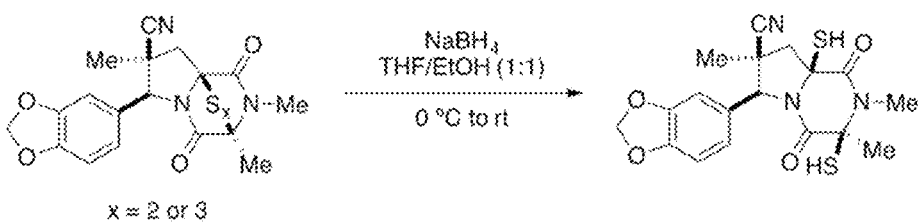
Figure 2A:
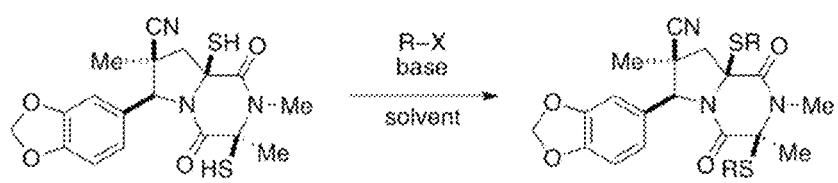
Figure 3:
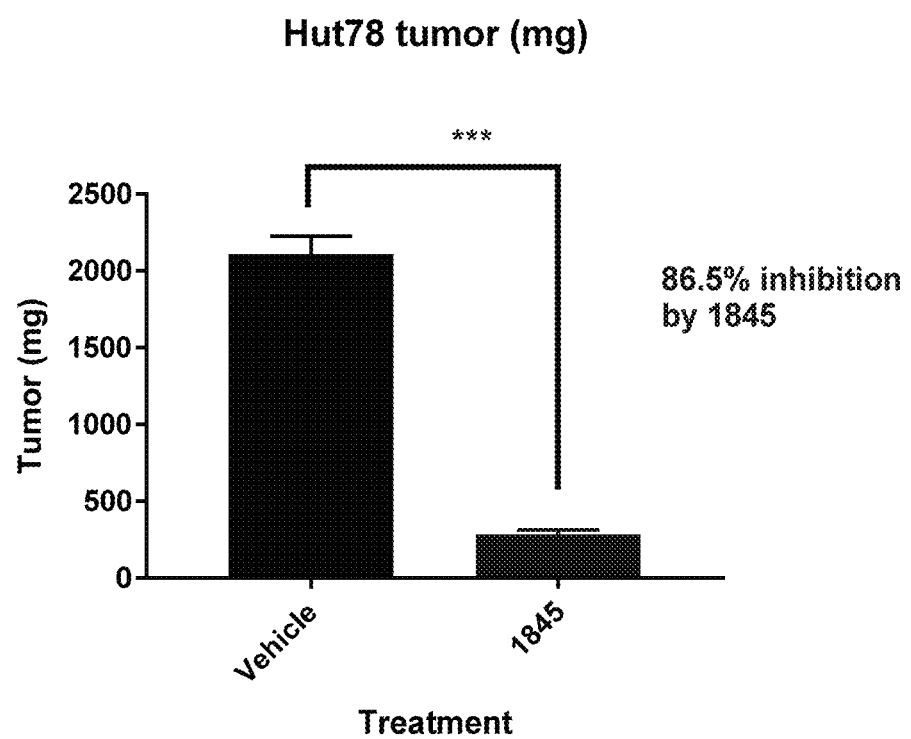
FIG. 3. Depicts the effect of S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) diethanethioate on in vivo inhibition of cutaneous T-cell lymphoma (CTCL) in mice.

Four examples of compounds of structure II with R=—C(O)R or —C(O)OR' were prepared as depicted in FIG. 2 and their in vitro cytotoxicity against two invasive cancer cell lines, DU145 (human prostate cancer) and A2058 (human melanoma) were determined. As shown in FIG. 2, LEO-16-1833, LEO-16-1835, LEO-16-1836 showed good activity against these two cancer cell lines, with LEO-16-1833 showing activity nearly identical to the corresponding ETP structure I (p=2).

Example 2. Synthesis and Characterization Data

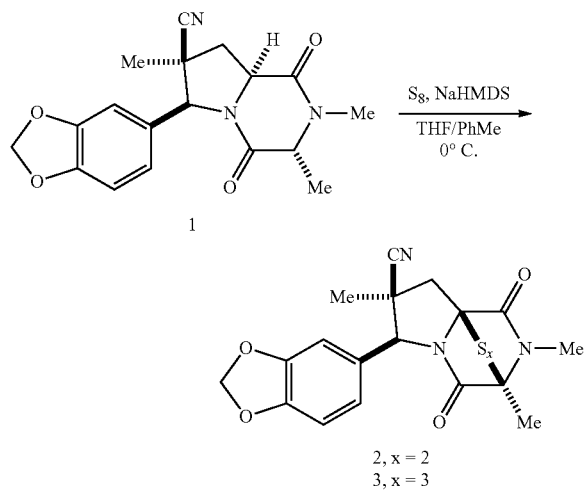

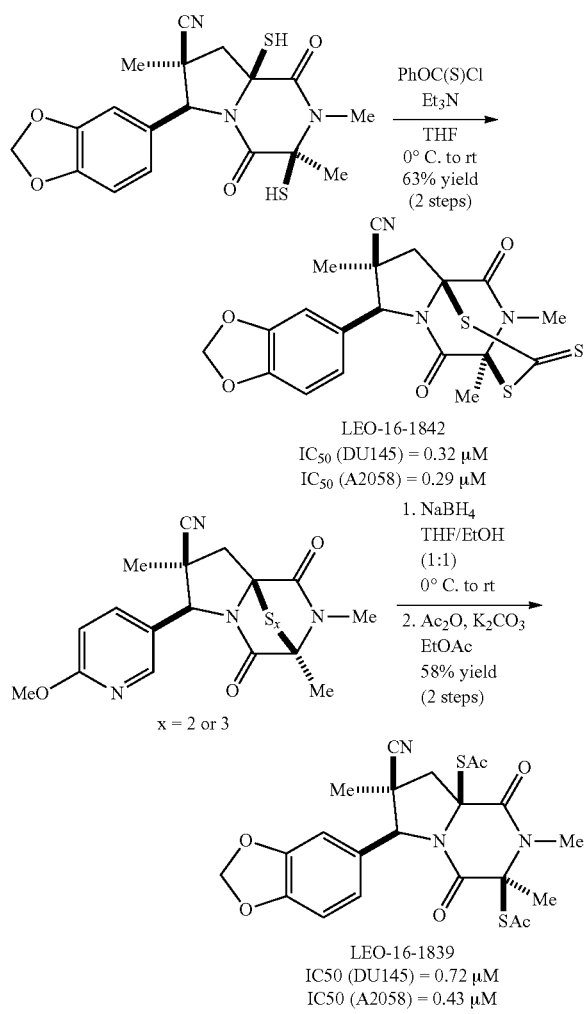

Rel-(3S,6S,7S,8aS)-6-(benzo[d][1,3]dioxol-5-yl)-2,3,7-trimethyl-1,4-dioxohexahydro-6H-3,8a-epidithiopyrrolo[1,2-c]pyrazine-7-carbonitrile (2) and Rel-(3S,6S,7S,8aS)-6-(benzo[d][1,3]dioxol-5-yl)-2,3,7-trimethyl-1,4-dioxohexahydro-6H-3,8a-epitrithiopyrrolo[1,2-c]pyrazine-7-carbonitrile (3). A three-neck 250 mL round bottom flask was fitted with an overhead mechanical stirrer with a grease-sealed glass fitting. The flask was charged with 1 (2.07 g, 6.1 mmol) and $S_8$ (1.56 g, 6.1 mmol) and fitted with two rubber septa. The flask was evacuated under vacuum and back-filled with Ar three times. The solids were suspended in anhydrous THF (60 mL) and the suspension was cooled in an ice bath. After 5 min., a solution of NaHMDS (0.6 M in PhMe, 60 mL, 36 mmol) was added over 10 min with vigorous stirring. The reaction was maintained at 0° C. for 3 h. The reaction was quenched with sat. aq. $NH_4Cl$ (50 mL) and $H_2O$ (50 mL). The biphasic mixture was extracted with EtOAc (3×150 mL). The combined organic extracts were dried over $Na_2SO_4$, filtered, and concentrated in vacuo. Flash chromatography (30×250 mm of $SiO_2$, 5 to 10% EtOAc in $CH_2Cl_2$ gradient elution) afforded a 2:1 mixture of 2 and 3 (880 mg, ca. 2.12 mmol, 35% yield) as an off-white solid.

Rel-S, S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) diethanethioate (4, LEO-16-1833). A mixture of 2 and 3 (53 mg, ca. 0.13 mmol) was suspended in degassed THF/EtOH (1:1, 1.3 mL) under Ar. The suspension was cooled in an ice bath. $NaBH_4$ (17 mg, 0.44 mmol) was added in 3 portions over 3 min. After 5 min, the cold bath was removed and the reaction was maintained at room temperature for 1 h. The solvent was removed in vacuo. The crude residue was suspended in EtOAc (2.5 mL) and $K_2CO_3$ (35 mg, 0.25 mmol) was added. $Ac_2O$ (30 µL, 0.32 mmol) was added and the reaction was maintained for 17 h. The reaction was diluted with $H_2O$ (10 mL) and extracted with EtOAc (3×10 mL). The combined organic extracts were dried over $Na_2SO_4$, filtered, and concentrated in vacuo. Flash chromatography (12×150 mm of $SiO_2$, 10% EtOAc in $CH_2Cl_2$) afforded bis-thioacetate 4 (60 mg, 0.12 mmol, 92% yield) as a colorless solid. $^1H$ NMR (500 MHz, $CDCl_3$): δ 6.97 (s, 1H), 6.88 (d, J=8.1 Hz, 1H), 6.84 (d, J=8.1 Hz, 1H), 6.00 (s, 2H), 4.86 (s, 1H), 4.34 (d, J=14.6 Hz, 1H), 3.18 (s, 3H), 2.41-2.37 (m, 7H), 2.10 (s, 3H), 1.70 (s, 3H); $^{13}C$ NMR (125 MHz, $CDCl_3$): δ 191.9 (C), 191.8 (C), 164.9 (C), 162.8 (C), 148.3 (C), 148.2 (C), 129.2 (C), 120.9 (C), 120.0 (CH), 108.8 (CH), 106.7 (CH), 101.5 ($CH_2$), 73.6 (C), 73.2 (CH), 72.1 (C), 44.8 ($CH_2$), 42.4 (C), 31.6 ($CH_3$), 31.5 ($CH_3$), 31.1 ($CH_3$), 25.3 ($CH_3$), 23.4 ($CH_3$); IR (thin film): 3059, 2986, 2919, 1693, 1504, 1492, 1446, 1366, 1252, 1105 $cm^{-1}$; HRMS (ESI) calculated for $C_{22}H_{23}N_3O_6S_2$ (M-Na) 512.0926, observed 512.0909.

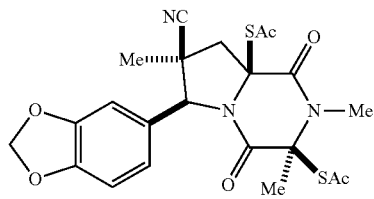

4

S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) diethanethioate (4, all S enantiomer; LEO-16-1845). 1H NMR (600 MHz, CDCl3): δ 6.97 (s, 1H), 6.88 (d, J=8.1 Hz, 1H), 6.84 (d, J=8.1 Hz, 1H), 6.00 (s, 2H), 4.86 (s, 1H), 4.34 (d, J=14.6 Hz, 1H), 3.18 (s, 3H), 2.41-2.37 (m, 7H), 2.10 (s, 3H), 1.70 (s, 3H); 13C NMR (125 MHz, CDCl3): δ 191.9 (C), 191.8 (C), 164.9 (C), 162.8 (C), 148.3 (C), 148.2 (C), 129.2 (C), 120.9 (C), 120.0 (CH), 108.8 (CH), 106.7 (CH), 101.5 (CH2), 73.6 (C), 73.2 (CH), 72.1 (C), 44.8 (CH2), 42.4 (C), 31.6 (CH3), 31.5 (CH3), 31.1 (CH3), 25.3 (CH3), 23.4 (CH3); IR (thin film): 3059, 2986, 2919, 1693, 1504, 1492, 1446, 1366, 1252, 1105 cm-1; $[\alpha]^{22.0}$ D+16.3°, $[\alpha]22.1577+27.2°$, $[\alpha]22.2546+30.7°$, $[\alpha]22.2435+67.2°$ (c=0.4, CHCl3); HRMS (ESI) calculated for C22H23N3O6S2Na (M-Na) 512.0926, observed 512.0909.

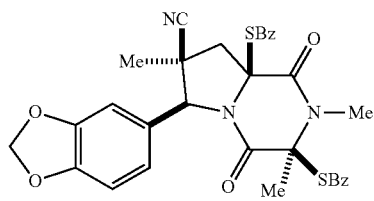

5

Rel-S,S'-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) dibenzothioate (5, LEO-16-1836). Prepared in analogous fashion to compound 4 from a mixture of 2 and 3 (51 mg, ca. 0.12 mmol) and benzoyl chloride (30 μL, 0.26 mmol). Afforded 5 (48 mg, 0.079 mmol, 66% yield) as a colorless solid. $^1$H NMR (600 MHz, CDCl$_3$): δ 7.90 (d, J=7.3 Hz, 2H), 7.87 (d, J=7.3 Hz, 2H), 7.62 (app t, J=7.4 Hz, 1H), 7.55 (app t, J=7.4 Hz, 1H), 7.46 (app t, J=7.7 Hz, 2H), 7.39 (app t, J=7.8 Hz, 2H), 7.01 (s, 1H), 6.92 (d, J=8.0 Hz, 1H), 6.79 (d, J=8.0 Hz, 1H), 5.98 (s, 2H), 4.94 (s, 1H), 4.43 (d, J=14.8 Hz, 1H), 3.29 (s, 3H), 2.59 (d, J=14.8 Hz, 1H), 2.23 (s, 3H), 1.73 (s, 3H); $^{13}$C NMR (125 MHz, CDCl$_3$): δ 188.35 (C), 188.32 (C), 165.1 (C), 163.2 (C), 148.3 (C), 148.2 (C), 137.1 (C), 136.9 (C), 134.2 (CH), 134.0 (CH), 129.2 (C), 129.0 (2CH), 128.9 (2CH), 128.0 (2CH), 127.8 (2CH), 120.8 (C), 120.0 (CH), 108.8 (CH), 107.0 (CH), 101.5 (CH2), 74.0 (C), 73.4 (CH), 72.0 (C), 45.8 (CH2), 42.4 (C), 31.4 (CH3), 25.3 (CH3), 24.2 (CH3); IR (thin film): 1682, 1491, 1446, 1360, 1251, 1200, 1038 cm$^{-1}$; HRMS (ESI) calculated for C$_{32}$H$_{27}$N$_3$O$_6$S$_2$Na (M-Na) 636.1239, observed 636.1212.

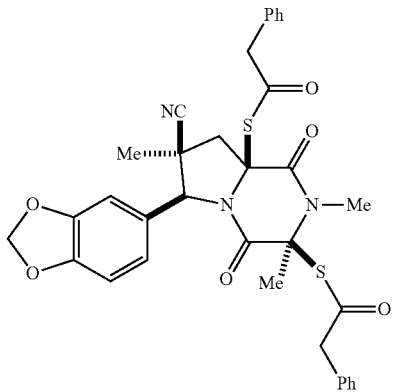

6

Rel-S,S'-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) bis(2-phenylethanethioate) (6, LEO-16-1835). Prepared in analogous fashion to compound 4 from a mixture of 2 and 3 (53 mg, ca. 0.13 mmol) and phenylacetyl chloride (40 μL, 0.30 mmol). Afforded 6 (59 mg, 0.091 mmol, 70% yield) as a colorless foam. $^1$H NMR (600 MHz, CDCl$_3$): δ 7.39 (app t, J=7.4 Hz, 2H), 7.34 (app t, J=6.7 Hz, 2H), 7.31-7.25 (m, 6H), 6.91 (s, 1H), 6.82-6.79 (m, 1H), 6.78 (d, J=8.0 Hz, 1H), 6.03 (d, J=1.3 Hz, 1H), 6.02 (d, J=1.3 Hz, 1H), 4.83 (s, 1H), 4.27 (d, J=14.6 Hz, 1H), 3.88 (d, J=16.1 Hz, 1H), 3.82 (d, J=16.1 Hz, 1H), 3.74 (app s, 2H), 3.09 (s, 3H), 2.36 (d, J=14.6 Hz, 1H), 2.04 (s, 3H), 1.66 (s, 3H); $^{13}$C NMR (125 MHz, CDCl$_3$): δ 193.3 (C), 193.2 (C), 164.9 (C), 162.5 (C), 148.3 (C), 148.2 (C), 132.6 (C), 132.3 (C), 130.3 (2CH), 129.9 (2CH), 129.1 (C), 129.0 (2CH), 128.7 (2CH), 127.9 (CH), 127.8 (CH), 120.9 (C), 120.0 (CH), 108.7 (CH), 106.8 (CH), 101.5 (CH$_2$), 73.8 (C), 73.1 (CH), 71.8 (C), 51.2 (CH$_2$), 50.9 (CH$_2$), 44.9 (CH$_2$), 42.3 (C), 30.9 (CH$_3$), 25.2 (CH$_3$), 23.3 (CH$_3$); IR (thin film): 3062, 3030, 2905, 1690, 1492, 1446, 1361, 1251, 1038 cm$^{-1}$; HRMS (ESI) calculated for C$_{34}$H$_{31}$N$_3$O$_6$S$_2$Na (M-Na), 664.1552, observed 664.1559.

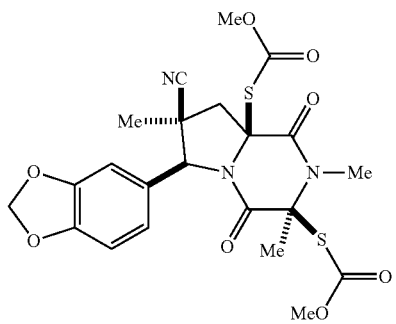

7

Rel-S,S' 4-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) O,O'-dimethyl bis(carbonothioate) (7, LEO-16-1837). Prepared in analogous fashion to compound 4 from a mixture of 2 and 3 (48 mg, ca. 0.12 mmol) and methyl chloroformate (20 μL, 0.26 mmol). Afforded 7 (36 mg, 0.070 mmol, 57% yield) as a colorless solid. $^1$H NMR (500 MHz, CDCl$_3$): δ 6.93 (d, J=1.3 Hz, 1H), 6.89 (dd, J=8.0, 1.3 Hz, 1H), 6.82 (d, J=8.0 Hz, 1H), 5.97 (s, 2H), 4.90 (s, 1H), 4.40 (d, J=14.7 Hz, 1H), 3.85 (s, 3H), 3.79

(s, 3H), 3.16 (s, 3H), 2.42 (d, J=14.7 Hz, 1H), 2.10 (s, 3H), 1.70 (s, 3H); $^{13}$C NMR (125 MHz, CDCl$_3$) δ 166.6 (C), 166.4 (C), 165.2 (C), 162.8 (C), 148.3 (C), 148.2 (C), 129.0 (C), 120.8 (C), 119.9 (CH), 108.7 (CH), 106.8 (CH), 101.5 (CH$_2$), 73.2 (CH), 72.9 (C), 70.9 (C), 54.9 (CH$_3$), 54.8 (CH$_3$), 45.2 (CH$_2$), 42.1 (CH), 30.6 (CH$_3$), 25.3 (CH$_3$), 23.9 (CH$_3$); IR (thin film): 2954, 1729, 1681, 1493, 1446, 1366, 1130 cm$^{-1}$; FIRMS (ESI) calculated for C$_{22}$H$_{23}$N$_3$O$_8$S$_2$Na (M-Na) 544.0825, observed 544.0793.

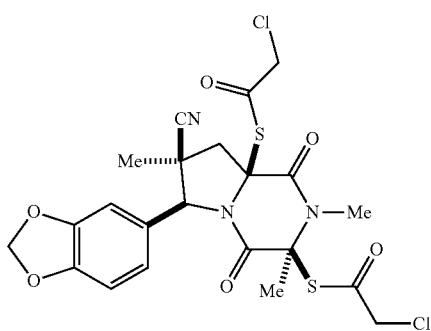

Rel-S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) bis(2-chloroethanethioate) (8, LEO-1840). Disulfide 2 (40 mg, 0.10 mmol) was suspended in degassed THF/EtOH (1:1, 1.0 mL) and cooled in an ice bath. Solid NaBH$_4$ (6.3 mg, 0.17 mmol) was added to the suspension. After 5 min, the cold bath was removed and the reaction was maintained for 30 min. The solvent was removed in vacuo. The residue was suspended in EtOAc (2 mL) and K$_2$CO$_3$ (32 mg, 0.23 mmol) was added. Neat chloroacetyl chloride (20 µL, 0.25 mmol) was added and the reaction was maintained for 30 min. The solution was diluted with distilled H$_2$O (5 mL) and extracted with EtOAc (3×10 mL). Combined extracts were dried over Na$_2$SO$_4$, filtered, and concentrated in vacuo. Flash chromatography (12×150 mm of SiO$_2$, 5% to 10% EtOAc in CH$_2$Cl$_2$) afforded 8 (20 mg, 0.036 mmol, 36% yield) as a colorless solid. $^1$H NMR (600 MHz, CDCl$_3$): δ 6.93 (d, J=1.2 Hz, 1H), 6.87 (dd, J=8.1, 1.2 Hz, 1H), 6.85 (d, J=8.1 Hz, 1H), 6.00 (s, 2H), 4.88 (s, 1H), 4.26 (s, 2H), 4.22 (d, J=14.6 Hz, 1H), 4.18 (s, 2H), 3.19 (s, 3H), 2.47 (d, J=14.6 Hz, 1H), 2.11 (s, 3H), 1.70 (s, 3H); $^{13}$C NMR (150 MHz, CDCl$_3$): P δ 190.1 (C), 189.4 (C), 164.3 (C), 162.4 (C), 148.2 (2C), 128.7 (C), 120.7 (C), 120.0 (CH), 108.9 (CH), 106.7 (CH), 101.6 (CH$_2$), 74.5 (C), 73.4 (CH), 72.5 (CH), 48.3 (CH$_2$), 48.2 (CH$_2$), 45.5 (CH$_2$), 42.4 (C), 31.3 (CH$_3$), 25.1 (CH$_3$), 23.9 (CH$_3$), missing 1C; IR (thin film): 2989, 2939, 2253, 1688, 1365, 1251, 1038, 728 cm$^{-1}$; HRMS (ESI) calculated for C$_{22}$H$_{21}$C$_{12}$N$_3$O$_6$S$_2$Na (M-Na) 580.0146, observed 580.0140.

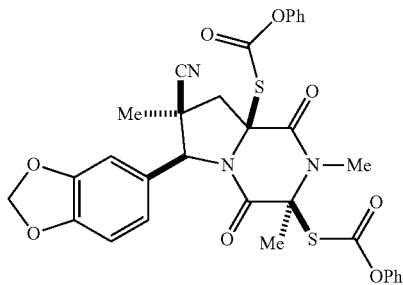

Rel-S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) O,O'-diphenyl bis(carbonothioate) (9, LEO-16-1841). A mixture of 2 and 3 (33 mg, ca. 0.082 mmol) was suspended in degassed THF/EtOH (1:1, 1 mL). The suspension was cooled in an ice bath and NaBH$_4$ (12.6 mg, 0.33 mmol) was added. After 5 min, the cold bath was removed and the reaction was maintained for 1 h. The solvent was removed in vacuo. The crude residue was suspended in anhydrous THF (1 mL) and cooled in an ice bath. To the cooled suspension neat Et$_3$N (50 µL, 0.36 mmol) and phenyl chloroformate (30 µL, 0.24 mmol) were added. After 1 h, the reaction was quenched with sat aq. NaHCO$_3$ (2 mL) and extracted with EtOAc (3×5 mL). Combined extracts were dried over Na$_2$SO$_4$, filtered and concentrated in vacuo. Flash chromatography ((12×150 mm of SiO$_2$, 2% to 5% EtOAc in CH$_2$Cl$_2$) afforded 9 (37 mg, 0.057 mmol, 69% yield) as a colorless solid. $^1$H NMR (500 MHz, CDCl$_3$): δ 7.40 (t, J=7.7 Hz, 4H), 7.32-7.21 (m, 4H), 7.15 (d, J=7.9 Hz, 2H), 7.07 (s, 1H), 7.00 (d, J=8.0 Hz, 1H), 6.89 (d, J=8.0 Hz, 1H), 6.04 (app s, 1H), 6.00 (app s, 1H), 5.00 (s, 1H), 4.49 (d, J=14.8 Hz, 1H), 3.27 (s, 3H), 2.48 (d, J=14.8 Hz, 1H), 2.21 (s, 3H), 1.76 (s, 3H); $^{13}$C NMR (125 MHz, CDCl$_3$): δ 165.3 (C), 165.0 (C), 164.9 (C), 162.5 (C), 150.9 (C), 150.8 (C), 148.4 (C), 148.3 (C), 129.64 (2CH), 129.63 (2CH), 128.9 (C), 126.7 (CH), 126.6 (CH), 121.5 (2CH), 121.2 (2CH), 120.8 (C), 120.1 (CH), 108.8 (CH), 106.8 (CH), 101.5 (CH$_2$), 73.4 (C), 73.3 (CH), 71.5 (C), 45.2 (CH$_2$), 42.2 (C), 30.8 (CH$_3$), 25.2 (CH$_3$), 23.9 (CH$_3$); IR (thin film): 2922, 1742, 1688, 1490, 1362, 1252, 1183, 1160, 1094, 1076 cm$^{-1}$; HRMS (ESI) calculated for C$_{32}$H$_{27}$N$_3$O$_8$S$_2$Na (M-Na) 668.1137, observed 668.1145.

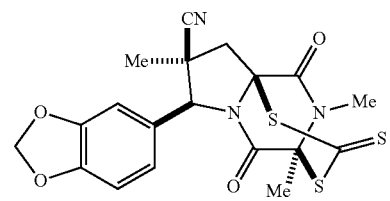

Rel-(4S,7S,8S,9aS)-7-(benzo[d][1,3]dioxol-5-yl)-4,8,11-trimethyl-5,10-dioxo-2-thioxotetrahydro-7H-4,9a-(epiminomethano)pyrrolo[2,1-d][1,3,5]dithiazepine-8-carbonitrile (10, LEO-16-1842). Prepared in analogous fashion to compound 9 from a mixture of 2 and 3 (36 mg, ca. 0.089 mmol) and phenyl chlorothionoformate (30 µL, 0.22 mmol). Afforded 10 (25 mg, 0.56 mmol, 63% yield) as a yellow solid. $^1$H NMR (600 MHz, CDCl$_3$): δ 6.83 (d, J=8.0 Hz, 1H), 6.71 (d, J=8.0 Hz, 1H), 6.69 (s, 1H), 5.98 (s, 2H), 4.91 (s, 1H), 3.12 (s, 3H), 3.10-3.06 (m, 2H), 1.89 (s, 3H), 1.70 (s, 3H); $^{13}$C NMR (125 MHz, CDCl$_3$): δ 214.0 (C), 164.6 (C), 161.4 (C), 148.7 (C), 148.5 (C), 127.6 (C), 120.3 (CH), 119.9 (C), 109.0 (CH), 106.8 (CH), 101.7 (CH$_2$), 75.0 (C), 73.6 (CH), 73.1 (C), 45.9 (CH$_2$), 43.2 (C), 28.7 (CH$_3$), 25.1 (CH$_3$), 19.9 (CH$_3$); IR (thin film): 2985, 2940, 2901, 2251, 1693, 1504, 1490, 1446, 1367, 1251, 1037 cm$^{-1}$; HRMS (ESI) calculated for C$_{19}$H$_{17}$N$_3$O$_4$S$_3$Na (M-Na) 470.0279, observed 470.0290.

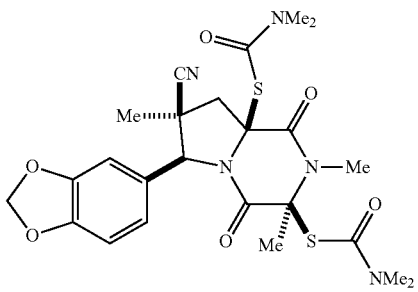

11

Rel-S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) bis(dimethylcarbamothioate) (11, LEO-16-1843). Prepared in analogous fashion to compound 9 from a mixture of 2 and 3 (29 mg, ca. 0.072 mmol) and phenyl chlorothionoformate (20 μL, 0.22 mmol). Afforded 11 (13 mg, 0.024 mmol, 33% yield) as a colorless solid. $^1$H NMR (500 MHz, CDCl$_3$): δ 7.05 (s, 1H), 6.90 (d, J=8.1 Hz, 1H), 6.81 (d, J=8.1 Hz, 1H), 5.97 (app s, 1H), 5.96 (app s, 1H), 4.90 (s, 1H), 4.61 (d, J=14.6 Hz, 1H), 3.21 (s, 3H), 2.08-2.94 (m, 12H), 2.37 (d, J=14.6 Hz, 1H), 2.10 (s, 3H), 1.69 (s, 3H); $^{13}$C NMR (125 MHz, CDCl$_3$): δ 165.4 (C), 163.89 (C), 163.88 (C), 163.7 (C), 148.1 (C), 148.0 (C), 129.7 (C), 121.0 (C), 120.2 (CH), 108.6 (CH), 107.0 (CH), 101.3 (CH$_2$), 73.5 (C), 73.3 (CH), 71.8 (C), 45.3 (CH$_2$), 42.2 (C), 37.2 (CH$_3$), 31.0 (2CH$_3$), 29.8 (2CH$_3$), 25.4 (CH$_3$), 24.4 (CH$_3$); IR (thin film): 2933, 2237, 1681, 1359, 1252, 1097, 1036 cm$^{-1}$; FIRMS (ESI) calculated for C$_{24}$H$_{29}$N$_5$O$_6$S$_2$Na (M-Na) 570.1457, observed 570.1443.

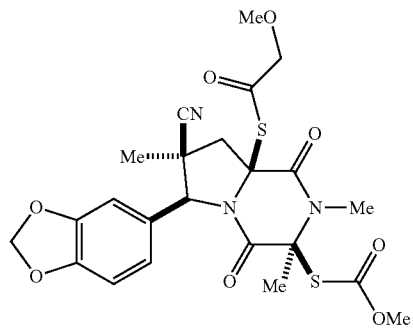

12

Rel-S,S'-((3S,6S,7S,8aS)-6-(benzo[d][1,3]dioxol-5-yl)-7-cyano-2,3,7-trimethyl-1,4-dioxohexahydropyrrolo[1,2-c]pyrazine-3,8a(6H)-diyl) bis(2-methoxyethanethioate) (12, LEO-16-1844). A mixture of 2 and 3 (33 mg, ca. 0.080 mmol) was suspended in degassed THF/EtOH (1:1, 1 mL). The suspension was cooled in an ice bath and NaBH$_4$ (12.1 mg, 0.32 mmol) was added. After 5 min, the cold bath was removed and the reaction was maintained for 1.5 h. The solvent was removed in vacuo. The crude residue was suspended in anhydrous THF (1 mL) and cooled in a −78° C. bath. To the cooled suspension neat Et$_3$N (40 μL, 0.29 mmol) and 2-methoxyacetyl chloride (20 μL, 0.22 mmol) were added. After 1 h, the reaction was quenched with sat aq. NaHCO$_3$ (2 mL) and extracted with EtOAc (3×5 mL). Combined extracts were dried over Na$_2$SO$_4$, filtered and concentrated in vacuo. Flash chromatography (12×150 mm of SiO$_2$, 2% to 5% EtOAc in CH$_2$Cl$_2$) afforded 12 (26 mg, 0.047 mmol, 58% yield) as a colorless solid. $^1$H NMR (500 MHz, CDCl$_3$): δ 6.97 (s, 1H), 6.88 (d, J=8.0 Hz, 1H), 6.82 (d, J=8.0 Hz, 1H), 5.98 (S, 2H), 4.88 (S, 1H), 4.34 (d, J=14.7 Hz, 1H), 4.15 (d, J=16.3 Hz, 1H), 4.13-4.01 (m, 3H), 3.54 (s, 3H), 3.49 (s, 3H), 3.16 (s, 3H), 2.44 (d, J=14.7 Hz, 1H), 2.09 (s, 3H), 1.70 (s, 3H). $^{13}$C NMR (125 MHz, CDCl$_3$): δ 196.18 (C), 196.17 (C), 165.0 (C), 162.9 (C), 148.3 (C), 148.2 (C), 129.2 (C), 121.0 (C), 120.0 (CH), 108.7 (CH), 106.7 (CH), 101.5 (CH$_2$), 77.8 (CH$_2$), 77.7 (CH$_2$), 73.3 (C), 73.1 (CH), 71.1 (C), 60.44 (CH$_3$), 60.43 (CH$_3$), 44.9 (CH$_2$), 42.3 (C), 31.0 (CH$_2$), 25.3 (CH$_3$), 23.8 (CH$_3$); IR (thin film): 2992, 2935, 2830, 2253, 1693, 1492, 1446, 1364, 1251, 1196, 1123, 1038 cm$^{-1}$; FIRMS (ESI) calculated for C$_{24}$H$_{27}$N$_3$O$_8$S$_2$Na (M-Na) 572.1137, observed 572.1130.

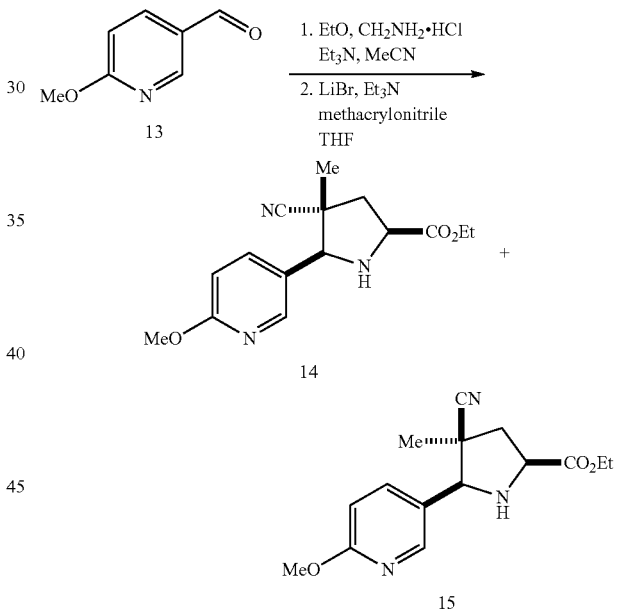

Ethyl Rel-(2S,4R,5S)-4-cyano-5-(6-methoxypyridin-3-yl)-4-methylpyrrolidine-2-carboxylate (14) and ethyl Rel-(2S,4S,5S)-4-cyano-5-(6-methoxypyridin-3-yl)-4-methylpyrrolidine-2-carboxylate (15). A 100 mL round-bottom flask was charged with 2-methoxypyridine-5-carbaldehyde (13, 1.33 g, 9.92 mmol) and glycine ethyl ester hydrochloride (1.66 g, 11.9 mmol) and MeCN (20 mL). To the suspension was added Et$_3$N (1.5 mL, 10.8 mmol) and the mixture was stirred vigorously for 16 h. The solvent was removed in vacuo and the crude residue was diluted with H$_2$O (20 mL) and extracted with CH$_2$Cl$_2$ (3×20 mL). Combined organic extracts were dried over Na$_2$SO$_4$, filtered through cotton, and concentrated in vacuo. The crude imine (2.11 g, 9.49 mmol, 96% yield) was dissolved in anhydrous THF (16 mL) under Ar. To the suspension was added LiBr (990 mg, 11.4 mmol) and Et$_3$N (1.6 mL, 11.5 mmol). After 2 min, methacrylonitrile (1.2 mL, 14.3 mmol) was added to the solution and the reaction was maintained for 16 h. The reaction was concentrated in vacuo. The residue was diluted with brine (20 mL) and extracted with $CH_2Cl_2$ (3×20 mL). The combined organic extracts were dried over $Na_2SO_4$, filtered through cotton, and concentrated in vacuo. Flash chromatography (28×250 mm of $SiO_2$, 20% to 50% EtOAc in hexanes) afforded pyrrolidine ester 14 (300 mg, 1.04 mmol, 11% yield) as a colorless solid and pyrrolidine ester 15 (1.74 g, 6.01 mmol, 63% yield) as a pale yellow oil. Data for 14: $^1$H NMR (600 MHz, $CDCl_3$): δ 8.24 (d, J=2.5 Hz, 1H), 7.70 (dd, J=8.6, 2.5 Hz, 1H), 6.76 (d, J=8.7 Hz, 1H), 4.54 (s, 1H), 4.25 (q, J=7.1 Hz, 2H), 4.06 (app t, J=7.3 Hz, 1H), 3.94 (s, 3H), 2.75 (dd, J=13.5, 9.7 Hz, 1H), 2.60 (br s, 1H), 2.25 (dd, J=13.5, 6.1 Hz, 1H), 1.31 (t, J=7.1 Hz, 3H), 1.03 (s, 3H); $^{13}$C NMR (125 MHz, $CDCl_3$): δ 173.0 (C), 164.5 (C), 145.9 (CH), 137.8 (CH), 125.1 (C), 123.8 (C), 110.9 (CH), 67.3 (CH), 61.7 ($CH_2$), 57.2 (CH), 53.7 ($CH_3$), 41.5 ($CH_2$), 40.2 (C), 20.5 ($CH_3$), 14.3 ($CH_3$); IR (thin film): 3344, 2983, 2947, 2904, 2850, 2235, 1737, 1608, 1495, 1285, 1202, 1028 $cm^{-1}$; FIRMS (ESI) calculated for $C_{15}H_{19}N_3O_3$ (M-Na) 312.1324, observed 312.1316. Data for 15: $^1$H NMR (600 MHz, $CDCl_3$): δ 8.12 (d, J=2.5 Hz, 1H), 7.96 (dd, J=8.6, 2.5 Hz, 1H), 6.81 (d, J=8.7 Hz, 1H), 4.33-4.23 (m, 2H), 3.97 (dd, J=9.7, 4.1 Hz, 1H), 3.93 (s, 3H), 3.90 (s, 1H), 2.83 (dd, J=13.7, 4.1 Hz, 1H), 2.69 (br s, 1H), 2.28 (dd, J=13.7, 9.7 Hz, 1H), 1.40 (s, 3H), 1.33 (t, J=7.1 Hz, 3H); $^{13}$C NMR (125 MHz, $CDCl_3$): δ 172.9 (C), 164.9 (C), 146.5 (CH), 137.7 (CH), 125.1 (C), 121.9 (C), 111.3 (CH), 69.7 (CH), 61.8 ($CH_2$), 57.3 (CH), 53.7 ($CH_3$), 43.8 (C), 42.1 ($CH_2$), 21.9 ($CH_3$), 14.3 ($CH_3$); IR (thin film): 3346, 2981, 2948, 2904, 2878, 2850, 2235, 1736, 1609, 1495, 1285, 1205, 1028 $cm^{-1}$; HRMS (ESI) calculated for $C_{15}H_{19}N_3O_3$ (M-Na) 312.1324, observed 312.1329.

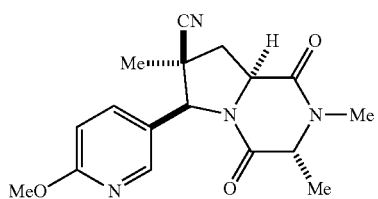

16

Rel-(3R,6S,7S,8aS)-6-(6-methoxypyridin-3-yl)-2,3,7-trimethyl-1,4-dioxooctahydropyrrolo[1,2-c]pyrazine-7-carbonitrile (16). In a 100 mL round bottom flask, pyrrolidine ester 15 (1.28 g, 4.42 mmol) was dissolved in anhydrous $CH_2Cl_2$ (15 mL). The solution was cooled in an ice bath. To the solution was added $Et_3N$ (740 μL, 5.3 mmol) and 2-chloropropionyl chloride (470 μL, 4.9 mmol). The reaction was maintained for 1 h, by which time starting material had been consumed (by TLC). The reaction was quenched with $H_2O$ (10 mL) and the biphasic mixture was stirred vigorously for 10 min. The biphasic mixture was extracted with $CH_2Cl_2$ (3×20 mL). The organic layer was concentrated in vacuo. The crude residue was dissolved in $CH_2Cl_2$ (20 mL) and a solution of $MeNH_2$ (40% in $H_2O$) and the biphasic mixture was stirred vigorously for 12 h. The mixture was extracted with $CH_2Cl_2$ (3×20 mL). Combined extracts were dried over $Na_2SO_4$, filtered through cotton, and concentrated in vacuo to afford a yellow foam. The residue was dissolved in $CH_2Cl_2$ (10 mL) and MeOH (10 mL). The solution was stirred under a stream of air until ca. 4 mL of solution remained. The suspension was cooled in the freezer for 18 h. Filtration afforded diketopiperazine 16 (490 mg, 1.50 mmol, 34% yield as a colorless solid. $^1$H NMR (600 MHz, $CDCl_3$): δ 7.97 (d, J=2.6 Hz, 1H), 7.37 (dd, J=8.6, 2.6 Hz, 1H), 6.76 (d, J=8.6 Hz, 1H), 4.87 (s, 1H), 4.37 (dd, J=11.3, 6.6 Hz, 1H), 3.92 (s, 3H), 3.89 (q, J=7.3 Hz, 1H), 3.03 (s, 3H), 2.77 (dd, J=13.4, 11.4 Hz, 1H), 2.50 (dd, J=13.4, 6.6 Hz, 1H), 1.69 (s, 3H), 1.48 (d, J=7.3 Hz, 3H); $^{13}$C NMR (125 MHz, $CDCl_3$): δ 166.8 (C), 165.9 (C), 164.7 (C), 144.8 (CH), 136.9 (CH), 125.4 (C), 119.9 (C), 111.5 (CH), 67.4 (CH), 60.9 (CH), 56.2 (CH), 53.7 ($CH_3$), 42.5 (C), 36.9 ($CH_2$), 32.2 ($CH_3$), 25.1 ($CH_3$), 15.5 ($CH_3$); IR (thin film): 2983, 2946, 2245, 1673, 1609, 1494, 1402, 1288, 1026 $cm^{-1}$; HRMS (ESI) calculated for $C_{17}H_{20}N_4O_3Na$ (M-Na) 351.1433, observed 351.1430.

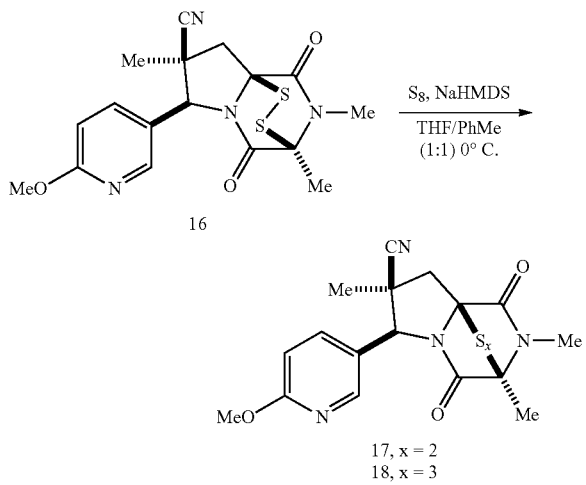

Rel-(3S,6S,7S,8aS)-6-(6-methoxypyridin-3-yl)-2,3,7-trimethyl-1,4-dioxohexahydro-6H-3,8a-epidithiopyrrolo[1,2-c]pyrazine-7-carbonitrile (17) and Rel-(3S,6S,7S,8aS)-6-(6-methoxypyridin-3-yl)-2,3,7-trimethyl-1,4-dioxohexahydro-6H-3,8a-epitrithiopyrrolo[1,2-c]pyrazine-7-carbonitrile (18). A 25 mL round bottom flask was charged with diketopiperazine 16 (120 mg, 0.37 mmol) and $S_8$ (100 mg, 0.39 mmol) and anhydrous THF (3.7 mL) under Ar. The suspension was cooled in an ice bath. A solution of NaHMDS (0.6 M in PhMe, 3.7 mL, 2.2 mmol) was added over 2 min. The reaction was maintained for 2 h and quenched with saturated aqueous $NH_4Cl$ (5 mL). The mixture was extracted with EtOAc (3×10 mL). The combined organic extracts were dried over $Na_2SO_4$, filtered, and concentrated in vacuo. Flash chromatography (30×250 mm of $SiO_2$, 5% to 10% acetone in $CH_2Cl_2$) afforded a mixture of 17 and 18 (68 mg, 0.17 mmol, ca. 47% yield) as a yellow solid. Data for 17: $^1$H NMR (600 MHz, $CDCl_3$): δ 8.16 (d, J=2.4 Hz, 1H), 7.64 (dd, J=8.6, 2.4 Hz, 1H), 6.84 (d, J=8.6 Hz, 1H), 4.86 (s, 1H), 3.96 (s, 3H), 3.31 (d, J=15.0 Hz, 1H), 3.08 (s, 3H), 3.00 (d, J=15.0 Hz, 1H), 1.94 (s, 3H), 1.69 (s, 3H); $^{13}$C NMR (125 MHz, $CDCl_3$): δ 165.5 (C), 165.0 (C), 162.1 (C), 145.5 (CH), 137.3 (CH), 122.5 (C), 120.2 (C), 111.7 (CH), 73.44 (C), 73.43 (C), 69.9 (CH), 53.8 ($CH_3$), 44.4 (C), 42.9 ($CH_2$), 27.9 ($CH_3$), 24.4 ($CH_3$), 18.2 ($CH_3$); IR (thin film): 2985, 2947, 2903, 2251, 1694, 1610, 1496, 1359, 1288, 1026 $cm^{-1}$; HRMS (ESI) calculated for $C_{17}H_{18}N_4O_3S_2Na$ (M-Na) 413.0718, observed 413.0716.

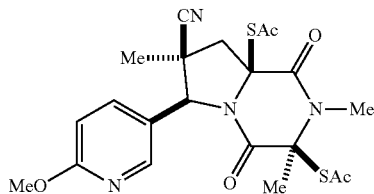

19

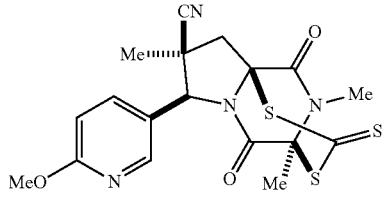

21

Rel-S,S'-((3S,6S,7S,8aS)-7-cyano-6-(6-methoxypyridin-3-yl)-2,3,7-trimethyl-1,4-dioxohexahydropyrrolo[1,2-c]pyrazine-3,8a(6H)-diyl) diethanethioate (19, LEO-16-1839). Prepared in analogous fashion to compound 5 from a mixture of 17 and 18 (52 mg, ca. 0.13 mmol) and acetic anhydride (40 μL, 0.42 mmol). Afforded 18 (37 mg, 0.078 mmol, 58% yield) as a colorless solid. $^1$H NMR (600 MHz, CDCl$_3$): δ 8.25 (d, J=2.5 Hz, 1H), 7.76 (dd, J=8.6, 2.5 Hz, 1H), 6.83 (d, J=8.6 Hz, 1H), 4.90 (s, 1H), 4.39 (d, J=14.6 Hz, 1H), 3.96 (s, 3H), 3.17 (s, 3H), 2.42 (d, J=14.6 Hz, 1H), 2.40 (s, 3H), 2.35 (s, 3H), 2.08 (s, 3H), 1.69 (s, 3H); $^{13}$C NMR (150 MHz, CDCl$_3$): δ 191.9 (C), 191.7 (C), 164.8 (C), 164.7 (C), 162.8 (C), 145.5 (CH), 137.0 (CH), 124.0 (C), 120.8 (C), 111.5 (CH), 73.6 (C), 72.0 (C), 71.1 (CH), 53.8 (CH$_3$), 44.7 (CH$_2$), 42.3 (C), 31.50 (CH$_3$), 31.48 (CH$_3$), 31.0 (CH$_3$), 25.1 (CH$_3$), 23.7 (CH$_3$); IR (thin film): 2980, 2923, 2850, 2361, 1686, 1610, 1496, 1365, 1288, 1109 cm$^{-1}$; HRMS (ESI) calculated for C$_{21}$H$_{24}$N$_4$O$_5$S$_2$Na (M-Na) 499.1086, observed 499.1077.

Rel-(4S,7S,8S,9aS)-7-(6-methoxypyridin-3-yl)-4,8,11-trimethyl-5,10-dioxo-2-thioxotetrahydro-7H-4,9a-(epiminomethano)pyrrolo[2,1-d][1,3,5]dithiazepine-8-carbonitrile (21, LEO-16-1858). Prepared in analogous fashion to compound 9 from a mixture of 17 and 18 (54 mg, ca. 0.14 mmol) and phenyl chlorothionoformate (30 μL, 0.22 mmol). Afforded 21 (22 mg, 0.56 mmol, 36% yield) as a yellow solid. $^1$H NMR (600 MHz, CDCl$_3$): δ 8.15 (d, J=2.5 Hz, 1H), 7.49 (dd, J=8.7, 2.5 Hz, 1H), 6.86 (d, J=8.7 Hz, 1H), 5.01 (s, 1H), 3.99 (s, 3H), 3.18-3.14 (m, 5H), 1.94 (s, 3H), 1.76 (s, 3H); $^{13}$C NMR (150 MHz, CDCl$_3$): δ 213.7 (C), 165.0 (C), 164.5 (C), 161.5 (C), 145.6 (CH), 136.7 (CH), 122.6 (C), 119.7 (C), 112.0 (CH), 75.0 (C), 73.0 (C), 71.3 (CH), 53.9 (CH$_3$), 45.8 (CH$_2$), 43.0 (C), 28.7 (CH$_3$), 24.7 (CH$_3$), 19.9 (CH$_3$); IR (thin film): 2985, 2946, 2240, 1690, 1495, 1369, 1288, 1002, 731 cm$^{-1}$; HRMS (ESI) calculated for C$_{18}$H$_{18}$N$_4$O$_3$S$_3$Na (M-Na) 457.0439, observed 457.0425.

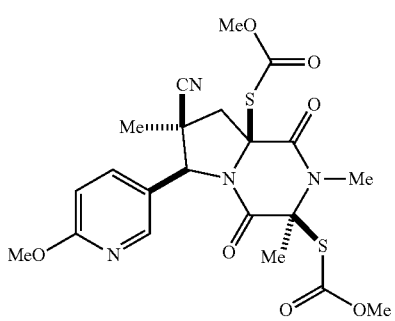

20

Rel-S,S'-((3S,6S,7S,8aS)-7-cyano-6-(6-methoxypyridin-3-yl)-2,3,7-trimethyl-1,4-dioxohexahydropyrrolo[1,2-c]pyrazine-3,8a(6H)-diyl) O,O'-dimethyl bis(carbonothioate) (20, LEO-16-1857). Prepared in analogous fashion to compound 7 from a mixture of 17 and 18 (55 mg, 0.14 mmol) and methyl chloroformate (30 μL, 0.39 mmol). Afforded 20 (44 mg, 0.087 mmol, 61% yield) as a colorless solid. $^1$H NMR (600 MHz, CDCl$_3$): δ 8.22 (d, J=2.5 Hz, 1H), 7.77 (dd, J=8.7, 2.5 Hz, 1H), 6.80 (d, J=8.7 Hz, 1H), 4.94 (s, 1H), 4.45 (d, J=14.8 Hz, 1H), 3.94 (s, 3H), 3.86 (s, 3H), 3.78 (s, 3H), 3.16 (s, 3H), 2.45 (d, J=14.8 Hz, 1H), 2.09 (s, 3H), 1.70 (s, 3H); $^{13}$C NMR (150 MHz, CDCl$_3$): δ166.5 (C), 166.4 (C), 165.1 (C), 164.7 (C), 163.0 (C), 145.6 (CH), 136.9 (CH), 123.9 (C), 120.7 (C), 111.5 (CH), 72.9 (C), 71.2 (CH), 70.9 (C), 55.0 (CH$_3$), 54.8 (CH$_3$), 53.7 (CH$_3$), 45.1 (CH$_2$), 42.0 (C), 30.6 (CH$_3$), 25.0 (CH$_3$), 24.1 (CH$_3$); IR (thin film): 2984, 2954, 2255, 1731, 1688, 1496, 1366, 1289, 1190, 1129 cm$^{-1}$; HRMS (ESI) calculated for C$_{21}$H$_{24}$N$_4$O$_7$S$_2$Na (M-Na) 531.0984, observed 531.1003.

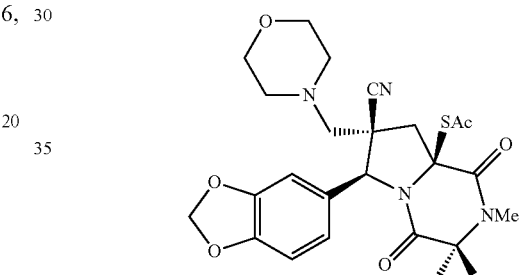

Leo-16-1862 v(R, S, S, S)-enantiomer. 1H NMR (600 MHz, CDCl3): δ 7.11 (d, J=1.9 Hz, 1H), 7.00 (dd, J=8.1, 1.9 Hz, 1H), 6.89 (d, J=8.1 Hz, 1H), 6.06 (s, br, 1H), 5.07 (s, 1H), 4.33 (d, J=14.3 Hz, 1H), 3.77-3.73 (m, 4H), 3.25 (s, 3H), 2.96 (d, J=14.1 Hz, 1H), 2.83 (d, J=14.1 Hz, 1H), 2.76-2.72 (m, 4H), 2.56 (d, J=14.3 Hz, 1H), 2.48 (s, 3H), 2.43 (s, 3H), 2.16 (s, 3H). HRMS (ESI) calculated for C$_{26}$H$_{30}$N$_4$O$_7$S$_2$Na (M-Na) 597.1454, observed 597.1446.

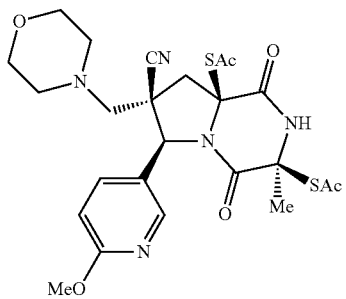

Leo-16-1866 (racemate). 1H NMR (600 MHz, CDCl3): δ 8.36 (d, J=2.5 Hz, 1H), 7.92 (dd, J=8.7, 12.5 Hz, 1H), 6.87 (d, J=8.7 Hz, 1H), 5.15 (s, 1H), 4.36 (d, J=14.5 Hz, 1H), 4.01

(s, 3H), 3.76-3.73 (m, 4H), 3.23 (s, 3H), 2.90 (d, J=14.0 Hz, 1H), 2.86 (d, J=14.0 Hz, 1H), 2.73-2.71 (m, 4H), 2.56 (d, J=14.5 Hz, 1H), 2.47 (s, 3H), 2.41 (s, 3H), 2.14 (s, 3H). HRMS (ESI) calculated for $C_{25}H_{31}N_5O_6S_2Na$ (M-Na) 584.1614, observed 584.1619.

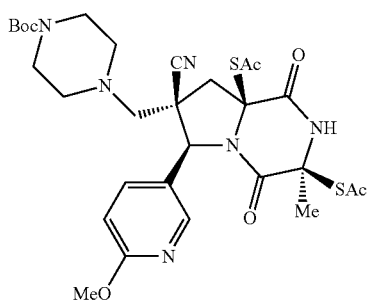

Leo-16-1867 (racemate). 1H NMR (600 MHz, CDCl3): δ 8.36 (d, J=2.5 Hz, 1H), 7.91 (dd, J=8.8, 2.5 Hz, 1H), 6.87 (d, J=8.8 Hz, 1H), 5.15 (s, 1H), 4.35 (d, J=14.0 Hz, 1H), 4.01 (s, 3H), 3.51-3.46 (m, 4H), 3.23 (s, 3H), 2.91 (d, J=13.8 Hz, 1H), 2.88 (d, J=13.8 Hz, 1H), 2.69-2.64 (m, 4H), 2.56 (d, J=14.0 Hz, 1H), 2.47 (s, 3H), 2.40 (s, 3H), 2.13 (s, 3H), 1.51 (s, 9H). HRMS (ESI) calculated for $C_{30}H_{40}N_6O_7S_2Na$ (M-Na) 683.2297, observed 683.2299.

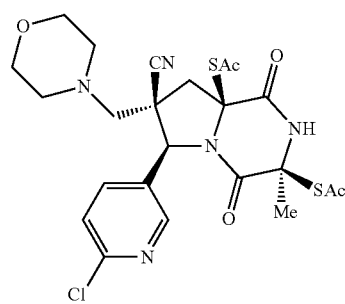

Leo-16-1868 (racemate). 1H NMR (600 MHz, CDCl3): δ 8.66 (d, J=2.7 Hz, 1H), 8.05 (dd, J=8.3, 2.7 Hz, 1H), 7.47 (d, J=8.3 Hz, 1H), 5.25 (s, 1H), 4.40 (d, J=14.6 Hz, 1H), 3.79-3.74 (m, 4H), 3.23 (s, 3H), 2.91 (d, J=14.7 Hz, 1H), 2.88 (d, J=14.7 Hz, 1H), 2.74-2.70 (m, 4H), 2.54 (d, J=14.6 Hz, 1H), 2.46 (s, 3H), 2.42 (s, 3H), 2.13 (s, 3H). HRMS (ESI) calculated for $C_{24}H_{28}ClN_5O_5S_2Na$ (M-Na) 588.1118, observed 588.1125.

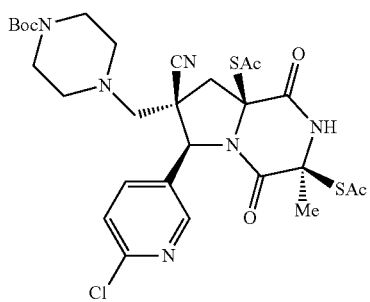

Leo-16-1869 (racemate). 1H NMR (600 MHz, CDCl3): δ 8.28 (d, J=2.8 Hz, 1H), 8.04 (dd, J=8.5, 2.8 Hz, 1H), 7.27 (d, J=8.5 Hz, 1H), 5.25 (s, 1H), 4.39 (d, J=14.7 Hz, 1H), 3.52-3.46 (m, 4H), 3.22 (s, 3H), 2.90 (t, J=13.9 Hz, 2H), 2.68-2.64 (m, 4H), 2.53 (d, J=14.7 Hz, 1H), 2.45 (s, 3H), 2.42 (s, 3H), 2.13 (s, 3H), 2.10 (s, 9H). HRMS (ESI) calculated for $C_{29}H_{37}ClN_6O_6S_2Na$ (M-Na) 687.1802, observed 687.1811.

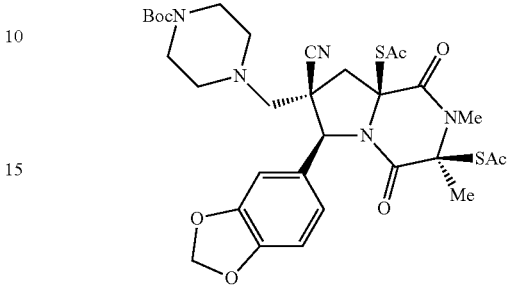

Leo-17-1876 (S, R, R, R)-enantiomer). 1H NMR (600 MHz, CDCl3): δ 7.10 (d, J=1.9 Hz, 1H), 6.98 (dd, J=8.0, 1.9 Hz, 1H), 6.88 (d, J=8.0 Hz, 1H), 6.05 (d, J=1.6 Hz, 1H), 6.04 (d, J=1.6 Hz, 1H), 5.06 (s, 1H), 4.31 (d, J=14.8 Hz, 1H), 3.48-3.46 (m, 4H), 3.24 (s, 3H), 2.95 (d, J=13.7 Hz, 1H), 2.84 (d, J=13.7 Hz, 1H), 2.69-2.66 (m, 4H), 2.55 (d, J=14.8 Hz, 1H), 2.46 (s, 3H), 2.42 (s, 3H), 2.14 (s, 3H), 1.50 (s, 9H). HRMS (ESI) calculated for $C_{31}H_{39}N_5O_8S_2Na$ (M-Na) 696.2138, observed 696.2135.

Example 3. Inhibition of Cutaneous T-Cell Lymphoma (CTCL) in Mice by S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) diethanethioate NSG (NOD. Cg-Prkdcscid Il2rgtm1Wjl/SzJ) mice (5 to 7 weeks of age) were obtained from an-animal in-house breeding facility. The facility mice stock derived from mice obtained from Jackson Laboratory. All animal experiments were conducted in accordance with protocol approved by the City of Hope Beckman Research Institute IACUC.

CTCL tumor model: 3 million of Hut 78 cells in 100 μl (cells in PBS:Matrigel=1:1) injected subcutaneously.

The compound stock of 60 mg/ml was made in DMSO and diluted to 2 mg/ml in 30% Solutol. The compound was administered orally (by gavage) at 10 μl per gram of mice body weight in a dose of 20 mg/kg for 3 consecutive days/week.

100 μl of 3×10⁶ Hut78 cells were injected subcutaneously into mice left flanks. The treatments were initiated when the tumor size reached approximately 200 mm³. The compound or the vehicle alone were administered for 3 consecutive days/week.

The obtained results have shown a significant effect of the compound on the mice tumor size. The data demonstrated 86.5% inhibition of the tumor size after the treatment with the compound.

EMBODIMENTS

Embodiment P1. A compound having the formula:

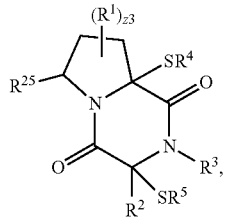

(I)

or a pharmaceutically acceptable salt thereof,
wherein:
$R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —C(O)$OR^{1A}$, —C(O)$NR^{1B}R^{1C}$, —$NO_2$, —$SR^{1D}$, —$S(O)_{n1}R^{1B}$, —$SO_{v1}NR^{1B}R^{1C}$, —$NHNR^{1B}R^{1C}$, —$ONR^{1B}R^{1C}$, —NHC(O)$NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$CF_3$, —$CCl_3$, —$CBr_3$, —$CI_3$, —CN, —CHO, —$COOR^{2A}$, —$CONR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_{n3}R^{3B}$, —$SO_{v3}NR^{3B}R^{3C}$, —$NHNR^{3B}R^{3C}$, —$ONR^{3B}R^{3C}$, —NHC(O)$NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is —C(O)-$L^1$-$R^{18}$ or —C(S)-$L^1$-$R^{18}$;
$R^5$ is —C(O)-$L^2$-$R^{19}$ or —C(S)-$L^2$-$R^{19}$; or
$R^4$ and $R^5$ may optionally be joined to form

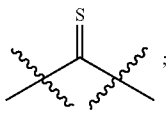 [SMILES: *C(*)=S]

;

$L^1$ is a bond, —O—, —NH—, substituted or unsubstituted alkylene, substituted or unsubstituted heteroalkylene;
$L^2$ is a bond, —O—, —NH—, substituted or unsubstituted alkylene, substituted or unsubstituted heteroalkylene;
$R^{18}$ and $R^{19}$ are independently halogen, substituted or unsubstituted $C_1$-$C_3$alkyl, substituted or unsubstituted aryl;
$R^{25}$ is hydrogen, halogen, —$N_3$, —$CF_3$, —$CCl_3$, —$CBr_3$, —$CI_3$, —CN, —CHO, —$OR^{25A}$, —$NR^{25B}R^{25C}$, —C(O)$OR^{25A}$, —C(O)$NR^{25B}R^{25C}$, —$NO_2$, —$SR^{25D}$, —$S(O)_{n25}R^{25B}$, —$SO_{v25}NR^{25B}R^{25C}$, —$NHNR^{25B}R^{25C}$, $ONR^{25B}R^{25C}$, —NHC(O)$NHNR^{25B}R^{25C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{25A}$, $R^{25B}$, $R^{25C}$, and $R^{25D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl or substituted or unsubstituted heteroaryl;

z3 is an integer from 0 to 5;
n1, n3, and n25 are independently an integer from 0 to 4; and
v1, v3, and v25 are independently 1 or 2.

Embodiment P2. The compound of embodiment P1, wherein the compound has the formula:

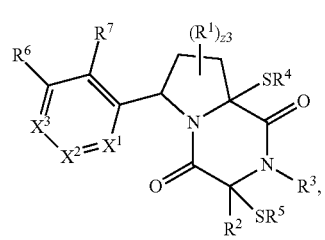

(II)

or a pharmaceutically acceptable salt thereof,
wherein:
$X^1$ is N or $CR^{10}$;
$X^2$ is N or $CR^{11}$;
$X^3$ is N or $CR^{12}$;
$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{v6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —$CONR^{7B}R^{7C}$, —$NO_2$, —$SR^{7D}$, —$SO_{n7}R^{7B}$, —$SO_{v7}NR^{7B}R^{7C}$, —$NHNR^{7B}R^{7C}$, —$ONR^{7B}R^{7C}$, —NHC(O)$NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $—N_3$, $—CF_3$, $—CCl_3$, $—CBr_3$, $—CI_3$, $—CN$, $—CHO$, $—OR^{10A}$, $—NR^{10B}R^{10C}$, $—COOR^{10A}$, $—CONR^{10B}R^{10C}$, $—NO_2$, $—SR^{10D}$, $—SO_{n10}R^{10B}$, $—SO_{v10}NR^{10B}R^{10C}$, $—NHNR^{10B}R^{10C}$, $—ONR^{10B}R^{10C}$, $—NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $—N_3$, $—CF_3$, $—CCl_3$, $—CBr_3$, $—CI_3$, $—CN$, $—CHO$, $—OR^{11A}$, $—NR^{11B}R^{11C}$, $—COOR^{11A}$, $—CONR^{11B}R^{11C}$, $—NO_2$, $—SR^{11D}$, $—SO_{n11}R^{11B}$, $—SO_{v11}NR^{11B}R^{11C}$, $—NHNR^{11B}R^{11C}$, $—ONR^{11B}R^{11C}$, $—NHC(O)NHNR^{11B}R^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ may optionally be joined to form a substituted or unsubstituted cycloalkyl, substituted or unsubstituted heterocycloalkyl;

$R^{12}$ is hydrogen, halogen, $—N_3$, $—CF_3$, $—CCl_3$, $—CBr_3$, $—CI_3$, $—CN$, $—CHO$, $—OR^{12A}$, $—NR^{12B}R^{12C}$, $—COOR^{12A}$, $—CONR^{12B}R^{12C}$, $—NO_2$, $—SR^{12D}$, $—SO_{n12}R^{12B}$, $—SO_{v12}NR^{12B}R^{12C}$, $—NHNR^{12B}R^{12C}$, $—ONR^{12B}R^{12C}$, $—NHC(O)NHNR^{12B}R^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R" and $R^{12}$ may optionally be joined to form a substituted or unsubstituted cycloalkyl, substituted or unsubstituted heterocycloalkyl;

$R^{6A}$, $R^{6B}$, $R^{6C}$, $R^{6D}$, $R^{7A}$, $R^{7B}$, $R^{7C}$, $R^{7D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen, halogen, $—CF_3$, $—CCl_3$, $—CBr_3$, $—CI_3$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)—OH$, $—NHOH$, $—OCF_3$, $—OCCl_3$, $—OCBr_3$, $—OCl_3$, $—OCHF_2$, $—OCHCl_2$, $—OCHBr_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{6B}$ and $R^{6C}$, $R^{7B}$ and $R^{7C}$, $R^{10B}$ and $R^{10C}$, $R^{11B}$ and $R^{11C}$, and $R^{12B}$ and $R^{12C}$, substituents bonded to the same nitrogen atom may optionally be joined to form a substituted or unsubstituted heterocycloalkyl or substituted or unsubstituted heteroaryl;

n6, n7, n10, n11 and n12 are independently an integer from 0 to 4; and v6, v7, v10, v11 and v12, are independently 1 or 2.

Embodiment P3. The compound of embodiment P2, wherein the compound has structural formula:

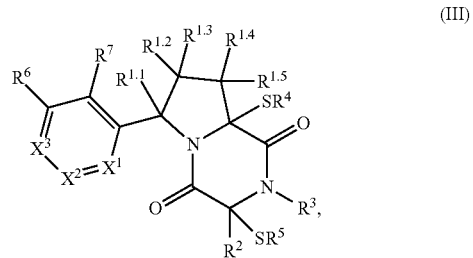

(III)

wherein:

$R^{1.1}$ is hydrogen, halogen, $—CF_3$, $—CCl_3$, $—CBr_3$, $—CI_3$, $—CN$, $—CHO$, $—COOR^{1.1A}$, $—CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, $—N_3$, $—CF_3$, $—CCl_3$, $—CBr_3$, $—CI_3$, $—CN$, $—CHO$, $—OR^{1.2A}$, $—NR^{1.2B}R^{1.2C}$, $—COOR^{1.2A}$, $—CONR^{1.2B}R^{1.2C}$, $—NO_2$, $—SR^{1.2D}$, $—SO_{n1.2}R^{1.2B}$, $—SO_{v1.2}NR^{1.2B}R^{1.2C}$, $—NHNR^{1.2B}R^{1.2C}$, $—ONR^{1.2B}R^{1.2C}$, $—NHC(O)NHNR^{1.2B}R^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.3}$ is hydrogen, halogen, $—N_3$, $—CF_3$, $—CCl_3$, $—CBr_3$, $—CI_3$, $—CN$, $—CHO$, $—OR^{1.3A}$, $—NR^{1.3B}R^{1.3C}$, $—COOR^{1.3A}$, $—CONR^{1.3B}R^{1.3C}$, $—NO_2$, $—SR^{1.3D}$, $—SO_{n1.3}R^{1.3B}$, $—SO_{v1.3}NR^{1.3B}R^{1.3C}$, $—NHNR^{1.3B}R^{1.3}C$, $—ONR^{1.3B}R^{1.3C}$, $—NHC(O)NHNR^{1.3B}R^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.4}$ is hydrogen, halogen, $—N_3$, $—CF_3$, $—CCl_3$, $—CBr_3$, $—CI_3$, $—CN$, $—CHO$, $—OR^{1.4A}$, $—NR^{1.4B}R^{1.4C}$, $—COOR^{1.4A}$, $—CONR^{1.4B}R^{1.4C}$, $—NO_2$, $—SR^{1.4D}$, $—SO_{n1.4}R^{1.4B}$, $—SO_{v1.4}NR^{1.4B}R^{1.4C}$, $—NHNR^{1.4B}R^{1.4}C$, $—ONR^{1.4B}R^{1.4C}$, $—NHC(O)NHNR^{1.4B}R^{1.4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.5}$ is hydrogen, halogen, $—N_3$, $—CF_3$, $—CCl_3$, $—CBr_3$, $—CI_3$, $—CN$, $—CHO$, $—OR^{1.5A}$, $—NR^{1.5B}R^{1.5C}$, $—COOR^{1.5A}$, $—CONR^{1.5B}R^{1.5C}$, $—NO_2$, $—SR^{1.5D}$, $—SO_{n1.5}R^{1.5B}$, $—SO_{v1.5}NR^{1.5B}R^{1.5C}$, $—NHNR^{1.5B}R^{1.5C}$, $—ONR^{1.5B}R^{1.5C}$, $—NHC(O)NHNR^{1.5B}R^{1.5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.1A}$, $R^{1.1B}$, $R^{1.1C}$, $R^{1.2A}$, $R^{1.2B}$, $R^{1.2C}$, $R^{1.2D}$, $R^{1.3A}$, $R^{1.3}B$, $R^{1.3C}$, $R^{1.3D}$, $R^{1.4A}$, $R^{1.4B}$, $R^{1.4C}$, $R^{1.4D}$, $R^{1.5A}$, $R^{1.5B}$, $R^{1.5C}$, and $R^{1.5D}$ are independently hydrogen, halogen, —CF₃, —CCl₃, —CBr₃, —CI₃, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{1.1B}$ and R$^{1.1C}$, R$^{1.2B}$ and R$^{1.2C}$, R$^{1.3B}$ and R$^{1.3C}$, R$^{1.4B}$ and R$^{1.4C}$, and R$^{1.5B}$ and R$^{1.5C}$ substituents bonded to the same nitrogen atom may optionally be joined to form a substituted or unsubstituted heterocycloalkyl or substituted or unsubstituted heteroaryl;

n1.2, n1.3, n1.4, and n1.5 are independently an integer from 0 to 4; and v1.2, v1.3, v1.4, and v1.5 are independently 1 or 2.

Embodiment P4. The compound of embodiment P3, wherein the compound has structural formula:

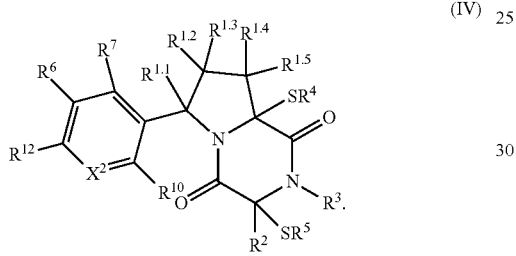

(IV)

Embodiment P5. The compound of any one of embodiments P2 to P4, wherein R$^{10}$ and R$^{11}$ or R$^{11}$ and R$^{12}$ are optionally joined to form a substituted or unsubstituted cycloalkyl or substituted or unsubstituted heterocycloalkyl having structural formula:

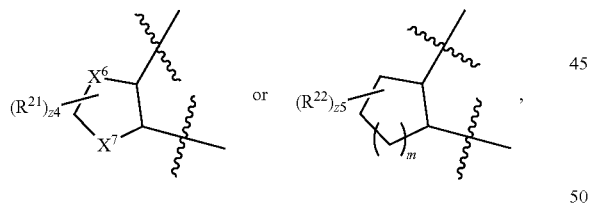

wherein:
X⁶ is O, NR$^{23A}$, or S;
X⁷ is O, NR$^{24A}$, or S;
z4 is an integer from 0 to 2;
z5 is an integer from 0 to 8;
m is 1 or 2;
R$^{21}$; R$^{22}$; R$^{23A}$, and R$^{24A}$ are independently hydrogen, halogen, —N₃, —CF₃, —CCl₃, —CBr₃, —CI₃, —CN, —CHO, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P6. The compound of embodiments P3 or P4, wherein the compound has the formula:

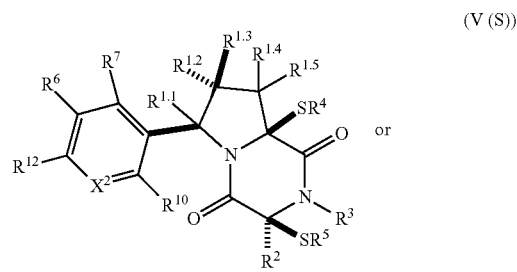

(V (S))

or

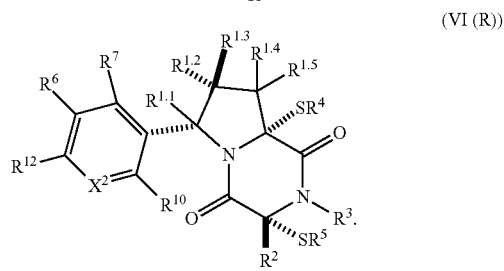

(VI (R))

Embodiment P7. The compound of embodiment P5, wherein the compound has the formula:

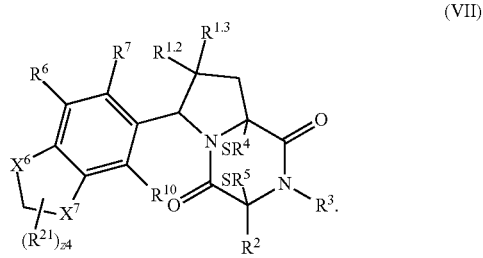

(VII)

Embodiment P8. The compound of embodiment P7, wherein the compound has the formula:

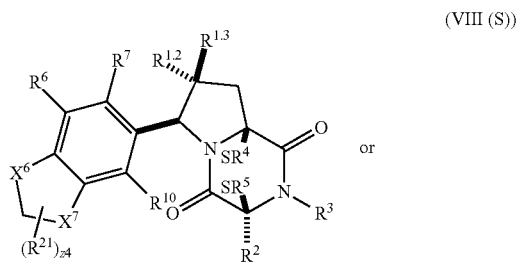

(VIII (S))

or

-continued

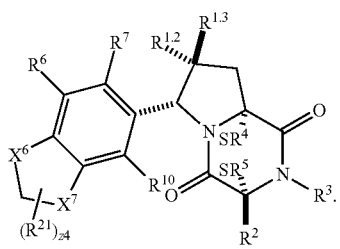

(IX (R))

Embodiment P9. The compound of embodiment P5, wherein the compound has the formula:

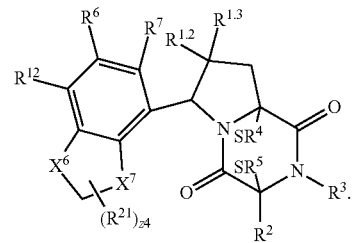

(X)

Embodiment P10. The compound of embodiment P9, wherein the compound has formula:

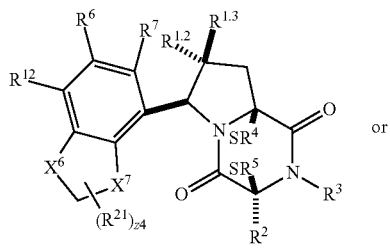

(XI (S))

or

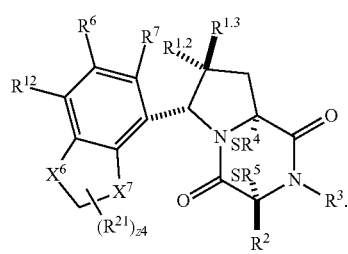

(XII (R))

Embodiment P11. The compound of embodiment P5, wherein the compound has the formula:

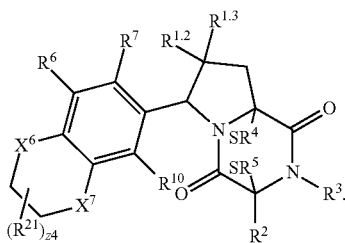

(XIII)

Embodiment P12. The compound of embodiment P11, wherein the compound has formula:

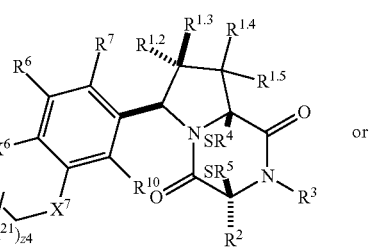

(XIV (S))

or

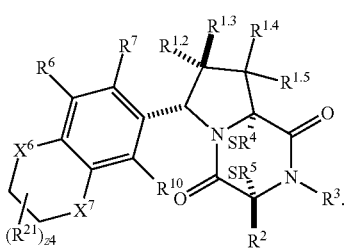

(XV (R))

Embodiment P13. The compound of embodiment P1, wherein the compound has structural formula:

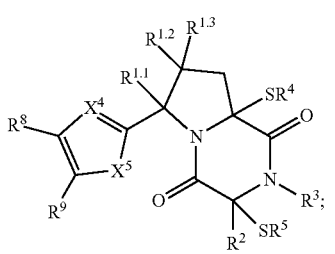

(XVI)

wherein:

$R^{1.1}$ is hydrogen, halogen, —$CF_3$, —$CCl_3$, —$CBr_3$, —$CI_3$, —CN, —CHO, —$COOR^{1.1A}$, —$CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, —$N_3$, —$CF_3$, —$CCl_3$, —$CBr_3$, —$CI_3$, —CN, —CHO, —$OR^{1.2A}$, —$NR^{1.2B}R^{1.2C}$, —$COOR^{1.2A}$, —$CONR^{1.2B}R^{1.2C}$, —$NO_2$, —$SR^{1.2D}$, —SO$_{n1.2}$R$^{1.2B}$, —SO$_{v1.2}$NR$^{1.2B}$R$^{1.2C}$, —NHNR$^{1.2B}$R$^{1.2C}$, —COOR$^{1.2A}$, —CONR$^{1.2B}$R$^{1.2C}$, —NHC(O)NHNR$^{1.2B}$R$^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1.3}$ is hydrogen, halogen, —N$_3$, —CF$_3$, —CCl$_3$, —CBr$_3$, —CI$_3$, —CN, —CHO, —OR$^{1.3A}$, —NR$^{1.3B}$R$^{1.3C}$, —COOR$^{1.3A}$, —CONR$^{1.3B}$R$^{1.3C}$, —NO$_2$, —SR$^{1.3D}$, —SO$_{n1.3}$R$^{1.3B}$, —SO$_{v1.3}$NR$^{1.3B}$R$^{1.3C}$, —NHNR$^{1.3B}$R$^{1.3}$C, —ONR$^{1.3B}$R$^{1.3C}$, —NHC(O)NHNR$^{1.3B}$R$^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^4$ is N or CR$^{13}$;

X$^5$ is CR$^{14}$R$^{15}$, S, O, or NR$^{20A}$;

R$^8$ is hydrogen, halogen, —N$_3$, —CF$_3$, —CCl$_3$, —CBr$_3$, —CI$_3$, —CN, —CHO, —OR$^{8A}$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, —NO$_2$, —SR$^{13D}$, —SO$_{n13}$R$^{13B}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, x substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$ is hydrogen, halogen, —N$_3$, —CF$_3$, —CCl$_3$, —CBr$_3$, —CI$_3$, —CN, —CHO, —OR$^{14A}$, —NR$^{14B}$R$^{14C}$, —COOR$^{14A}$, —CONR$^{14B}$R$^{14C}$, —NO$_2$, —SR$^{14D}$, —SO$_{n14}$R$^{14B}$, —SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, —CONR$^{15B}$R$^{15C}$, —NO$_2$, —SR$^{15D}$, —SO$_{n15}$R$^{15B}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1.1A}$, R$^{1.1B}$, R$^{1.1C}$, R$^{1.2A}$, R$^{1.2B}$, R$^{1.2C}$, R$^{1.2D}$, R$^{1.3A}$, R$^{1.3B}$, R$^{1.3C}$, R$^{1.3D}$, R$^{8A}$, R$^{8B}$, R$^{8C}$, R$^{8D}$, R$^{9A}$, R$^{9B}$, R$^{9C}$, R$^{9D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, and R$^{20A}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{1.1B}$ and R$^{1.1C}$, R$^{1.2B}$ and R$^{1.2C}$, R$^{1.3B}$ and R$^{1.3C}$, R$^{13B}$ and R$^{13C}$, R$^{14B}$ and R$^{14C}$, and R$^{15B}$ and R$^{15C}$, substituents bonded to the same nitrogen atom may optionally be joined to form a substituted or unsubstituted heterocycloalkyl or substituted or unsubstituted heteroaryl;

n1.2, n1.3, n8, n9, n13, n14, and n15 are independently an integer from 0 to 4; and v1.2, v1.3, v8, v9, v13, v14, and v15 are independently 1 or 2.

Embodiment P14. The compound of embodiment P13, wherein the compound has formula:

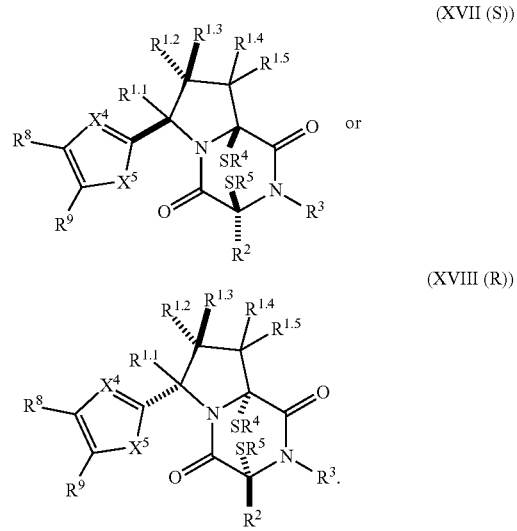

(XVII (S))

or (XVIII (R))

Embodiment P15. The compound of any one of embodiments P2 to P12, wherein R$^6$ and R$^7$ independently hydrogen.

Embodiment P16. The compound of any one of embodiments P2 to P6, wherein X$^2$ is N.

Embodiment P17. The compound of any one of embodiments P2 to P6, wherein R$^{12}$ is —OCH$_3$.

Embodiment P18. The compound of any one of embodiments P3 to P17, wherein R$^{1.2}$ is substituted or unsubstituted alkyl.

Embodiment P19. The compound of any one of embodiments P3 to P18, wherein R$^{1.2}$ is substituted or unsubstituted C$_1$-C$_3$alkyl.

Embodiment P20. The compound of any one of embodiments P3 to P19, wherein R$^{1.2}$ is methyl.

Embodiment P21. The compound of any one of embodiments P3 to P20, wherein R$^{1.3}$ is —CN.

Embodiment P22. The compound of any one of embodiments P1 to P21, wherein:
$R^4$ is —C(O)-$L^1$-$R^{18}$ or —C(S)-$L^1$-$R^{18}$; and
$R^5$ is —C(O)-$L^2$-$R^{19}$ or —C(S)-$L^2$-$R^{19}$.

Embodiment P23. The compound of any one of embodiments P1 to P22, wherein:
$R^4$ is —C(O)-$L^1$-$R^{18}$; and
$R^5$ is —C(O)-$L^2$-$R^{19}$.

Embodiment P24. The compound of any one of embodiments P1 to P22, wherein:
$R^4$ is —C(S)-$L^1$-$R^{18}$; and
$R^5$ is —C(S)-$L^2$-$R^{19}$.

Embodiment P25. The compound of any one of embodiments P1 to P24, wherein $L^1$ and $L^2$ are independently —O—.

Embodiment P26. The compound of any one of embodiments P1 to P24, wherein $L^1$ and $L^2$ are independently —NH—.

Embodiment P27. The compound of any one of embodiments P1 to P24, wherein $L^1$ and $L^2$ are independently a bond.

Embodiment P28. The compound of any one of embodiments P1 to P24, wherein:
$L^1$ is -$L^{1A}$-$L^{1B}$-, wherein $L^{1A}$ is bonded to —C(O)— or —C(S)—; and
$L^2$ is -$L^{2A}$-$L^{2B}$-, wherein $L^{2A}$ is bonded to —C(O)— or —C(S)—;
$L^{1A}$ is a bond or —(CH$_2$)$_{z1}$—;
$L^{1B}$ is a bond, —O— or —NR$^{16B}$—;
$L^{2A}$ is a bond or —(CH$_2$)$_{z2}$—;
$L^{2B}$ is a bond, —O— or —NR$^{17B}$—;
z1 and z2 are independently an integer from 1 to 10; and
$R^{16B}$ and $R^{17B}$ are independently hydrogen or substituted or unsubstituted alkyl.

Embodiment P29. The compound of embodiment P28, wherein $L^{1A}$ and $L^{2A}$ are independently —CH$_2$—.

Embodiment P30. The compound of embodiments P28 or P29, wherein:
$L^{1B}$ is —NR$^{16B}$;
$L^{2B}$ is —NR$^{17B}$; and
$R^{16B}$ and $R^{17B}$ are independently unsubstituted $C_1$-$C_3$alkyl.

Embodiment P31. The compound of any one of embodiments P1 to P30, wherein $R^{18}$ and $R^{19}$ are independently unsubstituted $C_1$-$C_3$alkyl or unsubstituted aryl.

Embodiment P32. The compound of any one of embodiments P1 to P31, wherein $R^{18}$ and $R^{19}$ are independently unsubstituted aryl.

Embodiment P33. The compound of any one of embodiments P1 to P30, wherein $R^{18}$ and $R^{19}$ are independently halogen.

Embodiment P34. The compound of any one of embodiments P1 to P21, wherein $R^4$ and $R^5$ are joined together to form:

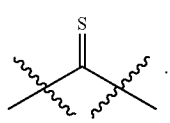

Embodiment P35. The compound of any one of embodiments P1 to P34, wherein $R^2$ is methyl.

Embodiment P36. The compound of embodiment P1, wherein the compound has the structure:

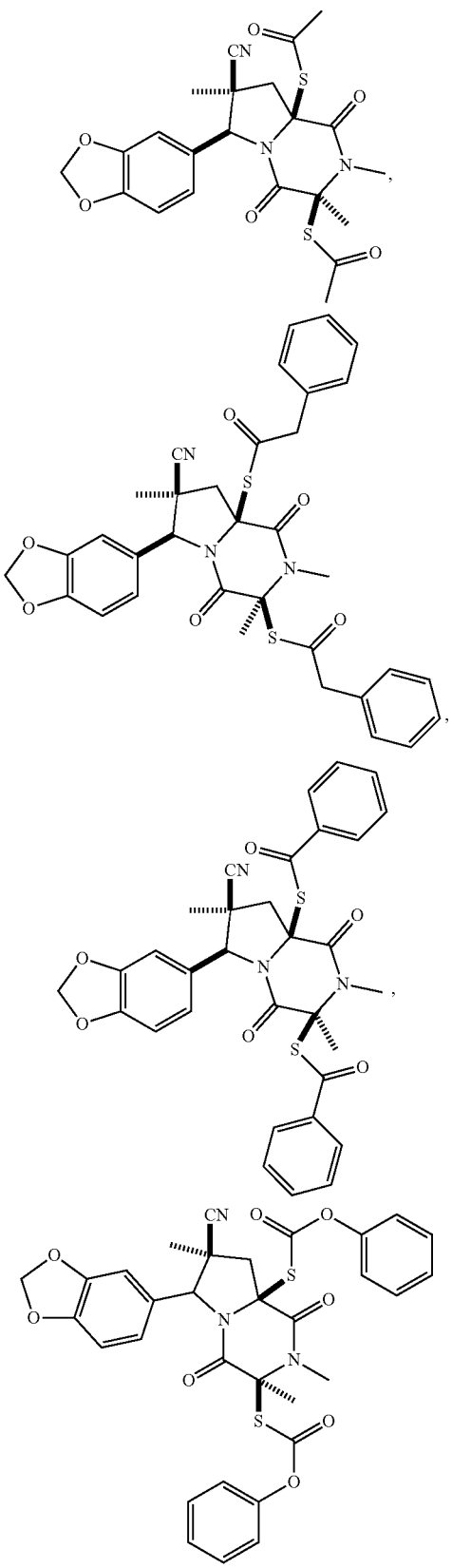

-continued
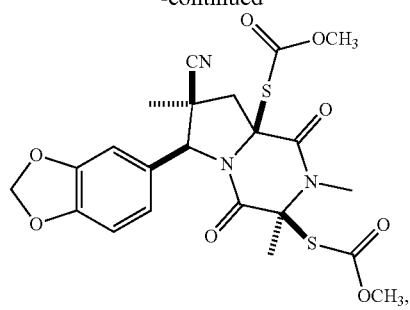
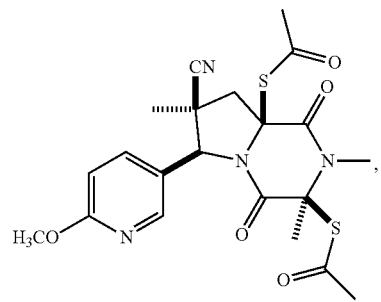
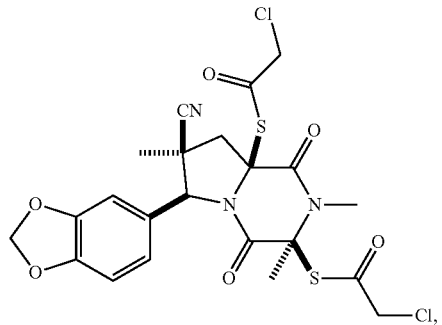
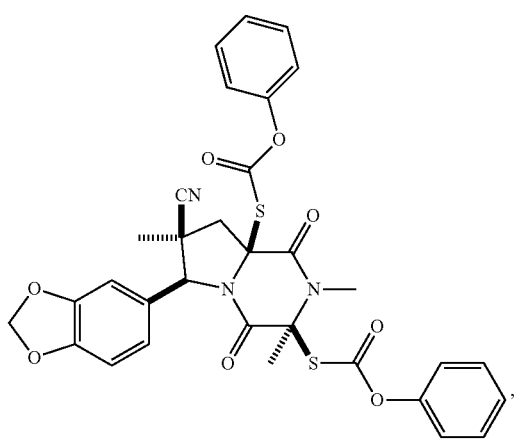
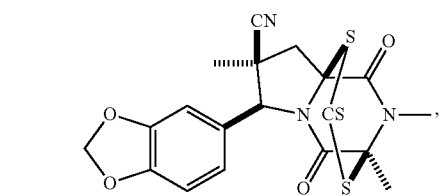
-continued
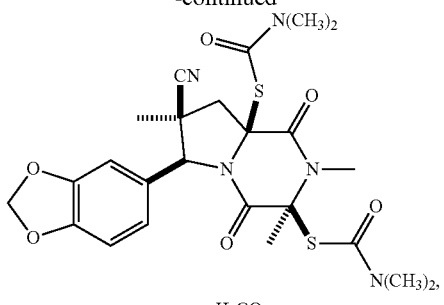
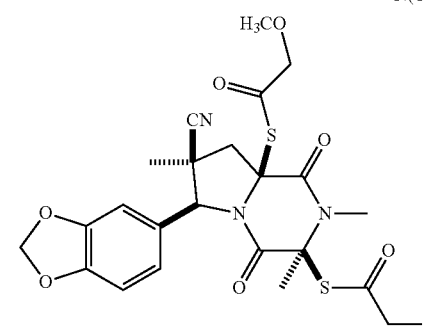
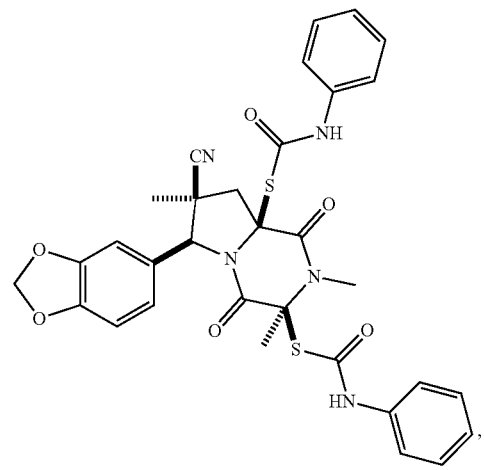
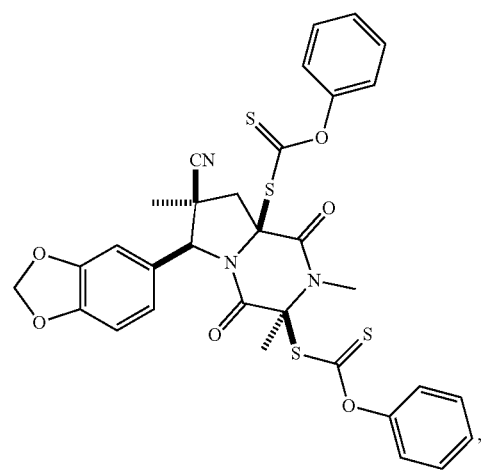

-continued

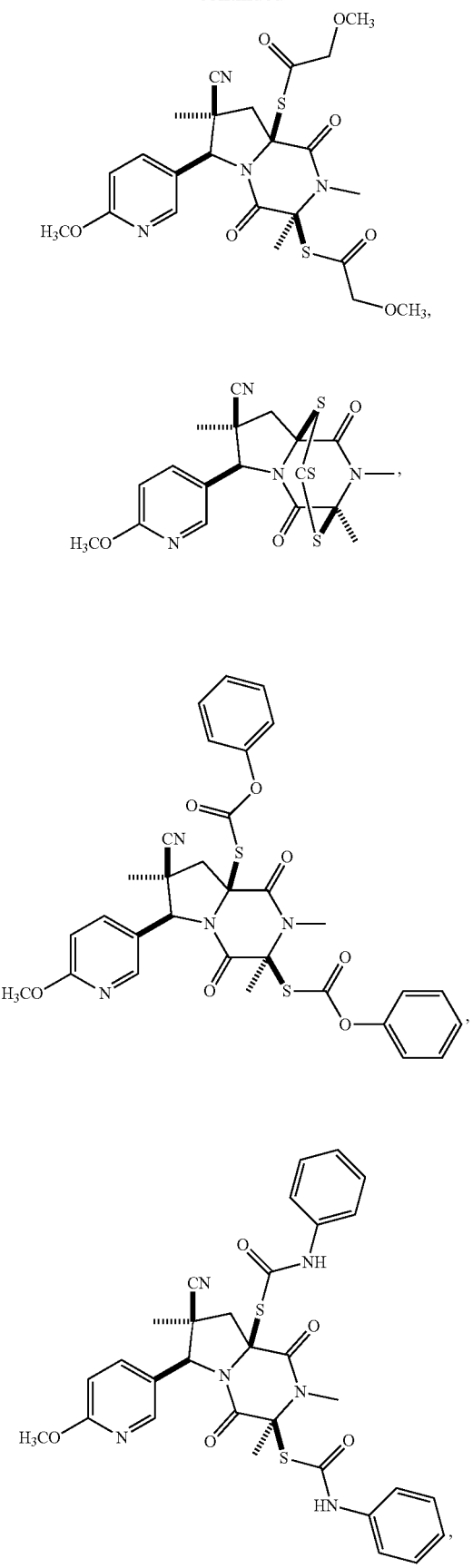

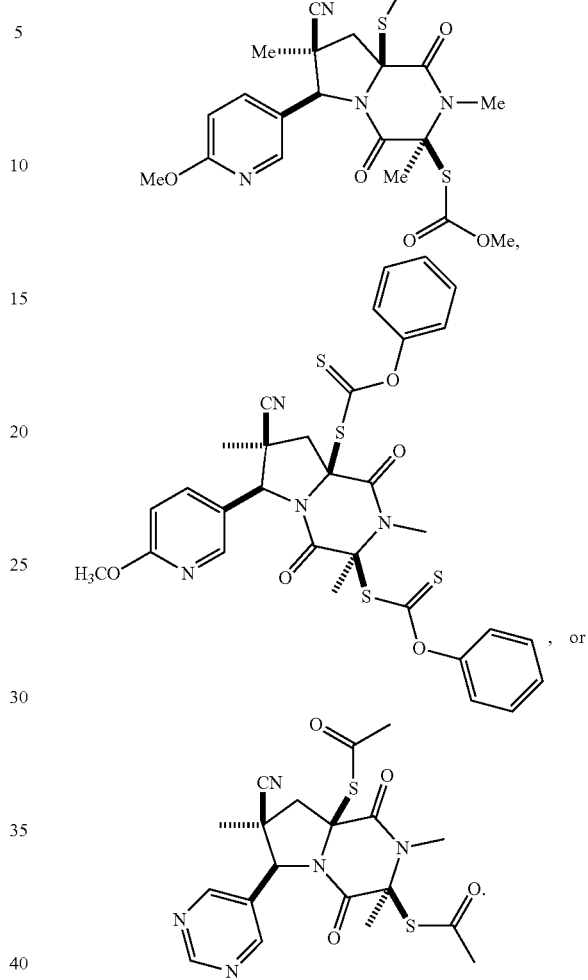

Embodiment P37. A method of treating cancer, comprising administering to a subject in need thereof a therapeutically effective amount of a compound of any one of embodiments P1 to P36.

Embodiment P38. The method of embodiment P37, wherein the cancer is a solid or blood tumor.

Embodiment P39. The method of embodiment P37, wherein the cancer is ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment P40. The method of any one of embodiments P37 to P39, further comprising administering at least one additional anticancer agent.

Embodiment 41. The method of embodiment 40, wherein the at least one additional anticancer agent comprises an epigenetic inhibitor or a multi-kinase inhibitor.

Embodiment 42. The method of any one of embodiments P37 to P41, wherein the method comprises administering a first amount of the compound and a second amount of at least one additional anticancer agent, wherein the first amount and second amount are together an effective amount to provide a synergistic therapeutic effect.

Embodiment P43. The method of any one of embodiments P40 to P42, wherein the additional anticancer agent is an epigenetic inhibitor.

Embodiment P44. The method of embodiment P43, wherein the epigenetic inhibitor is azacitidine or decitadine.

Embodiment P45. The method of embodiments P43 or P44, wherein the compound and the epigenetic inhibitor are co-administered as a pharmaceutical composition.

Embodiment P46. The method of any one of embodiments P40 to P42, wherein the additional anticancer agent is a multi-kinase inhibitor.

Embodiment P47. The method of embodiment P46, wherein the multi-kinase inhibitor is sorafenib.

Embodiment P48. The method of embodiments P46 or P47, wherein the compound and the multi-kinase inhibitor are co-administered as a pharmaceutical composition.

Embodiment P49. The method of embodiment P37 or P39, wherein the cancer is ovarian cancer.

Embodiment P50. A pharmaceutical composition comprising a compound of any one of embodiments P1 to P36 and a pharmaceutically acceptable excipient.

Embodiment P51. A pharmaceutical composition comprising a pharmaceutically acceptable excipient and a combination of a compound of any one of embodiments P1 to P36 and at least one additional anticancer agent.

Embodiment P52. The pharmaceutical composition of embodiment P51, wherein the at least one additional anticancer agent comprises a multi-kinase inhibitor or an epigenetic inhibitor.

Embodiment P53. The pharmaceutical composition of embodiment P51, wherein the combination includes a first amount of the compound and a second amount of a multi-kinase inhibitor, wherein the first amount and second amount are together an effective amount to provide a synergistic therapeutic effect.

Embodiment P54. The pharmaceutical composition of embodiment P51, wherein the combination includes a first amount of the compound and a second amount of an epigenetic inhibitor, wherein the first amount and second amount are together an effective amount to provide a synergistic therapeutic effect.

Embodiment P55. The pharmaceutical composition of embodiment P51, wherein the combination includes a first amount of the compound, a second amount of a multi-kinase inhibitor, and a third amount of an epigenetic inhibitor, wherein the first amount, second, and third amounts are together an effective amount to provide a synergistic therapeutic effect.

Embodiment P56. The pharmaceutical composition of embodiments P52 or P55, wherein the multi-kinase inhibitor is sorafenib and the epigenetic inhibitor is azacitidine or decitabine.

Embodiment P57. The pharmaceutical composition of any one of embodiment P50 to P56 for use in cancer.

Embodiment P58. The pharmaceutical composition of any one of embodiments P50 to P56 for use in solid and blood tumors, including ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment P59. The pharmaceutical composition of any one of embodiments P50 to P56 for use in non-small cell lung cancer.

Embodiment P60. The pharmaceutical composition of any one of embodiments P52, P55 or P56, wherein the compound and the multi-kinase inhibitor or the epigenetic inhibitor are co-administered as a single dosage form.

Embodiment P61. A method of inhibiting the growth of a cancer cell, comprising administering to a subject in need thereof a therapeutically effective amount of a compound of any one of embodiments P1 to P36.

Embodiment P62. The method of embodiment P61, wherein the cancer cell is an ovarian cancer cell, breast cancer cell, lung cancer cell, leukemia cell, AML cell, CML cell, lymphoma cell, pancreatic cancer cell, kidney cancer cell, melanoma cell, liver cancer cell, colon cancer cell, sarcoma cell, multiple myeloma cell, brain cancer cell, or prostate cancer cell.

EMBODIMENTS

Embodiment 1. A compound having the formula:

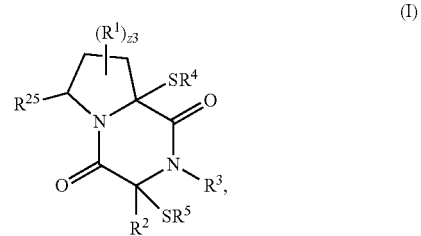

(I)

or a pharmaceutically acceptable salt thereof,
wherein:
$R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —C(O)$OR^{1A}$, —C(O)$NR^{1B}R^{1C}$, —$NO_2$, —$SR^{1D}$, —S(O)$_{n1}NR^{1B}$, —SO$_{v1}NR^{1B}R^{1C}$, —NHNR$^{1B}R^{1C}$, —ONR$^{1B}R^{1C}$, —NHC(O)NHNR$^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$CF_3$, —$CCl_3$, —$CBr_3$, —$CI_3$, —CN, —CHO, —COOR$^{2A}$, —CONR$^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —COOR$^{3A}$, —CONR$^{3B}R^{3C}$, —$NO_2$, —$SR^{3D}$, —SO$_{n3}R^{3B}$, —SO$_{v3}NR^{3B}R^{3C}$, —NHNR$^{3B}R^{3C}$, —ONR$^{3B}R^{3C}$, —NHC(O)NHNR$^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is —C(O)-$L^1$-$R^{18}$ or —C(S)-$L^1$-$R^{18}$;
$R^5$ is —C(O)-$L^2$-$R^{19}$ or —C(S)-$L^2$-$R^{19}$; or
$R^4$ and $R^5$ may optionally be joined to form

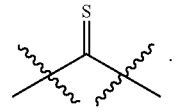

$L^1$ is a bond, —O—, —NH—, substituted or unsubstituted alkylene, substituted or unsubstituted heteroalkylene;

$L^2$ is a bond, —O—, —NH—, substituted or unsubstituted alkylene, substituted or unsubstituted heteroalkylene;

$R^{18}$ and $R^{19}$ are independently halogen, substituted or unsubstituted $C_1$-$C_3$alkyl, substituted or unsubstituted aryl;

$R^{25}$ is hydrogen, halogen, —$N_3$, —$CF_3$, —$CCl_3$, —$CBr_3$, —$CI_3$, —CN, —CHO, —$OR^{25A}$, —$NR^{25B}R^{25C}$, —$C(O)OR^{25A}$, —$C(O)NR^{25B}R^{25C}$, —$NO_2$, —$SR^{25D}$, —$S(O)_{n25}R^{25B}$, —$SO_{v25}NR^{25B}R^{25C}$, —$NHNR^{25B}R^{25C}$, —$ONR^{25B}R^{25C}$, —NHC(O)NHNR$^{25B}$R$^{25C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{3A}$, $R^{3B}$, $R^{3C}$, $R^{3D}$, $R^{25A}$, $R^{25B}$, $R^{25C}$, and $R^{25D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1B}$ and $R^{1C}$, $R^{2B}$ and $R^{2C}$, $R^{3B}$ and $R^{3C}$, and $R^{25B}$ and $R^{25C}$ substituents bonded to the same nitrogen atom may optionally be joined to form a substituted or unsubstituted heterocycloalkyl or substituted or unsubstituted heteroaryl;

z3 is an integer from 0 to 5;

n1, n3, and n25 are independently an integer from 0 to 4; and v1, v3, and v25 are independently 1 or 2.

Embodiment 2. The compound of embodiment 1, wherein the compound has the formula:

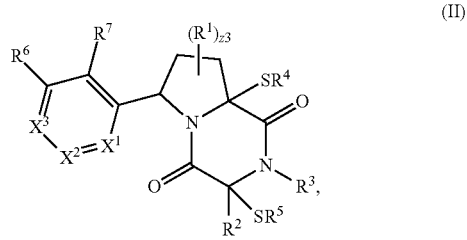

(II)

or a pharmaceutically acceptable salt thereof, wherein:

$X^1$ is N or $CR^{10}$;

$X^2$ is N or $CR^{11}$;

$X^3$ is N or $CR^{12}$;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{v6}NR^{6B}R^{6C}$, —$NHNR^{6B}R^{6C}$, —$ONR^{6B}R^{6C}$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —$CONR^{7B}R^{7C}$, —$NO_2$, —$SR^{7D}$, —$SO_{n7}R^{7B}$, —$SO_{v7}NR^{7B}R^{7C}$, —$NHNR^{7B}R^{7C}$, —$ONR^{7B}R^{7C}$, —NHC(O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$N_3$, —$CF_3$, —$CCl_3$, —$CBr_3$, —$CI_3$, —CN, —CHO, —$OR^{10A}$, —$NR^{10B}R^{10C}$, —$COOR^{10A}$, —$CONR^{10B}R^{10C}$, —$NO_2$, —$SR^{10D}$, —$SO_{n10}R^{10B}$, —$SO_{v10}NR^{10B}R^{10C}$, —$NHNR^{10B}R^{10C}$, —$ONR^{10B}R^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —$CONR^{11B}R^{11C}$, —$NO_2$, —$SR^{11D}$, —$SO_{n11}R^{11B}$, —$SO_{v11}NR^{11B}R^{11C}$, —$NHNR^{11B}R^{11C}$, —$ONR^{11B}R^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ may optionally be joined to form a substituted or unsubstituted cycloalkyl, substituted or unsubstituted heterocycloalkyl;

$R^{12}$ is hydrogen, halogen, —$N_3$, —$CF_3$, —$CCl_3$, —$CBr_3$, —$CI_3$, —CN, —CHO, —$OR^{12A}$, —$NR^{12B}R^{12C}$, —$COOR^{12A}$, —$CONR^{12B}R^{12C}$, —$NO_2$, —$SR^{12D}$, —$SO_{n12}R^{12B}$, —$SO_{v12}NR^{12B}R^{12C}$, —$NHNR^{12B}R^{12C}$, —$ONR^{12B}R^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ may optionally be joined to form a substituted or unsubstituted cycloalkyl, substituted or unsubstituted heterocycloalkyl;

$R^{6A}$, $R^{6B}$, $R^{6C}$, $R^{6D}$, $R^{7A}$, $R^{7B}$, $R^{7C}$, $R^{7D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2N_2$, —$NHNH_2$, —$ONH_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{6B}$ and $R^{6C}$, $R^{7B}$ and $R^{7C}$, $R^{10B}$ and $R^{10C}$, $R^{11B}$ and $R^{11C}$, and $R^{12B}$ and $R^{12C}$, substituents bonded to the same nitrogen atom may optionally be joined to form a substituted or unsubstituted heterocycloalkyl or substituted or unsubstituted heteroaryl;

n6, n7, n10, n11 and n12 are independently an integer from 0 to 4; and v6, v7, v10, v11 and v12, are independently 1 or 2.

Embodiment 3. The compound of embodiment 2, wherein the compound has structural formula:

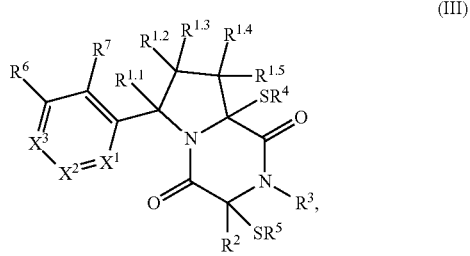

(III)

wherein:

$R^{1.1}$ is hydrogen, halogen, —$CF_3$, —$CCl_3$, —$CBr_3$, —$CI_3$, —CN, —CHO, —$COOR^{1.1A}$, —$CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, —$N_3$, —$CF_3$, —$CCl_3$, —$CBr_3$, —$CI_3$, —CN, —CHO, —$OR^{1.2A}$, —$NR^{1.2B}R^{1.2C}$, —$COOR^{1.2A}$, —$CONR^{1.2B}R^{1.2C}$, —$NO_2$, —$SR^{1.2D}$, —$SO_{n1.2}R^{1.2B}$, —$SO_{v1.2}NR^{1.2B}R^{1.2C}$, —$NHNR^{1.2B}R^{1.2C}$, —$ONR^{1.2B}R^{1.2C}$, —NHC(O)NHNR^{1.2B}R^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.3}$ is hydrogen, halogen, —$N_3$, —$CF_3$, —$CCl_3$, —$CBr_3$, —$CI_3$, —CN, —CHO, —$OR^{1.3A}$, —$NR^{1.3B}R^{1.3C}$, —$COOR^{1.3A}$, —$CONR^{1.3B}R^{1.3C}$, —$NO_2$, —$SR^{1.3D}$, —$SO_{n1.3}R^{1.3B}$, —$SO_{v1.3}NR^{1.3B}R^{1.3C}$, —$NHNR^{1.3B}R^{1.3C}$, —$ONR^{1.3B}R^{1.3C}$, —NHC(O)NHNR^{1.3B}R^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.4}$ is hydrogen, halogen, —$N_3$, —$CF_3$, —$CCl_3$, —$CBr_3$, —$CI_3$, —CN, —CHO, —$OR^{1.4A}$, —$NR^{1.4B}R^{1.4C}$, —$COOR^{1.4A}$, —$CONR^{1.4B}R^{1.4C}$, —$NO_2$, —$SR^{1.4D}$, —$SO_{n1.4}R^{1.4B}$, —$SO_{v1.4}NR^{1.4B}R^{1.4C}$, —$NHNR^{1.4B}R^{1.4C}$, —$ONR^{1.4B}R^{1.4C}$, —NHC(O)NHNR^{1.4B}R^{1.4C}$, substituted or unsubstituted alkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.5}$ is hydrogen, halogen, —$N_3$, —$CF_3$, —$CCl_3$, —$CBr_3$, —$CI_3$, —CN, —CHO, —$OR^{1.5A}$, —$NR^{1.5B}R^{1.5C}$, —$COOR^{1.5A}$, —$CONR^{1.5B}R^{1.5C}$, —$NO_2$, —$SR^{1.5D}$, —$SO_{n1.5}R^{1.5B}$, —$SO_{v1.5}NR^{1.5B}R^{1.5C}$, —$NHNR^{1.5B}R^{1.5C}$, —$ONR^{1.5B}R^{1.5C}$, —NHC(O)NHNR^{1.5B}R^{1.5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.1A}$, $R^{1.1B}$, $R^{1.1C}$, $R^{1.2A}$, and $R^{1.2B}$, $R^{1.2C}$, $R^{1.2D}$, $R^{1.3A}$, $R^{1.3B}$, and $R^{1.3C}$, $R^{1.3D}$, $R^{1.4A}$, $R^{1.4B}$, $R^{1.4C}$, and $R^{1.5D}$, $R^{1.5A}$, $R^{1.5B}$, $R^{1.5C}$, and $R^{1.5D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2$, —NHC(O)NH_2$, —NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1.1B}$ and $R^{1.1C}$, $R^{1.2B}$ and $R^{1.2C}$, $R^{1.3B}$ and $R^{1.3C}$, $R^{1.4B}$ and $R^{1.4C}$, and $R^{1.5B}$ and $R^{1.5C}$ substituents bonded to the same nitrogen atom may optionally be joined to form a substituted or unsubstituted heterocycloalkyl or substituted or unsubstituted heteroaryl;

n1.2, n1.3, n1.4, and n1.5 are independently an integer from 0 to 4; and v1.2, v1.3, v1.4, and v1.5 are independently 1 or 2.

Embodiment 4. The compound of embodiment 3, wherein the compound has structural formula:

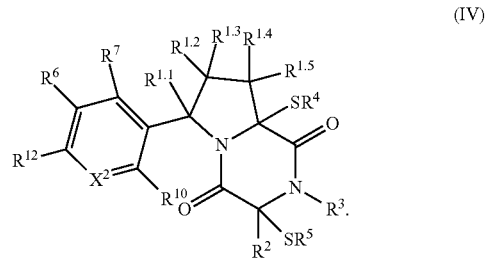

(IV)

Embodiment 5. The compound of any one of embodiments 2 to 4, wherein $R^{10}$ and $R^{11}$ or $R^{11}$ and $R^{12}$ are optionally joined to form a substituted or unsubstituted cycloalkyl or substituted or unsubstituted heterocycloalkyl having structural formula:

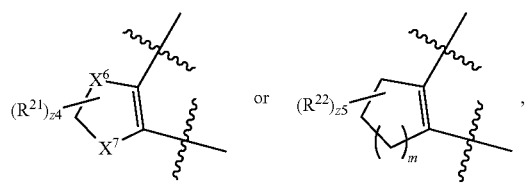

wherein:

$X^6$ is O, $NR^{23A}$, or S;

$X^7$ is O, $NR^{24A}$, or S;

z4 is an integer from 0 to 2;

z5 is an integer from 0 to 8;

m is 1 or 2;

$R^{21}$, $R^{22}$, $R^{23A}$, and $R^{24A}$ are independently hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2$, —NHC(O)NH_2$, —$NHSO_2H$, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 6. The compound of embodiments 3 or 4, wherein the compound has the formula:

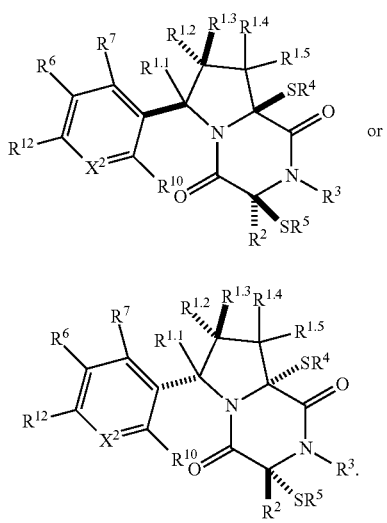

(V (S))

or (VI (R))

Embodiment 7. The compound of embodiment 5, wherein the compound has the formula:

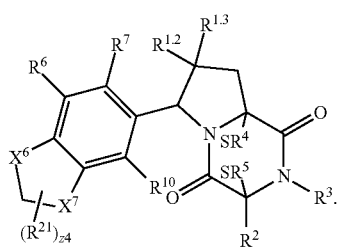

(VII)

Embodiment 8. The compound of embodiment 7, wherein the compound has the formula:

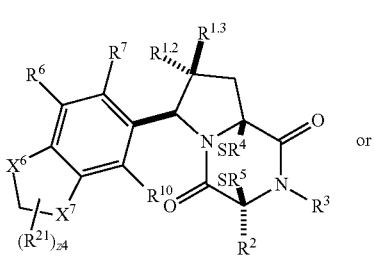

(VIII (S))

or

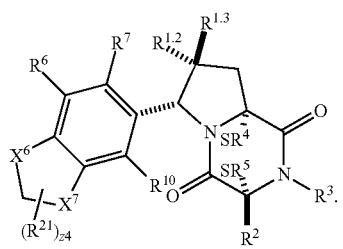

(IX (R))

Embodiment 9. The compound of embodiment 5, wherein the compound has the formula:

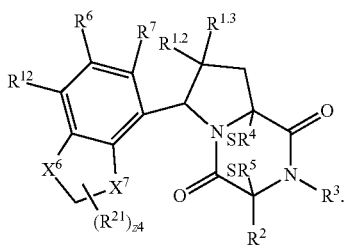

(X)

Embodiment 10. The compound of embodiment 9, wherein the compound has formula:

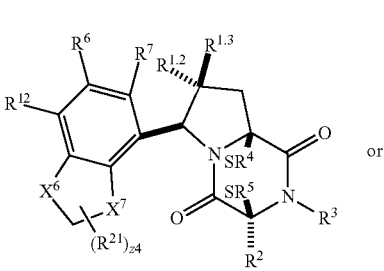

(XI (S))

or

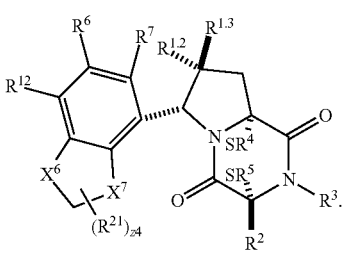

(XII (R))

Embodiment 11. The compound of embodiment 5, wherein the compound has the formula:

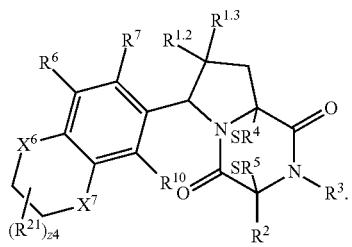

(XIII)

Embodiment 12. The compound of embodiment 11, wherein the compound has formula:

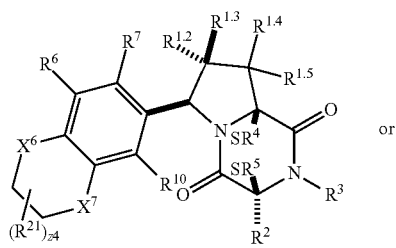

(XIV (S))

or

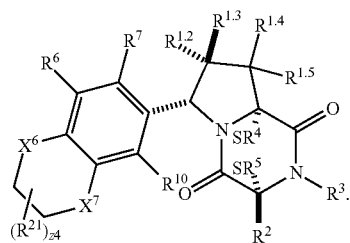

(XV (R))

Embodiment 13. The compound of embodiment 1, wherein the compound has structural formula:

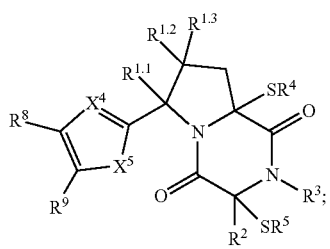

(XVI)

wherein:

$R^{1.1}$ is hydrogen, halogen, —CF$_3$, —CCl$_3$, CI$_3$, —CN, —CHO, —COOR$^{1.1A}$, —CONR$^{1.1B}$R$^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, —N$_3$, —CF$_3$, —CCl$_3$, CI$_3$, —CN, —CHO, —OR$^{1.2A}$, —NR$^{1.2B}$R$^{1.2C}$, —COOR$^{1.2A}$, —CONR$^{1.2B}$R$^{1.2C}$, —NO$_2$, —SR$^{1.2D}$, —SO$_{n1.2}$R$^{1.2B}$, —SO$_{v1.2}$NR$^{1.2B}$R$^{1.2C}$, —NHNR$^{1.2B}$R$^{1.2C}$, —ONR$^{1.2B}$R$^{1.2C}$, —NHC(O)NHNR$^{1.2B}$R$^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.3}$ is hydrogen, halogen, —N$_3$, —CF$_3$, —CCl$_3$, CI$_3$, —CN, —CHO, —OR$^{1.3A}$, —NR$^{1.3B}$R$^{1.3C}$, —COOR$^{1.3A}$, —CONR$^{1.3B}$R$^{1.3C}$, —NO$_2$, —SR$^{1.3D}$, —SO$_{n1.3}$R$^{1.3B}$, —SO$_{v1.3}$NR$^{1.3B}$R$^{1.3C}$, —NHNR$^{1.3B}$R$^{1.3C}$, —ONR$^{1.3B}$R$^{1.3C}$, —NHC(O)NHNR$^{1.3B}$R$^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^4$ is N or CR$^{13}$;

$X^5$ is CR$^{14}$R$^{15}$, S, O, or NR$^{20A}$;

$R^8$ is hydrogen, halogen, —N$_3$, —CF$_3$, —CCl$_3$, —CBr$_3$, —CI$_3$, —CN, —CHO, —OR$^{8A}$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, —NO$_2$, —SR$^{13D}$, —SO$_{n13}$R$^{13B}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, —N$_3$, —CF$_3$, —CCl$_3$, —CBr$_3$, —CI$_3$, —CN, —CHO, —OR$^{14A}$, —NR$^{14B}$R$^{14C}$, —COOR$^{14A}$, —CONR$^{14B}$R$^{14C}$, —NO$_2$, —SR$^{14D}$, —SO$_{n14}$R$^{14B}$, —SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, —CONR$^{15B}$R$^{15C}$, —SR$^{15D}$, —SO$_{n15}$R$^{15B}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.1A}$, $R^{1.1B}$, $R^{1.1C}$, $R^{1.2A}$, $R^{1.2B}$, $R^{1.2C}$, $R^{1.2D}$, $R^{1.3A}$, $R^{1.3B}$, $R^{1.3C}$, $R^{1.3D}$, $R^{8A}$, $R^{8B}$, $R^{8C}$, $R^{8D}$, $R^{9A}$, $R^{9B}$, $R^{9C}$, $R^{9D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, and $R^{20A}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1.1B}$ and $R^{1.1C}$, $R^{1.2B}$ and $R^{1.2C}$, $R^{1.3B}$ and $R^{1.3C}$, $R^{13B}$ and $R^{13C}$, $R^{14B}$ and $R^{14C}$, and $R^{15B}$ and $R^{15C}$, substituents bonded to the same nitrogen atom may optionally be joined to form a substituted or unsubstituted heterocycloalkyl or substituted or unsubstituted heteroaryl;

n1.2, n1.3, n8, n9, n13, n14, and n15 are independently an integer from 0 to 4; and v1.2, v1.3, v8, v9, v13, v14, and v15 are independently 1 or 2.

Embodiment 14. The compound of embodiment 13, wherein the compound has formula:

(XVII (S))

(XVIII (R))

Embodiment 15. The compound of any one of embodiments 2 to 12, wherein $R^6$ and $R^7$ independently hydrogen.

Embodiment 16. The compound of any one of embodiments 2 to 6, wherein $X^2$ is N.

Embodiment 17. The compound of any one of embodiments 2 to 6, wherein $R^{12}$ is —$OCH_3$.

Embodiment 18. The compound of any one of embodiments 3 to 17, wherein $R^{12}$ is substituted or unsubstituted alkyl.

Embodiment 19. The compound of any one of embodiments 3 to 18, wherein $R^{12}$ is substituted or unsubstituted $C_1$-$C_3$alkyl.

Embodiment 20. The compound of any one of embodiments 3 to 19, wherein $R^{1.2}$ is methyl.

Embodiment 21. The compound of any one of embodiments 3 to 20, wherein $R^{1.3}$ is —CN.

Embodiment 22. The compound of any one of embodiments 1 to 21, wherein:
$R^4$ is —C(O)-$L^1$-$R^{18}$ or —C(S)-$L^1$-$R^{18}$; and
$R^5$ is —C(O)-$L^2$-$R^{19}$ or —C(S)-$L^2$-$R^{19}$.

Embodiment 23. The compound of any one of embodiments 1 to 22, wherein:
$R^4$ is —C(O)-$L^1$-$R^{18}$; and
$R^5$ is —C(O)-$L^2$-$R^{19}$.

Embodiment 24. The compound of any one of embodiments 1 to 22, wherein:
$R^4$ is —C(S)-$L^1$-$R^{18}$; and
$R^5$ is —C(S)-$L^2$-$R^{19}$.

Embodiment 25. The compound of any one of embodiments 1 to 24, wherein $L^1$ and $L^2$ are independently —O—.

Embodiment 26. The compound of any one of embodiments 1 to 24, wherein $L^1$ and $L^2$ are independently —NH—.

Embodiment 27. The compound of any one of embodiments 1 to 24, wherein $L^1$ and $L^2$ are independently a bond.

Embodiment 28. The compound of any one of embodiments 1 to 24, wherein:
$L^1$ is -$L^{1A}$-$L^{1B}$-, wherein $L^{1A}$ is bonded to —C(O)— or —C(S)—; and
$L^2$ is -$L^{2A}$-$L^{2B}$-, wherein $L^{2A}$ is bonded to —C(O)— or —C(S)—;
$L^{1A}$ is a bond or —$(CH_2)_{z1}$—;
$L^{1B}$ is a bond, —O— or —$NR^{16B}$—;
$L^{2A}$ is a bond or —$(CH_2)_{z2}$—;
$L^{2B}$ is a bond, —O— or —$NR^{17B}$—;
z1 and z2 are independently an integer from 1 to 10; and
$R^{16B}$ and $R^{17B}$ are independently hydrogen or substituted or unsubstituted alkyl.

Embodiment 29. The compound of embodiment 28, wherein $L^{1A}$ and $L^{2A}$ are independently —$CH_2$—.

Embodiment 30. The compound of embodiments 28 or 29, wherein:
$L^{1B}$ is —$NR^{16B}$;
$L^{2B}$ is —$NR^{17B}$; and
$R^{16B}$ and $R^{17B}$ are independently unsubstituted $C_1$-$C_3$alkyl.

Embodiment 31. The compound of any one of embodiments 1 to 30, wherein $R^{18}$ and $R^{19}$ are independently unsubstituted $C_1$-$C_3$alkyl or unsubstituted aryl.

Embodiment 32. The compound of any one of embodiments 1 to 31, wherein $R^{18}$ and $R^{19}$ are independently unsubstituted aryl.

Embodiment 33. The compound of any one of embodiments 1 to 30, wherein $R^{18}$ and $R^{19}$ are independently halogen.

Embodiment 34. The compound of any one of embodiments 1 to 21, wherein $R^4$ and $R^5$ are joined together to form:

Embodiment 35. The compound of any one of embodiments 1 to 34, wherein $R^2$ is methyl.

Embodiment 36. The compound of embodiment 1, wherein the compound has the structure:

171
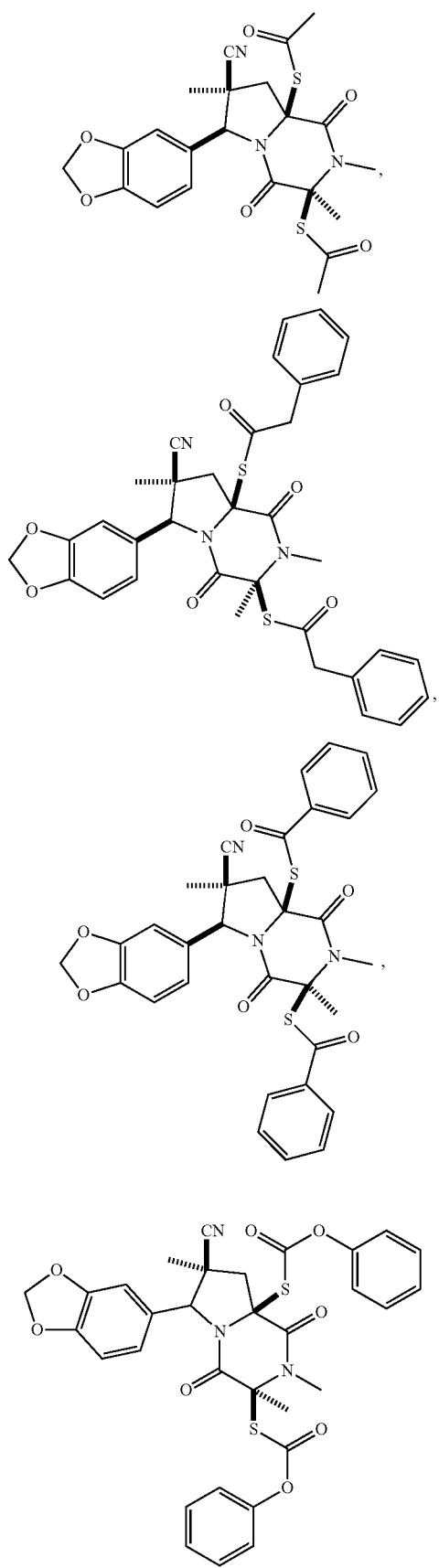
172
-continued
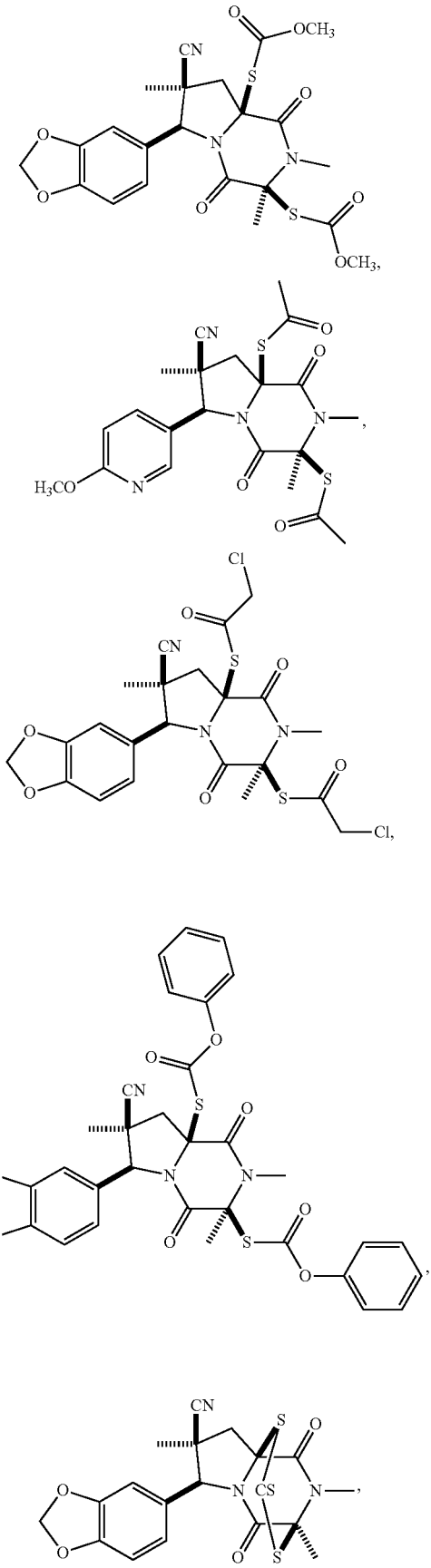

173
-continued
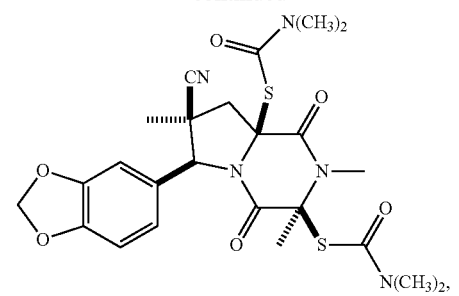
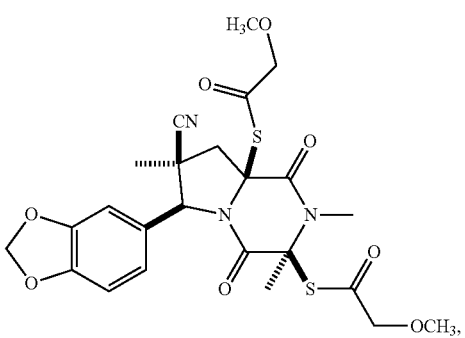
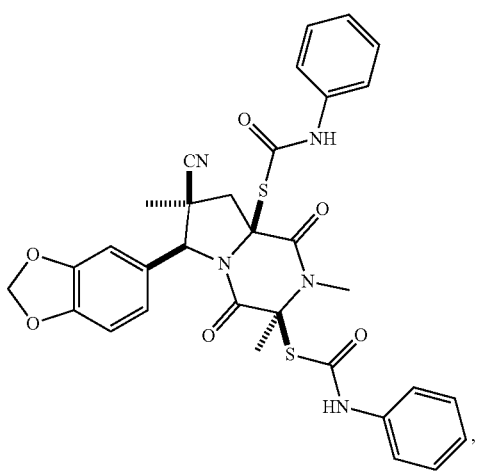
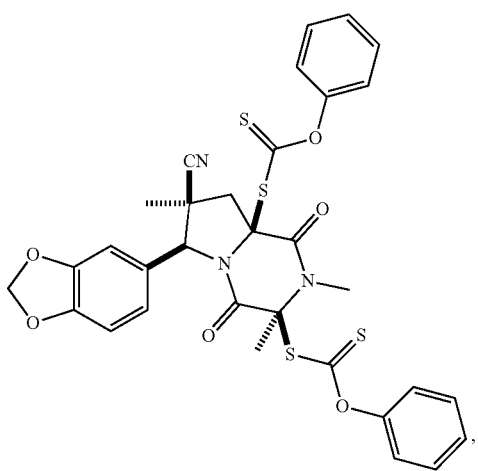
174
-continued
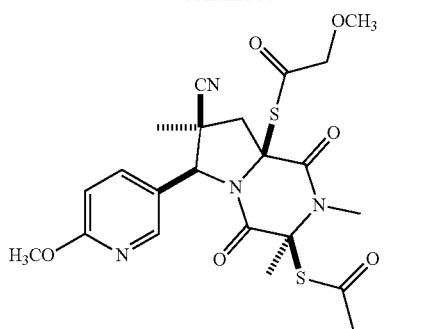
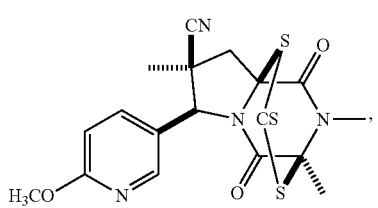
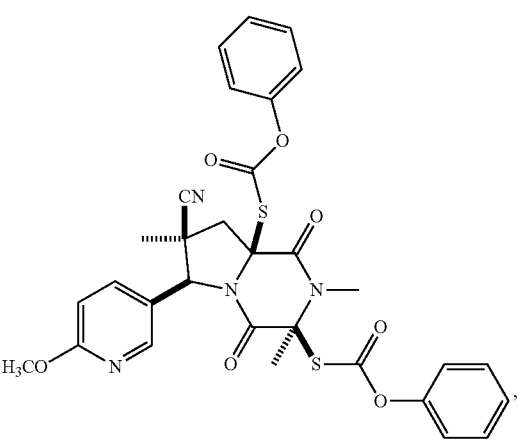
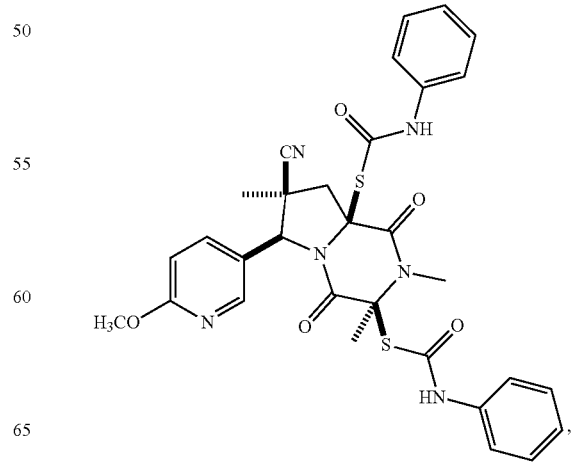

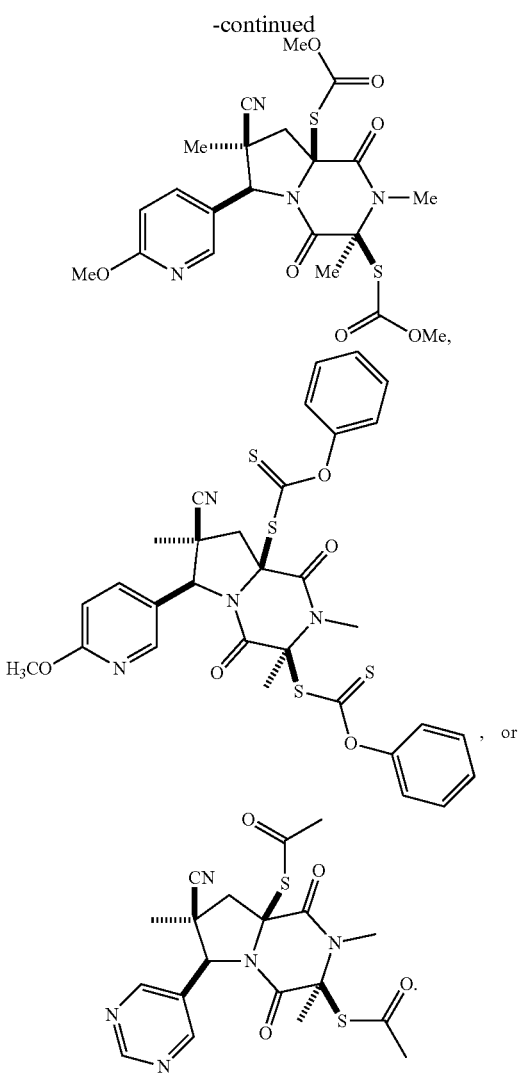

, or

Embodiment 37. A method of treating cancer, comprising administering to a subject in need thereof a therapeutically effective amount of a compound of any one of embodiments 1 to 36.

Embodiment 38. The method of embodiment 37, wherein the cancer is a solid or blood tumor.

Embodiment 39. The method of embodiment 37, wherein the cancer is ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment 40. The method of any one of embodiments 37 to 39, further comprising administering at least one additional anticancer agent.

Embodiment 41. The method of embodiment 40, wherein the at least one additional anticancer agent comprises an epigenetic inhibitor or a multi-kinase inhibitor.

Embodiment 42. The method of any one of embodiment 37 to 41, wherein the method comprises administering a first amount of the compound and a second amount of at least one additional anticancer agent, wherein the first amount and second amount are together an effective amount to provide a synergistic therapeutic effect.

Embodiment 43. The method of any one of embodiments 40 to 42, wherein the additional anticancer agent is an epigenetic inhibitor.

Embodiment 44. The method of embodiment 43, wherein the epigenetic inhibitor is azacitidine or decitadine.

Embodiment 45. The method of embodiments 43 or 44, wherein the compound and the epigenetic inhibitor are co-administered as a pharmaceutical composition.

Embodiment 46. The method of any one of embodiments 40 to 42, wherein the additional anticancer agent is a multi-kinase inhibitor.

Embodiment 47. The method of embodiment 46, wherein the multi-kinase inhibitor is sorafenib.

Embodiment 48. The method of embodiments 46 or 47, wherein the compound and the multi-kinase inhibitor are co-administered as a pharmaceutical composition.

Embodiment 49. The method of embodiment 37 or 39, wherein the cancer is ovarian cancer.

Embodiment 50. A pharmaceutical composition comprising a compound of any one of embodiments 1 to 36 and a pharmaceutically acceptable excipient.

Embodiment 51. A pharmaceutical composition comprising a pharmaceutically acceptable excipient and a combination of a compound of any one of embodiments 1 to 36 and at least one additional anticancer agent.

Embodiment 52. The pharmaceutical composition of embodiment 51, wherein the at least one additional anticancer agent comprises a multi-kinase inhibitor or an epigenetic inhibitor.

Embodiment 53. The pharmaceutical composition of embodiment 51, wherein the combination includes a first amount of the compound and a second amount of a multi-kinase inhibitor, wherein the first amount and second amount are together an effective amount to provide a synergistic therapeutic effect.

Embodiment 54. The pharmaceutical composition of embodiment 51, wherein the combination includes a first amount of the compound and a second amount of an epigenetic inhibitor, wherein the first amount and second amount are together an effective amount to provide a synergistic therapeutic effect.

Embodiment 55. The pharmaceutical composition of embodiment 51, wherein the combination includes a first amount of the compound, a second amount of a multi-kinase inhibitor, and a third amount of an epigenetic inhibitor, wherein the first amount, second, and third amounts are together an effective amount to provide a synergistic therapeutic effect.

Embodiment 56. The pharmaceutical composition of embodiment 52 or 55, wherein the multi-kinase inhibitor is sorafenib and the epigenetic inhibitor is azacitidine or decitabine.

Embodiment 57. The pharmaceutical composition of any one of embodiments 50 to 56 for use in cancer.

Embodiment 58. The pharmaceutical composition of any one of embodiments 50 to 56 for use in solid and blood tumors, including ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment 59. The pharmaceutical composition of any one of embodiments 50 to 56 for use in non-small cell lung cancer.

Embodiment 60. The pharmaceutical composition of any one of embodiments 52, 55 or 56, wherein the compound and the multi-kinase inhibitor or the epigenetic inhibitor are co-administered as a single dosage form.

Embodiment 61. A method of inhibiting the growth of a cancer cell, comprising administering to a subject in need thereof a therapeutically effective amount of a compound of any one of embodiments 1 to 36.

Embodiment 62. The method of embodiment 61, wherein the cancer cell is an ovarian cancer cell, breast cancer cell, lung cancer cell, leukemia cell, AML cell, CML cell, lymphoma cell, pancreatic cancer cell, kidney cancer cell, melanoma cell, liver cancer cell, colon cancer cell, sarcoma cell, multiple myeloma cell, brain cancer cell, or prostate cancer cell.

What is claimed is:

1. A compound having the formula (III):

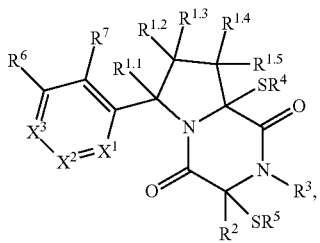

(III)

or a pharmaceutically acceptable salt thereof,
wherein:
$X^1$ is N or $CR^{10}$;
$X^2$ is N or $CR^{11}$;
$X^3$ is N or $CR^{12}$;
$R^{1.1}$ is hydrogen, halogen, $-CF_3$, $-CCl_3$, $-CBr_3$, $-CI_3$, $-CN$, $-CHO$, $-COOR^{1.1A}$, $-CONR^{1.1B}R^{1.1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.2}$ is hydrogen, halogen, $-N_3$, $-CF_3$, $-CCl_3$, $-CBr_3$, $-CI_3$, $-CN$, $-CHO$, $-OR^{1.2A}$, $-NR^{1.2B}R^{1.2C}$, $-COOR^{1.2A}$, $-CONR^{1.2B}R^{1.2C}$, $-NO_2$, $-SR^{1.2D}$, $-SO_{n1.2}R^{1.2B}$, $-SO_{v1.2}NR^{1.2B}R^{1.2C}$, $-NHNR^{1.2B}R^{1.2C}$, $-ONR^{1.2B}R^{1.2C}$, $-NHC(O)NHNR^{1.2B}R^{1.2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.3}$ is hydrogen, halogen, $-N_3$, $-CF_3$, $-CCl_3$, $-CBr_3$, $-CI_3$, $-CN$, $-CHO$, $-OR^{1.3A}$, $-NR^{1.3B}R^{1.3C}$, $-COOR^{1.3A}$, $-CONR^{1.3B}R^{1.3C}$, $-NO_2$, $-SR^{1.3D}$, $-SO_{n1.3}R^{1.3B}$, $-SO_{v1.3}NR^{1.3B}R^{1.3C}$, $-NHNR^{1.3B}R^{1.3C}$, $-ONR^{1.3B}R^{1.3C}$, $-NHC(O)NHNR^{1.3B}R^{1.3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.4}$ is hydrogen, halogen, $-N_3$, $-CF_3$, $-CCl_3$, $-CBr_3$, $-CI_3$, $-CN$, $-CHO$, $-OR^{1.4A}$, $-NR^{1.4B}R^{1.4C}$, $-COOR^{1.4A}$, $-CONR^{1.4B}R^{1.4C}$, $-NO_2$, $-SR^{1.4D}$, $-SO_{n1.4}R^{1.4B}$, $-SO_{v1.4}NR^{1.4B}R^{1.4C}$, $-NHNR^{1.4B}R^{1.4C}$, $-ONR^{1.4B}R^{1.4C}$, $-NHC(O)NHNR^{1.4B}R^{1.4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1.5}$ is hydrogen, halogen, $-N_3$, $-CF_3$, $-CCl_3$, $-CBr_3$, $-CI_3$, $-CN$, $-CHO$, $-OR^{1.5A}$, $-NR^{1.5B}R^{1.5C}$, $-COOR^{1.5A}$, $-CONR^{1.5B}R^{1.5C}$, $-NO_2$, $-SR^{1.5D}$, $-SO_{n1.5}R^{1.5B}$, $-SO_{v1.5}NR^{1.5B}R^{1.5C}$, $-NHNR^{1.5B}R^{1.5C}$, $-ONR^{1.5B}R^{1.5C}$, $-NHC(O)NHNR^{1.5B}R^{1.5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, $-CF_3$, $-CCl_3$, $-CBr_3$, $-CI_3$, $-CN$, $-CHO$, $-COOR^{2A}$, $-CONR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, halogen, $-N_3$, $-CF_3$, $-CCl_3$, $-CBr_3$, $-CI_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is $-C(O)-L^1-R^{18}$;
$R^5$ is $-C(O)-L^2-R^{19}$;
$L^1$ is a bond;
$L^2$ is a bond;
$R^{18}$ and $R^{19}$ are independently unsubstituted $C_1$-$C_3$alkyl;
$R^6$ is hydrogen, halogen, $-N_3$, $-CF_3$, $-CCl_3$, $-CBr_3$, $-CI_3$, $-CN$, $-CHO$, $-OR^{6A}$, $-NR^{6B}R^{6C}$, $-COOR^{6A}$, $-CONR^{6B}R^{6C}$, $-NO_2$, $-SR^{6D}$, $-SO_{n6}R^{6B}$, $-SO_{v6}NR^{6B}R^{6C}$, $-NHNR^{6B}R^{6C}$, $-ONR^{6B}R^{6C}$, $-NHC(O)NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is hydrogen, halogen, $-N_3$, $-CF_3$, $-CCl_3$, $-CBr_3$, $-CI_3$, $-CN$, $-CHO$, $-OR^{7A}$, $-NR^{7B}R^{7C}$, $-COOR^{7A}$, $-CONR^{7B}R^{7C}$, $-NO_2$, $-SR^{7D}$, $-SO_{n7}R^{7B}$, $-SO_{v7}NR^{7B}R^{7C}$, $-NHNR^{7B}R^{7C}$, $-ONR^{7B}R^{7C}$, $-NHC(O)NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10}$ is hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-CONR^{10B}R^{10C}$, $-NO_2$, $-SR^{10D}$, $-SO_{n10}R^{10B}$, $-SO_{v10}NR^{10B}R^{10C}$, $-NHNR^{10B}R^{10C}$, $-ONR^{10B}R^{10C}$, $-NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-CONR^{11B}R^{11C}$, $-NO_2$, $-SR^{11D}$, —SO$_{n11}$R$^{11B}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ and R$^{11}$ may optionally be joined to form a substituted or unsubstituted cycloalkyl, substituted or unsubstituted heterocycloalkyl;

R$^{12}$ is hydrogen, halogen, —N$_3$, —CF$_3$, —CCl$_3$, —CBr$_3$, —CI$_3$, —CN, —CHO, —OR$^{12A}$, —NR$^{12B}$R$^{12C}$, —COOR$^{12A}$, —CONR$^{12B}$R$^{12C}$, —NO$_2$, —SR$^{12D}$, —SO$_{n12}$R$^{12B}$, —SO$_{v12}$NR$^{12B}$R$^{12C}$, —NHNR$^{12B}$R$^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ and R$^{12}$ may optionally be joined to form a substituted or unsubstituted cycloalkyl, substituted or unsubstituted heterocycloalkyl;

R$^{1.1A}$, R$^{1.1B}$, R$^{1.1C}$, R$^{1.2A}$, and R$^{1.2B}$, R$^{1.2C}$, R$^{1.2D}$, R$^{1.3A}$, R$^{1.3B}$, and R$^{1.3C}$, R$^{1.3D}$, R$^{1.4A}$, R$^{1.4B}$, R$^{1.4C}$, R$^{1.4D}$, R$^{1.5A}$, R$^{1.5B}$, R$^{1.5C}$, and R$^{1.5D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{1.1B}$ and R$^{1.1C}$, R$^{1.2B}$ and R$^{1.2C}$, R$^{1.3B}$ and R$^{1.3C}$, R$^{1.4B}$ and R$^{1.4C}$, and R$^{1.5B}$ and R$^{1.5C}$ substituents bonded to the same nitrogen atom may optionally be joined to form a substituted or unsubstituted heterocycloalkyl or substituted or unsubstituted heteroaryl;

R$^{2A}$, R$^{2B}$, R$^{2C}$, R$^{3A}$, R$^{3B}$, R$^{3C}$, R$^{3D}$, R$^{6A}$, R$^{6B}$, R$^{6C}$, R$^{6D}$, R$^{7A}$, R$^{7B}$, R$^{7C}$, R$^{7D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, and R$^{12D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{6B}$ and R$^{6C}$, R$^{7B}$ and R$^{7C}$, R$^{10B}$ and R$^{10C}$, R$^{11B}$ and R$^{11C}$, and R$^{12B}$ and R$^{12C}$, substituents bonded to the same nitrogen atom may optionally be joined to form a substituted or unsubstituted heterocycloalkyl or substituted or unsubstituted heteroaryl;

n1.2, n1.3, n1.4, n1.5, n3, n6, n7, n10, n11 and n12 are independently an integer from 0 to 4; and v1.2, v1.3, v1.4, v1.5, v3, v6, v7, v10, v11 and v12, are independently 1 or 2.

2. The compound of claim 1, wherein the compound has the structure of Formula (IV):

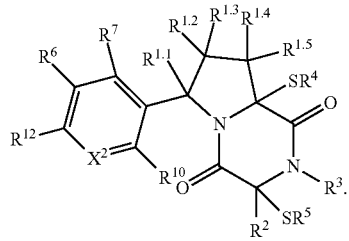

(IV)

3. The compound of claim 1, wherein R$^{10}$ and R$^{11}$ or R$^{11}$ and R$^{12}$ are joined to form a substituted or unsubstituted cycloalkyl or substituted or unsubstituted heterocycloalkyl having structural formula:

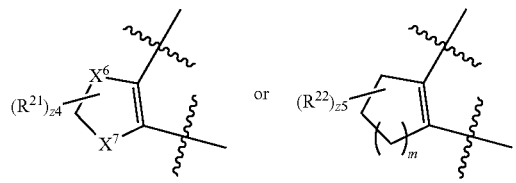

wherein:
X$^6$ is O, NR$^{23A}$, or S;
X$^7$ is O, NR$^{24A}$, or S;
z4 is an integer from 0 to 2;
z5 is an integer from 0 to 8;
m is 1 or 2; and
R$^{21}$, R$^{22}$, R$^{23A}$, and R$^{24A}$ are each independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

4. The compound of claim 2, wherein the compound has the formula:

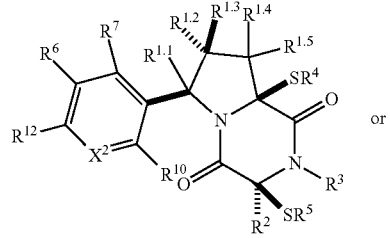

(V (S))

or

-continued

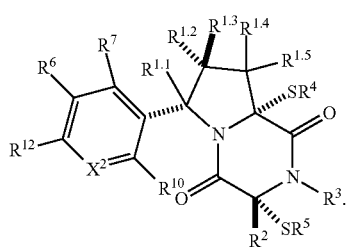
(VI (R))

5. The compound of claim 3, wherein the compound has the formula:

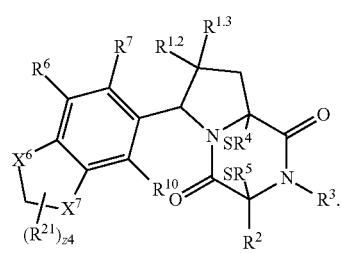
(VII)

6. The compound of claim 5, wherein the compound has the formula:

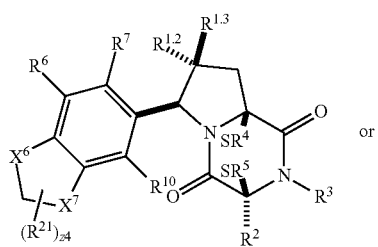
(VIII (S))

or

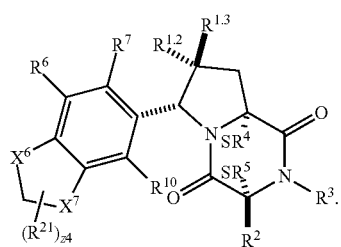
(IX (R))

7. The compound of claim 1, wherein $R^6$ and $R^7$ are each independently hydrogen.

8. The compound of claim 1, wherein $X^2$ is N.

9. The compound of claim 1, wherein $R^{12}$ is halogen or —$OR^{12.4}$.

10. The compound of claim 1, wherein $R^{1.2}$ is substituted or unsubstituted alkyl.

11. The compound of claim 1, wherein $R^{1.3}$ is —CN.

12. The compound of claim 1, wherein $R^2$ is substituted or unsubstituted alkyl.

13. The compound of claim 1, wherein the compound has the structure:

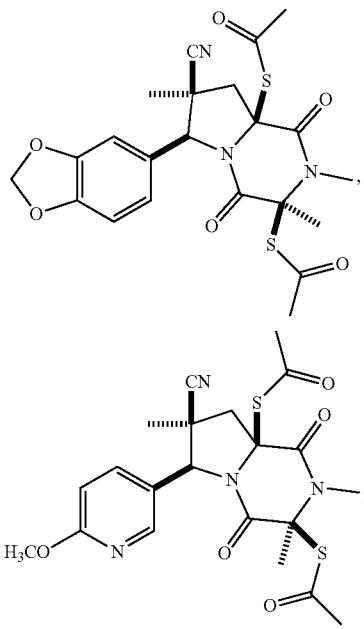

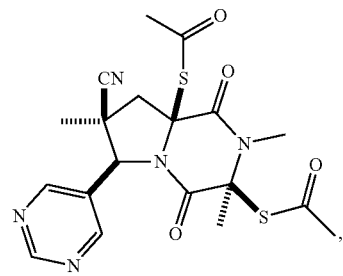

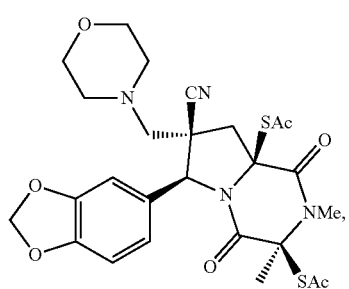

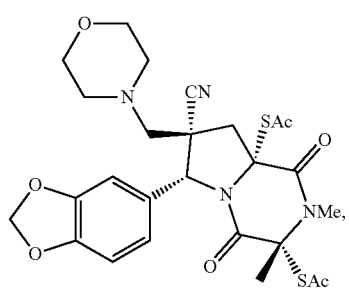

-continued

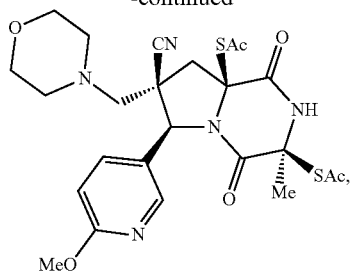

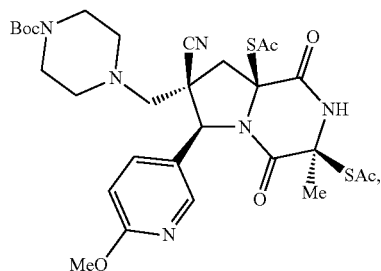

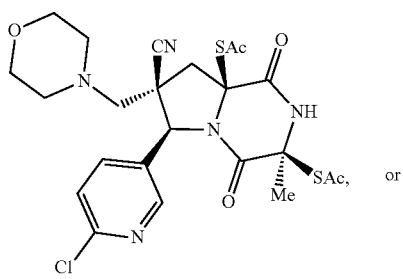

-continued

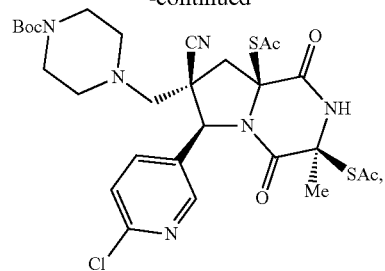

or a pharmaceutically acceptable salt thereof.

14. A pharmaceutical composition comprising a compound of claim 1, or a pharmaceutically acceptable salt thereof and a pharmaceutically acceptable excipient.

15. A method of treating cancer, comprising administering to a subject in need thereof a therapeutically effective amount of a compound of claim 1, or a pharmaceutically acceptable salt or solvate thereof, wherein the cancer is lymphoma, melanoma, prostate cancer, or lung cancer.

16. The method of claim 15, further comprising administering at least one additional anticancer agent, wherein the additional anticancer agent comprises an epigenetic inhibitor or a multi-kinase inhibitor.

17. The method of claim 16, wherein the epigenetic inhibitor is azacitidine or decitadine and the multi-kinase inhibitor is sorafenib.

18. A method of inhibiting the growth of a cancer cell, comprising administering to a subject in need thereof a therapeutically effective amount of a compound of claim 1, wherein the cancer cell is lymphoma cell, melanoma cell, lung cancer cell, or prostate cancer cell.

19. The method of claim 18, wherein lymphoma is cutaneous T-cell lymphoma.

* * * * *